US010202339B2

(12) United States Patent
Popovici-Muller et al.

(10) Patent No.: US 10,202,339 B2
(45) Date of Patent: Feb. 12, 2019

(54) THERAPEUTIC COMPOUNDS AND COMPOSITIONS

(71) Applicant: AGIOS PHARMACEUTICALS, INC., Cambridge, MA (US)

(72) Inventors: Janeta Popovici-Muller, Windham, NH (US); Francesco G. Salituro, Marlborough, MA (US); Jeffrey O. Saunders, Lincoln, MA (US); Jeremy Travins, Southborough, MA (US); Shunqi Yan, Irvine, CA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/435,674

(22) PCT Filed: Oct. 11, 2013

(86) PCT No.: PCT/US2013/064601
§ 371 (c)(1),
(2) Date: Apr. 14, 2015

(87) PCT Pub. No.: WO2014/062511
PCT Pub. Date: Apr. 24, 2014

(65) Prior Publication Data

US 2015/0299115 A1 Oct. 22, 2015

Related U.S. Application Data

(60) Provisional application No. 61/714,179, filed on Oct. 15, 2012.

(51) Int. Cl.

| | |
|---|---|
| ***C07C 311/44*** | (2006.01) |
| ***A61K 31/17*** | (2006.01) |
| ***A61K 31/18*** | (2006.01) |
| ***A61K 31/351*** | (2006.01) |
| ***A61K 31/381*** | (2006.01) |
| ***A61K 31/397*** | (2006.01) |
| ***A61K 31/422*** | (2006.01) |
| ***A61K 31/4402*** | (2006.01) |
| ***A61K 31/4406*** | (2006.01) |
| ***A61K 31/4436*** | (2006.01) |
| ***A61K 31/505*** | (2006.01) |
| ***A61K 31/5377*** | (2006.01) |
| ***A61K 31/541*** | (2006.01) |
| ***A61K 31/553*** | (2006.01) |
| ***A61K 45/06*** | (2006.01) |
| ***C07D 213/40*** | (2006.01) |
| ***C07D 213/74*** | (2006.01) |
| ***C07D 239/42*** | (2006.01) |
| ***C07D 267/10*** | (2006.01) |
| ***C07D 295/26*** | (2006.01) |
| ***C07D 309/14*** | (2006.01) |
| ***C07D 333/20*** | (2006.01) |
| ***C07D 409/12*** | (2006.01) |
| ***C07D 413/12*** | (2006.01) |

(52) U.S. Cl.
CPC ............ *C07C 311/44* (2013.01); *A61K 31/17* (2013.01); *A61K 31/18* (2013.01); *A61K 31/351* (2013.01); *A61K 31/381* (2013.01); *A61K 31/397* (2013.01); *A61K 31/422* (2013.01); *A61K 31/4402* (2013.01); *A61K 31/4406* (2013.01); *A61K 31/4436* (2013.01); *A61K 31/505* (2013.01); *A61K 31/5377* (2013.01); *A61K 31/541* (2013.01); *A61K 31/553* (2013.01); *A61K 45/06* (2013.01); *C07D 213/40* (2013.01); *C07D 213/74* (2013.01); *C07D 239/42* (2013.01); *C07D 267/10* (2013.01); *C07D 295/26* (2013.01); *C07D 309/14* (2013.01); *C07D 333/20* (2013.01); *C07D 409/12* (2013.01); *C07D 413/12* (2013.01)

(58) Field of Classification Search
None
See application file for complete search history.

(56) References Cited

U.S. PATENT DOCUMENTS 2,390,529 A 12/1945 Friedheim
3,755,322 A 8/1973 Winter et al.
(Continued)

FOREIGN PATENT DOCUMENTS

CN 101575408 A 11/2009
CN 102659765 A 9/2012
(Continued)

OTHER PUBLICATIONS

PUBCHEM CID 4078245 [online]. Sep. 13, 2005 [retrieved on Feb. 4, 2012]; retrieved from http://pubchem.ncbi.nim.nih.gov/; 2d-structure.*
Shehata, MT. et al. Sulfamido-o-toluic acid azide and its urea and urethane derivatives. Proceedings of the Indian National Science Academy. 1986, vol. 52, p. 1413.*
US Pharmacopeial Convention. USP 30 (467) Residual Solvents. Table 2. Class 2 Residual Solvents. Published Mar. 23, 2007. Accessed Apr. 20, 2017.*
Wang, Science, vol. 340, 622-626, 2013. (Year: 2013).*
Dang, Trends in Molecular Medicine vol. 16(9), 387-397, 2010. (Year: 2010).*
Yen, Oncogene, vol. 29, 6409-6417, 2010. (Year: 2010).*
(Continued)

*Primary Examiner* — D Margaret M Seaman
(74) *Attorney, Agent, or Firm* — Goodwin Procter LLP

(57) ABSTRACT

Provided are aryl sulfonamide diarylurea derivative compounds that are inhibitors of mutant isocitrate dehydrogenase 1/2 (IDH 1/2), useful for treating cancer. Also provided are methods of treating cancer comprising administering to a subject in need thereof a compound described herein. Cancers that are treatable by the compounds of the invention are glioblastoma, myelodysplastic syndrome, myeloproliferative neoplasm, acute myelogenous leukemia, sarcoma, melanoma, non-small cell lung cancer, chondrosarcoma, and non-Hodgkin's lymphoma (NHL).

11 Claims, No Drawings

(56) References Cited

U.S. PATENT DOCUMENTS

| | | | |
|---|---|---|---|
| 3,867,383 A | 2/1975 | Winter | |
| 4,084,053 A | 4/1978 | Desai et al. | |
| 4,977,062 A * | 12/1990 | Yagihara | G03C 1/061 430/264 |
| 5,021,421 A | 6/1991 | Hino et al. | |
| 5,489,591 A | 2/1996 | Kobayashi et al. | |
| 5,807,876 A | 9/1998 | Armistead et al. | |
| 5,834,485 A | 11/1998 | Dyke et al. | |
| 5,965,559 A | 10/1999 | Faull et al. | |
| 5,984,882 A | 11/1999 | Rosenschein et al. | |
| 6,262,113 B1 | 7/2001 | Widdowson et al. | |
| 6,274,620 B1 | 8/2001 | Labrecque et al. | |
| 6,313,127 B1 | 11/2001 | Waterson et al. | |
| 6,399,358 B1 | 6/2002 | Williams et al. | |
| 6,723,730 B2 | 4/2004 | Bakthavatchalam et al. | |
| 6,979,675 B2 | 12/2005 | Tidmarsh | |
| 7,173,025 B1 | 2/2007 | Stocker et al. | |
| 7,858,782 B2 | 12/2010 | Tao et al. | |
| 8,133,900 B2 | 3/2012 | Hood et al. | |
| 8,465,673 B2 | 6/2013 | Yasuda et al. | |
| 2002/0188027 A1 | 12/2002 | Robinson et al. | |
| 2003/0095958 A1 | 5/2003 | Bhisetti et al. | |
| 2003/0109527 A1 | 6/2003 | Jin et al. | |
| 2003/0207882 A1 | 11/2003 | Stocker et al. | |
| 2003/0213405 A1 | 11/2003 | Harada et al. | |
| 2004/0067234 A1 | 4/2004 | Einat et al. | |
| 2004/0248221 A1 | 12/2004 | Stockwell | |
| 2006/0084645 A1 | 4/2006 | Pal et al. | |
| 2006/0281122 A1 | 12/2006 | Bryant et al. | |
| 2007/0244088 A1 | 10/2007 | Brickmann et al. | |
| 2008/0300208 A1 | 12/2008 | Einat et al. | |
| 2009/0093526 A1 | 4/2009 | Miller et al. | |
| 2009/0163508 A1 | 6/2009 | Kori et al. | |
| 2009/0163545 A1 * | 6/2009 | Goldfarb | A61K 31/122 514/312 |
| 2010/0129350 A1 | 5/2010 | Zacharie et al. | |
| 2010/0144722 A1 | 6/2010 | Alexander et al. | |
| 2010/0273808 A1 | 10/2010 | Armitage et al. | |
| 2010/0331307 A1 | 12/2010 | Salituro et al. | |
| 2011/0073007 A1 | 3/2011 | Yasuda et al. | |
| 2011/0086088 A1 | 4/2011 | Berry | |
| 2011/0288065 A1 | 11/2011 | Fujihara et al. | |
| 2012/0121515 A1 | 5/2012 | Dang et al. | |
| 2012/0129865 A1 | 5/2012 | Wang et al. | |
| 2012/0164143 A1 | 6/2012 | Teeling et al. | |
| 2012/0202818 A1 | 8/2012 | Tao et al. | |
| 2012/0238576 A1 | 9/2012 | Tao et al. | |
| 2012/0277233 A1 | 11/2012 | Tao et al. | |
| 2013/0035329 A1 | 2/2013 | Saunders et al. | |
| 2013/0109643 A1 | 5/2013 | Riggins et al. | |
| 2013/0183281 A1 | 7/2013 | Su et al. | |
| 2013/0184222 A1 | 7/2013 | Popovici-Muller et al. | |
| 2013/0190249 A1 | 7/2013 | Lemieux et al. | |
| 2013/0190287 A1 | 7/2013 | Cianchetta et al. | |
| 2014/0187435 A1 | 7/2014 | Dang et al. | |
| 2015/0018328 A1 | 1/2015 | Konteatis et al. | |
| 2015/0031627 A1 | 1/2015 | Lemieux et al. | |
| 2015/0044716 A1 | 2/2015 | Balss et al. | |

FOREIGN PATENT DOCUMENTS

| | | | |
|---|---|---|---|
| CN | 103097340 | A | 5/2013 |
| DE | 3314663 | A1 | 10/1983 |
| DE | 3512630 | A1 | 10/1986 |
| DE | 10155684 | * | 5/2003 |
| EP | 0022958 | A1 | 1/1981 |
| EP | 0384228 | A1 | 8/1990 |
| EP | 0385237 | A2 | 9/1990 |
| EP | 0945446 | A1 | 9/1999 |
| FR | 2735127 | A1 | 12/1996 |
| JP | 4099768 | | 3/1992 |
| JP | 9291034 | A | 11/1997 |
| JP | 11158073 | | 6/1999 |
| JP | 2004107220 | A | 4/2004 |
| JP | 2009237115 | A | 10/2009 |
| JP | 2010079130 | A | 4/2010 |
| JP | 2010181540 | A | 8/2010 |
| JP | 4753336 | B2 | 8/2011 |
| MX | 2013/000614 | A | 6/2013 |
| WO | 97/28128 | A1 | 8/1997 |
| WO | 97/28129 | A1 | 8/1997 |
| WO | 9932463 | A1 | 7/1999 |
| WO | 2001016097 | A1 | 3/2001 |
| WO | 2002102313 | A2 | 12/2002 |
| WO | 030016289 | A1 | 2/2003 |
| WO | 2004009562 | A1 | 1/2004 |
| WO | 2004046120 | A2 | 6/2004 |
| WO | 2004050033 | A2 | 6/2004 |
| WO | 2004/073619 | A2 | 9/2004 |
| WO | 2004/074438 | A2 | 9/2004 |
| WO | 2005035507 | A2 | 4/2005 |
| WO | 2005060956 | A1 | 7/2005 |
| WO | 2005065691 | A1 | 7/2005 |
| WO | 2006-038594 | A1 | 4/2006 |
| WO | 2006070198 | A1 | 7/2006 |
| WO | 2006079791 | A1 | 8/2006 |
| WO | 2007023186 | A1 | 3/2007 |
| WO | 2008/050168 | A1 | 5/2008 |
| WO | 2008070661 | A1 | 6/2008 |
| WO | 2008076883 | A2 | 6/2008 |
| WO | 2008131547 | A1 | 11/2008 |
| WO | 2008154026 | A1 | 12/2008 |
| WO | 2009013126 | A1 | 1/2009 |
| WO | 2009016410 | A2 | 2/2009 |
| WO | 2009118567 | A2 | 10/2009 |
| WO | 2009126863 | A2 | 10/2009 |
| WO | WO 2009/129371 | A1 * | 10/2009 |
| WO | 2009150248 | A1 | 12/2009 |
| WO | 2010007756 | A1 | 1/2010 |
| WO | 2010/028099 | A1 | 3/2010 |
| WO | 2010105243 | A1 | 9/2010 |
| WO | 2010/129596 | A1 | 11/2010 |
| WO | 2010144338 | A1 | 12/2010 |
| WO | 2010144404 | A1 | 12/2010 |
| WO | 201105210 | A1 | 1/2011 |
| WO | 2011002817 | A1 | 1/2011 |
| WO | 2011/072174 | A1 | 6/2011 |
| WO | 2012/009678 | A1 | 1/2012 |
| WO | 2012074999 | A1 | 6/2012 |
| WO | 2012160034 | A1 | 11/2012 |
| WO | 2012171506 | A1 | 12/2012 |
| WO | 2013/004332 | A1 | 1/2013 |
| WO | 2013102431 | A1 | 7/2013 |
| WO | 2013107291 | A1 | 7/2013 |
| WO | 2013107405 | A1 | 7/2013 |
| WO | 2013133367 | A1 | 9/2013 |
| WO | 2014015422 | A1 | 1/2014 |
| WO | 2015/003360 | A2 | 1/2015 |

OTHER PUBLICATIONS

Aghili et al. "Hydroxyglutaric aciduria and malignant brain tumor: a case report and literature review", Journal of Neuroncology (2008) 91 pp. 233-236.

Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.

Balss, "Analysis of the IDH1 codon 132 mutation in brain tumors", Acta Neuropathol (2008) vol. 116, pp. 597-602.

Benner et al, "Evolution, language and analogy in functional genomics", Trends in Genetics (2001) vol. 17, pp. 414-418.

Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.

Bleeker et al., "IDH1 mutations at residue p. R132 (IDH1 (R132)) occur frequently in high-grade 18-22 gliomas but not in other solid tumors." Hum Muta1., (2009) vol. 30, No. 1, pp. 7-11.

Braun et al. "Triazine-based polymers: 4. MALDI-MS of triazine-based polyamines" Polymer (1996) vol. 37, No. 5, pp. 777-783.

(56) References Cited

OTHER PUBLICATIONS

Cairns et al. "Oncogenic Isocitrate Dehydrogenase Mutations: Mechanisms, Models, and Clinical Opportunities" Cancer Discovery (2013) vol. 3, Iss 7, pp. 730-741 .
Cecil Text Book of Medicine, edited by Bennet and Plum, (1997) 20th edition, vol. 1, pp. 1004-1010.
Chan et al. "Multi-domain hydrogen-bond forming metal chelates: X-ray crystal structures of dicyclopalladated 2,3-bis[6-(2-amino-4-phenylamino-1 ,3,5-triazinyl)]pyrazine (H2L) [Pd2Br2L] and 2,6-bis[6-(2-amino-4-phenylamino-1,3,5-triazinylium)]-pyridine dichloride" Chemical Communications (1996) No. 1, pp. 81-83.
Chapman et al. "Substituted aminopyrimidine protein kinase B (PknB) inhibitors show activity against Mycobacterium tuberculosis" Bioorganic & Medicinal Chemistry Letters (2012) vol. 22, pp. 3349-3353.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry (1995) vol. 32, pp. 543-545.
Dang et al., "Cancer-associated IDH1 mutations produce 2-hydroxyglutarate." Nature (2009) vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Dermer "another Anniversary for the War on Cancer" Bio/Technology (1994) vol. 12, p. 320.
Dohner et al. "Impact of Genetic Features on Treatment Decisions in AML" American Society of Hematology (2011) pp. 36-42.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
EP Search Report & Written Opinion for EP 10825706 dated Mar. 20, 2013.
European Search Report for Application No. 10751525.6 dated Dec. 14, 2012.
European Search Report for European Application No. 12799802.9 dated Sep. 24, 2014.
European Search Report for European Application No. EP 12800001.5 dated Oct. 10, 2014.
Eurpoean Search Report for EP Application No. 11763425.3 dated Sep. 23, 2013.
Freshney et al. "Culture of Animal Cells, A Manual of Basic Techniques" Alan R. Liss, Inc. (1983) pp. 1-6.
Gewald et al. "Discovery of triazines as potent, selective and orally active PDE4 inhibitors" Bioorganic & medicinal Chemistry Letters (2013) vol. 23, pp. 4308-4314.
Golub et al. "Molecular Classification of Cancer: Class Discovery and Class Prediction by Gene Expression Monitoring" Science (1999) vol. 286, pp. 531-537.
Hartmann et al. "Type and Frequency of IDH1 and IDH2 mutations are related to astrocytic and oligodendroglial differentiation and age: a study of 1010 diffuse gliomas" Acta Neuropathologica (2009) vol. 118, pp. 469-474.
Holmes et al. "750 MHz 1H NMR spectroscopy characterisation of the complex metabolic pattern of urine from patients with inborn errors of metabolism: 2-hydroxyglutaric aciduria and maple syrup urine disease" Journal of Pharmaceutical and Biomedical Analysis (1997) vol. 15, pp. 1647-1659.
International Preliminary Report for related application No. PCT/US2010/059778 dated Jun. 12, 2012.
International Preliminary Report on Patentability for PCT/CN2012/000841 dated Dec. 17, 2013.
International Preliminary Report on Patentability for PCT/CN2012/077096 dated Dec. 17, 2013.
International Preliminary Report on Patentability for PCT/US2010/027253 dated Sep. 13, 2011.
International Preliminary Report on Patentability for PCT/US2010/040486 dated Jan. 12, 2012.
International Preliminary Report on Patentability for PCT/US2010/053623 dated Apr. 24, 2012.
International Preliminary Report on Patentability for PCT/US2010/053624 dated Apr. 7, 2011.
International Preliminary Report on Patentability for PCT/US2011/030692 dated Oct. 2, 2012.
International Preliminary Report on Patentability for PCT/US2011/067752 dated Apr. 11, 2013.
International Search Report & Written Opinion for PCT/CN2013/070755 dated Apr. 25, 2013.
International Search Report and Written Opinion for International Application No. PCT/CN2013/080105 dated Jul. 11, 2014.
International Search Report and Written Opinion for International Application No. PCT/CN2013/081170 dated Apr. 30, 2014.
International Search Report and Written Opinion for International Application No. PCT/CN2014/081957 dated Sep. 30, 2014.
International Search Report and Written Opinion for International Application No. PCT/CN2014/081958 dated Sep. 29, 2014.
International Search Report and Written Opinion for International Application No. PCT/US2014/046202 dated Sep. 30, 2014.
International Search Report and Written Opinion for International Application No. PCT/US2014/049469 dated Jan. 22, 2015.
International Search Report for International Application No. PCT/CN2013/079184 dated Jan. 12, 2015.
International Search Report for International Application No. PCT/CN2013/079200 dated Jan. 12, 2015.
International Search Report for International Application No. PCT/CN2014/082869 dated Sep. 30, 2014.
International Search Report for International Application No. PCT/US2014/046204 dated Oct. 1, 2014.
International Search Report for PCT/2011/030692 dated Jul. 27, 2011.
International Search Report for PCT/CN2012/000841 dated Sep. 27, 2012.
Struys et al. "Investigations by mass isotopomer analysis of the formation of D-2-hydroxyglutarate by cultured lymphoblasts from two patients with D-2-hydroxyglutaric aciduria" FEBS Letters (2004) vol. 557, pp. 115-120.
Struys et al. "Mutations in the D-2-hydroxyglutarate dehydrogenase gene cause D-2-hydroxyglutaric aciduria" American Journal of Human Genetics (2005) vol. 76, pp. 358-360.
Supplementary European Search Report for EP 10751525 dated Dec. 14, 2012.
Supplementary European Search Report for EP Application No. 10825707.2 dated Jun. 28, 2013.
Supplementary Search Report for EP10794668 dated Oct. 18, 2012.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
Thompson, "Metabolic Enzymes as Oncogenes or Tumor Suppressors." The New England Journal of Medicine (2009) vol. 360, No. 8, pp. 813-815.
Van Schaftingen et al. "L-2-Hydroglutaric aciduria, a disorder of metabolite repair" J Inherit. Metab. Dis. (2009) vol. 32, pp. 135-142.
Wang et al "Facile Synthesis of 2,4-Dianiino-6-alkyi—or 6-Aryl-Pyrimidine Derivatives" Journal of Heterocyclic Chemistry (2010) vol. 47 pp. 1056-1061.
Wang et al. "A novel ligand N,N'-di(2-pyridyl)-2,4-diamino-6-phenyl-1,3,5-triazine (dpdapt) and its complexes: [Cu (dpdapt)Cl2] and [Cu(dpdapt)(NO3)(H2O)] •NO3 • H2O" Polyhedron (2006) vol. 25, No. 1, pp. 195-202.
Ward et al. "The Common Feature of Leukemia-Associated IDH1 and IDH2 Mutations Is a Neomorphic Enzyme Activity Converting [alpha]-Ketoglutarate to 2-Hydroxyglutarate" Cancer Cell (2010) vol. 17, No. 3 pp. 225-234.
Watanabe et al., "IDH1 Mutations Are Early Events in the Development of Astrocytomas and Oligodendrogliomas". American Journal of Pathology (2009) vol. 174, No. 4, pp. 1149-1153.
Written Opinion for PCT/US2010/027253 dated Aug. 19, 2010.

(56) References Cited

OTHER PUBLICATIONS

Written Opinion of International Search Authority for PCT/CN2013/000009 dated Apr. 18, 2013.
Written Opinion of Search Authority for PCT/US2010/53623 dated Jan. 18, 2011.
Written Opinion of the International Searching Authority for PCT/US2011/067752 dated Mar. 5, 2012.
Yan et al., "IDH1 and IDH2 Mutations in Gliomas." The New England Journal of Medicine, (2009) vol. 360, No. 8, pp. 765-773.
Zhao et al. "Glioma-derived mutations in IDH1 dominantly inhibit IDH1 catalytic activity and induce HIF-1alpha", Science (2009) vol. 324, No. 5924, pp. 261-265.
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Genetics Home Reference, "L2HGDH". <http:..ghr.nlm.nih.gove/gene/L2HGDH> accessed on Sep. 4, 2015.
International Preliminary Report for related application No. PCT/US2011/067752 dated Apr. 11, 2013.
International Preliminary Report on Patentability for International Application No. PCT/CN2012/000841 dated Dec. 17, 2013.
International Preliminary Report on Patentability for International Application No. PCT/CN2012/077096 dated Sep. 17, 2013.
International Search Report and Written Opinion for Internatinal Application No. PCT/US2013/064601 dated Feb. 24, 2014.
International Search Report and Written Opinion for International Application No. PCT/US15/020349 dated Jun. 15, 2015.
International Search Report and Written Opinion for International Application No. PCT/US2015/020346 dated Jun. 18, 2015.
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Lou, "IDH1: function follows form" SciBX (2009) vol. 2, No. 48, pp. 1-2.
Paronikyan et al. "Synthesis and biological activity of 3-piperazinylpyrano [3,4-C] pyridines" Armyanskii Khimicheskii Zhurnal (1990) vol. 43, No_ 8, pp. 518-523.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Sosnovik et al. "Emerging concepts in molecular MRI" Current Opinions in Biotechnology (2007) vol. 18, pp. 4-10.
Struys, EA. et al. "Measurement of Urinary D- and L-2-Hydroxyglutarate Enantiomers by Stable-Isotope-Dilution LiquidChromatography—Tandem Mass Spectrometry after Derivatization with Diacetyi-L-Tartaric Anhydride." Clinical Chemistry (2004) 501391-1395.
The radiation fact sheet published by the National Cancer Institute, http://www.cancergov/about-cancer/treatment/types/radiation-therapy/radiation-fact-sheet, reviewed Jun. 30, 2010.
Zheng et al. "Synthesis and antitumor evaluation of a novel series of triaminotriazine derivatives" Bioorganic & Medicinal Chemistry (2007) vol. 15, pp. 1815-1827.
International Search Report for PCT/CN2012/077096 dated Oct. 4, 2012.
International Search Report for PCT/CN2013/000009 dated Apr. 18, 2013.
International Search Report for PCT/CN2013/000068 dated Apr. 25, 2013.
International Search Report for PCT/US10/040486 dated Sep. 1, 2010.
International Search Report for PCT/US2010/027253 dated Aug. 19, 2010.
International Search Report for PCT/US2010/059778 dated Mar. 17, 2011.
International Search Report for PCT/US2010/53623 dated Jan. 18, 2011.
International Search Report for PCT/US2010053624 dated Apr. 7, 2011.
International Search Report for PCT/US2011/067752 dated Feb. 22, 2012.
International Search Report for PCT/US2011044254 dated May 10, 2011.
International Search Report for PCT/US2013/064601 dated Feb. 24, 2014.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jennings et al. "Expression and mutagenesis of mammalian cytosolic NADP+-specific isocitrate dehydrogenase" Biochemistry (1997) vol. 36, pp. 13743-13747.
Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al. "Identification and Functional Characterization of a Novel, Tissue-specific NAD+-dependent Isocitrate Dehydrogenase b Subunit Isoform" JBC (1999) vol. 274, No. 52, pp. 36866-36875.
Kim et al. "Ser95, Asn97, and Thr78 are important for the catalytic function of porcine NADP-dependent isocitrate dehydrogenase" Protein Science (2005) vol. 14, pp. 140-147.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kusakabe et al. Chemical Abstracts vol. 152, No. 191956, Abstract for WO2010007756 (2010).
Lee et al. "Combinatorial Solid-Phase Synthesis of 6-Aryl-1,3,4-triazines via Suzuki Coupling" Aust. J. Chem. (2011) vol. 64, pp. 540-544.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
May et al. "How many species are there on earth" Science (1988) vol. 241, p. 1441.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Parsons et al. "An Integrated Genomic Analysis of Human Glioblastoma Multiforme" Science (2008) vol. 321, pp. 1807-1812 and Supplemental Data.
Pollard et al, "Cancer. Puzzling patterns of predisposition." Science (2009) vol. 324, pp. 192-194.
Popovici-Muller et al. "Discovery of the First Potent Inhibitors of Mutant IDH1 That Lower Tumor2-HG in Vivo" ACS Medicinal Chemistry Letters (2012) vol. 3, No. 10, pp. 850-855.
Pubchem CID 4854170 [online]; Sep. 17, 2005 [retrieved on Feb. 4, 2012]; retrieved from http://pubchem.ncbi.nim.nih.gov/; 2d-structure.
Raynaud et al. "Absence of R140Q Mutation of Isocitrate Dehydrogenase 2 in Gliomas and Breast Cancers" Oncology Letters (2010) vol. 1, No. 5, pp. 883-884.

(56) References Cited

OTHER PUBLICATIONS

Reitman et al. "Isocitrate Dehydrogenase 1 and 2 Mutations in Cancer: Alterations at a Crossroads of Cellular Metabolism" Journal of the National Cancer Institute (2010) vol. 102, No. 13, pp. 932-941.

Rohle et al. "An Inhibitor of Mutant IDH1 Delays Growth and Promotes Differentiation of Glioma Cells" Science (2013) vol. 340, No. 6132, pp. 626-630.

Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.

Shih et al. "The Role of Mutations in Epigenetic Regulators in Myeloid Malignancies" Nature Reviews Cancer (2012) vol. 12, No. 9, pp. 599-612.

Sirkanyan et al "Synthesis of new derivatives of piperazine-substituted pyrano[3,4-c]pyridines" Hayastani Kimiakan Handes (2009) vol. 62, No. 3-4 pp. 378-385. English Abstract Only.

Sonoda et al. "Analysis of IDH1 and IDH2 mutations in Japanese glioma patients" Cancer Science, vol. 100, No. 10, pp. 1996-1998.

STN File CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".

STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".

STN File CA, Registry No. 134538-28-6, entered STN on Jun. 28, 1991, Chemical Abstracts Index Name "1H-Pyrano[3,4-c]pyridine-5-carbonitrile, 3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.

STN File CA, Registry No. 134538-29-7, entered STN on Jun. 28, 1991, Chemical Abstracts Index Name "1H-Pyrano[3,4-c]pyridine-5-carbonitrile, 3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.

STN File CA, Registry No. 134538-30-0, entered STN on Jun. 28, 1991, Chemical Abstracts Index Name "1H-Pyrano[3,4-c]pyridine-5-carbonitrile, 6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.

STN File CA, Registry No. 134538-31-1, entered STN on Jun. 28, 1991, Chemical Abstracts Index Name "1H-Pyrano[3,4-c]pyridine-5-carbonitrile, 6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.

STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".

STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".

STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".

STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".

STN Registry, L23 Answer 2 of 3 (CAS No. 1032450-21-7), Database: ASINEX Ltd.,Entered STN: Jul. 3, 2008 (Jul. 3, 2008).

STN Registry. L23 Answer 1 of 3 (CAS No. 1038821-72-5),Database: ChemDB (University of California Irvine), Entered STN: Aug. 5, 2008 (May 8, 2008).

Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.

Rao et al., "Polymorphism in Drugs and its Significance in Therapeutics". Journal of Scientific & Industrial Research vol. 46 Oct. 1987 pp. 450-455.

Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.

Extended European Search Report for European application No. 16152308.9 dated Jul. 18, 2016.

Registry (STN) [online], entered STN Apr. 18, 2005, CAS registration No. 848658-32-2.

Registry (STN) [online], entered STN Aug. 12, 2003, CAS registration No. 565165-17-5.

Registry (STN) [online], entered STN Aug. 24, 2004, CAS registration No. 731816-64-1.

Registry (STN) [online], entered STN Dec. 1, 2004, CAS registration No. 793678-13-4.

Registry (STN) [online], entered STN Dec. 31, 2001, CAS registration No. 379707-06-9.

Registry (STN) [online], entered STN Jan. 2, 2002, CAS registration No. 380169-59-5.

Registry (STN) [online], entered STN Jan. 3, 2002, CAS registration No. 380320-85-4.

Registry (STN) [online], entered STN Jan. 3, 2002, CAS registration No. 380322-34-9.

Registry (STN) [online], entered STN Sep. 23, 2004, CAS registration No. 749890-71-9.

* cited by examiner

THERAPEUTIC COMPOUNDS AND COMPOSITIONS

CLAIM OF PRIORITY

This application is a national stage application under 35 U.S.C. § 371 of International Application No. PCT/US2013/064601, filed Oct. 11, 2013, published as International Publication No. WO 2014/062511 on Apr. 24, 2014, which claims priority from U.S. Ser. No. 61/714,179, filed Oct. 15, 2012, each of which is incorporated herein by reference in its entirety.

BACKGROUND OF INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1/2 (isocitrate dehydrogenase 1/2 (NADP+), mitochondrial) are also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex.

Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November 1992) to the EMBL/GenBank/DDBJ databases; and The MGC Project Team, Genome Res. 14:2121-2127(2004).

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (December 2008) to UniProtKB; Kullmann et al., Submitted (June 1996) to the EMBL/GenBank/DDBJ databases; and Sjoeblom et al., Science 314:268-274(2006).

Non-mutant, e.g., wild type, IDH 1/2 catalyzes the oxidative decarboxylation of isocitrate to α-ketoglutarate (α-KG) thereby reducing $NAD^+$ ($NADP^+$) to NADP (NADPH), e.g., in the forward reaction:

$$\text{Isocitrate}+NAD^+(NADP^+)\rightarrow \alpha\text{-KG}+CO_2+NADH(NADPH)+H^+.$$

It has been discovered that mutations of IDH 1/2 present in certain cancer cells result in a new ability of the enzyme to catalyze the NADPH-dependent reduction of α-ketoglutarate to R(−)-2-hydroxyglutarate (2HG). 2HG is not formed by wild-type IDH 1/2. The production of 2HG is believed to contribute to the formation and progression of cancer (Dang, L et al, Nature 2009, 462:739-44).

The inhibition of mutant IDH 1/2 and their alpha hydroxyl neoactivity are therefore a potential therapeutic treatment for cancer. Accordingly, there is an ongoing need for inhibitors of IDH 1/2 mutants having alpha hydroxyl neoactivity.

SUMMARY OF INVENTION

Described herein are compounds of Formula (I), or a pharmaceutically acceptable salt or hydrate thereof:

(I)

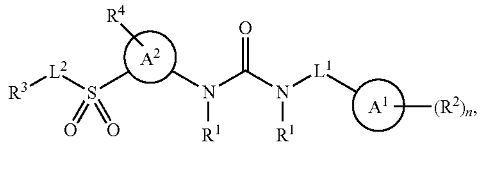

wherein each $R^1$ is independently hydrogen or $C_{1-6}$ alkyl;

$L^1$ is a bond or $C_{1-6}$ alkylene;

$A^1$ is $C_{3-8}$ cycloalkyl, aryl, heteroaryl or heterocyclyl;

$A^2$ is $C_{3-8}$ cycloalkyl, aryl, heteroaryl or heterocyclyl;

$L^2$ is a bond or —$NR^5$—;

each $R^2$ is independently halo, hydroxyl, $C_{1-6}$ alkyl, $C_{2-6}$ alkenyl, $C_{2-6}$ alkynyl, $C_{1-6}$ alkoxy, $C_{1-6}$ thioalkoxy, $C_{1-6}$ haloalkyl, $C_{1-6}$ haloalkoxy, $C_{1-6}$ alkyl-OH, aryl, aralkyl, aryloxy, —$NO^2$, —C(O)—O—$C_{1-6}$ alkyl, —$S(O)_2$—NH-aryl, —$S(O)_2$—$C_{1-6}$ alkyl or —S(O)—$C_{1-6}$ alkyl, wherein each said aryl moiety may be substituted with 0-3 occurrences of $R^6$;

$R^3$ is $C_{1-6}$ alkyl, $C_{2-6}$ alkenyl, $C_{3-8}$ cycloalkyl, aryl, aralkyl, heteroaryl, heteroaralkyl or heterocyclyl, each of which may be substituted with 0-3 occurrences of $R^6$;

each $R^4$ is independently halo, $C_{1-6}$ alkyl, $C_{2-6}$ alkenyl, $C_{2-6}$ alkynyl, $C_{1-6}$ alkoxy, $C_{1-6}$ thioalkyl, $C_{3-8}$ cycloalkyl, $C_{3-8}$ cycloalkenyl, aryl, heteroaryl, heterocyclyl, —S(O)—$C_{1-6}$ alkyl, —$S(O)_2$—$C_{1-6}$ alkyl, —O-aryl, —O-heteroaryl, —O-heterocyclyl, —$N(R^5)$—$C_{1-6}$ alkyl or —$N(R^5)$-aryl;

each $R^5$ is independently hydrogen or $C_{1-6}$ alkyl;

each $R^6$ is independently halo, hydroxyl, $C_{1-6}$ alkyl, $C_{1-6}$ haloalkyl, $C_{1-6}$ alkoxy, $C_{3-8}$ cycloalkyl, cyano, $NO_2$, —$CO_2H$, —C(O)—$C_{1-6}$ alkyl, —$S(O)_2$—$C_{1-6}$ alkyl, —O—$S(O)_2$—$C_{1-6}$ alkyl, —O—$C_{1-6}$ alkyl-C(O)OH, —O—$C_{1-6}$ alkyl-C(O)—O—$C_{1-6}$ alkyl, —$N(R^5)$—C(O)—$C_{1-6}$ alkyl, —$N(R^5)$—$C_{1-6}$ alkyl-C(O)—O—$C_{1-6}$ alkyl, aryl, heteroaryl or heterocyclyl; or adjacent $R^6$ moieties, taken together with the atoms to which they are attached form a heterocyclyl;

each $R^7$ is independently $C_{1-6}$ alkyl, $C_{1-6}$ alkoxy, $C_{3-8}$ cycloalkyl, hydroxyl, halo, —NHC(O)—$C_{1-6}$ alkyl, —$S(O)_2$—$C_{1-6}$ alkyl, aryl, heteroaryl or heterocyclyl; and n is 0, 1, 2, 3 or 4;

wherein when $L^1$ is a bond, $A^1$ and the adjacent $N(R^1)$ can be taken together to form a heterocyclic ring; and wherein when $L^2$ is a bond, $R^3$ is heterocyclyl; and provided that:

(1) when $L^1$ is a bond, $L^2$ is a bond, $A^2$ is phenyl, and $R^4$ is methoxy, Cl, F, or methyl and $R^4$ is para to the $N(R^1)C(O)N(R^1)$ moiety, then $R^3$ is not 1-piperidinyl, 1-pyrrolidinyl, N-morpholinyl, or N-azepanyl;

(2) when $L^2$ is —$N(R^5)$— wherein $R^5$ is H, $A^2$ is phenyl, and $R^4$ is methyl and $R^4$ is para to the $N(R^1)C(O)N(R^1)$ moiety, then $R^3$ is not methyl;

(3) when $L^2$ is —N($R^5$)—, $R^5$ is H, $A^2$ is phenyl, and $R^4$ is methyl and $R^4$ is ortho to the N($R^1$)C(O)N($R^1$) moiety, then $R^3$ is not methyl;

(4) when $L^2$ is —N($R^5$)—, $R^5$ is H, $A^2$ is phenyl, and $R^4$ is methoxy and $R^4$ is ortho to the N($R^1$)C(O)N($R^1$) moiety, then $R^3$ is not cyclopropyl;

(5) when $L^1$ is a bond, $A^1$ is phenyl, $L^2$ is —N($R^5$)— wherein $R^5$ is H, $A^2$ is phenyl, and $R^4$ is methyl, methoxy, Cl, 1-piperidiniyl, 1-pyrrolidinyl, N-morpholinyl, or N-azepanyl and $R^4$ is ortho to the N($R^1$) C(O)N($R^1$) moiety, then $R^3$ is not dodecyl or phenyl optionally substituted with 0-3 occurrences of $R^6$;

(6) when $L^2$ is a bond, $A^2$ is phenyl, and $R^4$ is methyl, methoxy, ethoxy, Cl, OH, tetrahydro-2-furanylmethyl-amino, 4-methyl-piperazinyl, 4-ethyl-piperazinyl, 1-pyrrolidinyl, 1-piperidinyl, 4-methyl-1-piperidinyl, or —$OCH_2CF_3$ and $R^4$ is ortho to the N($R^1$)C(O)N($R^1$) moiety, then $R^3$ is not 1-piperidinyl, 1-pyrrolidinyl, N-morpholinyl or 4-methyl-1-piperidinyl; and (7) is not a compound selected from: N'-[4-ethoxy-3-(1-pyrrolidinylsulfonyl)phenyl]-N-methyl-N-(4-methyl-cyclohexyl)-urea;

N-[5-chloro-3-[[[[4-chloro-3-[(dodecylamino)sulfonyl]phenyl]amino]carbonyl]amino]-2-hydroxyphenyl]-acetamide;

4-butyl-1-[3-[[[[4-chloro-3-[[[4-(2-formylhydrazinyl)phenyl]amino]sulfonyl]phenyl]-amino]-carbonyl]amino]propyl]-3,5-dimethyl-pyridinium;

N-(2-methoxyphenyl)-5-[[[[1-methyl-1-[3-(1-methylethenyl)phenyl]ethyl]amino]-carbonyl]-amino]-2-(1-piperidinyl)-benzenesulfonamide;

2-chloro-N-(4-ethoxyphenyl)-5-[[[[1-methyl-1-[3-(1-methylethenyl)phenyl]ethyl]amino]carbonyl]amino]-benzenesulfonamide;

2-(diethylamino)-N-(2-methoxyphenyl)-5-[[[[1-methyl-1-[3-(1-methylethenyl)phenyl]ethyl]amino]carbonyl]amino]-benzenesulfonamide;

N-(3-chlorophenyl)-2-methyl-5-[[[[1-methyl-1-[3-(1-methylethenyl)phenyl]ethyl]amino]carbonyl]amino]-benzenesulfonamide;

4-butyl-1-[3-[[[[4-chloro-3-[[[4-(2-formylhydrazinyl)phenyl]amino]sulfonyl]phenyl]amino]carbonyl]amino]propyl]-3,5-dimethyl-pyridinium chloride;

N'-[4-chloro-3-(1-pyrrolidinylsulfonyl)phenyl]-N-methyl-N-[(2-methyl-5-thiazolyl)methyl]-urea;

N'-[4-methoxy-3-(1-piperidinylsulfonyl)phenyl]-N-methyl-N-[(2-methyl-5-thiazolyl)methyl]-urea;

N-[3-[(hexahydro-1H-azepin-1-yl)sulfonyl]-4-methylphenyl]-N'-[1-methyl-1-[3-(1-methylethenyl)phenyl]ethyl]-urea;

N-butyl-4-methoxy-3-[[[[4-[6-(4-morpholinylmethyl)-3-pyridinyl]-1-naphthalenyl]amino]carbonyl]amino]-benzenesulfonamide;

N-[3-[2,4-bis(1,1-dimethylpropyl)phenoxy]propyl]-4-chloro-3-[[[(3,5-dichloro-2-hydroxy-4-methylphenyl)amino]carbonyl]amino]-benzenesulfonamide;

N-(2,5-dichlorophenyl)-4-(diethylamino)-3-[[[(4-nitrophenyl)amino]carbonyl]amino]-benzenesulfonamide;

3-[[[[6-[[4-[bis(2-cyanoethyl)amino]-2-methylphenyl]imino]-3,4-dicyano-5-(trifluoromethyl)-6H-pyrrolo[1,2-b]pyrazol-2-yl]amino]carbonyl]amino]-4-chloro-N-hexadecyl-benzenesulfonamide;

3-[[[[4-[[4-[bis(2-hydroxyethyl)amino]-2-methylphenyl]methylene]-2-phenyl-4H-imidazol-5-yl]amino]carbonyl]amino]-N-hexadecyl-4-methoxy-benzenesulfonamide;

3,3'-[(3,7-dichloro-5-oxo-1H,5H-diimidazo[1,2-a:2',1'-d][1,3,5]triazine-2,8-diyl)bis(iminocarbonylimino)]bis[N-[3-(dodecyloxy)propyl]-4-methoxy-benzenesulfonamide;

N-[2-(diethylamino)-5-(4-morpholinylsulfonyl)phenyl]-N'-(3-methylphenyl)-urea;

N-[2-methyl-5-(1-piperidinylsulfonyl)phenyl]-N'-(3,5,7-trimethyltricyclo[3.3.1.13,7]dec-1-yl)-urea;

N-(4-chlorophenyl)-N'-[5-(4-morpholinylsulfonyl)-2-(2-oxo-1-pyrrolidinyl)phenyl]-urea;

and

N-[2-chloro-5-[(hexahydro-1H-azepin-1-yl)sulfonyl]phenyl]-N'-(4-nitrophenyl)-urea.

The compounds of Formula (I) are inhibitors of mutant IDH1/2, particularly mutant IDH1 or IDH2 having alpha hydroxyl neoactivity. Also described herein are pharmaceutical compositions comprising a compound of Formula (I) and methods of using such compositions to treat cancers characterized by the presence of a mutant IDH1 or IDH2.

DETAILED DESCRIPTION

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions:

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, —$CH_2CH_2CH_2$— and —$CH_2CH(CH_3)CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkoxy" refers to an —O-alkyl radical. The term "haloalkoxy" refers to an alkoxy in which one or more hydrogen atoms are replaced by halo, and includes alkoxy moieties in which all hydrogens have been replaced by halo (e.g., perfluoroalkoxy).

The term "aryl" refers to a fully aromatic monocyclic, bicyclic, or tricyclic hydrocarbon ring system. Examples of aryl moieties are phenyl, naphthyl, and anthracenyl. Unless otherwise specified, any ring atom in an aryl can be substituted by one or more substituents.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, S(O) and $S(O)_2$).

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, S(O) and $S(O)_2$). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl. Heterocyclyl groups include fully saturated ring systems, and partially saturated ring systems.

Bicyclic and tricyclic ring systems containing one or more heteroatoms and both aromatic and non-aromatic rings are considered to be heterocyclyl groups. Bicyclic or tricyclic ring systems where an aryl or a heteroaryl is fused to a carbocyclyl or heterocyclyl and the point of attachment from the ring system to the rest of the molecule is through an aromatic ring are considered to be aryl or heteroaryl groups.

Aryl, heteroaryl, carbocyclyl (including cycloalkyl), and heterocyclyl groups, either alone or a part of a group (e.g., the aryl portion of an aralkyl group), are optionally substituted at one or more substitutable atoms with, unless specified otherwise, substituents independently selected from: halo, —C≡N, $C_1$-$C_4$ alkyl, =O, —$OR^b$, —$OR^{b'}$, —$SR^b$, —$SR^{b'}$, —($C_1$-$C_4$ alkyl)-N($R^b$)($R^b$), —($C_1$-$C_4$ alkyl)-N($R^b$)($R^{b'}$), —N($R^b$)($R^b$), —N($R^b$)($R^{b'}$), —O—($C_1$-$C_4$ alkyl)-N($R^b$)($R^b$), —O—($C_1$-$C_4$ alkyl)-N($R^b$)($R^{b'}$), —($C_1$-$C_4$ alkyl)-O—($C_1$-$C_4$ alkyl)-N($R^b$)($R^b$), —($C_1$-$C_4$ alkyl)-O—($C_1$-$C_4$ alkyl)-N($R^b$)($R^{b'}$), —C(O)—N($R^b$)($R^b$), —($C_1$-$C_4$ alkyl)-C(O)—N($R^b$)($R^b$), —($C_1$-$C_4$ alkyl)-C(O)—N($R^b$)($R^{b'}$), —$OR^{b'}$, $R^{b'}$, —C(O)($C_1$-$C_4$ alkyl), —C(O)$R^{b'}$, —C(O)N($R^{b'}$)($R^b$), —N($R^b$)C(O)($R^b$), —N($R^b$)C(O)($R^{b'}$), —N($R^b$)$SO_2$($R^b$), —$SO_2$N($R^b$)($R^b$), —N($R^b$)$SO_2$($R^{b'}$), and —$SO_2$N($R^b$)($R^{b'}$), wherein any alkyl substituent is optionally further substituted with one or more of —OH, —O—($C_1$-$C_4$ alkyl), halo, —$NH_2$, —NH($C_1$-$C_4$ alkyl), or —N($C_1$-$C_4$ alkyl)$_2$;

each $R^b$ is independently selected from hydrogen, and —$C_1$-$C_4$ alkyl; or two $R^b$s are taken together with the nitrogen atom to which they are bound to form a 4- to 8-membered heterocyclyl optionally comprising one additional heteroatom selected from N, S, and O; and each $R^{b'}$ is independently selected from $C_3$-$C_7$ carbocyclyl, phenyl, heteroaryl, and heterocyclyl, wherein one or more substitutable positions on said phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —$NH_2$, —NH($C_1$-$C_4$ alkyl), or —N($C_1$-$C_4$ alkyl)$_2$.

Heterocyclyl groups, either alone or as part of a group, are optionally substituted on one or more any substitutable nitrogen atom with oxo, —$C_1$-$C_4$ alkyl, or fluoro-substituted $C_1$-$C_4$ alkyl.

The term "substituted" refers to the replacement of a hydrogen atom by another group.

As used herein, the term "elevated levels of 2HG" means 10%, 20% 30%, 50%, 75%, 100%, 200%, 500% or more 2HG then is present in a subject that does not carry a mutant IDH2 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (e.g., a cancer), lessen the severity of the disease/disorder (e.g., a cancer) or improve the symptoms associated with the disease/disorder (e.g., a cancer).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compounds

Provided is a compound of Formula (I), or a pharmaceutically acceptable salt or hydrate thereof:

(I)

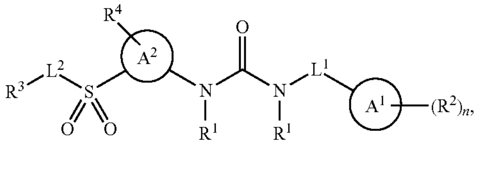

wherein each $R^1$ is independently hydrogen or $C_{1-6}$ alkyl;

$L^1$ is a bond or $C_{1-6}$ alkylene;

$A^1$ is $C_{3-8}$ cycloalkyl, aryl, heteroaryl or heterocyclyl;

$A^2$ is $C_{3-8}$ cycloalkyl, aryl, heteroaryl or heterocyclyl;

$L^2$ is a bond or —$NR^5$—;

each $R^2$ is independently halo, hydroxyl, $C_{1-6}$ alkyl, $C_{2-6}$ alkenyl, $C_{2-6}$ alkynyl, $C_{1-6}$ alkoxy, $C_{1-6}$ thioalkoxy, $C_{1-6}$ haloalkyl, $C_{1-6}$ haloalkoxy, $C_{1-6}$ alkyl-OH, aryl, aralkyl, aryloxy, —$NO^2$, —C(O)—O—$C_{1-6}$ alkyl, —$S(O)_2$—NH-aryl, —$S(O)_2$—$C_{1-6}$ alkyl or —S(O)—$C_{1-6}$ alkyl, wherein each said aryl moiety may be substituted with 0-3 occurrences of $R^6$;

$R^3$ is $C_{1-6}$ alkyl, $C_{2-6}$ alkenyl, $C_{3-8}$ cycloalkyl, aryl, aralkyl, heteroaryl, heteroaralkyl or heterocyclyl, each of which may be substituted with 0-3 occurrences of $R^6$;

each $R^4$ is independently halo, $C_{1-6}$ alkyl, $C_{2-6}$ alkenyl, $C_{2-6}$ alkynyl, $C_{1-6}$ alkoxy, $C_{1-6}$ thioalkyl, $C_{3-8}$ cycloalkyl, $C_{3-8}$ cycloalkenyl, aryl, heteroaryl, heterocyclyl, —S(O)—$C_{1-6}$ alkyl, —$S(O)_2$—$C_{1-6}$ alkyl, —O-aryl, —O-heteroaryl, —O-heterocyclyl, —$N(R^5)$—$C_{1-6}$ alkyl or —$N(R^5)$-aryl;

each $R^5$ is independently hydrogen or $C_{1-6}$ alkyl;

each $R^6$ is independently halo, hydroxyl, $C_{1-6}$ alkyl, $C_{1-6}$ haloalkyl, $C_{1-6}$ alkoxy, $C_{3-8}$ cycloalkyl, cyano, $NO_2$, —$CO_2H$, —C(O)—$C_{1-6}$ alkyl, —$S(O)_2$—$C_{1-6}$ alkyl, —O—$S(O)_2$—$C_{1-6}$ alkyl, —O—$C_{1-6}$ alkyl-C(O)OH, —O—$C_{1-6}$ alkyl-C(O)—O—$C_{1-6}$ alkyl, —$N(R^5)$—C(O)—$C_{1-6}$ alkyl, —$N(R^5)$—$C_{1-6}$ alkyl-C(O)— O—$C_{1-6}$ alkyl, aryl, heteroaryl or heterocyclyl; or adjacent $R^6$ moieties, taken together with the atoms to which they are attached form a heterocyclyl;

each $R^7$ is independently $C_{1-6}$ alkyl, $C_{1-6}$ alkoxy, $C_{3-8}$ cycloalkyl, hydroxyl, halo, —NHC(O)—$C_{1-6}$ alkyl, —$S(O)_2$—$C_{1-6}$ alkyl, aryl, heteroaryl or heterocyclyl; and n is 0, 1, 2, 3 or 4;

wherein when $L^1$ is a bond, $A^1$ and the adjacent $N(R^1)$ can be taken together to form a heterocyclic ring; and wherein when $L^2$ is a bond, $R^3$ is heterocyclyl; and provided that:

(1) when $L^1$ is a bond, $L^2$ is a bond, $A^2$ is phenyl, and $R^4$ is methoxy, Cl, F, or methyl and $R^4$ is para to the $N(R^1)C(O)N(R^1)$ moiety, then $R^3$ is not 1-piperidinyl, 1-pyrrolidinyl, N-morpholinyl, or N-azepanyl;

(2) when $L^2$ is —$N(R^5)$— wherein $R^5$ is H, $A^2$ is phenyl, and $R^4$ is methyl and $R^4$ is para to the $N(R^1)C(O)N(R^1)$ moiety, then $R^3$ is not methyl;

(3) when $L^2$ is —$N(R^5)$—, $R^5$ is H, $A^2$ is phenyl, and $R^4$ is methyl and $R^4$ is ortho to the $N(R^1)C(O)N(R^1)$ moiety, then $R^3$ is not methyl;

(4) when $L^2$ is —$N(R^5)$—, $R^5$ is H, $A^2$ is phenyl, and $R^4$ is methoxy and $R^4$ is ortho to the $N(R^1)C(O)N(R^1)$ moiety, then $R^3$ is not cyclopropyl;

(5) when $L^1$ is a bond, $A^1$ is phenyl, $L^2$ is —$N(R^5)$— wherein $R^5$ is H, $A^2$ is phenyl, and $R^4$ is methyl, methoxy, Cl, 1-piperidiniyl, 1-pyrrolidinyl, N-morpholinyl, or N-azepanyl and $R^4$ is ortho to the $N(R^1)C(O)N(R^1)$ moiety, then $R^3$ is not dodecyl or phenyl optionally substituted with 0-3 occurrences of $R^6$;

(6) when $L^2$ is a bond, $A^2$ is phenyl, and $R^4$ is methyl, methoxy, ethoxy, Cl, OH, tetrahydro-2-furanylmethyl-amino, 4-methyl-piperazinyl, 4-ethyl-piperazinyl, 1-pyrrolidinyl, 1-piperidinyl, 4-methyl-1-piperidinyl, or —$OCH_2CF_3$ and $R^4$ is ortho to the $N(R^1)C(O)N(R^1)$ moiety, then $R^3$ is not 1-piperidinyl, 1-pyrrolidinyl, N-morpholinyl or 4-methyl-1-piperidinyl; and (7) is not a compound selected from: N'-[4-ethoxy-3-(1-pyrrolidinylsulfonyl)phenyl]-N-methyl-N-(4-methyl-cyclohexyl)-urea;

N-[5-chloro-3-[[[[4-chloro-3-[(dodecylamino)sulfonyl]phenyl]amino]carbonyl]amino]-2-hydroxyphenyl]-acetamide;

4-butyl-1-[3-[[[[4-chloro-3-[[[4-(2-formylhydrazinyl)phenyl]amino]sulfonyl]phenyl]-amino]-carbonyl]amino]propyl]-3,5-dimethyl-pyridinium;

N-(2-methoxyphenyl)-5-[[[[1-methyl-1-[3-(1-methylethenyl)phenyl]ethyl]amino]-carbonyl]-amino]-2-(1-piperidinyl)-benzenesulfonamide;

2-chloro-N-(4-ethoxyphenyl)-5-[[[[1-methyl-1-[3-(1-methylethenyl)phenyl]ethyl]amino]carbonyl]amino]-benzenesulfonamide;

2-(diethylamino)-N-(2-methoxyphenyl)-5-[[[[1-methyl-1-[3-(1-methylethenyl)phenyl]ethyl]amino]carbonyl]amino]-benzenesulfonamide;

N-(3-chlorophenyl)-2-methyl-5-[[[[1-methyl-1-[3-(1-methylethenyl)phenyl]ethyl]amino]carbonyl]amino]-benzenesulfonamide;

4-butyl-1-[3-[[[[4-chloro-3-[[[4-(2-formylhydrazinyl)phenyl]amino]sulfonyl]phenyl]amino]carbonyl]amino]propyl]-3,5-dimethyl-pyridinium chloride;

N'-[4-chloro-3-(1-pyrrolidinylsulfonyl)phenyl]-N-methyl-N-[(2-methyl-5-thiazolyl)methyl]-urea;

N'-[4-methoxy-3-(1-piperidinylsulfonyl)phenyl]-N-methyl-N-[(2-methyl-5-thiazolyl)methyl]-urea;

N-[3-[(hexahydro-1H-azepin-1-yl)sulfonyl]-4-methylphenyl]-N'-[1-methyl-1-[3-(1-methylethenyl)phenyl]ethyl]-urea;

N-butyl-4-methoxy-3-[[[[4-[6-(4-morpholinylmethyl)-3-pyridinyl]-1-naphthalenyl]amino]carbonyl]amino]-benzenesulfonamide;

N-[3-[2,4-bis(1,1-dimethylpropyl)phenoxy]propyl]-4-chloro-3-[[[(3,5-dichloro-2-hydroxy-4-methylphenyl)amino]carbonyl]amino]-benzenesulfonamide;

N-(2,5-dichlorophenyl)-4-(diethylamino)-3-[[[(4-nitrophenyl)amino]carbonyl]amino]-benzenesulfonamide;

3-[[[[6-[[4-[bis(2-cyanoethyl)amino]-2-methylphenyl]imino]-3,4-dicyano-5-(trifluoromethyl)-6H-pyrrolo[1,2-b]pyrazol-2-yl]amino]carbonyl]amino]-4-chloro-N-hexadecyl-benzenesulfonamide;

3-[[[[4-[[4-[bis(2-hydroxyethyl)amino]-2-methylphenyl]methylene]-2-phenyl-4H-imidazol-5-yl]amino]carbonyl]amino]-N-hexadecyl-4-methoxy-benzenesulfonamide;

3,3'-[(3,7-dichloro-5-oxo-1H,5H-diimidazo[1,2-a:2',1'-d][1,3,5]triazine-2,8-diyl)bis(iminocarbonylimino)]bis[N-[3-(dodecyloxy)propyl]-4-methoxy-benzenesulfonamide;

N-[2-(diethylamino)-5-(4-morpholinylsulfonyl)phenyl]-N'-(3-methylphenyl)-urea;

N-[2-methyl-5-(1-piperidinylsulfonyl)phenyl]-N'-(3,5,7-trimethyltricyclo[3.3.1.13,7]dec-1-yl)-urea;

N-(4-chlorophenyl)-N'-[5-(4-morpholinylsulfonyl)-2-(2-oxo-1-pyrrolidinyl)phenyl]-urea;

and

N-[2-chloro-5-[(hexahydro-1H-azepin-1-yl)sulfonyl]phenyl]-N'-(4-nitrophenyl)-urea.

In certain embodiments, each $R^1$ is independently hydrogen.

In certain embodiments, $L^1$ is a bond. In some aspects of this embodiment, $A^1$ is aryl (e.g., phenyl or naphthyl). In some aspects of this embodiment, $A^1$ is heteroaryl (e.g., a 5 or 6-membered heteroaryl). In some aspects of this embodiment, $A^1$ is 5-membered heteroaryl (e.g., 3-thiophenyl, 2-thiazolyl, 3-pyrazolyl, 2-oxazolyl or 3-isoxazolyl). In some aspects of this embodiment, $A^1$ is 6-membered heteroaryl (e.g., 2-pyridinyl, 3-pyridinyl, 4-pyridinyl or 2-pyrimidinyl). In some aspects of this embodiment, $A^1$ is $C_{3-8}$ cycloalkyl (e.g., cyclopropyl, cyclopentyl or cyclohexyl). In some aspects of this embodiment, $A^1$ is heterocyclyl (e.g., benzo-1,3-dioxole or 2,3-dihydrobenzofuran). In some aspects of this embodiment, $L^1$ is a bond and $A^1$ and the adjacent $N(R^1)$ are taken together to form a heteroaryl (e.g., indolyl).

In certain embodiments, $L^1$ is $C_{1-6}$ alkylenyl (e.g., methylene or ethylene). In some embodiments, when $L^1$ is ethylene, $A^1$ is attached at the 2-position of the ethylene moiety. In some embodiments, when $L^1$ is ethylene, $A^1$ is attached at the 1-position of the ethylene moiety. In some aspects of this embodiments, $A^1$ is aryl (e.g., phenyl or naphthyl).

In some embodiments, n is 0.

In some embodiments, n is 1. In some aspects of this embodiment, $R^2$ is hydroxyl. In some aspects of this embodiment, $R^2$ is $C_{1-6}$ alkyl (e.g., methyl, ethyl, n-butyl, isopropyl or t-butyl). In some aspects of this embodiment, $R^2$ is $C_{1-6}$ alkoxy (e.g., methoxy). In some aspects of this embodiment, $R^2$ is halo (e.g., bromo, fluoro, iodo or chloro). In some aspects of this embodiment, $R^2$ is $C_{1-6}$ haloalkyl (e.g., trifluoromethyl). In some aspects of this embodiment, $R^2$ is $C_{1-6}$ haloalkoxy (e.g., trifluoromethoxy or difluoromethoxy). In some aspects of this embodiment, $R^2$ is $C_{2-6}$ alkynyl (e.g., ethynyl). In some aspects of this embodiment, $R^2$ is aryloxy (e.g., phenoxy). In some aspects of this embodiment, $R^2$ is $C_{1-6}$ thioalkoxy (e.g., thiomethoxy). In some aspects of this embodiment, $R^2$ is $—NO_2$. In some aspects of this embodiment, $R^2$ is —C(O)—O—$C_{1-6}$ alkyl (e.g., —C(O)OMe). In some aspects of this embodiment, $R^2$ is aralkyl (e.g., benzyl). In some aspects of this embodiment, $R^2$ is $—S(O)_2—$NH-aryl (e.g., $—S(O)_2—$NH-phenyl, $—S(O)_2—$NH-4-chlorophenyl or $—S(O)_2—$NH-2,6-dichlorophenyl). In some aspects of this embodiment, $R^2$ is $—S(O)_2—C_{1-6}$ alkyl (e.g., $—S(O)_2$-Me). In some aspects of this embodiment, $R^2$ is $C_{1-6}$ alkyl-OH (e.g., ethyl-OH). In some aspects of this embodiment, $R^2$ is —S(O)—$C_{1-6}$ alkyl (e.g., —S(O)-Me). In some aspects of this embodiment, $R^2$ is aryl (e.g., phenyl).

In certain embodiments, n is 2. In some aspects of this embodiment, both $R^2$ are halo (e.g., chloro, fluoro or bromo). In some aspects of this embodiment, one $R^2$ is $C_{1-6}$ haloalkyl (e.g., trifluoromethyl) and the other $R^2$ is halo (e.g., fluoro). In some aspects of this embodiment, one $R^2$ is $C_{1-6}$ haloalkoxy (e.g., trifluoromethoxy) and the other $R^2$ is halo (e.g., fluoro or bromo). In some aspects of this embodiment, one $R^2$ is $C_{1-6}$ alkyl (e.g., methyl) and the other $R^2$ is halo (e.g., fluoro, chloro or bromo). In some aspects of this embodiment, one $R^2$ is $—NO_2$ and the other $R^2$ is halo (e.g., fluoro or chloro). In some aspects of this embodiment, both $R^2$ are $C_{1-6}$ alkyl (e.g., methyl or ethyl). In some aspects of this embodiment, one $R^2$ is $—NO_2$ and the other is $C_{1-6}$ alkyl (e.g., methyl). In some aspects of this embodiment, both $R^2$ are $C_{1-6}$ alkoxy (e.g., methoxy). In some aspects of this embodiment, one $R^2$ is $C_{1-6}$ alkoxy (e.g., methoxy) and the other is halo (e.g., chloro). In some aspects of this embodiment, one $R^2$ is $—NO_2$ and the other $R^2$ is $C_{1-6}$ alkoxy (e.g., methoxy). In some aspects of this embodiment, one $R^2$ is $C_{1-6}$ alkyl (e.g., methyl) and the other $R^2$ is aryl (e.g., phenyl). In some aspects of this embodiment, one $R^2$ is $—S(O)_2—$NH-aryl (e.g., $—S(O)_2—$NH-4-chlorophenyl) and the other is $C_{1-6}$ alkyl (e.g., methyl).

In certain embodiments, n is 3. In some aspects of this embodiment, all $R^2$ are halo (e.g., fluoro, chloro or bromo). In some aspects of this embodiment, two $R^2$ are $C_{1-6}$ alkyl (e.g., methyl) and the other is halo (e.g., fluoro or chloro). In some aspects of this embodiment, two $R^2$ are $C_{1-6}$ alkoxy (e.g., methoxy) and one is halo (e.g., fluoro or chloro).

In certain embodiments, $A^2$ is aryl (e.g., phenyl). In some embodiments, $A^2$ is heteroaryl (e.g., 3-pyridinyl).

In some aspects of this embodiment, $R^4$ is $C_{1-6}$ alkyl (e.g., methyl or ethyl) substituted with 0-3 occurrences of $R^7$. In some aspects of this embodiment, $R^4$ is $C_{1-6}$ alkyl (e.g., methyl or ethyl) substituted with 0 occurrences of $R^7$.

In some aspects of this embodiment, $R^4$ is heteroaryl (e.g., 2-thiophenyl, 3-thiophenyl, 2-pyridinyl, 3-pyridinyl or 4-pyridinyl) substituted with 0-3 occurrences of $R^7$. In some aspects of this embodiment, $R^4$ is heteroaryl (e.g., 2-thiophenyl, 3-thiophenyl, 2-pyridinyl, 3-pyridinyl or 4-pyridinyl) substituted with 0 occurrences of $R^7$.

In some aspects of this embodiment, $R^4$ is heterocyclyl (e.g., 2-thiazolyl, 3-pyrazolyl, 1,4-oxazepanyl, morpholinyl, 1-imidazolyl, 2-tetrahydrofuranyl, 3-tetrahydrofuranyl, 2-tetrahydro-2H-pyranyl, 3-tetrahydro-2H-pyranyl or 3,6-dihydro-2H-pyranyl) substituted with 0-3 occurrences of $R^7$. In some aspects of this embodiment, $R^4$ is heterocyclyl (e.g., 2-thiazolyl, 3-pyrazolyl, 1,4-oxazepanyl, morpholinyl, 1-imidazolyl, 2-tetrahydrofuranyl, 3-tetrahydrofuranyl, 2-tetrahydro-2H-pyranyl, 3-tetrahydro-2H-pyranyl or 3,6-dihydro-2H-pyranyl) substituted with 0 occurrences of $R^7$. In some aspects of this embodiment, $R^4$ is heterocyclyl (e.g., 1-imidazolyl) substituted with 1 occurrence of $R^7$ wherein $R^7$ is $C_{1-6}$ alkyl (e.g., methyl).

In some aspects of this embodiment, $R^4$ is aryl (e.g., phenyl) substituted with 0-3 occurrences of $R^7$. In some aspects of this embodiment, $R^4$ is aryl (e.g., phenyl) substituted with 0 occurrences of $R^7$. In some aspects of this embodiment, $R^4$ is aryl (e.g., phenyl substituted with 1 occurrence of $R^7$. In some further aspects of this embodiment, $R^7$ is $C_{1-6}$ alkyl (e.g., methyl). In some further aspects of this embodiment, $R^7$ is hydroxyl. In some further aspects of this embodiment, $R^7$ is $C_{1-6}$ alkoxy (e.g., methoxy). In some further aspects of this embodiment, $R^7$ is halo (e.g., fluoro, chloro). In some further aspects of this embodiment, $R^7$ is —NHC(O)—$C_{1-6}$ alkyl (e.g., —NHC(O)-Me). In some further aspects of this embodiment, $R^7$ is $—S(O)_2—C_{1-6}$ alkyl (e.g., $—S(O)_2$-Me).

In some aspects of this embodiment, $R^4$ is $C_{1-6}$ alkoxy (e.g., methoxy, isopropoxy or ethoxy) substituted with 0-3 occurrences of $R^7$. In some aspects of this embodiment, $R^4$ is $C_{1-6}$ alkoxy (e.g., ethoxy or isopropoxy) substituted with 0 occurrences of $R^7$. In some aspects of this embodiment, $R^4$ is $C_{1-6}$ alkoxy (e.g., methoxy) substituted with 1 occurrence of $R^7$. In some further aspects of this embodiment, $R^7$ is $C_{3-8}$ cycloalkyl (e.g., cyclopropyl). In some further aspects of this embodiment, $R^7$ is heterocyclyl (e.g., 2-tetrahydrofuranyl, 3-tetrahydrofuranyl, 4-tetrahydropyranyl). In some further aspects of this embodiment, $R^7$ is heteroaryl (e.g., 3-pyridinyl). In some further aspects of this embodiment, $R^7$ is aryl (e.g., phenyl).

In some aspects of this embodiment, $R^4$ is —O-heterocyclyl (e.g., —O-4-tetrahydropyranyl) substituted with 0-3 occurrences of $R^7$. In some aspects of this embodiment, $R^4$ is —O-heterocyclyl (e.g., —O-4-tetrahydropyranyl) substituted with 0 occurrences of $R^7$.

In some aspects of this embodiment, $R^4$ is —O-heteroaryl (e.g., —O-3-pyridinyl) substituted with 0-3 occurrences of $R^7$. In some aspects of this embodiment, $R^4$ is —O-heteroaryl (e.g., —O-3-pyridinyl) substituted with 0 occurrences of $R^7$.

In some aspects of this embodiment, $R^4$ is —O-aryl (e.g., —O-phenyl) substituted with 0-3 occurrences of $R^7$. In some aspects of this embodiment, $R^4$ is —O-aryl (e.g., —O-phenyl) substituted with 0 occurrences of $R^7$.

In some aspects of this embodiment, $R^4$ is $C_{1-6}$ thioalkyl (e.g., thioethyl) substituted with 0-3 occurrences of $R^7$. In some aspects of this embodiment, $R^4$ is $C_{1-6}$ thioalkyl (e.g., thioethyl) substituted with 0 occurrences of $R^7$.

In some aspects of this embodiment, $R^4$ is —S(O)—$C_{1-6}$ alkyl (e.g., —S(O)-ethyl) substituted with 0-3 occurrences of $R^7$. In some aspects of this embodiment, $R^4$ is —S(O)—$C_{1-6}$ alkyl (e.g., —S(O)-ethyl) substituted with 0 occurrences of $R^7$.

In some aspects of this embodiment, $R^4$ is —$S(O)_2$—$C_{1-6}$ alkyl (e.g., —$S(O)_2$-ethyl) substituted with 0-3 occurrences of $R^7$. In some aspects of this embodiment, $R^4$ is —$S(O)_2$—$C_{1-6}$ alkyl (e.g., —$S(O)_2$-ethyl) substituted with 0 occurrences of $R^7$.

In some aspects of this embodiment, $R^4$ is $C_{2-6}$ alkynyl (e.g., ethynyl) substituted with 0-3 occurrences of $R^7$. In some aspects of this embodiment, $R^4$ is $C_{2-6}$ alkynyl (e.g., ethynyl) substituted with 0 occurrences of $R^7$.

In some aspects of this embodiment, $R^4$ is —N($R^5$)—$C_{1-6}$ alkyl (e.g., —N(Me)-isopropyl) substituted with 0-3 occurrences of $R^7$. In some aspects of this embodiment, $R^4$ is —N($R^5$)—$C_{1-6}$ alkyl (e.g., —N(Me)-isopropyl) substituted with 0 occurrences of $R^7$.

In some aspects of this embodiment, $R^4$ is —N($R^5$)-aryl (e.g., —N(H)-phenyl or —N(Me)-phenyl) substituted with 0-3 occurrences of $R^7$. In some aspects of this embodiment, $R^4$ is —N($R^5$)-aryl (e.g., —N(H)-phenyl or —N(Me)-phenyl) substituted with 0 occurrences of $R^7$.

In some embodiments, $L^2$ is a bond. In some aspects of this embodiment, $R^3$ is heterocyclyl (e.g., piperazinyl, morpholinyl, thiomorpholinyl-1,1-dioxide, azetidinyl or pyrrolidinyl) substituted with 0-3 occurrences of $R^6$. In some aspects of this embodiment, $R^3$ is heterocyclyl (e.g., piperazinyl, morpholinyl, thiomorpholinyl-1,1-dioxide, azetidinyl or pyrrolidinyl) substituted with 0 occurrences of $R^6$.

In some embodiments, $L^2$ is —N($R^5$)— wherein $R^5$ is hydrogen. In some aspects of this embodiment, $R^3$ is aryl (e.g., phenyl) substituted with 0-3 occurrences of $R^6$. In some aspects of this embodiment, $R^3$ is aryl (e.g., phenyl) substituted with 0 occurrences of $R^6$. In some aspects of this embodiment, $R^3$ is aryl (e.g., phenyl) substituted with 1 occurrence of $R^6$. In some further aspects of this embodiment, $R^6$ is halo (e.g., fluoro or chloro). In some further aspects of this embodiment, $R^6$ is hydroxyl. In some further aspects of this embodiment, $R^6$ is $C_{1-6}$ haloalkyl (e.g., trifluoromethyl). In some further aspects of this embodiment, $R^6$ is $C_{1-6}$ alkyl (e.g., methyl). In some further aspects of this embodiment, $R^6$ is $C_{2-6}$ alkynyl (e.g., ethynyl). In some further aspects of this embodiment, $R^6$ is $C_{1-6}$ alkoxy (e.g., propoxy). In some further aspects of this embodiment, $R^6$ is cyano. In some further aspects of this embodiment, $R^6$ is —O—$S(O)_2$—$C_{1-6}$ alkyl (e.g., —O—$S(O)_2$-methyl). In some further aspects of this embodiment, $R^6$ is —O—$C_{1-6}$ alkyl-C(O)—O—$C_{1-6}$ alkyl (e.g., —O—$CH_2$—C(O)—O-ethyl or —O—$CH_2(CH_3)$—C(O)—O-ethyl). In some further aspects of this embodiment, $R^6$ is —N($R^5$)—C(O)—$C_{1-6}$ alkyl (e.g., —N(H)—C(O)-methyl). In some further aspects of this embodiment, $R^6$ is —N($R^5$)—$C_{1-6}$ alkyl-C(O)—O—$C_{1-6}$ alkyl (e.g., —N(H)—$CH_2$—C(O)—O-ethyl). In some further aspects of this embodiment, $R^6$ is —$CO_2H$. In some further aspects of this embodiment, $R^6$ is —$S(O)_2$—$C_{1-6}$ alkyl (e.g., —$S(O)_2$-methyl). In some further aspects of this embodiment, $R^6$ is $C_{1-6}$ aralkyl (e.g., phenethyl). In some further aspects of this embodiment, $R^6$ is —C(O)—$C_{1-6}$ alkyl (e.g., —C(O)-methyl). In some further aspects of this embodiment, $R^6$ is —O—$C_{1-6}$ alkyl-C(O)OH (e.g., —O—$CH_2$—C(O)OH). In some aspects of this embodiment, $R^3$ is aryl (e.g., phenyl) substituted with 2 occurrences of $R^6$. In some further aspects of this embodiment, both $R^6$ are halo (e.g., fluoro, chloro or bromo). In some further aspects of this embodiment, one $R^6$ is $C_{1-6}$ alkyl (e.g., methyl) and the other $R^6$ is halo (e.g., fluoro or chloro). In some aspects of this embodiment, $R^3$ is aryl (e.g., phenyl) substituted with 3 occurrences of $R^6$. In some further aspects of this embodiment, all $R^6$ are halo (e.g., fluoro, chloro or bromo).

In some aspects of this embodiment, $R^3$ is heteroaryl (e.g., indolyl, quinolinyl, tetrazolyl, benzimidazolyl, 3-pyrazolyl, 2-pyridinyl, 3-pyridinyl) substituted with 0-3 occurrences of $R^6$. In some aspects of this embodiment, $R^3$ is heteroaryl (e.g., indolyl, quinolinyl, tetrazolyl, benzimidazolyl, 3-pyrazolyl, 2-pyridinyl, 3-pyridinyl) substituted with 0 occurrences of $R^6$.

In some aspects of this embodiment, $R^3$ is $C_{3-8}$ cycloalkyl (e.g., cyclopropyl, cyclobutyl or cyclopentyl) substituted with 0-3 occurrences of $R^6$. In some aspects of this embodiment, $R^3$ is $C_{3-8}$ cycloalkyl (e.g., cyclopropyl, cyclobutyl or cyclopentyl) substituted with 0 occurrences of $R^6$. In some aspects of this embodiment, $R^3$ is $C_{3-8}$ cycloalkyl (e.g., cyclopropyl) substituted with 1 occurrence of $R^6$. In some further aspects of this embodiment, $R^6$ is cyano. In some further aspects of this embodiment, $R^6$ is $C_{1-6}$ alkyl (e.g., methyl).

In some aspects of this embodiment, $R^3$ is heterocyclyl (e.g., 2,3-dihydrobenzodioxinyl, 4-tetrahydropyranyl or 3-oxetanyl) substituted with 0-3 occurrences of $R^6$. In some aspects of this embodiment, $R^3$ is heterocyclyl (e.g., 2,3-dihydrobenzodioxinyl, 4-tetrahydropyranyl or 3-oxetanyl) substituted with 0 occurrences of $R^6$.

In some aspects of this embodiment, $R^3$ is $C_{1-6}$ alkoxy (e.g., methoxy or ethoxy) substituted with 0-3 occurrences of $R^6$. In some aspects of this embodiment, $R^3$ is $C_{1-6}$ alkoxy (e.g., methoxy or ethoxy) substituted with 0 occurrences of $R^6$.

In some aspects of this embodiment, $R^3$ is $C_{1-6}$ alkyl (e.g., methyl, ethyl, isopropyl, isobutyl, sec-butyl, n-propyl, n-butyl or isopentyl) substituted with 0-3 occurrences of $R^6$. In some aspects of this embodiment, $R^3$ is $C_{1-6}$ alkyl (e.g., methyl, ethyl, isopropyl, isobutyl, sec-butyl, n-propyl, n-butyl or isopentyl) substituted with 0 occurrences of $R^6$. In some aspects of this embodiment, $R^3$ is $C_{1-6}$ alkyl (e.g., methyl, ethyl, n-propyl or isopentyl) substituted with 1 occurrences of $R^6$. In some further aspects of this embodiment, $R^6$ is hydroxyl. In some further aspects of this embodiment, $R^6$ is $C_{1-6}$ alkoxy (e.g., methoxy). In some further aspects of embodiment, $R^6$ is $C_{3-8}$ cycloalkyl (e.g., cyclopropyl, cyclobutyl or cyclopentyl). In some further aspects of this embodiment, $R^6$ is heterocyclyl (e.g., 4-tetrahydropyranyl or 4-tetrahydrothiopyranyl). In some further aspects of this embodiment, $R^6$ is aryl (e.g., phenyl).

In some aspects of this embodiment, $R^3$ is $C_{1-6}$ alkyl (e.g., methyl or ethyl) substituted with 2 occurrences of $R^6$. In some further aspects of this embodiment, one $R^6$ is $C_{1-6}$ alkyl (e.g., methyl) and the other $R^6$ is aryl (e.g., phenyl).

In some aspects of this embodiment, $R^3$ is $C_{1-6}$ alkyl (e.g., methyl or ethyl) substituted with 3 occurrences of $R^6$. In some further aspects of this embodiment, all three $R^6$ are halo (e.g., fluoro). In some aspects of this embodiment, $R^3$ is 2,2,2-trifluoroethyl.

In some aspects of this embodiment, $R^3$ is $C_{2-6}$ alkenyl (e.g., propenyl) substituted with 0-3 occurrences of $R^6$. In some aspects of this embodiment, $R^3$ is $C_{2-6}$ alkenyl (e.g., propenyl) substituted with 0 occurrences of $R^6$.

In some embodiments, $L^2$ is —N($R^5$)— wherein $R^5$ is $C_{1-6}$ alkyl (e.g., methyl). In some aspects of this embodiment, $R^3$ is $C_{1-6}$ alkyl (e.g., methyl) substituted with 0-3 occurrences of $R^6$.

In some aspects of this embodiment, $R^3$ is $C_{1-6}$ alkyl (e.g., methyl) substituted with 0 occurrences of $R^6$.

In some aspects of this embodiment, $R^3$ is aryl (e.g., phenyl) substituted with 0-3 occurrences of $R^6$. In some aspects of this embodiment, $R^3$ is aryl (e.g., phenyl) substituted with 0 occurrences of $R^6$.

In certain embodiments, the compound of Formula (I) is a compound of Formula (II):

(II)

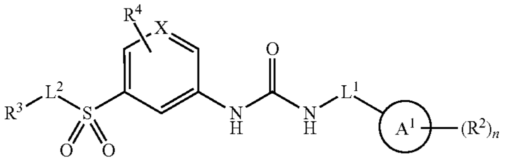

wherein

X is CH or N; and $L^1$, $L^2$, $A^1$, $R^2$, $R^3$, $R^4$, $R^5$, $R^6$, $R^7$ and n are as defined in Formula (I);

provided that:

(1) when $L^1$ is a bond, $L^2$ is a bond, X is CH, and $R^4$ is methoxy, Cl, F, or methyl and $R^4$ is para to the N($R^1$)C(O)N($R^1$) moiety, then $R^3$ is not 1-piperidinyl, 1-pyrrolidinyl, N-morpholinyl, or N-azepanyl;

(2) when $L^2$ is —N($R^5$)— wherein $R^5$ is H, X is CH, and $R^4$ is methyl and $R^4$ is para to the N($R^1$)C(O)N($R^1$) moiety, then $R^3$ is not methyl;

(3) when $L^2$ is —N($R^5$)—, $R^5$ is H, X is CH, and $R^4$ is methyl and $R^4$ is ortho to the N(H)C(O)N(H) moiety, then $R^3$ is not methyl;

(4) when $L^2$ is —N($R^5$)—, $R^5$ is H, X is CH, and $R^4$ is methoxy and $R^4$ is ortho to the N(H)C(O)N(H) moiety, then $R^3$ is not cyclopropyl;

(5) when $L^1$ is a bond, $A^1$ is phenyl, $L^2$ is —N($R^5$)— wherein $R^5$ is H, X is CH, and $R^4$ is methyl, methoxy, Cl, 1-piperidiniyl, 1-pyrrolidinyl, N-morpholinyl, or N-azepanyl and $R^4$ is ortho to the N(H)C(O)N(H) moiety, then $R^3$ is not dodecyl or phenyl optionally substituted with 0-3 occurrences of $R^6$;

(6) when $L^2$ is a bond, X is CH, and $R^4$ is methyl, methoxy, ethoxy, Cl, OH, tetrahydro-2-furanylmethyl-amino, 4-methyl-piperazinyl, 4-ethyl-piperazinyl, 1-pyrrolidinyl, 1-piperidinyl, 4-methyl-1-piperidinyl, or —$OCH_2CF_3$ and $R^4$ is ortho to the N(H)C(O)N(H) moiety, then $R^3$ is not 1-piperidinyl, 1-pyrrolidinyl, N-morpholinyl or 4-methyl-1-piperidinyl; and (7) is not a compound selected from: N'-[4-ethoxy-3-(1-pyrrolidinylsulfonyl)phenyl]-N-methyl-N-(4-methyl-cyclohexyl)-urea;

N-[5-chloro-3-[[[[4-chloro-3-[(dodecylamino)sulfonyl]phenyl]amino]carbonyl]amino]-2-hydroxyphenyl]-acetamide;

4-butyl-1-[3-[[[[4-chloro-3-[[[4-(2-formylhydrazinyl)phenyl]amino]sulfonyl]phenyl]-amino]-carbonyl]amino]propyl]-3,5-dimethyl-pyridinium;

N-(2-methoxyphenyl)-5-[[[[1-methyl-1-[3-(1-methylethenyl)phenyl]ethyl]amino]-carbonyl]-amino]-2-(1-piperidinyl)-benzenesulfonamide;

2-chloro-N-(4-ethoxyphenyl)-5-[[[[1-methyl-1-[3-(1-methylethenyl)phenyl]ethyl]amino]carbonyl]amino]-benzenesulfonamide;

2-(diethylamino)-N-(2-methoxyphenyl)-5-[[[[1-methyl-1-[3-(1-methylethenyl)phenyl]ethyl]amino]carbonyl]amino]-benzenesulfonamide;

N-(3-chlorophenyl)-2-methyl-5-[[[[1-methyl-1-[3-(1-methylethenyl)phenyl]ethyl]amino]carbonyl]amino]-benzenesulfonamide;

4-butyl-1-[3-[[[[4-chloro-3-[[[4-(2-formylhydrazinyl)phenyl]amino]sulfonyl]phenyl]amino]carbonyl]amino]propyl]-3,5-dimethyl-pyridinium chloride;

N'-[4-chloro-3-(1-pyrrolidinylsulfonyl)phenyl]-N-methyl-N-[(2-methyl-5-thiazolyl)methyl]-urea;

N'-[4-methoxy-3-(1-piperidinylsulfonyl)phenyl]-N-methyl-N-[(2-methyl-5-thiazolyl)methyl]-urea;

N-[3-[(hexahydro-1H-azepin-1-yl)sulfonyl]-4-methylphenyl]-N'-[1-methyl-1-[3-(1-methylethenyl)phenyl]ethyl]-urea;

N-butyl-4-methoxy-3-[[[[4-[6-(4-morpholinylmethyl)-3-pyridinyl]-1-naphthalenyl]amino]carbonyl]amino]-benzenesulfonamide;

N-[3-[2,4-bis(1,1-dimethylpropyl)phenoxy]propyl]-4-chloro-3-[[[(3,5-dichloro-2-hydroxy-4-methylphenyl)amino]carbonyl]amino]-benzenesulfonamide;

N-(2,5-dichlorophenyl)-4-(diethylamino)-3-[[[(4-nitrophenyl)amino]carbonyl]amino]-benzenesulfonamide;

3-[[[[6-[[4-[bis(2-cyanoethyl)amino]-2-methylphenyl]imino]-3,4-dicyano-5-(trifluoromethyl)-6H-pyrrolo[1,2-b]pyrazol-2-yl]amino]carbonyl]amino]-4-chloro-N-hexadecyl-benzenesulfonamide;

3-[[[[4-[[4-[bis(2-hydroxyethyl)amino]-2-methylphenyl]methylene]-2-phenyl-4H-imidazol-5-yl]amino]carbonyl]amino]-N-hexadecyl-4-methoxy-benzenesulfonamide;

3,3'-[(3,7-dichloro-5-oxo-1H,5H-diimidazo[1,2-a:2',1'-d][1,3,5]triazine-2,8-diyl)bis(iminocarbonylimino)]bis[N-[3-(dodecyloxy)propyl]-4-methoxy-benzenesulfonamide;

N-[2-(diethylamino)-5-(4-morpholinylsulfonyl)phenyl]-N'-(3-methylphenyl)-urea;

N-[2-methyl-5-(1-piperidinylsulfonyl)phenyl]-N'-(3,5,7-trimethyltricyclo[3.3.1.13,7]dec-1-yl)-urea;

N-(4-chlorophenyl)-N'-[5-(4-morpholinylsulfonyl)-2-(2-oxo-1-pyrrolidinyl)phenyl]-urea;

and

N-[2-chloro-5-[(hexahydro-1H-azepin-1-yl)sulfonyl]phenyl]-N'-(4-nitrophenyl)-urea.

In some embodiments, the compound of Formula (II) is a compound of Formula (IIa):

(IIa)

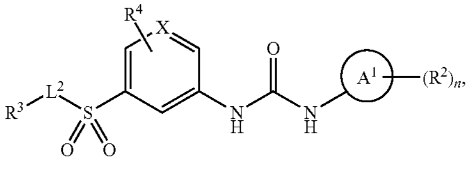

wherein X, $L^2$, $A^1$, $R^2$, $R^3$, $R^4$, $R^5$, $R^6$, $R^7$ and n are as defined in Formula (II).

In some embodiments, the compound of Formula (II) is a compound of Formula (IIb):

(IIb)

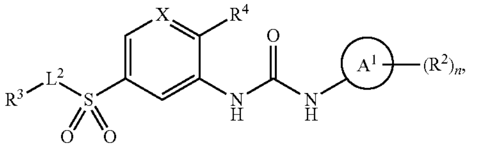

wherein X, $L^2$, $A^1$, $R^2$, $R^3$, $R^4$, $R^5$, $R^6$, $R^7$ and n are as defined in Formula (II).

In certain embodiments, the compound of formula (I) is a compound of Formula (III):

(III)

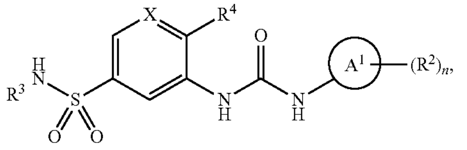

wherein X, $A^1$, $R^2$, $R^3$, $R^4$, $R^5$, $R^6$, $R^7$ and n are as defined in Formula (II);

provided that:

(1) when X is CH, and $R^4$ is methyl, then $R^3$ is not methyl;

(2) when X is CH, and $R^4$ is methoxy, then $R^3$ is not cyclopropyl;

(3) when $A^1$ is phenyl, X is CH, and $R^4$ is methyl, methoxy, Cl, 1-piperidiniyl, 1-pyrrolidinyl, N-morpholinyl, or N-azepanyl, then $R^3$ is not dodecyl or phenyl optionally substituted with 0-3 occurrences of $R^6$; and (4) is not a compound selected from: N-butyl-4-methoxy-3-[[[[4-[6-(4-morpholinylmethyl)-3-pyridinyl]-1-naphthalenyl]amino]carbonyl]amino]-benzenesulfonamide;

N-[3-[2,4-bis(1,1-dimethylpropyl)phenoxy]propyl]-4-chloro-3-[[[(3,5-dichloro-2-hydroxy-4-methylphenyl) amino]carbonyl]amino]-benzenesulfonamide;

N-(2,5-dichlorophenyl)-4-(diethylamino)-3-[[[(4-nitrophenyl)amino]carbonyl]amino]-benzenesulfonamide;

3-[[[[6-[[4-[bis(2-cyanoethyl)amino]-2-methylphenyl] imino]-3,4-dicyano-5-(trifluoromethyl)-6H-pyrrolo[1,2-b]pyrazol-2-yl]amino]carbonyl]amino]-4-chloro-N-hexadecyl-benzenesulfonamide;

3-[[[[4-[[4-[bis(2-hydroxyethyl)amino]-2-methylphenyl] methylene]-2-phenyl-4H-imidazol-5-yl]amino]carbonyl] amino]-N-hexadecyl-4-methoxy-benzenesulfonamide;

3,3'-[(3,7-dichloro-5-oxo-1H,5H-diimidazo[1,2-a:2',1'-d][1,3,5]triazine-2,8-diyl)bis(iminocarbonylimino)]bis[N-[3-(dodecyloxy)propyl]-4-methoxy-benzenesulfonamide;

N-[2-(diethylamino)-5-(4-morpholinylsulfonyl)phenyl]-N'-(3-methylphenyl)-urea;

N-[2-methyl-5-(1-piperidinylsulfonyl)phenyl]-N'-(3,5,7-trimethyltricyclo[3.3.1.13,7]dec-1-yl)-urea;

N-(4-chlorophenyl)-N'-[5-(4-morpholinylsulfonyl)-2-(2-oxo-1-pyrrolidinyl)phenyl]-urea;

and

N-[2-chloro-5-[(hexahydro-1H-azepin-1-yl) sulfonyl]phenyl]-N'-(4-nitrophenyl)-urea.

In certain embodiments, the compound of Formula (III) is a compound of Formula (Ma):

(IIIa)

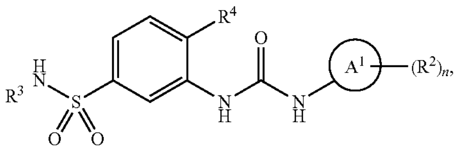

wherein $A^1$, $R^2$, $R^3$, $R^4$, $R^5$, $R^6$, $R^7$ and n are as defined in Formula (III).

In certain embodiments, the compound of Formula (I) is a compound of Formula (IV):

(IV)

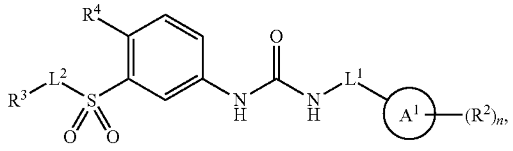

wherein $L^1$, $L^2$, $A^1$, $R^2$, $R^3$, $R^4$, $R^5$, $R^6$, $R^7$ and n are as defined in Formula (I);

provided that:

(1) when $L^1$ is a bond, $L^2$ is a bond, and $R^4$ is methoxy, Cl, F, or methyl, then $R^3$ is not 1-piperidinyl, 1-pyrrolidinyl, N-morpholinyl, or N-azepanyl; and (2) when $L^2$ is —N($R^5$)— wherein $R^5$ is H, and $R^4$ is methyl, then $R^3$ is not methyl;

(3) is not a compound selected from: N'-[4-ethoxy-3-(1-pyrrolidinylsulfonyl)phenyl]-N-methyl-N-(4-methylcyclohexyl)-urea;

N-[5-chloro-3-[[[[4-chloro-3-[(dodecylamino)sulfonyl]phenyl]amino]carbonyl]amino]-2-hydroxyphenyl]-acetamide;

4-butyl-1-[3-[[[[4-chloro-3-[[[4-(2-formylhydrazinyl)phenyl]amino]sulfonyl]phenyl]-amino]-carbonyl]amino]propyl]-3,5-dimethyl-pyridinium;

N-(2-methoxyphenyl)-5-[[[[1-methyl-1-[3-(1-methylethenyl)phenyl]ethyl]amino]-carbonyl]-amino]-2-(1-piperidinyl)-benzenesulfonamide;

2-chloro-N-(4-ethoxyphenyl)-5-[[[[1-methyl-1-[3-(1-methylethenyl)phenyl]ethyl]amino]carbonyl]amino]-benzenesulfonamide;

2-(diethylamino)-N-(2-methoxyphenyl)-5-[[[[1-methyl-1-[3-(1-methylethenyl)phenyl]ethyl]amino]carbonyl] amino]-benzenesulfonamide;

N-(3-chlorophenyl)-2-methyl-5-[[[[1-methyl-1-[3-(1-methylethenyl)phenyl]ethyl]amino]carbonyl]amino]-benzenesulfonamide;

4-butyl-1-[3-[[[[4-chloro-3-[[[4-(2-formylhydrazinyl)phenyl]amino]sulfonyl]phenyl]amino]carbonyl]amino]propyl]-3,5-dimethyl-pyridinium chloride;

N'-[4-chloro-3-(1-pyrrolidinylsulfonyl)phenyl]-N-methyl-N-[(2-methyl-5-thiazolyl)methyl]-urea;

N'-[4-methoxy-3-(1-piperidinylsulfonyl)phenyl]-N-methyl-N-[(2-methyl-5-thiazolyl)methyl]-urea; and N-[3-[(hexahydro-1H-azepin-1-yl)sulfonyl]-4-methylphenyl]-N'-[1-methyl-1-[3-(1-methylethenyl)phenyl]ethyl]-urea.

In some embodiments, the compound of Formula (IV) is a compound of Formula (IVa):

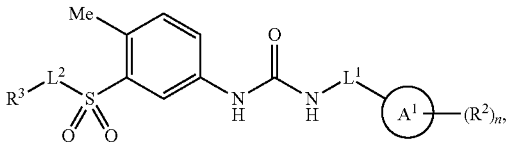

wherein $L^1$, $L^2$, $A^1$, $R^2$, $R^3$, $R^5$, $R^6$, $R^7$ and n are as defined in Formula (IV).

In some embodiments, the compound of Formula (IV) is a compound of Formula (IVb):

(IVb)

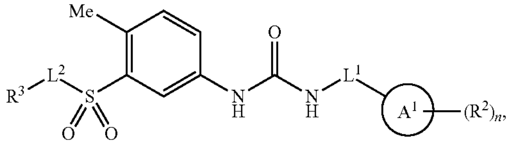

wherein $L^1$, $A^1$, $R^2$, $R^3$, $R^5$, $R^6$, $R^7$ and n are as defined in Formula (IV).

In some embodiments, the compound of Formula (IV) is a compound of Formula (IVc):

(IVc)

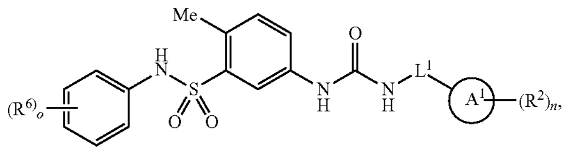

wherein o is 0, 1, 2, 3 or 4; and $L^1$, $A^1$, $R^2$, $R^3$, $R^5$, $R^6$, $R^7$ and n are as defined in Formula (IV).

In another embodiment, the compound of formula (I), (II), (III) or (IV) is selected from any one of the compounds set forth in Table 1, below.

TABLE 1

Representative Compounds

| Cmpd # | Structure |
|---|---|
| 205 | 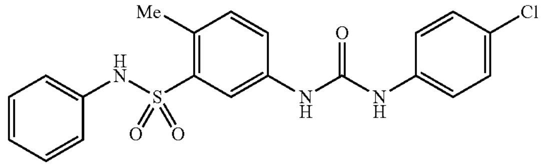 [SMILES: Cc1ccc(NC(=O)Nc2ccc(Cl)cc2)cc1S(=O)(=O)Nc1ccccc1] |
| 206 | 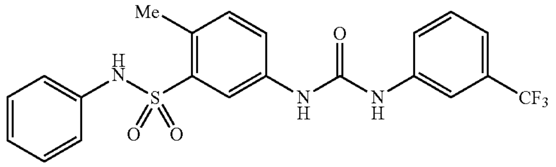 [SMILES: Cc1ccc(NC(=O)Nc2cccc(C(F)(F)F)c2)cc1S(=O)(=O)Nc1ccccc1] |
| 207 | 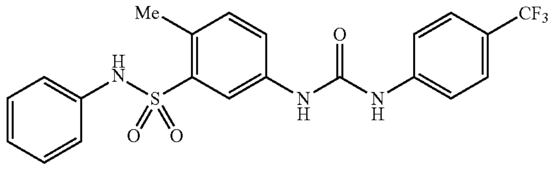 [SMILES: Cc1ccc(NC(=O)Nc2ccc(C(F)(F)F)cc2)cc1S(=O)(=O)Nc1ccccc1] |
| 208 | 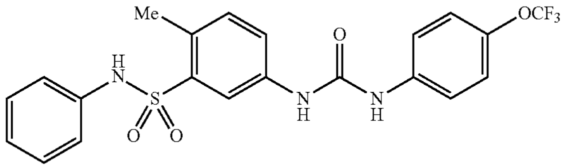 [SMILES: Cc1ccc(NC(=O)Nc2ccc(OC(F)(F)F)cc2)cc1S(=O)(=O)Nc1ccccc1] |
| 209 | 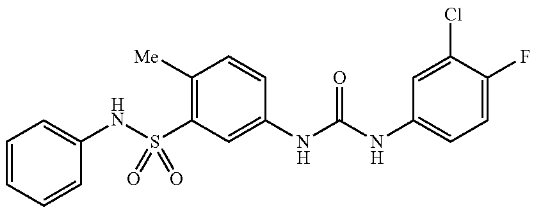 [SMILES: Cc1ccc(NC(=O)Nc2ccc(F)c(Cl)c2)cc1S(=O)(=O)Nc1ccccc1] |

TABLE 1-continued
| Representative Compounds | |
|---|---|
| Cmpd # | Structure |
| 210 | 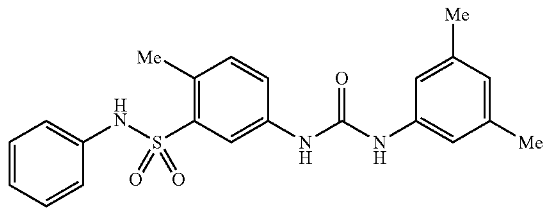 [SMILES: Cc1cc(C)cc(NC(=O)Nc2ccc(C)c(S(=O)(=O)Nc3ccccc3)c2)c1] |
| 211 | 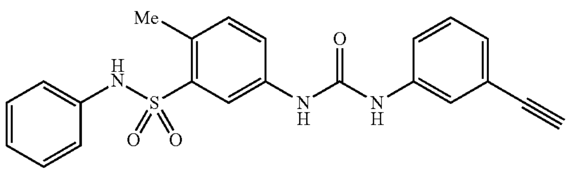 [SMILES: C#Cc1cccc(NC(=O)Nc2ccc(C)c(S(=O)(=O)Nc3ccccc3)c2)c1] |
| 212 | 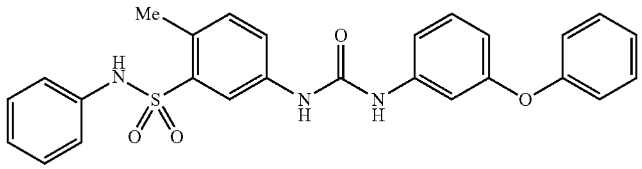 [SMILES: Cc1ccc(NC(=O)Nc2cccc(Oc3ccccc3)c2)cc1S(=O)(=O)Nc1ccccc1] |
| 213 | 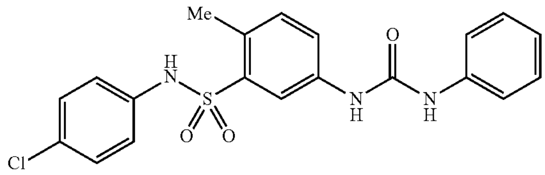 [SMILES: Cc1ccc(NC(=O)Nc2ccccc2)cc1S(=O)(=O)Nc1ccc(Cl)cc1] |
| 214 | 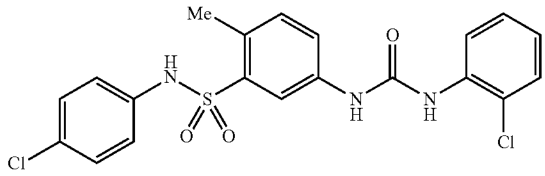 [SMILES: Cc1ccc(NC(=O)Nc2ccccc2Cl)cc1S(=O)(=O)Nc1ccc(Cl)cc1] |
| 215 | 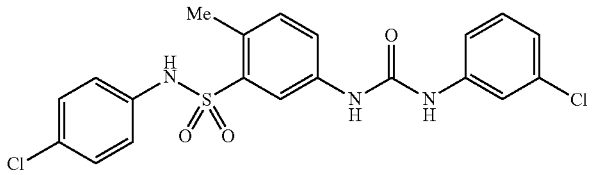 [SMILES: Cc1ccc(NC(=O)Nc2cccc(Cl)c2)cc1S(=O)(=O)Nc1ccc(Cl)cc1] |
| 216 | 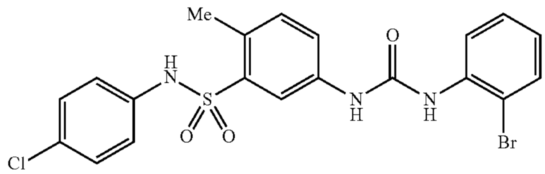 [SMILES: Cc1ccc(NC(=O)Nc2ccccc2Br)cc1S(=O)(=O)Nc1ccc(Cl)cc1] |
| 217 | 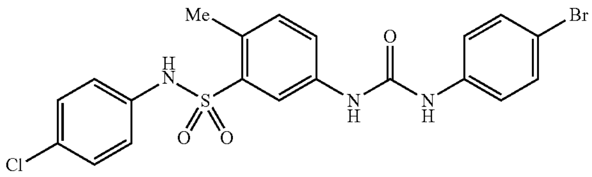 [SMILES: Cc1ccc(NC(=O)Nc2ccc(Br)cc2)cc1S(=O)(=O)Nc1ccc(Cl)cc1] |

TABLE 1-continued
| Representative Compounds | |
|---|---|
| Cmpd # | Structure |
| 218 | 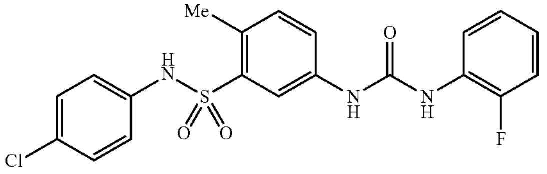 [SMILES: Cc1ccc(NC(=O)Nc2ccccc2F)cc1S(=O)(=O)Nc1ccc(Cl)cc1] |
| 219 | 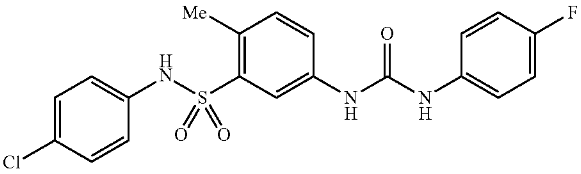 [SMILES: Cc1ccc(NC(=O)Nc2ccc(F)cc2)cc1S(=O)(=O)Nc1ccc(Cl)cc1] |
| 220 | 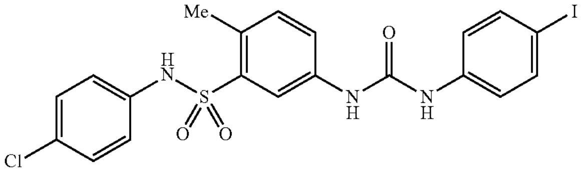 [SMILES: Cc1ccc(NC(=O)Nc2ccc(I)cc2)cc1S(=O)(=O)Nc1ccc(Cl)cc1] |
| 221 | 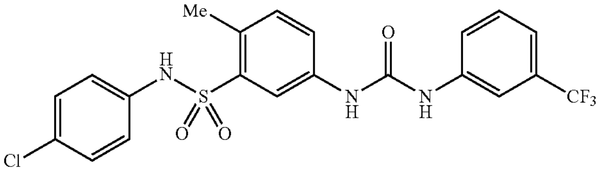 [SMILES: Cc1ccc(NC(=O)Nc2cccc(C(F)(F)F)c2)cc1S(=O)(=O)Nc1ccc(Cl)cc1] |
| 222 | 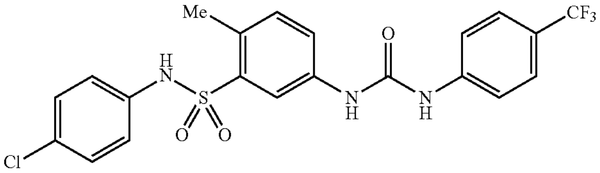 [SMILES: Cc1ccc(NC(=O)Nc2ccc(C(F)(F)F)cc2)cc1S(=O)(=O)Nc1ccc(Cl)cc1] |
| 223 | 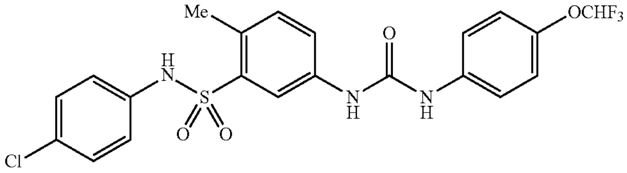 |
| 224 | 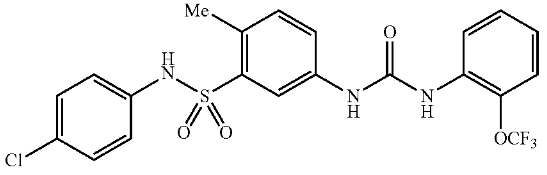 [SMILES: Cc1ccc(NC(=O)Nc2ccccc2OC(F)(F)F)cc1S(=O)(=O)Nc1ccc(Cl)cc1] |
| 225 | 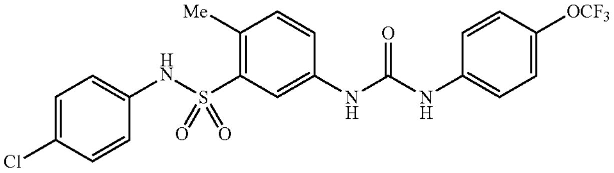 [SMILES: Cc1ccc(NC(=O)Nc2ccc(OC(F)(F)F)cc2)cc1S(=O)(=O)Nc1ccc(Cl)cc1] |

TABLE 1-continued
| Representative Compounds | |
|---|---|
| Cmpd # | Structure |
| 227 | 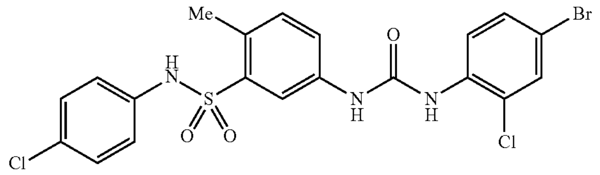 [SMILES: Cc1ccc(NC(=O)Nc2ccc(Br)cc2Cl)cc1S(=O)(=O)Nc1ccc(Cl)cc1] |
| 228 | 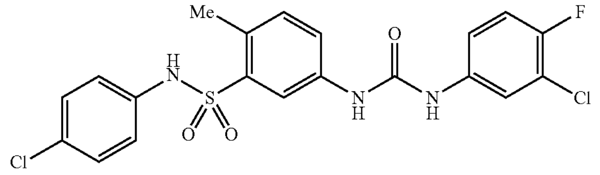 [SMILES: Cc1ccc(NC(=O)Nc2ccc(F)c(Cl)c2)cc1S(=O)(=O)Nc1ccc(Cl)cc1] |
| 229 | 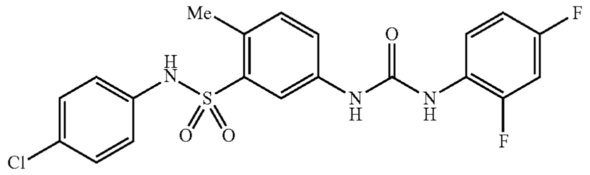 [SMILES: Cc1ccc(NC(=O)Nc2ccc(F)cc2F)cc1S(=O)(=O)Nc1ccc(Cl)cc1] |
| 230 | 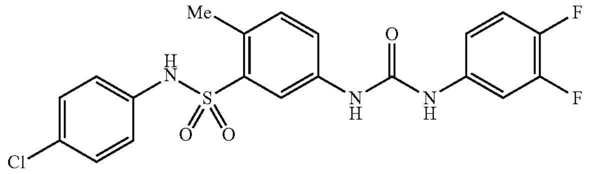 [SMILES: Cc1ccc(NC(=O)Nc2ccc(F)c(F)c2)cc1S(=O)(=O)Nc1ccc(Cl)cc1] |
| 231 | 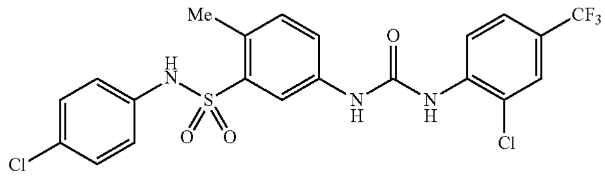 [SMILES: Cc1ccc(NC(=O)Nc2ccc(C(F)(F)F)cc2Cl)cc1S(=O)(=O)Nc1ccc(Cl)cc1] |
| 232 | 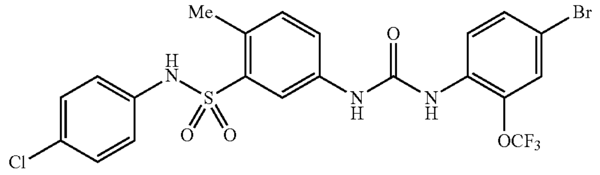 [SMILES: Cc1ccc(NC(=O)Nc2ccc(Br)cc2OC(F)(F)F)cc1S(=O)(=O)Nc1ccc(Cl)cc1] |
| 233 | 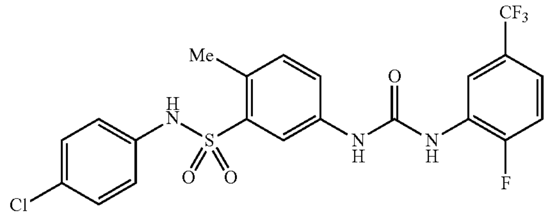 [SMILES: Cc1ccc(NC(=O)Nc2cc(C(F)(F)F)ccc2F)cc1S(=O)(=O)Nc1ccc(Cl)cc1] |
| 234 | 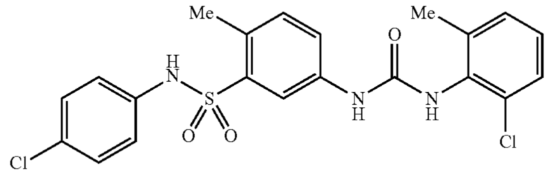 [SMILES: Cc1ccc(NC(=O)Nc2c(C)cccc2Cl)cc1S(=O)(=O)Nc1ccc(Cl)cc1] |

TABLE 1-continued
| Representative Compounds | |
|---|---|
| Cmpd # | Structure |
| 235 | 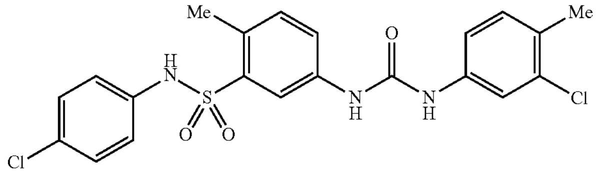 [SMILES: Cc1ccc(NC(=O)Nc2ccc(C)c(S(=O)(=O)Nc3ccc(Cl)cc3)c2)cc1Cl] |
| 236 | 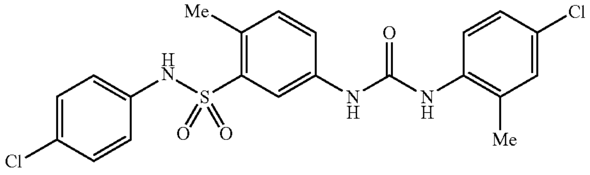 [SMILES: Cc1cc(Cl)ccc1NC(=O)Nc1ccc(C)c(S(=O)(=O)Nc2ccc(Cl)cc2)c1] |
| 237 | 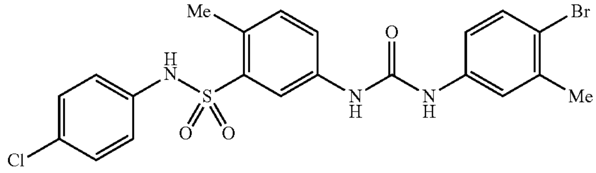 [SMILES: Cc1cc(NC(=O)Nc2ccc(C)c(S(=O)(=O)Nc3ccc(Cl)cc3)c2)ccc1Br] |
| 238 | 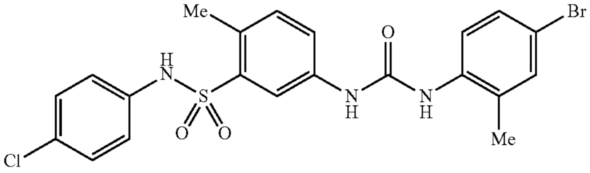 [SMILES: Cc1cc(Br)ccc1NC(=O)Nc1ccc(C)c(S(=O)(=O)Nc2ccc(Cl)cc2)c1] |
| 239 | 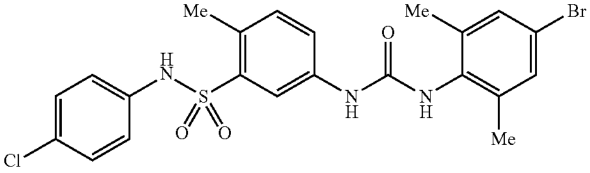 [SMILES: Cc1ccc(NC(=O)Nc2c(C)cc(Br)cc2C)cc1S(=O)(=O)Nc1ccc(Cl)cc1] |
| 240 | 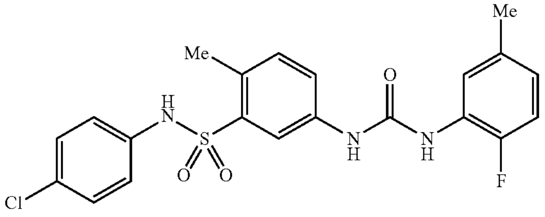 [SMILES: Cc1ccc(F)c(NC(=O)Nc2ccc(C)c(S(=O)(=O)Nc3ccc(Cl)cc3)c2)c1] |
| 241 | 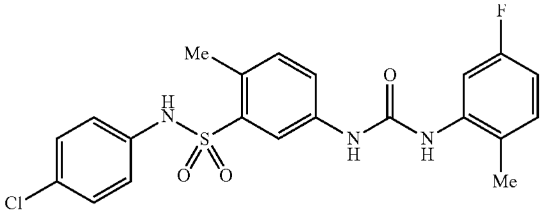 [SMILES: Cc1ccc(F)cc1NC(=O)Nc1ccc(C)c(S(=O)(=O)Nc2ccc(Cl)cc2)c1] |
| 242 | 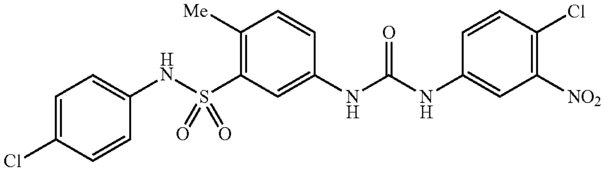 [SMILES: Cc1ccc(NC(=O)Nc2ccc(Cl)c([N+](=O)[O-])c2)cc1S(=O)(=O)Nc1ccc(Cl)cc1] |

TABLE 1-continued
| Representative Compounds | |
|---|---|
| Cmpd # | Structure |
| 243 | 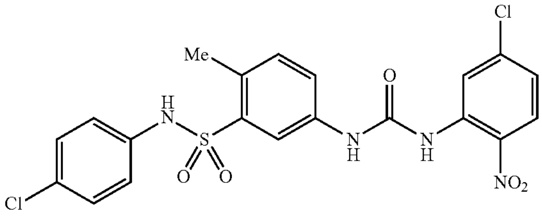 [SMILES: Cc1ccc(NC(=O)Nc2cc(Cl)ccc2[N+](=O)[O-])cc1S(=O)(=O)Nc1ccc(Cl)cc1] |
| 244 | 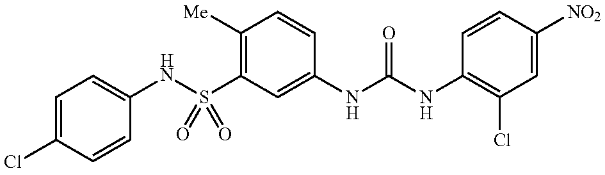 [SMILES: Cc1ccc(NC(=O)Nc2ccc([N+](=O)[O-])cc2Cl)cc1S(=O)(=O)Nc1ccc(Cl)cc1] |
| 245 | 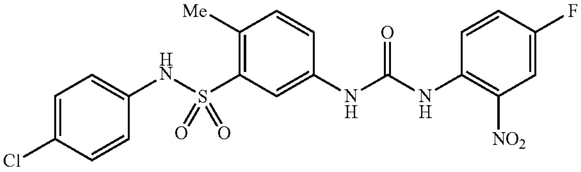 [SMILES: Cc1ccc(NC(=O)Nc2ccc(F)cc2[N+](=O)[O-])cc1S(=O)(=O)Nc1ccc(Cl)cc1] |
| 246 | 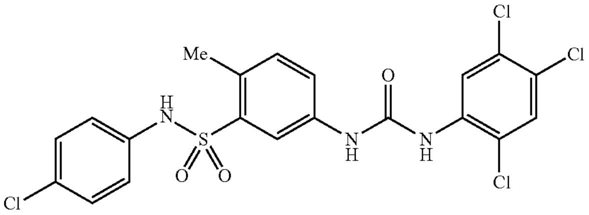 [SMILES: Cc1ccc(NC(=O)Nc2cc(Cl)c(Cl)cc2Cl)cc1S(=O)(=O)Nc1ccc(Cl)cc1] |
| 247 | 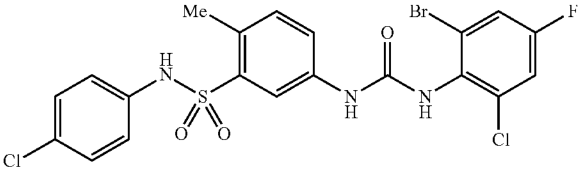 [SMILES: Cc1ccc(NC(=O)Nc2c(Cl)cc(F)cc2Br)cc1S(=O)(=O)Nc1ccc(Cl)cc1] |
| 248 | 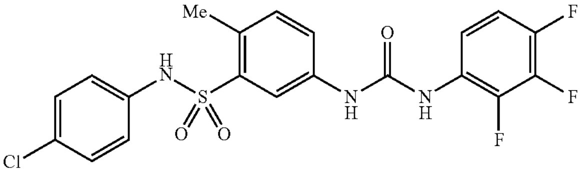 [SMILES: Cc1ccc(NC(=O)Nc2ccc(F)c(F)c2F)cc1S(=O)(=O)Nc1ccc(Cl)cc1] |
| 249 | 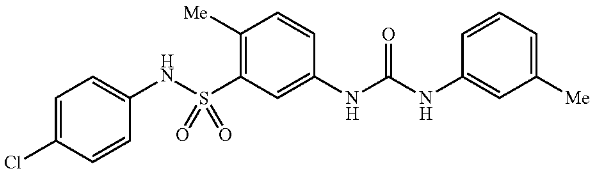 [SMILES: Cc1cccc(NC(=O)Nc2ccc(C)c(S(=O)(=O)Nc3ccc(Cl)cc3)c2)c1] |
| 250 | 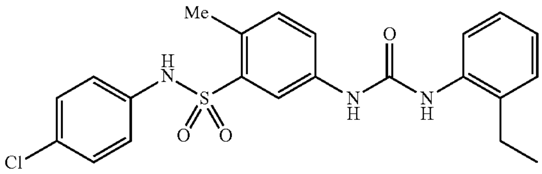 [SMILES: CCc1ccccc1NC(=O)Nc1ccc(C)c(S(=O)(=O)Nc2ccc(Cl)cc2)c1] |

TABLE 1-continued
| Representative Compounds | |
|---|---|
| Cmpd # | Structure |
| 251 | 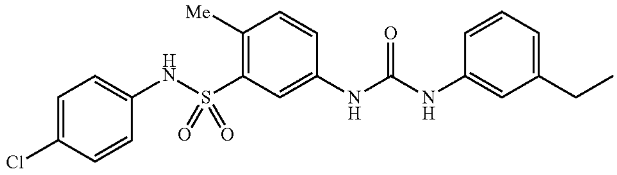 [SMILES: CCc1cccc(NC(=O)Nc2ccc(C)c(S(=O)(=O)Nc3ccc(Cl)cc3)c2)c1] |
| 252 | 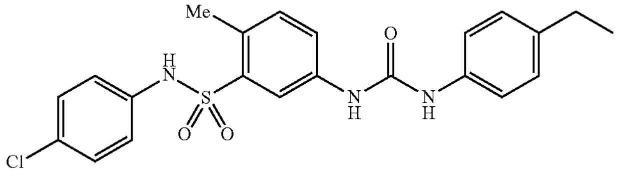 [SMILES: CCc1ccc(NC(=O)Nc2ccc(C)c(S(=O)(=O)Nc3ccc(Cl)cc3)c2)cc1] |
| 253 | 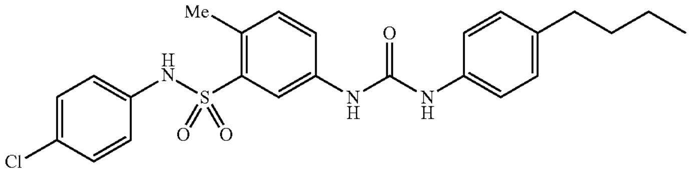 [SMILES: CCCCc1ccc(NC(=O)Nc2ccc(C)c(S(=O)(=O)Nc3ccc(Cl)cc3)c2)cc1] |
| 254 | 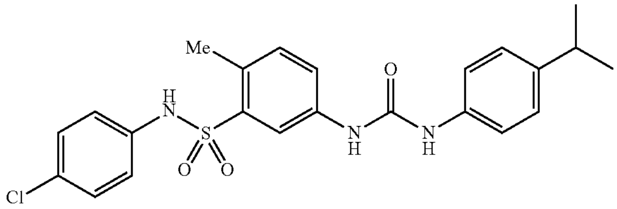 [SMILES: Cc1ccc(NC(=O)Nc2ccc(C(C)C)cc2)cc1S(=O)(=O)Nc1ccc(Cl)cc1] |
| 255 | 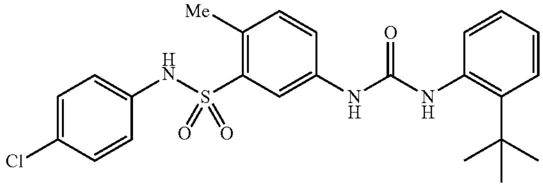 [SMILES: Cc1ccc(NC(=O)Nc2ccccc2C(C)(C)C)cc1S(=O)(=O)Nc1ccc(Cl)cc1] |
| 256 | 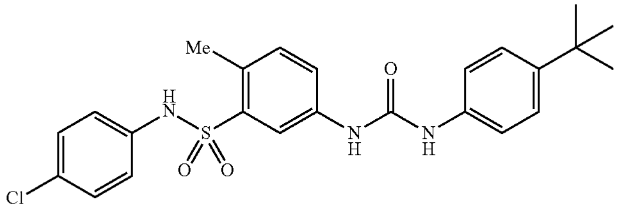 [SMILES: Cc1ccc(NC(=O)Nc2ccc(C(C)(C)C)cc2)cc1S(=O)(=O)Nc1ccc(Cl)cc1] |
| 257 | 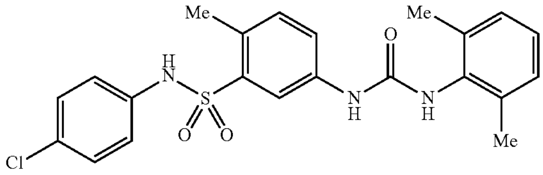 [SMILES: Cc1ccc(NC(=O)Nc2c(C)cccc2C)cc1S(=O)(=O)Nc1ccc(Cl)cc1] |
| 258 | 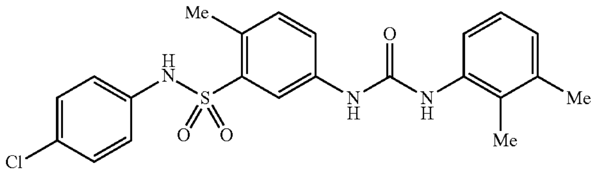 [SMILES: Cc1ccc(NC(=O)Nc2cccc(C)c2C)cc1S(=O)(=O)Nc1ccc(Cl)cc1] |

TABLE 1-continued
| Representative Compounds | |
|---|---|
| Cmpd # | Structure |
| 259 | 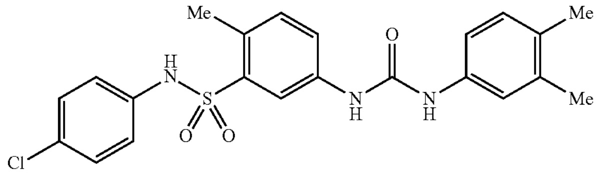 [SMILES: Cc1ccc(NC(=O)Nc2ccc(C)c(S(=O)(=O)Nc3ccc(Cl)cc3)c2)cc1C] |
| 260 | 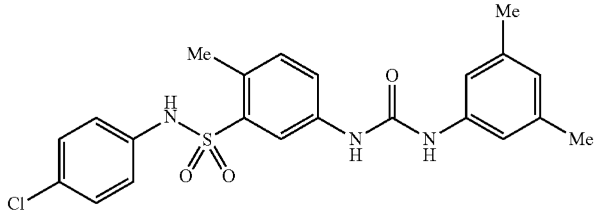 [SMILES: Cc1cc(C)cc(NC(=O)Nc2ccc(C)c(S(=O)(=O)Nc3ccc(Cl)cc3)c2)c1] |
| 261 | 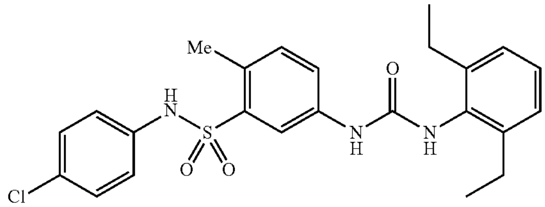 [SMILES: CCc1cccc(CC)c1NC(=O)Nc1ccc(C)c(S(=O)(=O)Nc2ccc(Cl)cc2)c1] |
| 262 | 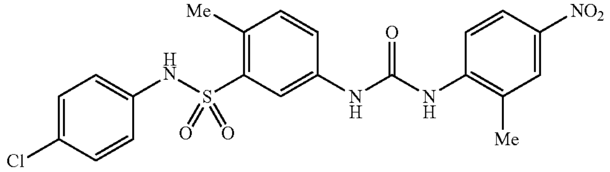 [SMILES: Cc1cc([N+](=O)[O-])ccc1NC(=O)Nc1ccc(C)c(S(=O)(=O)Nc2ccc(Cl)cc2)c1] |
| 263 | 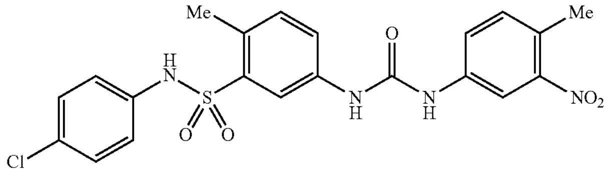 [SMILES: Cc1ccc(NC(=O)Nc2ccc(C)c(S(=O)(=O)Nc3ccc(Cl)cc3)c2)cc1[N+](=O)[O-]] |
| 264 | 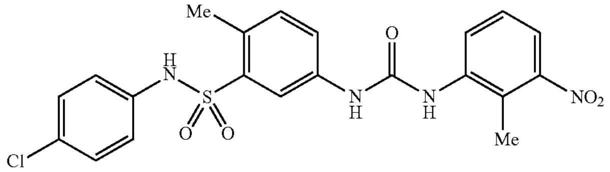 [SMILES: Cc1ccc(NC(=O)Nc2cccc([N+](=O)[O-])c2C)cc1S(=O)(=O)Nc1ccc(Cl)cc1] |
| 265 | 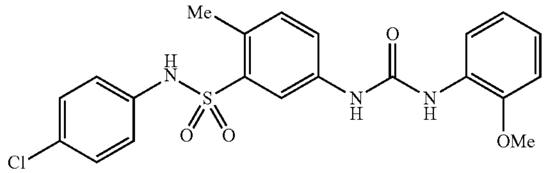 [SMILES: COc1ccccc1NC(=O)Nc1ccc(C)c(S(=O)(=O)Nc2ccc(Cl)cc2)c1] |
| 266 | 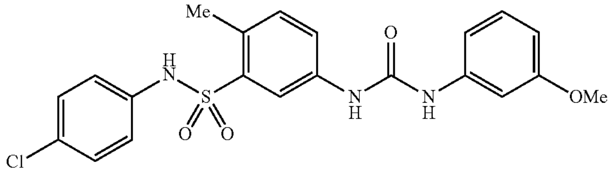 [SMILES: COc1cccc(NC(=O)Nc2ccc(C)c(S(=O)(=O)Nc3ccc(Cl)cc3)c2)c1] |

TABLE 1-continued
| Representative Compounds | |
|---|---|
| Cmpd # | Structure |
| 267 | 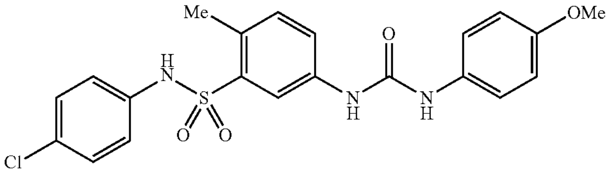 [SMILES: COc1ccc(NC(=O)Nc2ccc(C)c(S(=O)(=O)Nc3ccc(Cl)cc3)c2)cc1] |
| 268 | 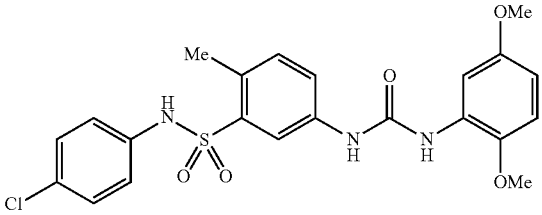 [SMILES: COc1ccc(OC)c(NC(=O)Nc2ccc(C)c(S(=O)(=O)Nc3ccc(Cl)cc3)c2)c1] |
| 269 | 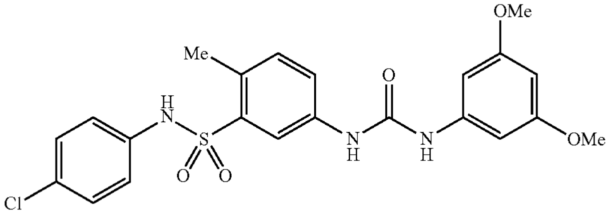 [SMILES: COc1cc(NC(=O)Nc2ccc(C)c(S(=O)(=O)Nc3ccc(Cl)cc3)c2)cc(OC)c1] |
| 270 | 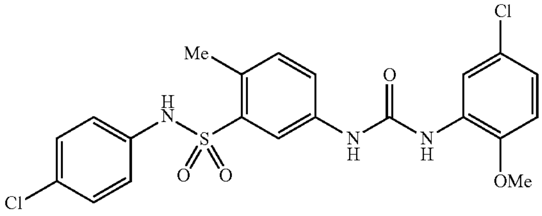 [SMILES: COc1ccc(Cl)cc1NC(=O)Nc1ccc(C)c(S(=O)(=O)Nc2ccc(Cl)cc2)c1] |
| 271 | 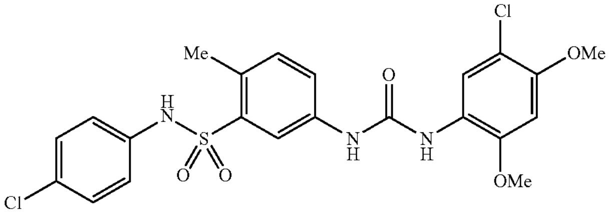 [SMILES: COc1cc(OC)c(NC(=O)Nc2ccc(C)c(S(=O)(=O)Nc3ccc(Cl)cc3)c2)cc1Cl] |
| 272 | 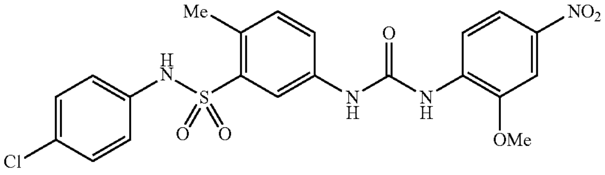 [SMILES: COc1cc([N+](=O)[O-])ccc1NC(=O)Nc1ccc(C)c(S(=O)(=O)Nc2ccc(Cl)cc2)c1] |
| 273 | 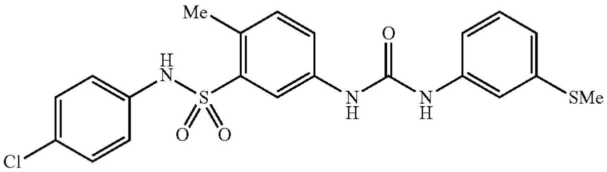 [SMILES: CSc1cccc(NC(=O)Nc2ccc(C)c(S(=O)(=O)Nc3ccc(Cl)cc3)c2)c1] |

TABLE 1-continued
| Representative Compounds | |
|---|---|
| Cmpd # | Structure |
| 274 | 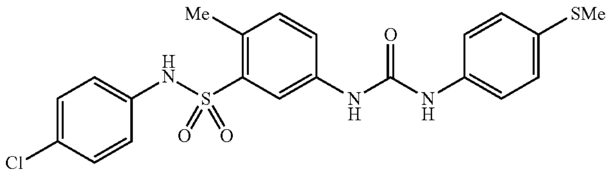 [SMILES: CSc1ccc(NC(=O)Nc2ccc(C)c(S(=O)(=O)Nc3ccc(Cl)cc3)c2)cc1] |
| 275 | 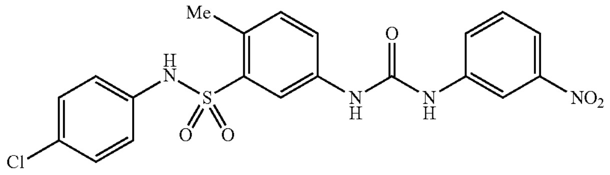 [SMILES: Cc1ccc(NC(=O)Nc2cccc([N+](=O)[O-])c2)cc1S(=O)(=O)Nc1ccc(Cl)cc1] |
| 276 | 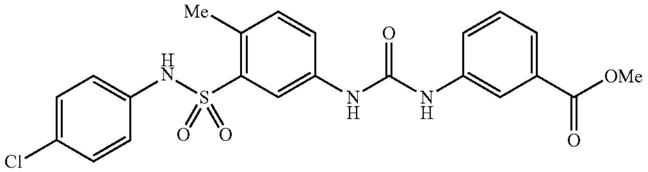 [SMILES: COC(=O)c1cccc(NC(=O)Nc2ccc(C)c(S(=O)(=O)Nc3ccc(Cl)cc3)c2)c1] |
| 277 | 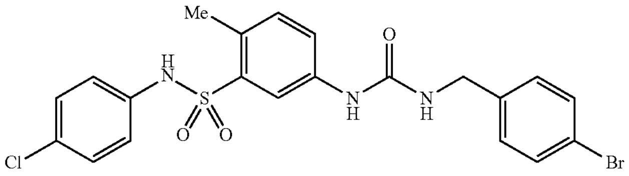 [SMILES: Cc1ccc(NC(=O)NCc2ccc(Br)cc2)cc1S(=O)(=O)Nc1ccc(Cl)cc1] |
| 278 | 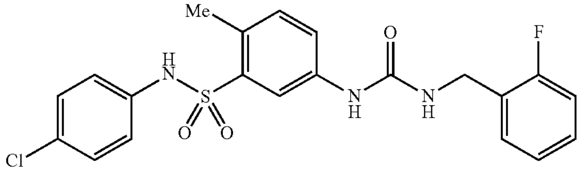 [SMILES: Cc1ccc(NC(=O)NCc2ccccc2F)cc1S(=O)(=O)Nc1ccc(Cl)cc1] |
| 279 | 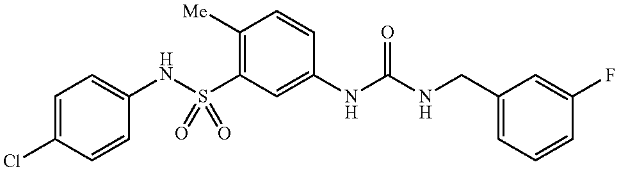 [SMILES: Cc1ccc(NC(=O)NCc2cccc(F)c2)cc1S(=O)(=O)Nc1ccc(Cl)cc1] |
| 280 | 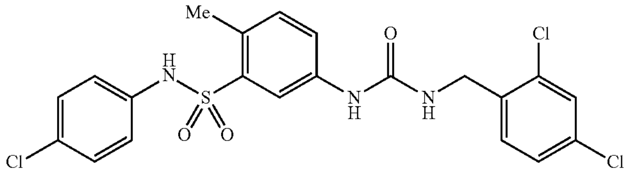 [SMILES: Cc1ccc(NC(=O)NCc2ccc(Cl)cc2Cl)cc1S(=O)(=O)Nc1ccc(Cl)cc1] |
| 282 | 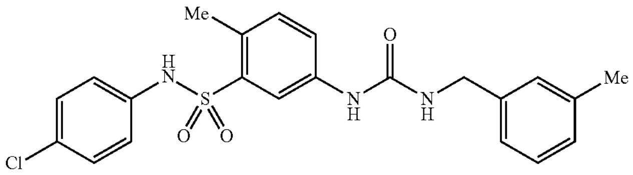 [SMILES: Cc1cccc(CNC(=O)Nc2ccc(C)c(S(=O)(=O)Nc3ccc(Cl)cc3)c2)c1] |

TABLE 1-continued
| Representative Compounds | |
|---|---|
| Cmpd # | Structure |
| 283 | 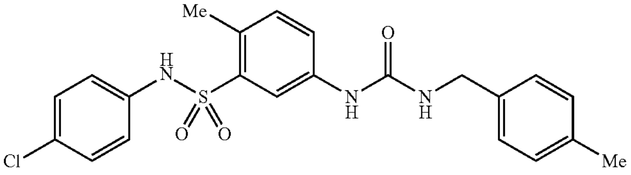 [SMILES: Cc1ccc(CNC(=O)Nc2ccc(C)c(S(=O)(=O)Nc3ccc(Cl)cc3)c2)cc1] |
| 284 | 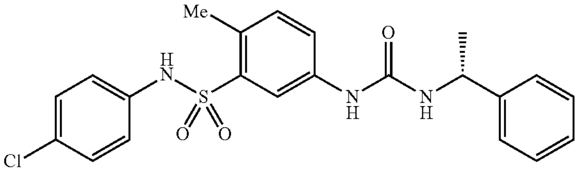 [SMILES: Cc1ccc(NC(=O)N[C@H](C)c2ccccc2)cc1S(=O)(=O)Nc1ccc(Cl)cc1] |
| 285 | 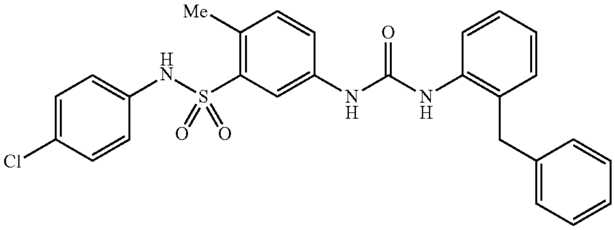 [SMILES: Cc1ccc(NC(=O)Nc2ccccc2Cc2ccccc2)cc1S(=O)(=O)Nc1ccc(Cl)cc1] |
| 286 | 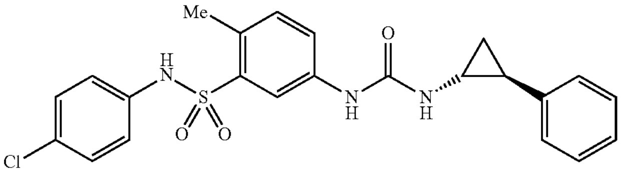 |
| 287 | 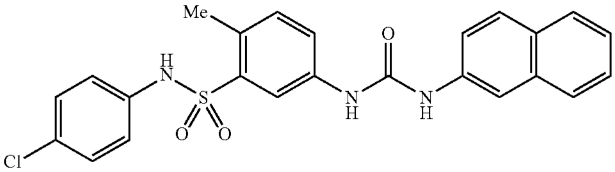 [SMILES: Cc1ccc(NC(=O)Nc2ccc3ccccc3c2)cc1S(=O)(=O)Nc1ccc(Cl)cc1] |
| 288 | 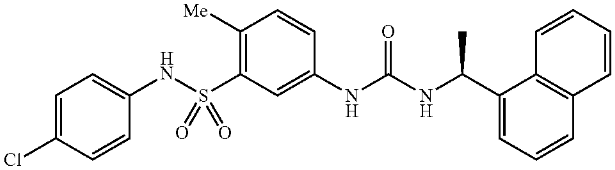 [SMILES: Cc1ccc(NC(=O)N[C@@H](C)c2cccc3ccccc23)cc1S(=O)(=O)Nc1ccc(Cl)cc1] |
| 289 | 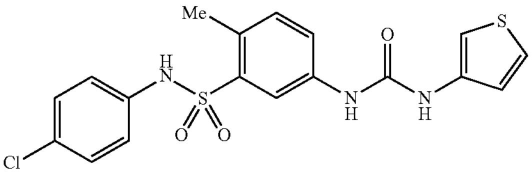 [SMILES: Cc1ccc(NC(=O)Nc2ccsc2)cc1S(=O)(=O)Nc1ccc(Cl)cc1] |
| 290 | 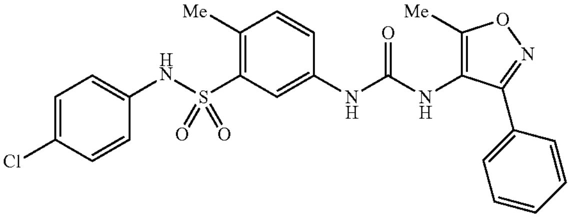 [SMILES: Cc1ccc(NC(=O)Nc2c(-c3ccccc3)noc2C)cc1S(=O)(=O)Nc1ccc(Cl)cc1] |

TABLE 1-continued
| Representative Compounds | |
|---|---|
| Cmpd # | Structure |
| 291 | 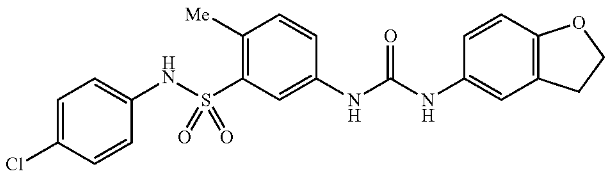 [SMILES: Cc1ccc(NC(=O)Nc2ccc3c(c2)CCO3)cc1S(=O)(=O)Nc1ccc(Cl)cc1] |
| 292 | 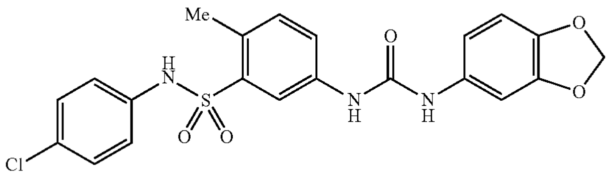 [SMILES: Cc1ccc(NC(=O)Nc2ccc3c(c2)OCO3)cc1S(=O)(=O)Nc1ccc(Cl)cc1] |
| 293 | 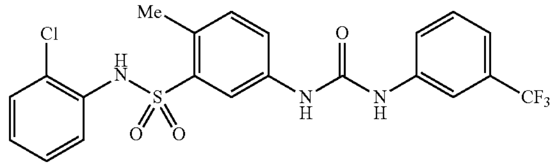 [SMILES: Cc1ccc(NC(=O)Nc2cccc(C(F)(F)F)c2)cc1S(=O)(=O)Nc1ccccc1Cl] |
| 294 | 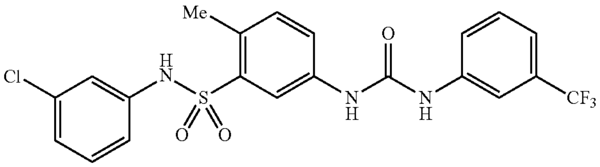 [SMILES: Cc1ccc(NC(=O)Nc2cccc(C(F)(F)F)c2)cc1S(=O)(=O)Nc1cccc(Cl)c1] |
| 295 | 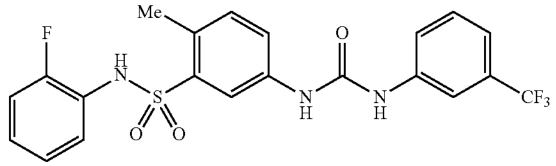 [SMILES: Cc1ccc(NC(=O)Nc2cccc(C(F)(F)F)c2)cc1S(=O)(=O)Nc1ccccc1F] |
| 296 | 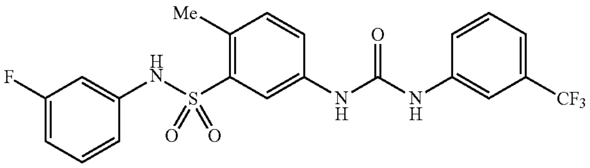 [SMILES: Cc1ccc(NC(=O)Nc2cccc(C(F)(F)F)c2)cc1S(=O)(=O)Nc1cccc(F)c1] |
| 297 | 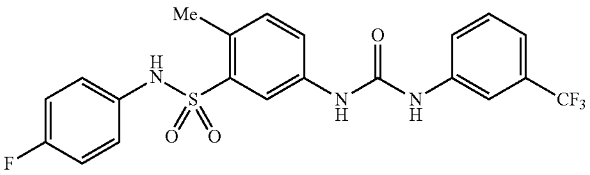 [SMILES: Cc1ccc(NC(=O)Nc2cccc(C(F)(F)F)c2)cc1S(=O)(=O)Nc1ccc(F)cc1] |
| 298 | 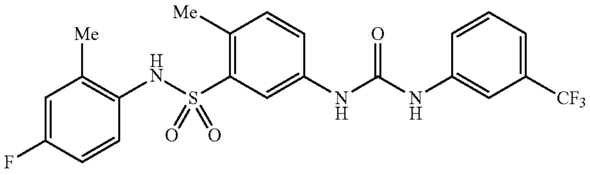 [SMILES: Cc1cc(F)ccc1NS(=O)(=O)c1cc(NC(=O)Nc2cccc(C(F)(F)F)c2)ccc1C] |

TABLE 1-continued
| Representative Compounds | |
|---|---|
| Cmpd # | Structure |
| 299 | 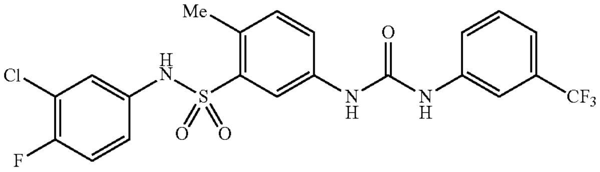 [SMILES: Cc1ccc(NC(=O)Nc2cccc(C(F)(F)F)c2)cc1S(=O)(=O)Nc1ccc(F)c(Cl)c1] |
| 301 | 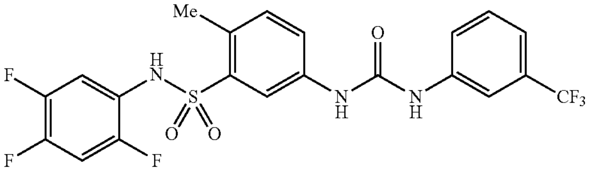 [SMILES: Cc1ccc(NC(=O)Nc2cccc(C(F)(F)F)c2)cc1S(=O)(=O)Nc1cc(F)c(F)cc1F] |
| 302 | 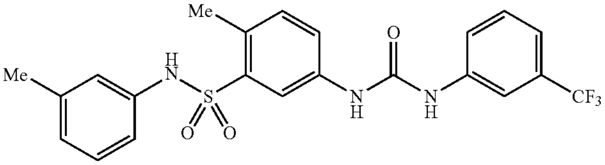 [SMILES: Cc1ccc(NC(=O)Nc2cccc(C(F)(F)F)c2)cc1S(=O)(=O)Nc1cccc(O)c1] |
| 324 | 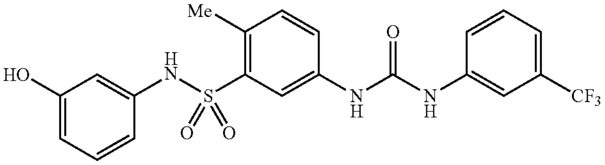 |
| 304 | 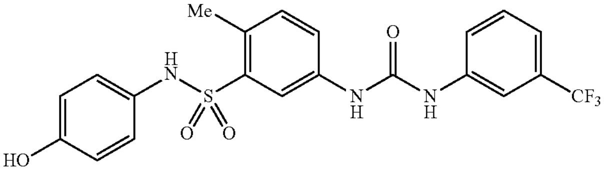 [SMILES: Cc1ccc(NC(=O)Nc2cccc(C(F)(F)F)c2)cc1S(=O)(=O)Nc1ccc(O)cc1] |
| 305 | 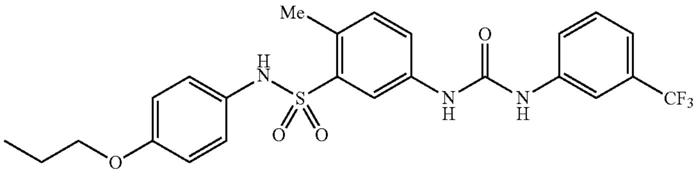 [SMILES: CCCOc1ccc(NS(=O)(=O)c2cc(NC(=O)Nc3cccc(C(F)(F)F)c3)ccc2C)cc1] |
| 306 | 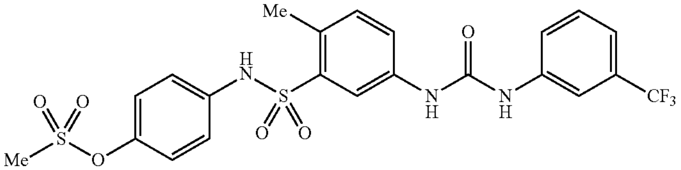 [SMILES: Cc1ccc(NC(=O)Nc2cccc(C(F)(F)F)c2)cc1S(=O)(=O)Nc1ccc(OS(C)(=O)=O)cc1] |
| 308 | 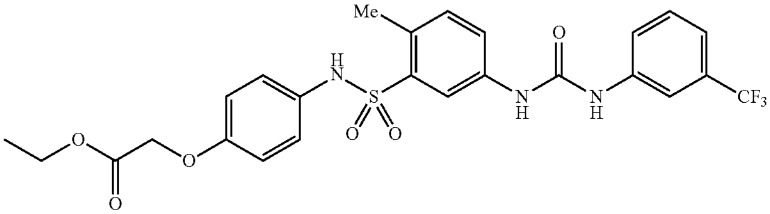 [SMILES: CCOC(=O)COc1ccc(NS(=O)(=O)c2cc(NC(=O)Nc3cccc(C(F)(F)F)c3)ccc2C)cc1] |

TABLE 1-continued
| Representative Compounds | |
|---|---|
| Cmpd # | Structure |
| 309 | 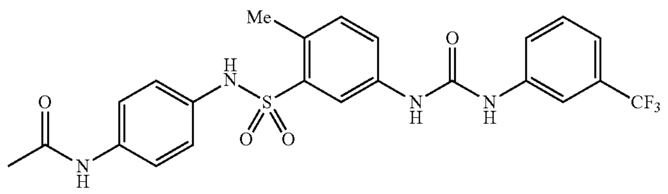 [SMILES: CC(=O)Nc1ccc(NS(=O)(=O)c2cc(NC(=O)Nc3cccc(C(F)(F)F)c3)ccc2C)cc1] |
| 310 | 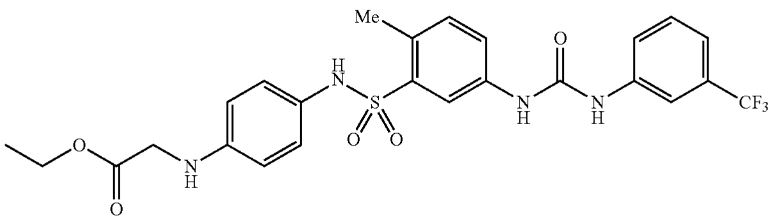 [SMILES: CCOC(=O)CNc1ccc(NS(=O)(=O)c2cc(NC(=O)Nc3cccc(C(F)(F)F)c3)ccc2C)cc1] |
| 311 | 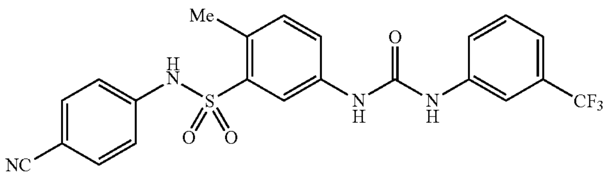 [SMILES: Cc1ccc(NC(=O)Nc2cccc(C(F)(F)F)c2)cc1S(=O)(=O)Nc1ccc(C#N)cc1] |
| 312 | 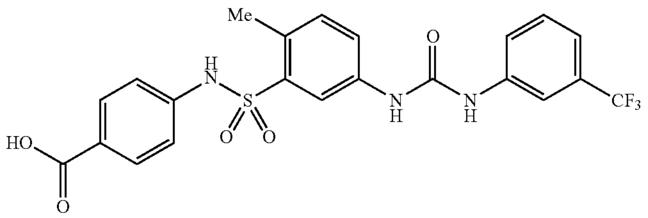 [SMILES: Cc1ccc(NC(=O)Nc2cccc(C(F)(F)F)c2)cc1S(=O)(=O)Nc1ccc(C(=O)O)cc1] |
| 313 | 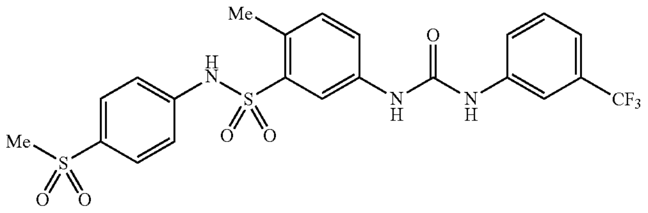 [SMILES: Cc1ccc(NC(=O)Nc2cccc(C(F)(F)F)c2)cc1S(=O)(=O)Nc1ccc(S(C)(=O)=O)cc1] |
| 314 | 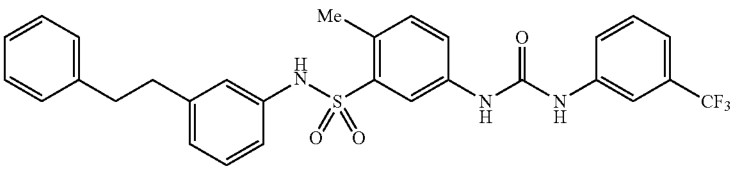 [SMILES: Cc1ccc(NC(=O)Nc2cccc(C(F)(F)F)c2)cc1S(=O)(=O)Nc1cccc(CCc2ccccc2)c1] |
| 315 | 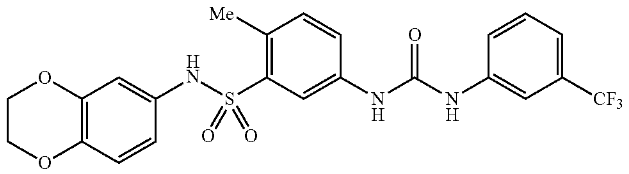 [SMILES: Cc1ccc(NC(=O)Nc2cccc(C(F)(F)F)c2)cc1S(=O)(=O)Nc1ccc2c(c1)OCCO2] |

TABLE 1-continued
| Representative Compounds | |
|---|---|
| Cmpd # | Structure |
| 316 | 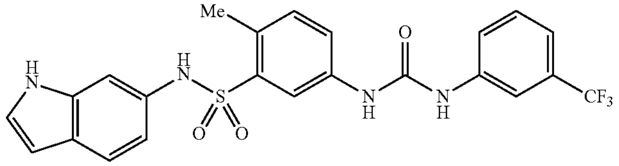 [SMILES: Cc1ccc(NC(=O)Nc2cccc(C(F)(F)F)c2)cc1S(=O)(=O)Nc1ccc2cc[nH]c2c1] |
| 317 | 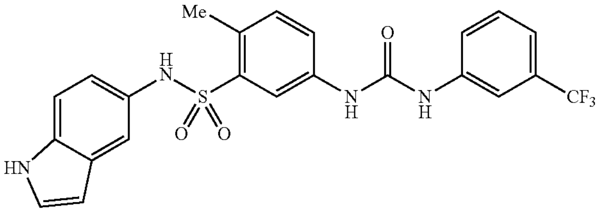 |
| 318 | 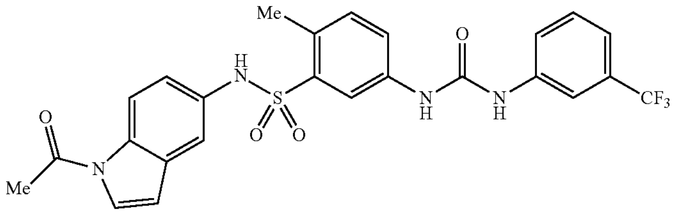 [SMILES: CC(=O)n1ccc2cc(NS(=O)(=O)c3cc(NC(=O)Nc4cccc(C(F)(F)F)c4)ccc3C)ccc21] |
| 319 | 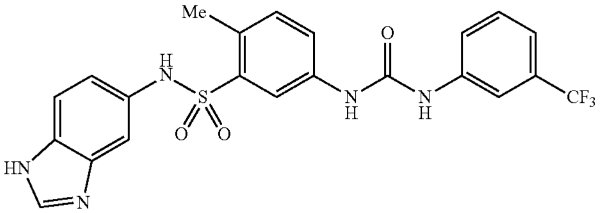 [SMILES: Cc1ccc(NC(=O)Nc2cccc(C(F)(F)F)c2)cc1S(=O)(=O)Nc1ccc2[nH]cnc2c1] |
| 320 | 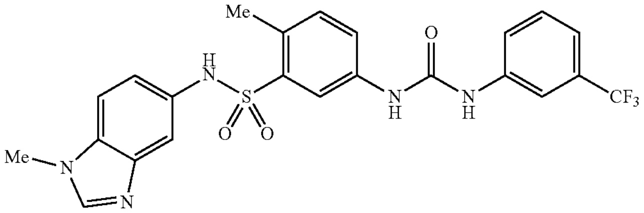 [SMILES: Cc1ccc(NC(=O)Nc2cccc(C(F)(F)F)c2)cc1S(=O)(=O)Nc1ccc2c(c1)ncn2C] |
| 321 | 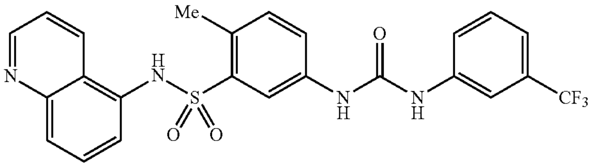 [SMILES: Cc1ccc(NC(=O)Nc2cccc(C(F)(F)F)c2)cc1S(=O)(=O)Nc1cccc2ncccc12] |
| 322 | 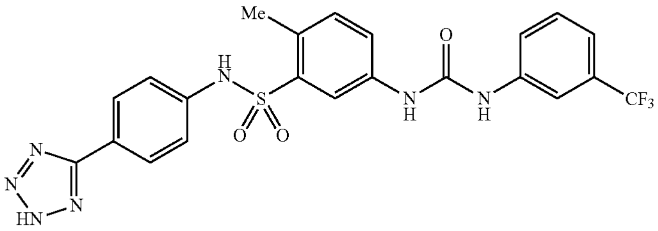 [SMILES: Cc1ccc(NC(=O)Nc2cccc(C(F)(F)F)c2)cc1S(=O)(=O)Nc1ccc(-c2nn[nH]n2)cc1] |

TABLE 1-continued
| Representative Compounds | |
|---|---|
| Cmpd # | Structure |
| 323 | 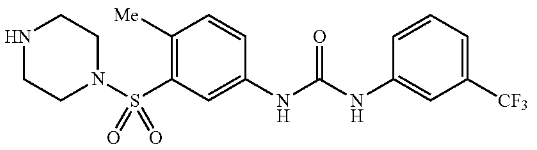 [SMILES: Cc1ccc(NC(=O)Nc2cccc(C(F)(F)F)c2)cc1S(=O)(=O)N1CCNCC1] |
| 324 | 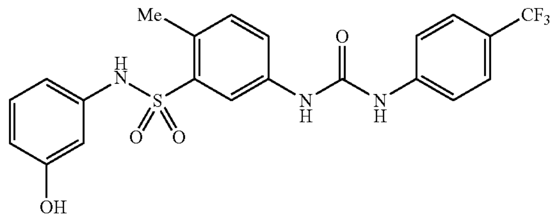 [SMILES: Cc1ccc(NC(=O)Nc2ccc(C(F)(F)F)cc2)cc1S(=O)(=O)Nc1cccc(O)c1] |
| 325 | 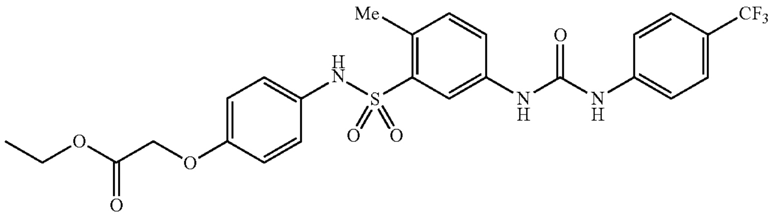 [SMILES: CCOC(=O)COc1ccc(NS(=O)(=O)c2cc(NC(=O)Nc3ccc(C(F)(F)F)cc3)ccc2C)cc1] |
| 326 | 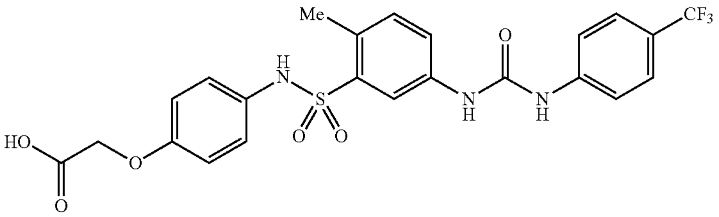 [SMILES: Cc1ccc(NC(=O)Nc2ccc(C(F)(F)F)cc2)cc1S(=O)(=O)Nc1ccc(OCC(=O)O)cc1] |
| 327 | 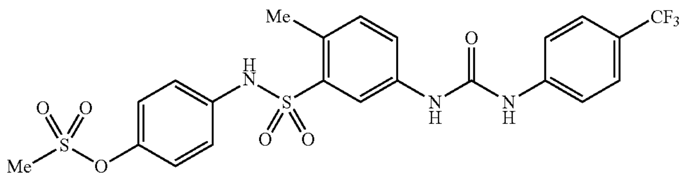 [SMILES: Cc1ccc(NC(=O)Nc2ccc(C(F)(F)F)cc2)cc1S(=O)(=O)Nc1ccc(OS(C)(=O)=O)cc1] |
| 328 | 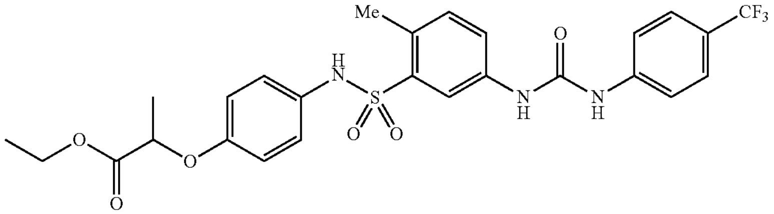 [SMILES: CCOC(=O)C(C)Oc1ccc(NS(=O)(=O)c2cc(NC(=O)Nc3ccc(C(F)(F)F)cc3)ccc2C)cc1] |
| 329 | 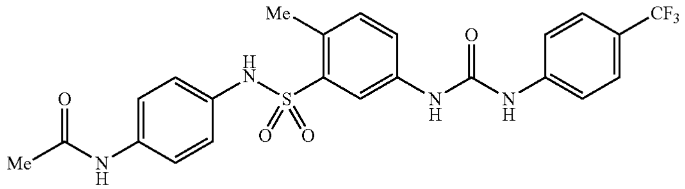 [SMILES: CC(=O)Nc1ccc(NS(=O)(=O)c2cc(NC(=O)Nc3ccc(C(F)(F)F)cc3)ccc2C)cc1] |

TABLE 1-continued
| Representative Compounds | |
| --- | --- |
| Cmpd # | Structure |
| 330 | 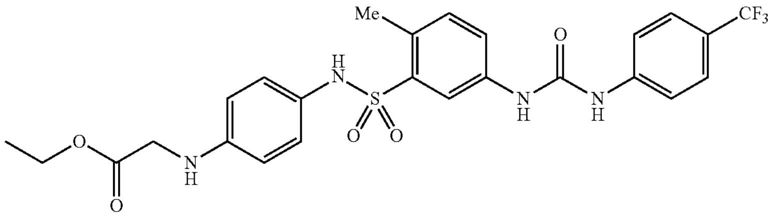 [SMILES: CCOC(=O)CNc1ccc(NS(=O)(=O)c2cc(NC(=O)Nc3ccc(C(F)(F)F)cc3)ccc2C)cc1] |
| 331 | 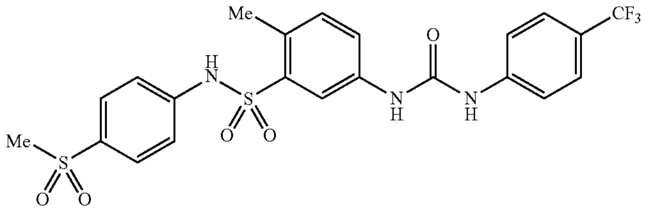 [SMILES: Cc1ccc(NC(=O)Nc2ccc(C(F)(F)F)cc2)cc1S(=O)(=O)Nc1ccc(S(C)(=O)=O)cc1] |
| 332 | 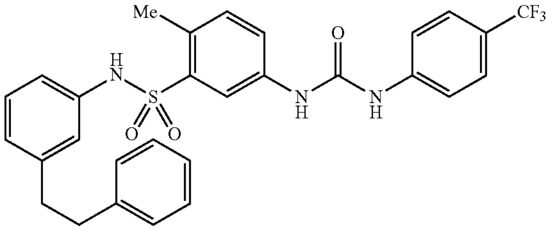 [SMILES: Cc1ccc(NC(=O)Nc2ccc(C(F)(F)F)cc2)cc1S(=O)(=O)Nc1cccc(CCc2ccccc2)c1] |
| 333 | 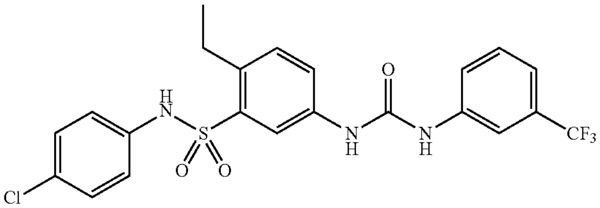 [SMILES: CCc1ccc(NC(=O)Nc2cccc(C(F)(F)F)c2)cc1S(=O)(=O)Nc1ccc(Cl)cc1] |
| 334 | 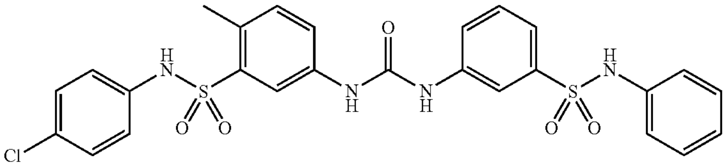 [SMILES: Cc1ccc(NC(=O)Nc2cccc(S(=O)(=O)Nc3ccccc3)c2)cc1S(=O)(=O)Nc1ccc(Cl)cc1] |
| 335 | 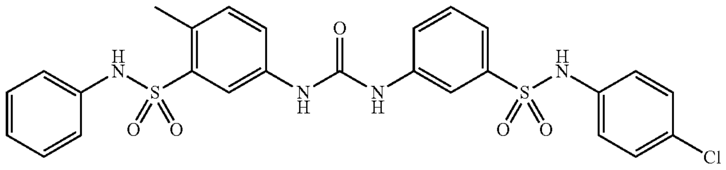 [SMILES: Cc1ccc(NC(=O)Nc2cccc(S(=O)(=O)Nc3ccc(Cl)cc3)c2)cc1S(=O)(=O)Nc1ccccc1] |
| 336 | 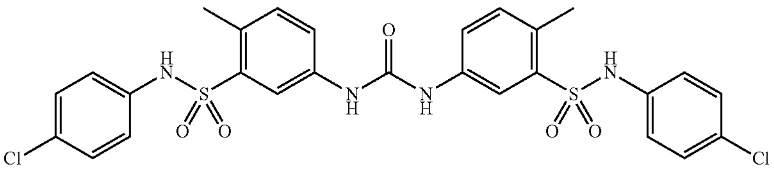 [SMILES: Cc1ccc(NC(=O)Nc2ccc(C)c(S(=O)(=O)Nc3ccc(Cl)cc3)c2)cc1S(=O)(=O)Nc1ccc(Cl)cc1] |

TABLE 1-continued
| Representative Compounds | |
|---|---|
| Cmpd # | Structure |
| 352 | 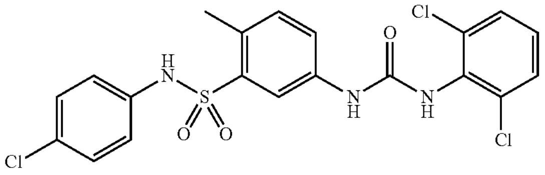 [SMILES: Cc1ccc(NC(=O)Nc2c(Cl)cccc2Cl)cc1S(=O)(=O)Nc1ccc(Cl)cc1] |
In another embodiment, the compound of formula (I), (II), (III) or (IV) is selected from any one of the compounds set forth in Table 2, below.
TABLE 2
| Representative Compounds | |
|---|---|
| Cmpd # | Structure |
| 1 | 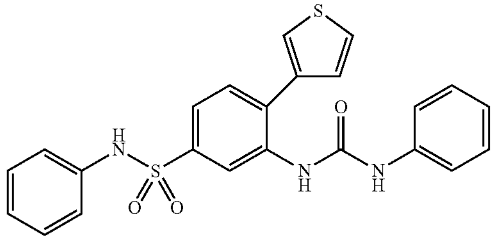 [SMILES: O=C(Nc1ccccc1)Nc1cc(S(=O)(=O)Nc2ccccc2)ccc1-c1ccsc1] |
| 2 | 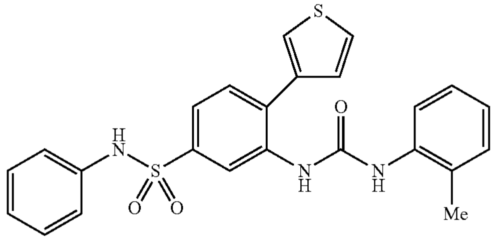 [SMILES: Cc1ccccc1NC(=O)Nc1cc(S(=O)(=O)Nc2ccccc2)ccc1-c1ccsc1] |
| 3 | 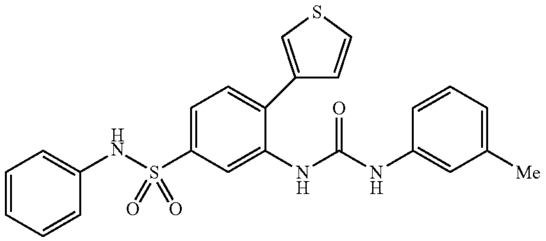 [SMILES: Cc1cccc(NC(=O)Nc2cc(S(=O)(=O)Nc3ccccc3)ccc2-c2ccsc2)c1] |
| 4 | 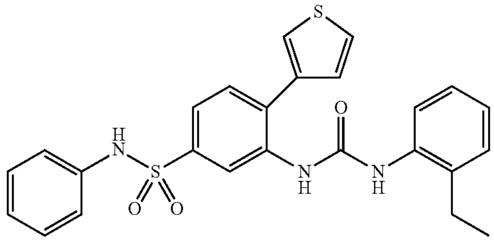 [SMILES: CCc1ccccc1NC(=O)Nc1cc(S(=O)(=O)Nc2ccccc2)ccc1-c1ccsc1] |

TABLE 2-continued
| Representative Compounds | |
|---|---|
| Cmpd # | Structure |
| 5 | 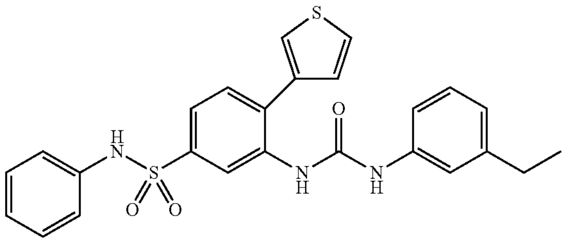 [SMILES: CCc1cccc(NC(=O)Nc2cc(S(=O)(=O)Nc3ccccc3)ccc2-c2ccsc2)c1] |
| 6 | 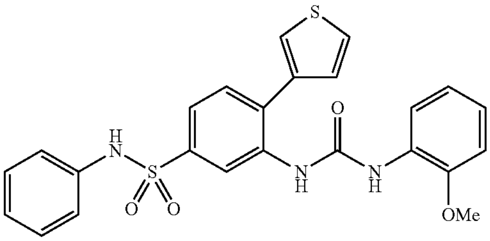 [SMILES: COc1ccccc1NC(=O)Nc1cc(S(=O)(=O)Nc2ccccc2)ccc1-c1ccsc1] |
| 7 | 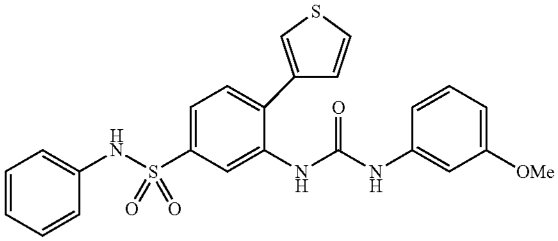 [SMILES: COc1cccc(NC(=O)Nc2cc(S(=O)(=O)Nc3ccccc3)ccc2-c2ccsc2)c1] |
| 8 | 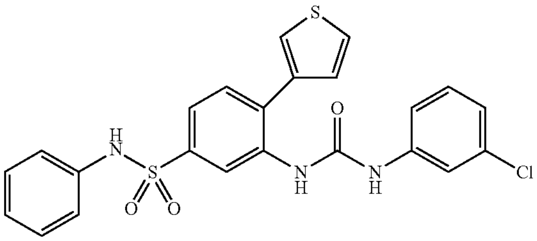 [SMILES: O=C(Nc1cccc(Cl)c1)Nc1cc(S(=O)(=O)Nc2ccccc2)ccc1-c1ccsc1] |
| 9 | 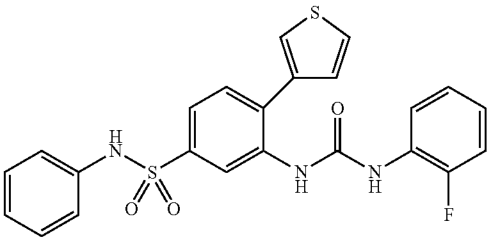 [SMILES: O=C(Nc1ccccc1F)Nc1cc(S(=O)(=O)Nc2ccccc2)ccc1-c1ccsc1] |
| 10 | 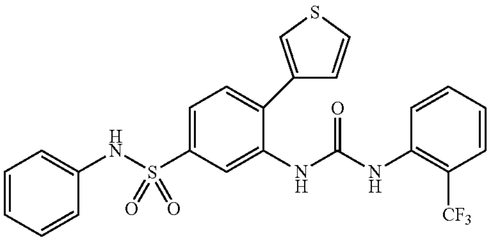 [SMILES: O=C(Nc1cc(S(=O)(=O)Nc2ccccc2)ccc1-c1ccsc1)Nc1ccccc1C(F)(F)F] |

TABLE 2-continued
| Representative Compounds | |
|---|---|
| Cmpd # | Structure |
| 11 | 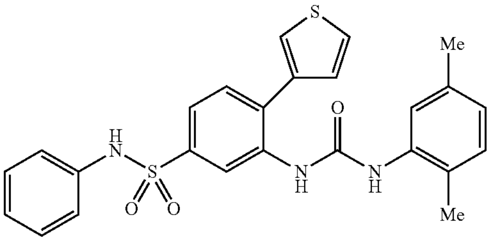 [SMILES: Cc1ccc(C)c(NC(=O)Nc2cc(S(=O)(=O)Nc3ccccc3)ccc2-c2ccsc2)c1] |
| 12 | 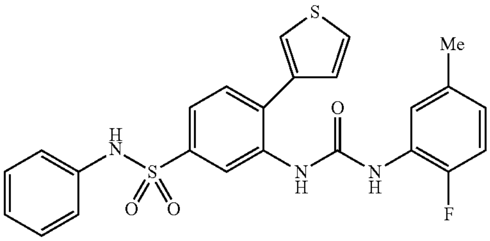 [SMILES: Cc1ccc(F)c(NC(=O)Nc2cc(S(=O)(=O)Nc3ccccc3)ccc2-c2ccsc2)c1] |
| 13 | 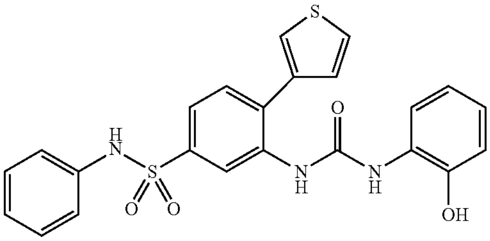 [SMILES: O=C(Nc1ccccc1O)Nc1cc(S(=O)(=O)Nc2ccccc2)ccc1-c1ccsc1] |
| 14 | 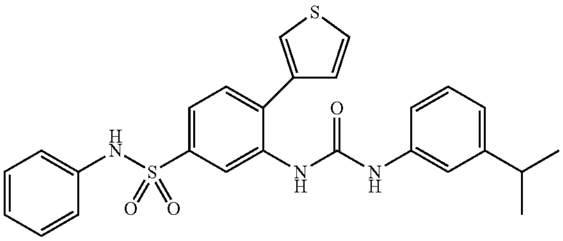 [SMILES: CC(C)c1cccc(NC(=O)Nc2cc(S(=O)(=O)Nc3ccccc3)ccc2-c2ccsc2)c1] |
| 15 | 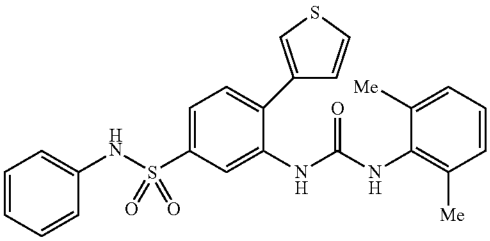 [SMILES: Cc1cccc(C)c1NC(=O)Nc1cc(S(=O)(=O)Nc2ccccc2)ccc1-c1ccsc1] |
| 16 | 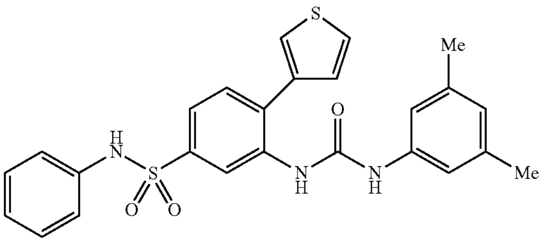 [SMILES: Cc1cc(C)cc(NC(=O)Nc2cc(S(=O)(=O)Nc3ccccc3)ccc2-c2ccsc2)c1] |

TABLE 2-continued
| Representative Compounds | |
|---|---|
| Cmpd # | Structure |
| 17 | 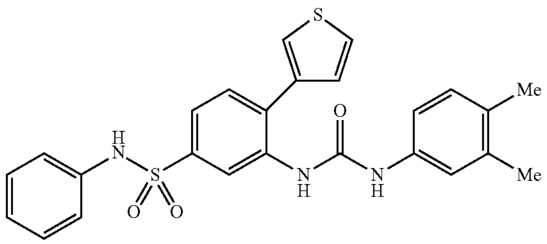 [SMILES: Cc1ccc(NC(=O)Nc2cc(S(=O)(=O)Nc3ccccc3)ccc2-c2ccsc2)cc1C] |
| 18 | 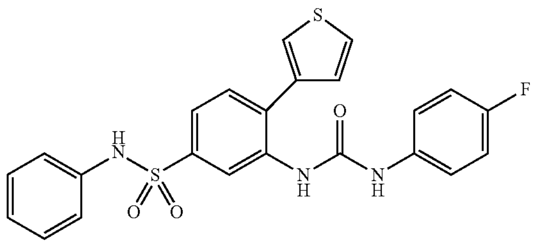 [SMILES: O=C(Nc1ccc(F)cc1)Nc1cc(S(=O)(=O)Nc2ccccc2)ccc1-c1ccsc1] |
| 19 | 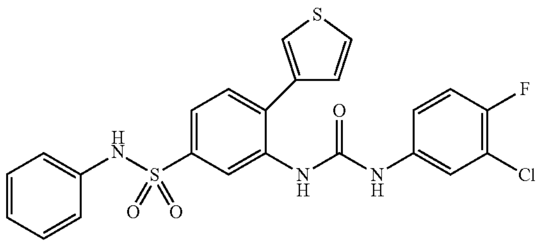 [SMILES: O=C(Nc1ccc(F)c(Cl)c1)Nc1cc(S(=O)(=O)Nc2ccccc2)ccc1-c1ccsc1] |
| 20 | 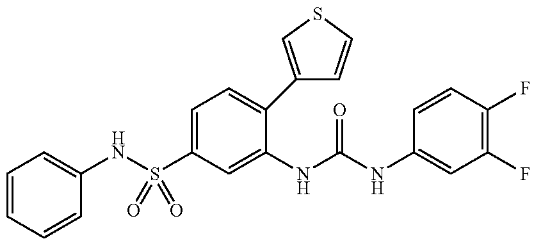 [SMILES: O=C(Nc1ccc(F)c(F)c1)Nc1cc(S(=O)(=O)Nc2ccccc2)ccc1-c1ccsc1] |
| 21 | 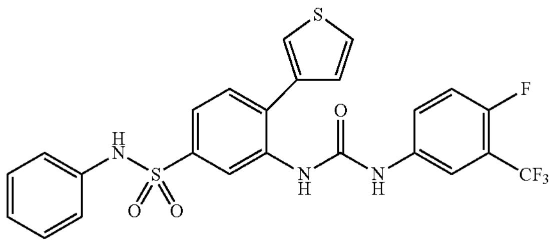 [SMILES: O=C(Nc1ccc(F)c(C(F)(F)F)c1)Nc1cc(S(=O)(=O)Nc2ccccc2)ccc1-c1ccsc1] |
| 22 | 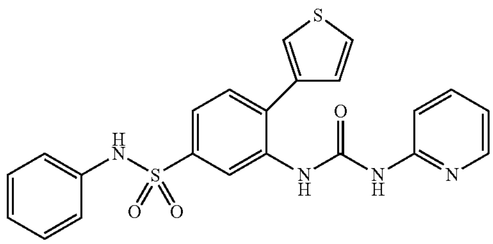 [SMILES: O=C(Nc1ccccn1)Nc1cc(S(=O)(=O)Nc2ccccc2)ccc1-c1ccsc1] |

TABLE 2-continued
| Representative Compounds | |
|---|---|
| Cmpd # | Structure |
| 23 | 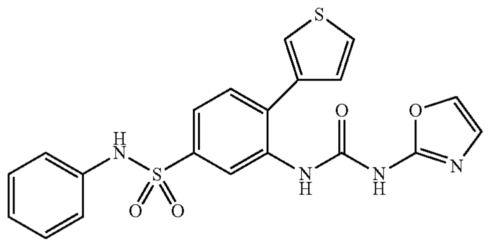 [SMILES: O=C(Nc1ncco1)Nc1cc(S(=O)(=O)Nc2ccccc2)ccc1-c1ccsc1] |
| 24 | 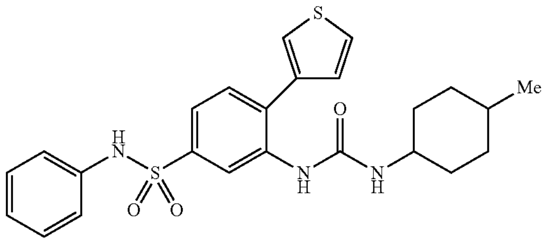 [SMILES: CC1CCC(NC(=O)Nc2cc(S(=O)(=O)Nc3ccccc3)ccc2-c2ccsc2)CC1] |
| 25 | 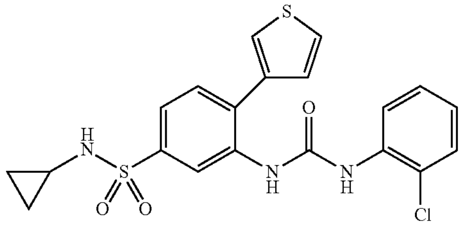 [SMILES: O=C(Nc1ccccc1Cl)Nc1cc(S(=O)(=O)NC2CC2)ccc1-c1ccsc1] |
| 26 | 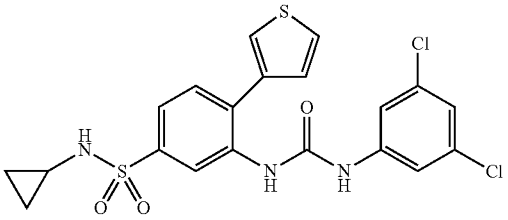 [SMILES: O=C(Nc1cc(Cl)cc(Cl)c1)Nc1cc(S(=O)(=O)NC2CC2)ccc1-c1ccsc1] |
| 27 | 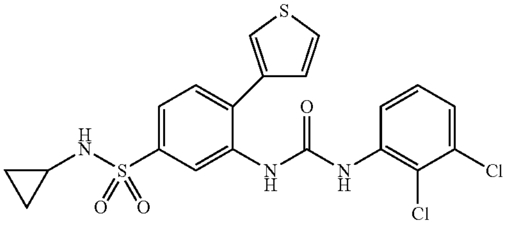 [SMILES: O=C(Nc1cc(S(=O)(=O)NC2CC2)ccc1-c1ccsc1)Nc1cccc(Cl)c1Cl] |
| 28 | 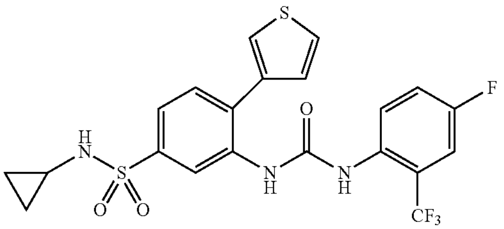 [SMILES: O=C(Nc1cc(S(=O)(=O)NC2CC2)ccc1-c1ccsc1)Nc1ccc(F)cc1C(F)(F)F] |

TABLE 2-continued
| Representative Compounds | |
|---|---|
| Cmpd # | Structure |
| 29 | 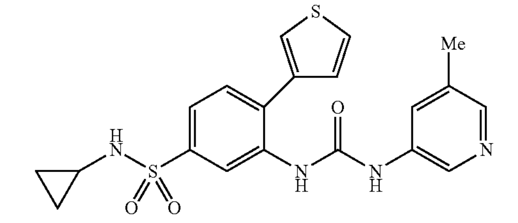 [SMILES: Cc1cncc(NC(=O)Nc2cc(S(=O)(=O)NC3CC3)ccc2-c2ccsc2)c1] |
| 30 | 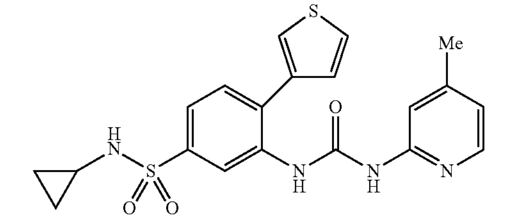 [SMILES: Cc1ccnc(NC(=O)Nc2cc(S(=O)(=O)NC3CC3)ccc2-c2ccsc2)c1] |
| 31 | 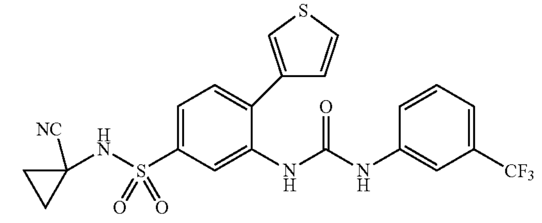 [SMILES: N#CC1(NS(=O)(=O)c2ccc(-c3ccsc3)c(NC(=O)Nc3cccc(C(F)(F)F)c3)c2)CC1] |
| 32 | 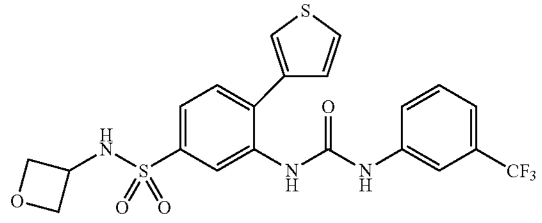 [SMILES: O=C(Nc1cccc(C(F)(F)F)c1)Nc1cc(S(=O)(=O)NC2COC2)ccc1-c1ccsc1] |
| 33 | 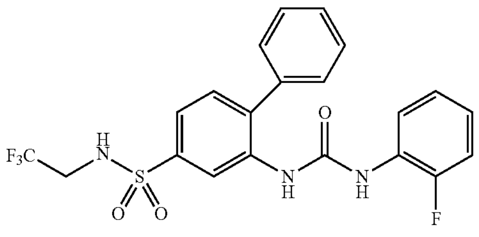 [SMILES: O=C(Nc1ccccc1F)Nc1cc(S(=O)(=O)NCC(F)(F)F)ccc1-c1ccccc1] |
| 34 | 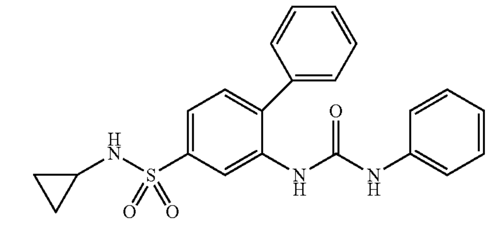 [SMILES: O=C(Nc1ccccc1)Nc1cc(S(=O)(=O)NC2CC2)ccc1-c1ccccc1] |

TABLE 2-continued
| Representative Compounds | |
|---|---|
| Cmpd # | Structure |
| 35 | 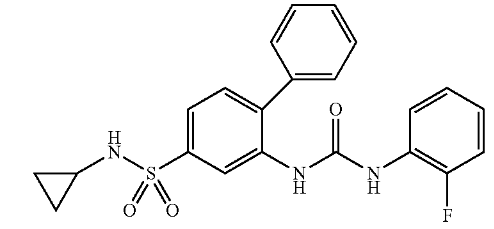 [SMILES: O=C(Nc1ccccc1F)Nc1cc(S(=O)(=O)NC2CC2)ccc1-c1ccccc1] |
| 36 | 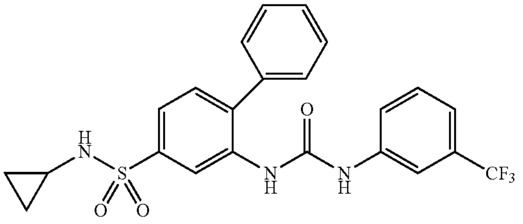 [SMILES: O=C(Nc1cccc(C(F)(F)F)c1)Nc1cc(S(=O)(=O)NC2CC2)ccc1-c1ccccc1] |
| 37 | 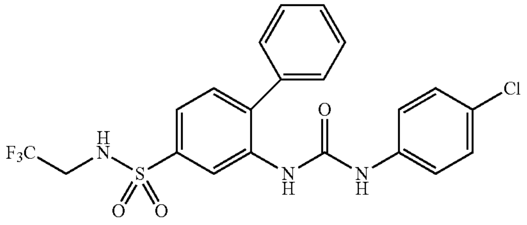 [SMILES: O=C(Nc1ccc(Cl)cc1)Nc1cc(S(=O)(=O)NCC(F)(F)F)ccc1-c1ccccc1] |
| 38 | 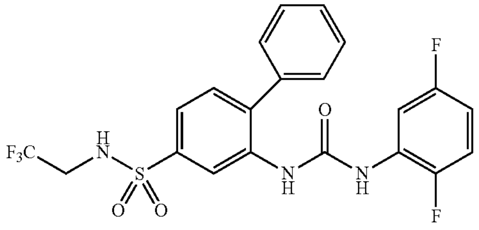 [SMILES: O=C(Nc1cc(F)ccc1F)Nc1cc(S(=O)(=O)NCC(F)(F)F)ccc1-c1ccccc1] |
| 39 | 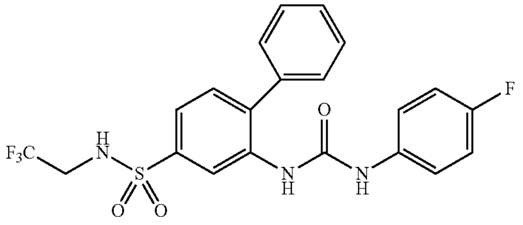 [SMILES: O=C(Nc1ccc(F)cc1)Nc1cc(S(=O)(=O)NCC(F)(F)F)ccc1-c1ccccc1] |
| 40 | 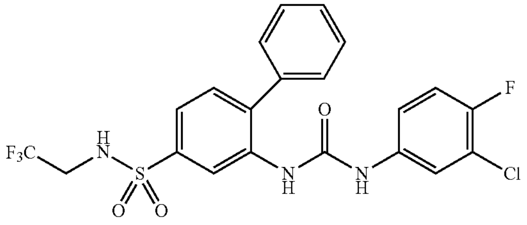 [SMILES: O=C(Nc1ccc(F)c(Cl)c1)Nc1cc(S(=O)(=O)NCC(F)(F)F)ccc1-c1ccccc1] |

TABLE 2-continued
| Representative Compounds | |
|---|---|
| Cmpd # | Structure |
| 41 | 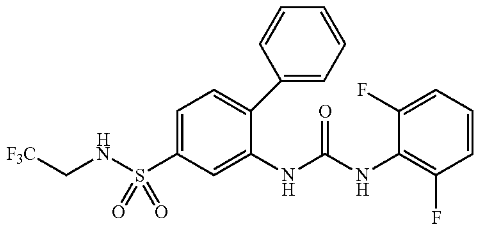 [SMILES: O=C(Nc1cc(S(=O)(=O)NCC(F)(F)F)ccc1-c1ccccc1)Nc1c(F)cccc1F] |
| 42 | 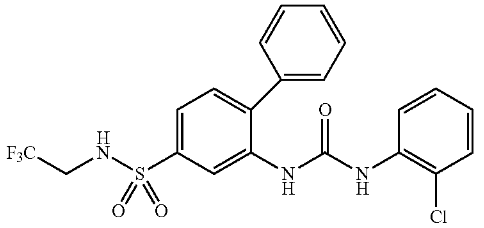 [SMILES: O=C(Nc1ccccc1Cl)Nc1cc(S(=O)(=O)NCC(F)(F)F)ccc1-c1ccccc1] |
| 43 | 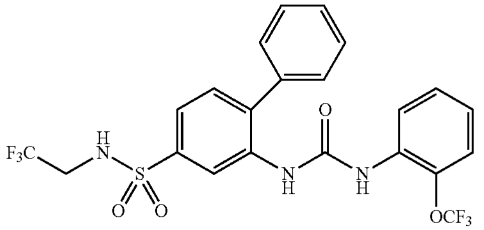 [SMILES: O=C(Nc1ccccc1OC(F)(F)F)Nc1cc(S(=O)(=O)NCC(F)(F)F)ccc1-c1ccccc1] |
| 44 | 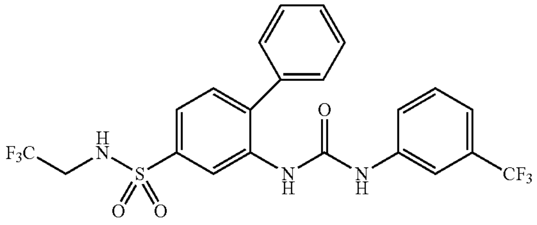 |
| 45 | 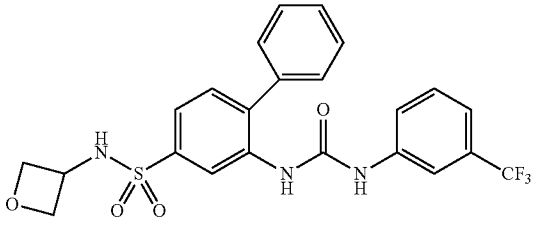 [SMILES: O=C(Nc1cccc(C(F)(F)F)c1)Nc1cc(S(=O)(=O)NC2COC2)ccc1-c1ccccc1] |
| 46 | 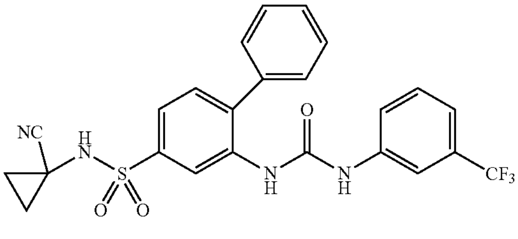 [SMILES: N#CC1(NS(=O)(=O)c2ccc(-c3ccccc3)c(NC(=O)Nc3cccc(C(F)(F)F)c3)c2)CC1] |

TABLE 2-continued
| Representative Compounds | |
|---|---|
| Cmpd # | Structure |
| 47 | 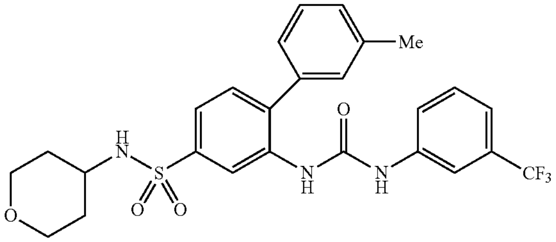 [SMILES: Cc1cccc(-c2ccc(S(=O)(=O)NC3CCOCC3)cc2NC(=O)Nc2cccc(C(F)(F)F)c2)c1] |
| 48 | 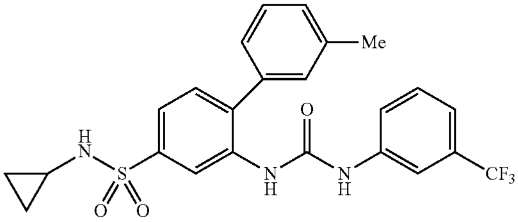 [SMILES: Cc1cccc(-c2ccc(S(=O)(=O)NC3CC3)cc2NC(=O)Nc2cccc(C(F)(F)F)c2)c1] |
| 49 | 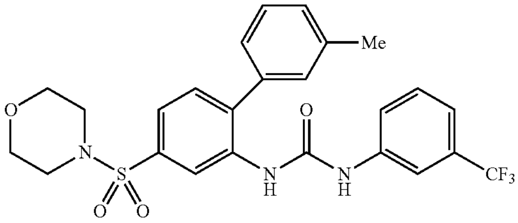 [SMILES: Cc1cccc(-c2ccc(S(=O)(=O)N3CCOCC3)cc2NC(=O)Nc2cccc(C(F)(F)F)c2)c1] |
| 50 | 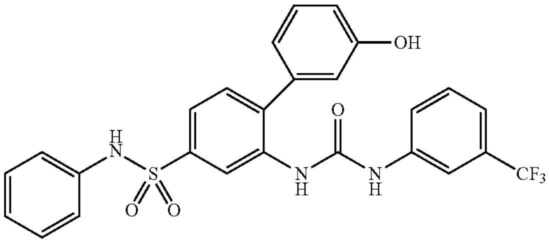 [SMILES: O=C(Nc1cccc(C(F)(F)F)c1)Nc1cc(S(=O)(=O)Nc2ccccc2)ccc1-c1cccc(O)c1] |
| 51 | 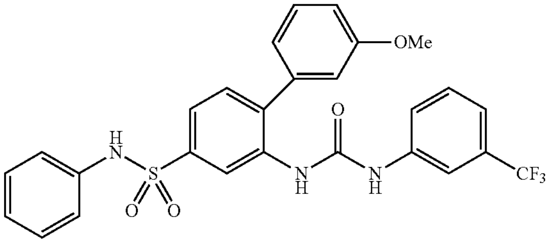 [SMILES: COc1cccc(-c2ccc(S(=O)(=O)Nc3ccccc3)cc2NC(=O)Nc2cccc(C(F)(F)F)c2)c1] |
| 52 | 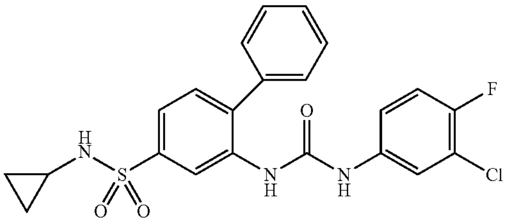 [SMILES: O=C(Nc1ccc(F)c(Cl)c1)Nc1cc(S(=O)(=O)NC2CC2)ccc1-c1ccccc1] |

TABLE 2-continued
| Representative Compounds | |
|---|---|
| Cmpd # | Structure |
| 53 | 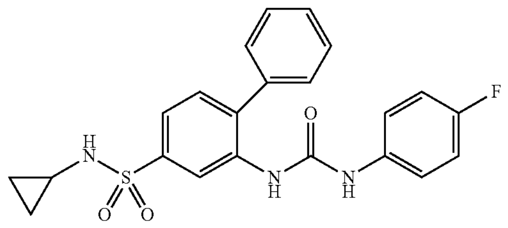 [SMILES: O=C(Nc1ccc(F)cc1)Nc1cc(S(=O)(=O)NC2CC2)ccc1-c1ccccc1] |
| 54 | 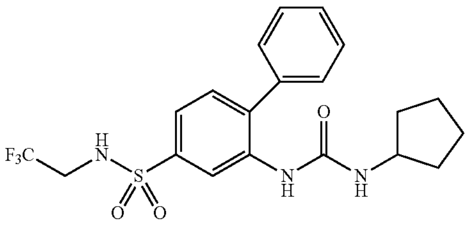 [SMILES: O=C(Nc1cc(S(=O)(=O)NCC(F)(F)F)ccc1-c1ccccc1)NC1CCCC1] |
| 55 | 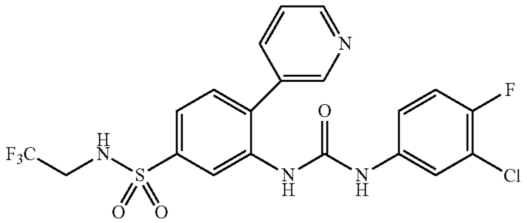 [SMILES: O=C(Nc1ccc(F)c(Cl)c1)Nc1cc(S(=O)(=O)NCC(F)(F)F)ccc1-c1cccnc1] |
| 56 | 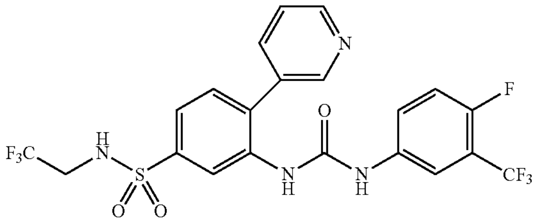 [SMILES: O=C(Nc1ccc(F)c(C(F)(F)F)c1)Nc1cc(S(=O)(=O)NCC(F)(F)F)ccc1-c1cccnc1] |
| 57 | 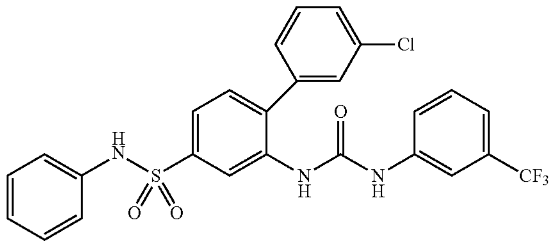 [SMILES: O=C(Nc1cccc(C(F)(F)F)c1)Nc1cc(S(=O)(=O)Nc2ccccc2)ccc1-c1cccc(Cl)c1] |
| 58 | 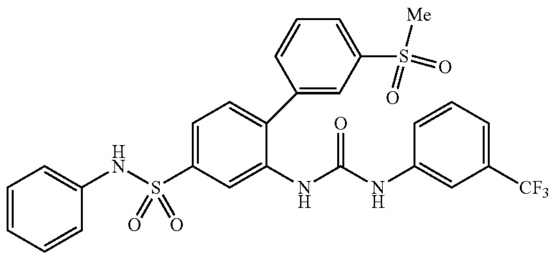 [SMILES: CS(=O)(=O)c1cccc(-c2ccc(S(=O)(=O)Nc3ccccc3)cc2NC(=O)Nc2cccc(C(F)(F)F)c2)c1] |

TABLE 2-continued
| Representative Compounds | |
|---|---|
| Cmpd # | Structure |
| 59 | 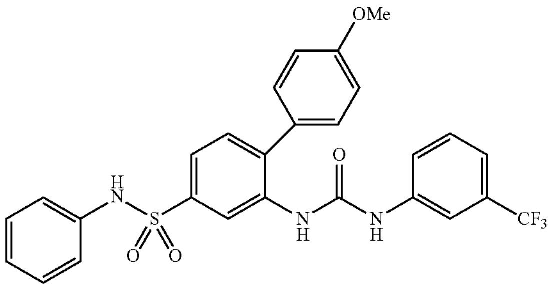 [SMILES: COc1ccc(-c2ccc(S(=O)(=O)Nc3ccccc3)cc2NC(=O)Nc2cccc(C(F)(F)F)c2)cc1] |
| 60 | 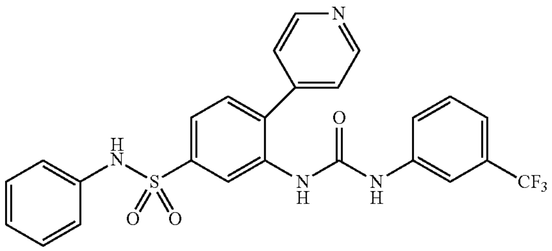 [SMILES: O=C(Nc1cccc(C(F)(F)F)c1)Nc1cc(S(=O)(=O)Nc2ccccc2)ccc1-c1ccncc1] |
| 61 | 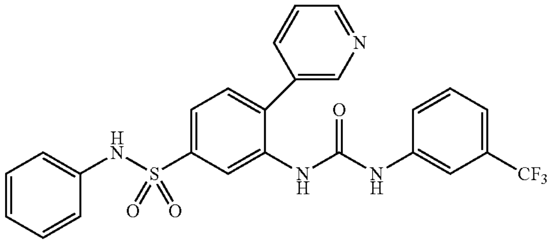 [SMILES: O=C(Nc1cccc(C(F)(F)F)c1)Nc1cc(S(=O)(=O)Nc2ccccc2)ccc1-c1cccnc1] |
| 62 | 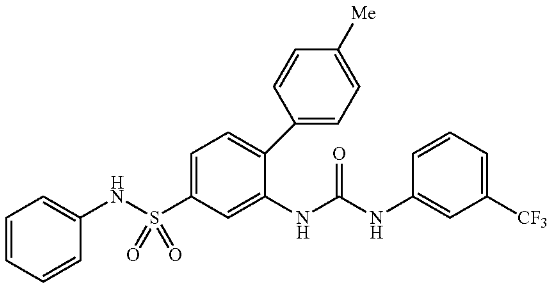 [SMILES: Cc1ccc(-c2ccc(S(=O)(=O)Nc3ccccc3)cc2NC(=O)Nc2cccc(C(F)(F)F)c2)cc1] |
| 63 | 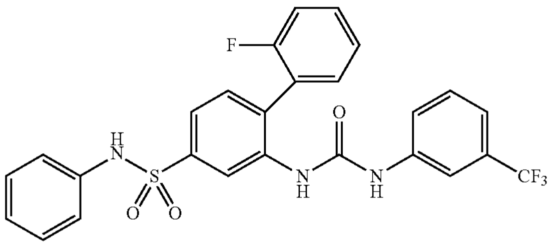 [SMILES: O=C(Nc1cccc(C(F)(F)F)c1)Nc1cc(S(=O)(=O)Nc2ccccc2)ccc1-c1ccccc1F] |

TABLE 2-continued
| Representative Compounds | |
|---|---|
| Cmpd # | Structure |
| 64 | 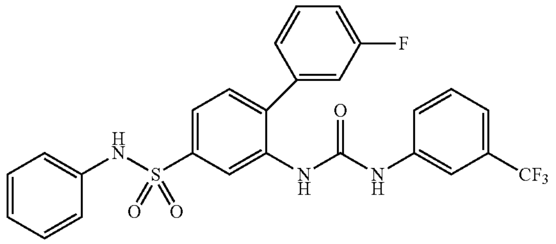 [SMILES: O=C(Nc1cccc(C(F)(F)F)c1)Nc1cc(S(=O)(=O)Nc2ccccc2)ccc1-c1cccc(F)c1] |
| 65 | 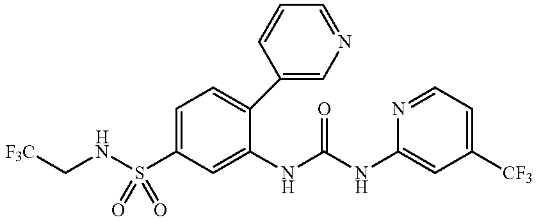 [SMILES: O=C(Nc1cc(C(F)(F)F)ccn1)Nc1cc(S(=O)(=O)NCC(F)(F)F)ccc1-c1cccnc1] |
| 66 | 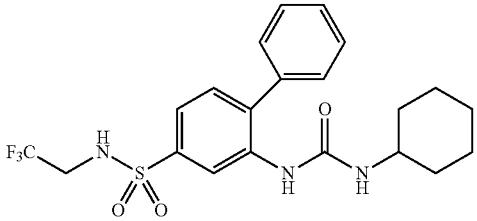 [SMILES: O=C(Nc1cc(S(=O)(=O)NCC(F)(F)F)ccc1-c1ccccc1)NC1CCCCC1] |
| 67 | 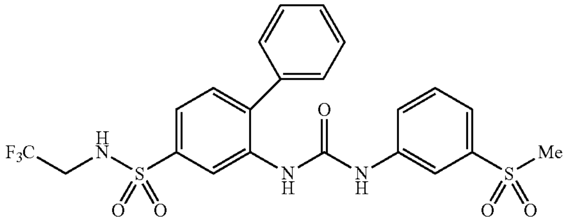 [SMILES: CS(=O)(=O)c1cccc(NC(=O)Nc2cc(S(=O)(=O)NCC(F)(F)F)ccc2-c2ccccc2)c1] |
| 68 | 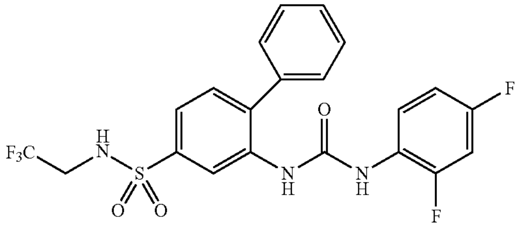 [SMILES: O=C(Nc1ccc(F)cc1F)Nc1cc(S(=O)(=O)NCC(F)(F)F)ccc1-c1ccccc1] |
| 69 | 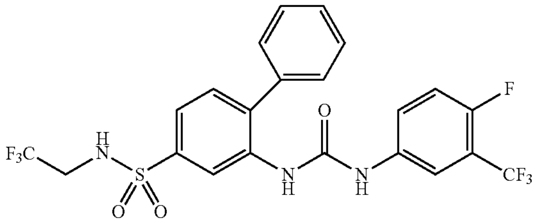 [SMILES: O=C(Nc1ccc(F)c(C(F)(F)F)c1)Nc1cc(S(=O)(=O)NCC(F)(F)F)ccc1-c1ccccc1] |

TABLE 2-continued
| Representative Compounds | |
|---|---|
| Cmpd # | Structure |
| 70 | 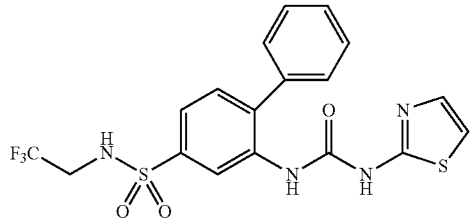 [SMILES: O=C(Nc1nccs1)Nc1cc(S(=O)(=O)NCC(F)(F)F)ccc1-c1ccccc1] |
| 71 | 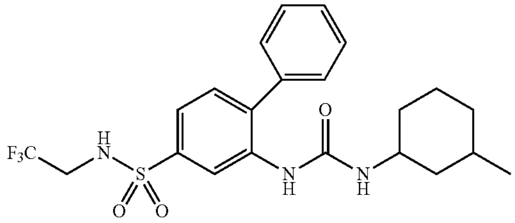 [SMILES: CC1CCCC(NC(=O)Nc2cc(S(=O)(=O)NCC(F)(F)F)ccc2-c2ccccc2)C1] |
| 72 | 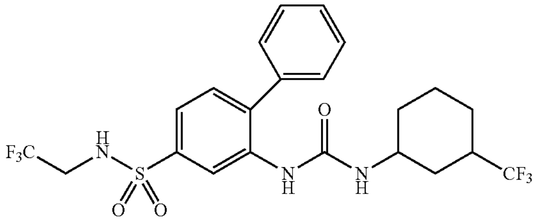 [SMILES: O=C(Nc1cc(S(=O)(=O)NCC(F)(F)F)ccc1-c1ccccc1)NC1CCCC(C(F)(F)F)C1] |
| 73 | 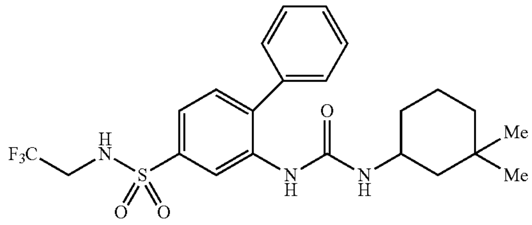 [SMILES: CC1(C)CCCC(NC(=O)Nc2cc(S(=O)(=O)NCC(F)(F)F)ccc2-c2ccccc2)C1] |
| 74 | 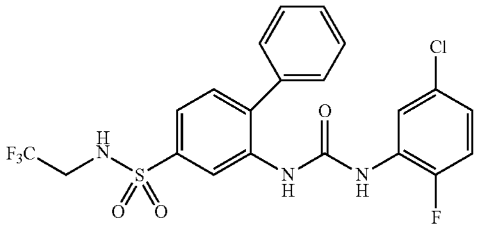 [SMILES: O=C(Nc1cc(Cl)ccc1F)Nc1cc(S(=O)(=O)NCC(F)(F)F)ccc1-c1ccccc1] |
| 76 | 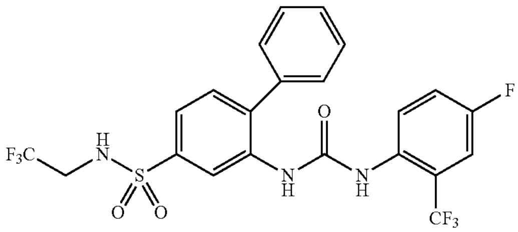 [SMILES: O=C(Nc1cc(S(=O)(=O)NCC(F)(F)F)ccc1-c1ccccc1)Nc1ccc(F)cc1C(F)(F)F] |

TABLE 2-continued
| Representative Compounds | |
|---|---|
| Cmpd # | Structure |
| 77 | 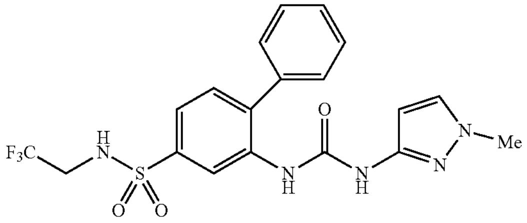 [SMILES: Cn1ccc(NC(=O)Nc2cc(S(=O)(=O)NCC(F)(F)F)ccc2-c2ccccc2)n1] |
| 78 | 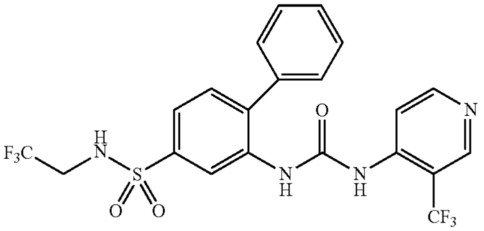 [SMILES: O=C(Nc1cc(S(=O)(=O)NCC(F)(F)F)ccc1-c1ccccc1)Nc1ccncc1C(F)(F)F] |
| 79 | 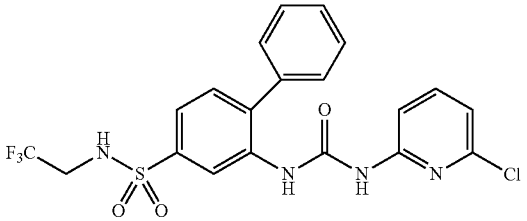 [SMILES: O=C(Nc1cccc(Cl)n1)Nc1cc(S(=O)(=O)NCC(F)(F)F)ccc1-c1ccccc1] |
| 80 | 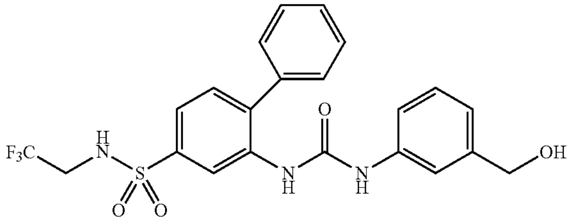 [SMILES: O=C(Nc1cccc(CO)c1)Nc1cc(S(=O)(=O)NCC(F)(F)F)ccc1-c1ccccc1] |
| 81 | 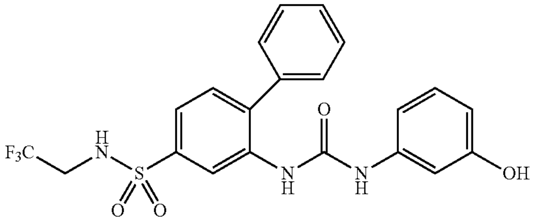 |
| 82 | 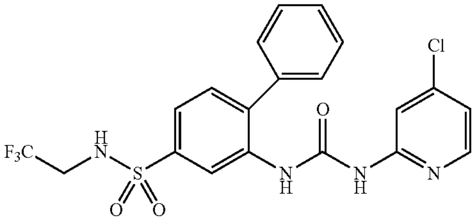 [SMILES: O=C(Nc1cc(Cl)ccn1)Nc1cc(S(=O)(=O)NCC(F)(F)F)ccc1-c1ccccc1] |

TABLE 2-continued
| Cmpd # | Structure |
|---|---|
| Representative Compounds | |
| 83 | 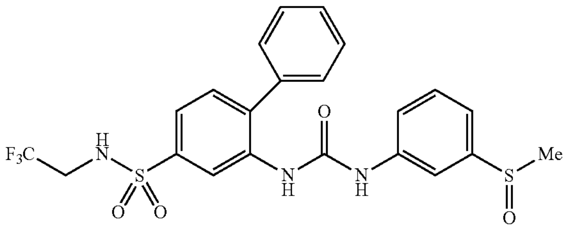 [SMILES: CS(=O)c1cccc(NC(=O)Nc2cc(S(=O)(=O)NCC(F)(F)F)ccc2-c2ccccc2)c1] |
| 84 | 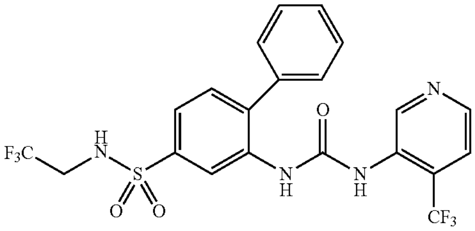 [SMILES: O=C(Nc1cc(S(=O)(=O)NCC(F)(F)F)ccc1-c1ccccc1)Nc1cnccc1C(F)(F)F] |
| 85 | 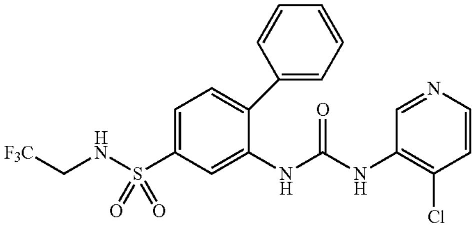 [SMILES: O=C(Nc1cnccc1Cl)Nc1cc(S(=O)(=O)NCC(F)(F)F)ccc1-c1ccccc1] |
| 86 | 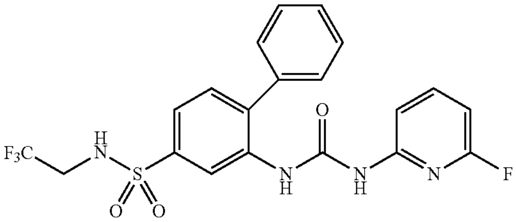 [SMILES: O=C(Nc1cccc(F)n1)Nc1cc(S(=O)(=O)NCC(F)(F)F)ccc1-c1ccccc1] |
| 87 | 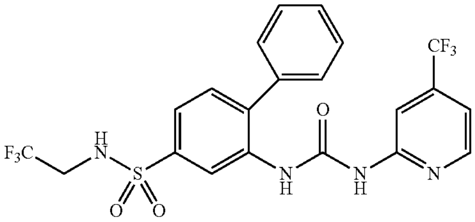 [SMILES: O=C(Nc1cc(C(F)(F)F)ccn1)Nc1cc(S(=O)(=O)NCC(F)(F)F)ccc1-c1ccccc1] |
| 88 | 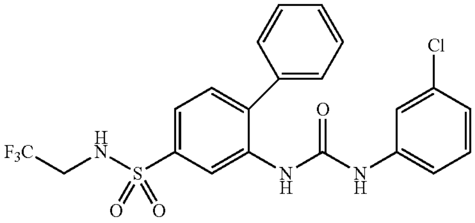 [SMILES: O=C(Nc1cccc(Cl)c1)Nc1cc(S(=O)(=O)NCC(F)(F)F)ccc1-c1ccccc1] |

TABLE 2-continued
| Representative Compounds | |
|---|---|
| Cmpd # | Structure |
| 89 | 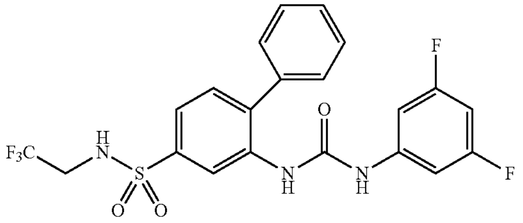 [SMILES: O=C(Nc1cc(F)cc(F)c1)Nc1cc(S(=O)(=O)NCC(F)(F)F)ccc1-c1ccccc1] |
| 90 | 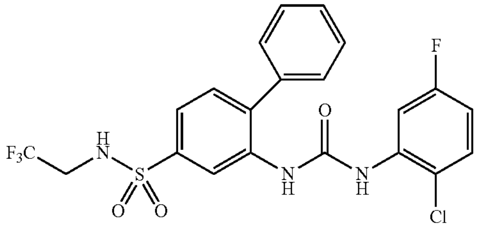 |
| 91 | 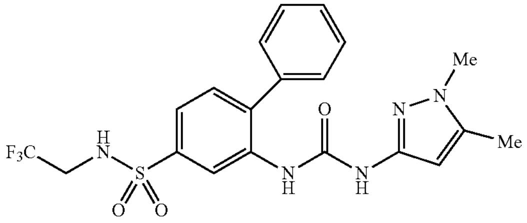 [SMILES: Cc1cc(NC(=O)Nc2cc(S(=O)(=O)NCC(F)(F)F)ccc2-c2ccccc2)nn1C] |
| 92 | 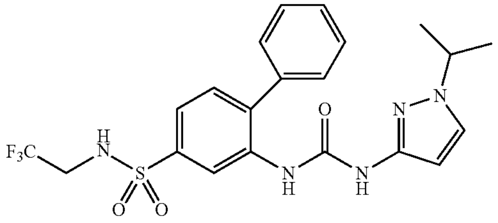 [SMILES: CC(C)n1ccc(NC(=O)Nc2cc(S(=O)(=O)NCC(F)(F)F)ccc2-c2ccccc2)n1] |
| 93 | 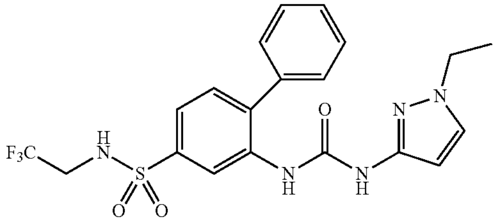 [SMILES: CCn1ccc(NC(=O)Nc2cc(S(=O)(=O)NCC(F)(F)F)ccc2-c2ccccc2)n1] |
| 94 | 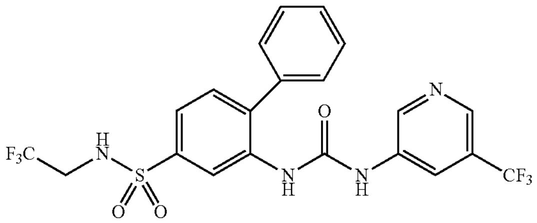 [SMILES: O=C(Nc1cncc(C(F)(F)F)c1)Nc1cc(S(=O)(=O)NCC(F)(F)F)ccc1-c1ccccc1] |

TABLE 2-continued
| Representative Compounds | |
|---|---|
| Cmpd # | Structure |
| 95 | 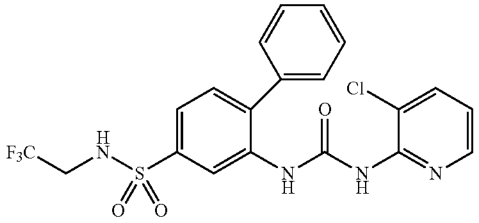 [SMILES: O=C(Nc1cc(S(=O)(=O)NCC(F)(F)F)ccc1-c1ccccc1)Nc1ncccc1Cl] |
| 96 | 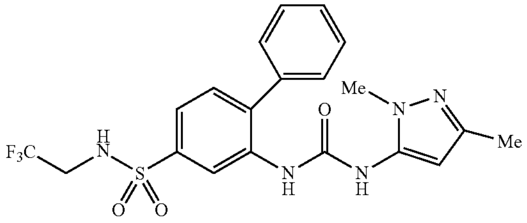 [SMILES: Cc1cc(NC(=O)Nc2cc(S(=O)(=O)NCC(F)(F)F)ccc2-c2ccccc2)n(C)n1] |
| 97 | 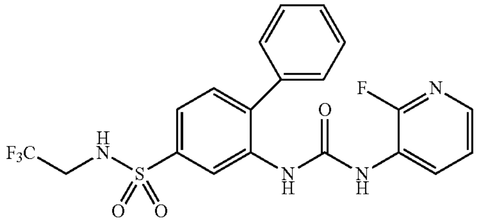 [SMILES: O=C(Nc1cc(S(=O)(=O)NCC(F)(F)F)ccc1-c1ccccc1)Nc1cccnc1F] |
| 98 | 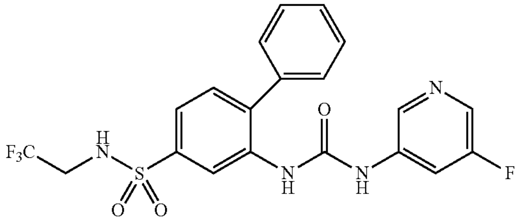 [SMILES: O=C(Nc1cncc(F)c1)Nc1cc(S(=O)(=O)NCC(F)(F)F)ccc1-c1ccccc1] |
| 99 | 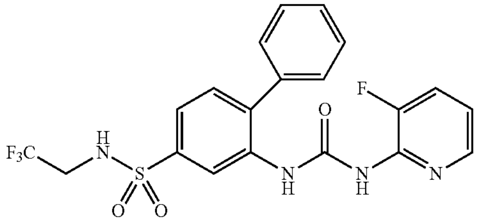 [SMILES: O=C(Nc1cc(S(=O)(=O)NCC(F)(F)F)ccc1-c1ccccc1)Nc1ncccc1F] |
| 100 | 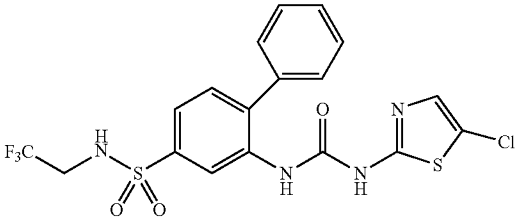 [SMILES: O=C(Nc1ncc(Cl)s1)Nc1cc(S(=O)(=O)NCC(F)(F)F)ccc1-c1ccccc1] |

TABLE 2-continued
| Representative Compounds | |
|---|---|
| Cmpd # | Structure |
| 101 | 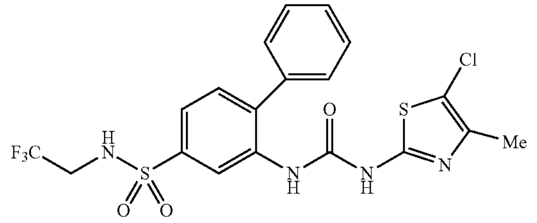 [SMILES: Cc1nc(NC(=O)Nc2cc(S(=O)(=O)NCC(F)(F)F)ccc2-c2ccccc2)sc1Cl] |
| 102 | 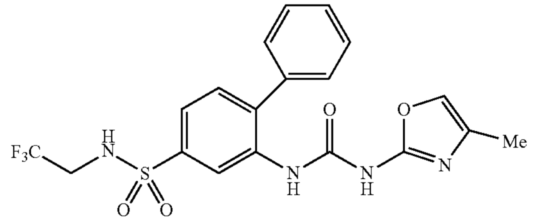 [SMILES: Cc1coc(NC(=O)Nc2cc(S(=O)(=O)NCC(F)(F)F)ccc2-c2ccccc2)n1] |
| 103 | 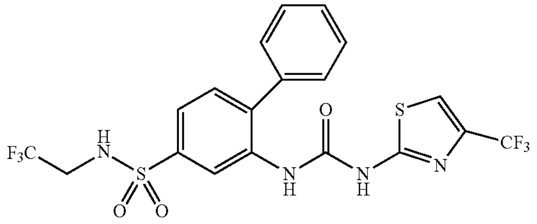 [SMILES: O=C(Nc1nc(C(F)(F)F)cs1)Nc1cc(S(=O)(=O)NCC(F)(F)F)ccc1-c1ccccc1] |
| 104 | 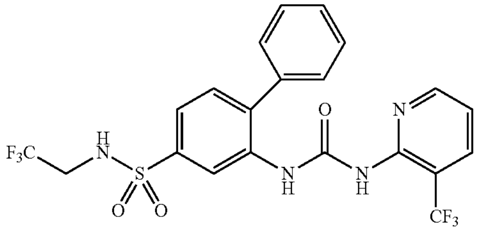 [SMILES: O=C(Nc1cc(S(=O)(=O)NCC(F)(F)F)ccc1-c1ccccc1)Nc1ncccc1C(F)(F)F] |
| 105 | 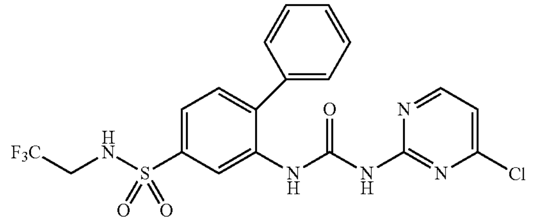 [SMILES: O=C(Nc1nccc(Cl)n1)Nc1cc(S(=O)(=O)NCC(F)(F)F)ccc1-c1ccccc1] |
| 106 | 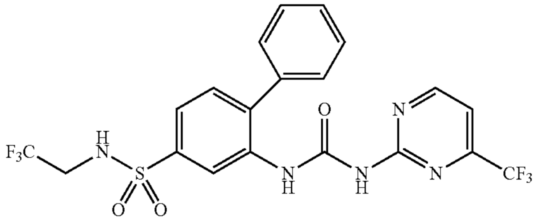 [SMILES: O=C(Nc1nccc(C(F)(F)F)n1)Nc1cc(S(=O)(=O)NCC(F)(F)F)ccc1-c1ccccc1] |

TABLE 2-continued
| Representative Compounds | |
|---|---|
| Cmpd # | Structure |
| 107 | 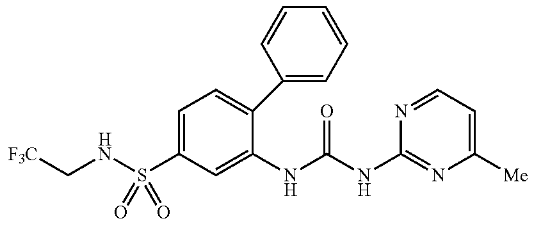 [SMILES: Cc1ccnc(NC(=O)Nc2cc(S(=O)(=O)NCC(F)(F)F)ccc2-c2ccccc2)n1] |
| 108 | 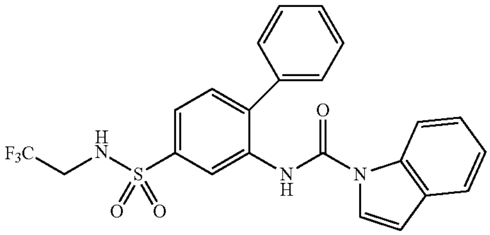 [SMILES: O=C(Nc1cc(S(=O)(=O)NCC(F)(F)F)ccc1-c1ccccc1)n1ccc2ccccc21] |
| 109 | 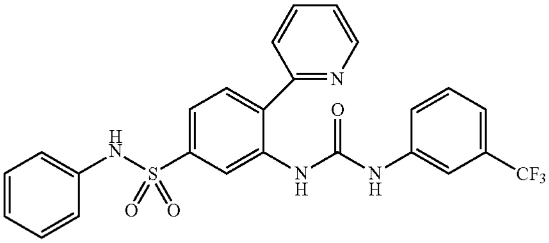 [SMILES: O=C(Nc1cccc(C(F)(F)F)c1)Nc1cc(S(=O)(=O)Nc2ccccc2)ccc1-c1ccccn1] |
| 110 | 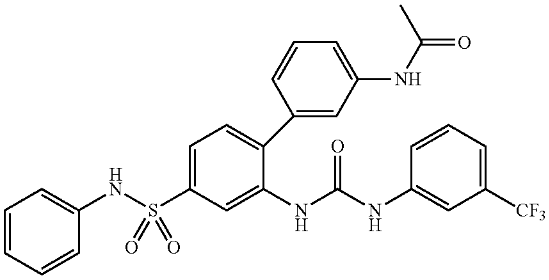 [SMILES: CC(=O)Nc1cccc(-c2ccc(S(=O)(=O)Nc3ccccc3)cc2NC(=O)Nc2cccc(C(F)(F)F)c2)c1] |
| 111 | 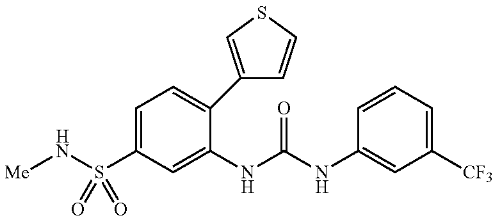 [SMILES: CNS(=O)(=O)c1ccc(-c2ccsc2)c(NC(=O)Nc2cccc(C(F)(F)F)c2)c1] |
| 112 | 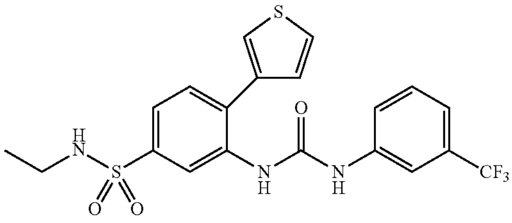 [SMILES: CCNS(=O)(=O)c1ccc(-c2ccsc2)c(NC(=O)Nc2cccc(C(F)(F)F)c2)c1] |

TABLE 2-continued
| Representative Compounds | |
|---|---|
| Cmpd # | Structure |
| 113 | 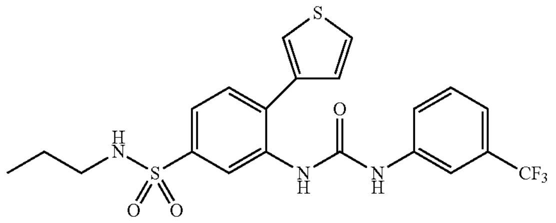 [SMILES: CCCNS(=O)(=O)c1ccc(-c2ccsc2)c(NC(=O)Nc2cccc(C(F)(F)F)c2)c1] |
| 114 | 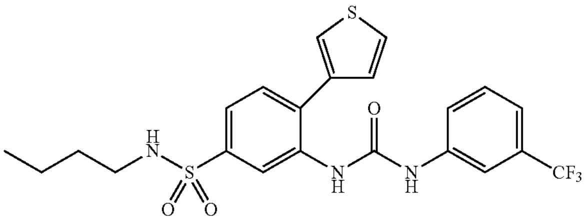 [SMILES: CCCCNS(=O)(=O)c1ccc(-c2ccsc2)c(NC(=O)Nc2cccc(C(F)(F)F)c2)c1] |
| 115 | 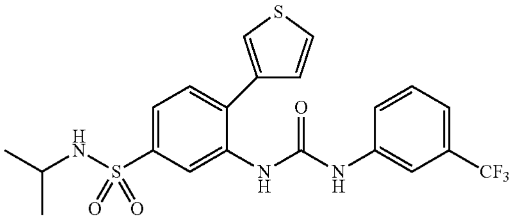 [SMILES: CC(C)NS(=O)(=O)c1ccc(-c2ccsc2)c(NC(=O)Nc2cccc(C(F)(F)F)c2)c1] |
| 116 | 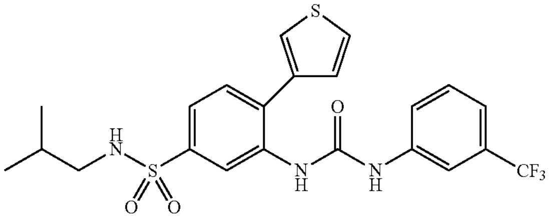 [SMILES: CC(C)CNS(=O)(=O)c1ccc(-c2ccsc2)c(NC(=O)Nc2cccc(C(F)(F)F)c2)c1] |
| 117 | 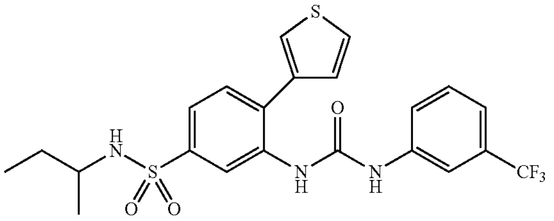 [SMILES: CCC(C)NS(=O)(=O)c1ccc(-c2ccsc2)c(NC(=O)Nc2cccc(C(F)(F)F)c2)c1] |
| 118 | 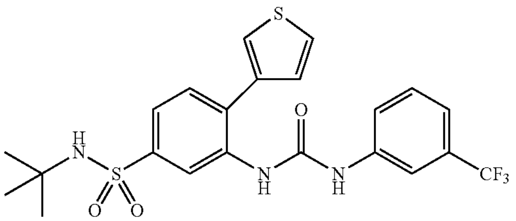 [SMILES: CC(C)(C)NS(=O)(=O)c1ccc(-c2ccsc2)c(NC(=O)Nc2cccc(C(F)(F)F)c2)c1] |

TABLE 2-continued
| Representative Compounds | |
|---|---|
| Cmpd # | Structure |
| 119 | 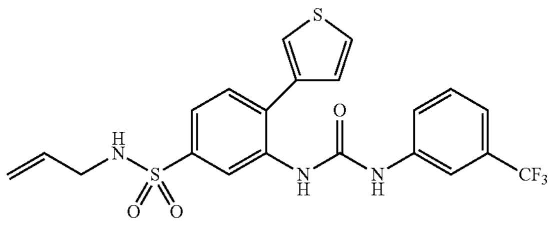 [SMILES: C=CCNS(=O)(=O)c1ccc(-c2ccsc2)c(NC(=O)Nc2cccc(C(F)(F)F)c2)c1] |
| 120 | 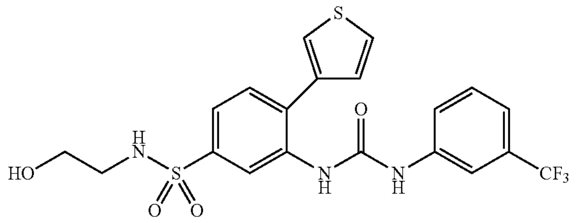 [SMILES: O=C(Nc1cccc(C(F)(F)F)c1)Nc1cc(S(=O)(=O)NCCO)ccc1-c1ccsc1] |
| 121 | 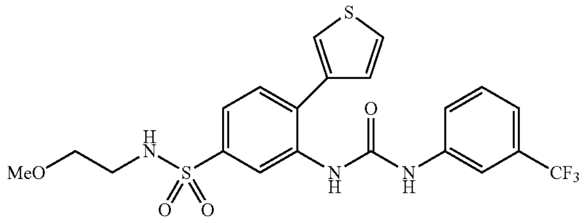 [SMILES: COCCNS(=O)(=O)c1ccc(-c2ccsc2)c(NC(=O)Nc2cccc(C(F)(F)F)c2)c1] |
| 122 | 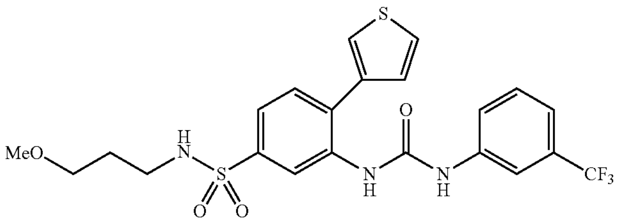 [SMILES: COCCCNS(=O)(=O)c1ccc(-c2ccsc2)c(NC(=O)Nc2cccc(C(F)(F)F)c2)c1] |
| 123 | 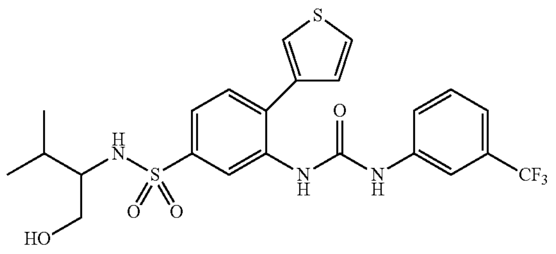 [SMILES: CC(C)C(CO)NS(=O)(=O)c1ccc(-c2ccsc2)c(NC(=O)Nc2cccc(C(F)(F)F)c2)c1] |
| 124 | 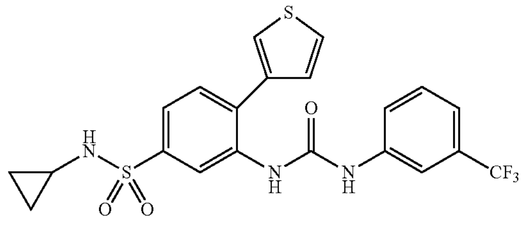 [SMILES: O=C(Nc1cccc(C(F)(F)F)c1)Nc1cc(S(=O)(=O)NC2CC2)ccc1-c1ccsc1] |

TABLE 2-continued
| Representative Compounds | |
|---|---|
| Cmpd # | Structure |
| 125 | 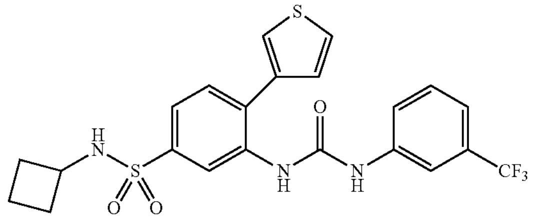 [SMILES: O=C(Nc1cccc(C(F)(F)F)c1)Nc1cc(S(=O)(=O)NC2CCC2)ccc1-c1ccsc1] |
| 126 | 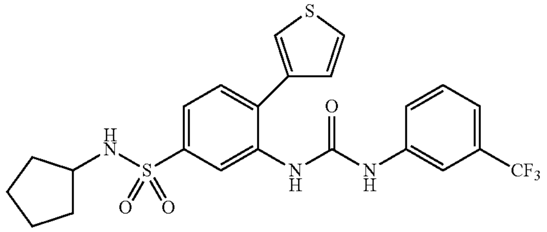 [SMILES: O=C(Nc1cccc(C(F)(F)F)c1)Nc1cc(S(=O)(=O)NC2CCCC2)ccc1-c1ccsc1] |
| 127 | 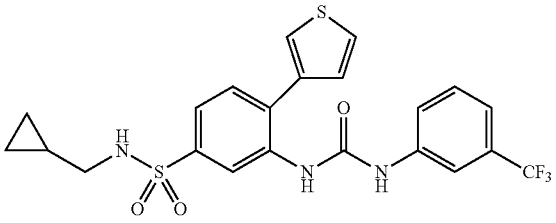 [SMILES: O=C(Nc1cccc(C(F)(F)F)c1)Nc1cc(S(=O)(=O)NCC2CC2)ccc1-c1ccsc1] |
| 128 | 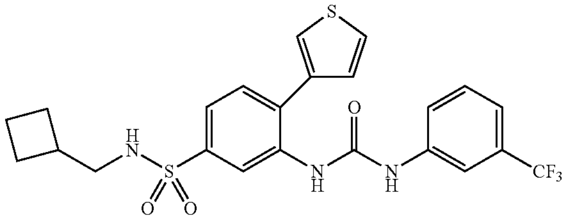 [SMILES: O=C(Nc1cccc(C(F)(F)F)c1)Nc1cc(S(=O)(=O)NCC2CCC2)ccc1-c1ccsc1] |
| 129 | 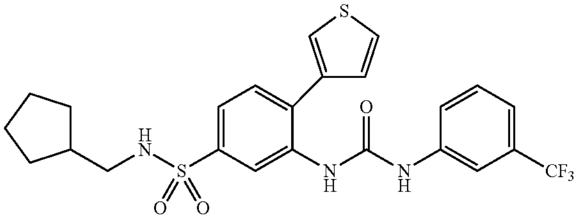 [SMILES: O=C(Nc1cccc(C(F)(F)F)c1)Nc1cc(S(=O)(=O)NCC2CCCC2)ccc1-c1ccsc1] |
| 130 | 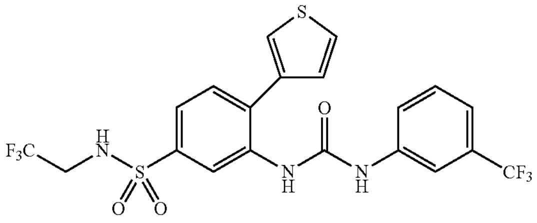 [SMILES: O=C(Nc1cccc(C(F)(F)F)c1)Nc1cc(S(=O)(=O)NCC(F)(F)F)ccc1-c1ccsc1] |

TABLE 2-continued
| Representative Compounds | |
|---|---|
| Cmpd # | Structure |
| 131 | 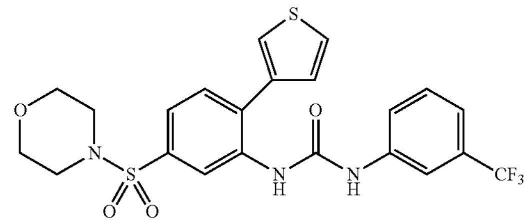 [SMILES: O=C(Nc1cccc(C(F)(F)F)c1)Nc1cc(S(=O)(=O)N2CCOCC2)ccc1-c1ccsc1] |
| 132 | 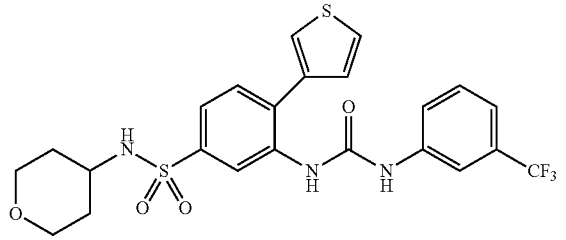 [SMILES: O=C(Nc1cccc(C(F)(F)F)c1)Nc1cc(S(=O)(=O)NC2CCOCC2)ccc1-c1ccsc1] |
| 133 | 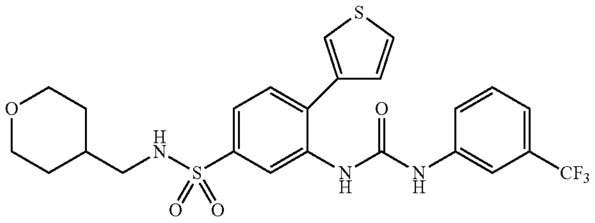 [SMILES: O=C(Nc1cccc(C(F)(F)F)c1)Nc1cc(S(=O)(=O)NCC2CCOCC2)ccc1-c1ccsc1] |
| 134 | 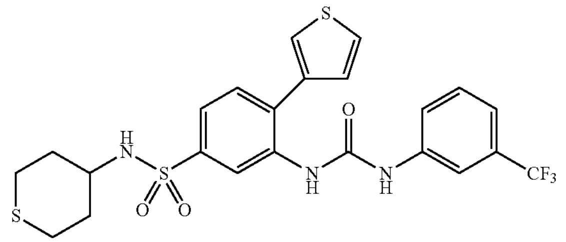 [SMILES: O=C(Nc1cccc(C(F)(F)F)c1)Nc1cc(S(=O)(=O)NC2CCSCC2)ccc1-c1ccsc1] |
| 135 | 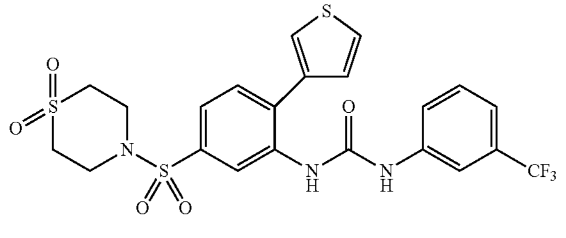 [SMILES: O=C(Nc1cccc(C(F)(F)F)c1)Nc1cc(S(=O)(=O)N2CCS(=O)(=O)CC2)ccc1-c1ccsc1] |
| 136 | 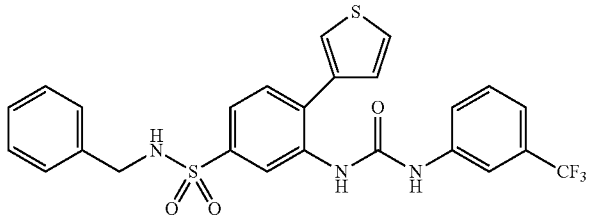 [SMILES: O=C(Nc1cccc(C(F)(F)F)c1)Nc1cc(S(=O)(=O)NCc2ccccc2)ccc1-c1ccsc1] |

TABLE 2-continued
| Representative Compounds | |
|---|---|
| Cmpd # | Structure |
| 137 | 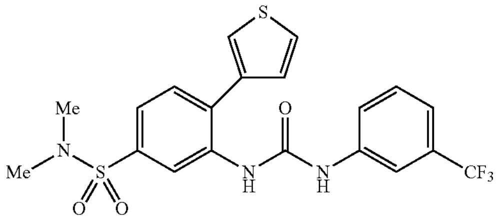 [SMILES: CN(C)S(=O)(=O)c1ccc(-c2ccsc2)c(NC(=O)Nc2cccc(C(F)(F)F)c2)c1] |
| 138 | 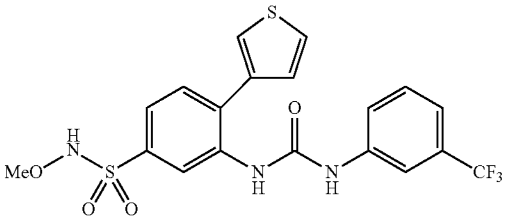 [SMILES: CONS(=O)(=O)c1ccc(-c2ccsc2)c(NC(=O)Nc2cccc(C(F)(F)F)c2)c1] |
| 139 | 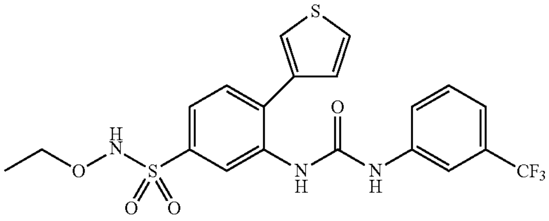 [SMILES: CCONS(=O)(=O)c1ccc(-c2ccsc2)c(NC(=O)Nc2cccc(C(F)(F)F)c2)c1] |
| 140 | 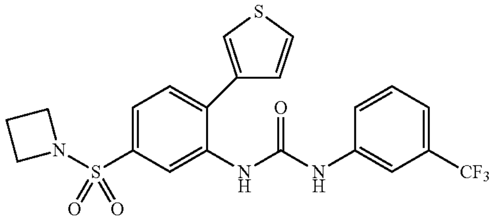 [SMILES: O=C(Nc1cccc(C(F)(F)F)c1)Nc1cc(S(=O)(=O)N2CCC2)ccc1-c1ccsc1] |
| 141 | 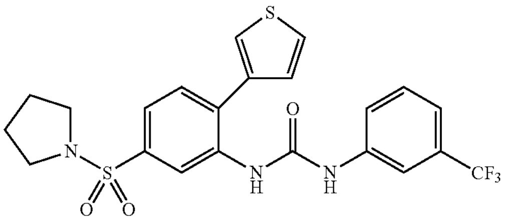 [SMILES: O=C(Nc1cccc(C(F)(F)F)c1)Nc1cc(S(=O)(=O)N2CCCC2)ccc1-c1ccsc1] |
| 142 | 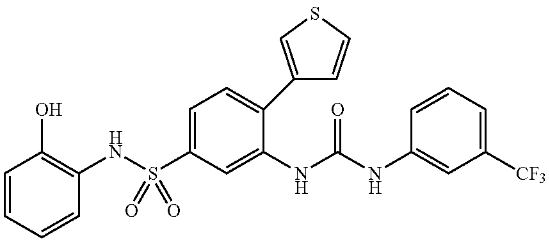 [SMILES: O=C(Nc1cccc(C(F)(F)F)c1)Nc1cc(S(=O)(=O)Nc2ccccc2O)ccc1-c1ccsc1] |

TABLE 2-continued
| Representative Compounds | |
|---|---|
| Cmpd # | Structure |
| 143 | 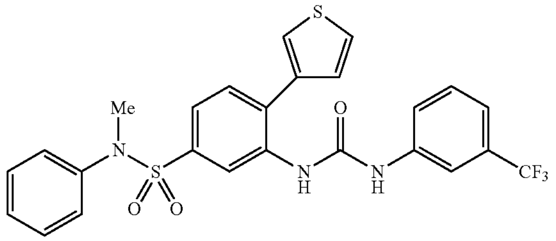 [SMILES: CN(c1ccccc1)S(=O)(=O)c1ccc(-c2ccsc2)c(NC(=O)Nc2cccc(C(F)(F)F)c2)c1] |
| 144 | 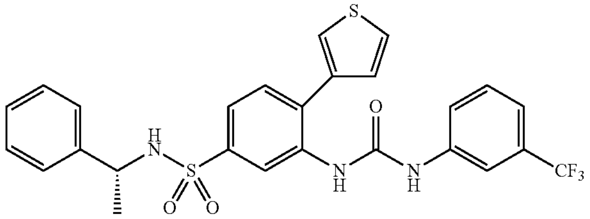 [SMILES: C[C@@H](NS(=O)(=O)c1ccc(-c2ccsc2)c(NC(=O)Nc2cccc(C(F)(F)F)c2)c1)c1ccccc1] |
| 145 | 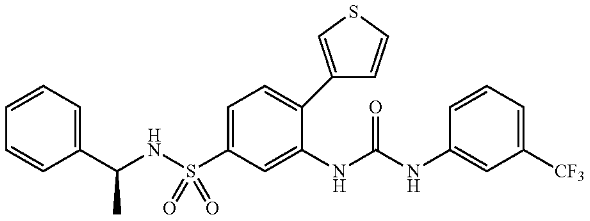 [SMILES: C[C@H](NS(=O)(=O)c1ccc(-c2ccsc2)c(NC(=O)Nc2cccc(C(F)(F)F)c2)c1)c1ccccc1] |
| 146 | 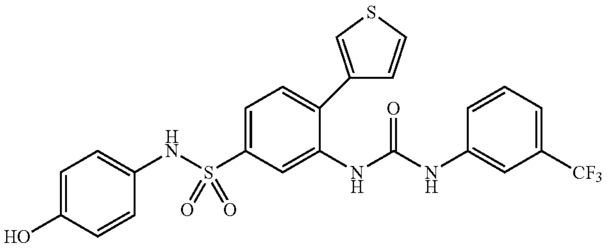 [SMILES: O=C(Nc1cccc(C(F)(F)F)c1)Nc1cc(S(=O)(=O)Nc2ccc(O)cc2)ccc1-c1ccsc1] |
| 147 | 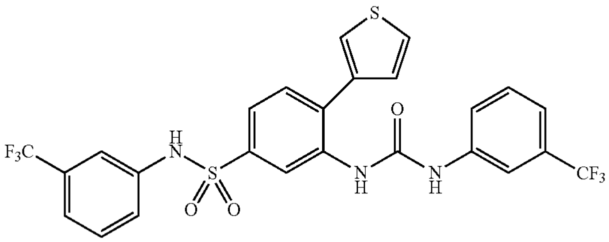 [SMILES: O=C(Nc1cccc(C(F)(F)F)c1)Nc1cc(S(=O)(=O)Nc2cccc(C(F)(F)F)c2)ccc1-c1ccsc1] |
| 148 | 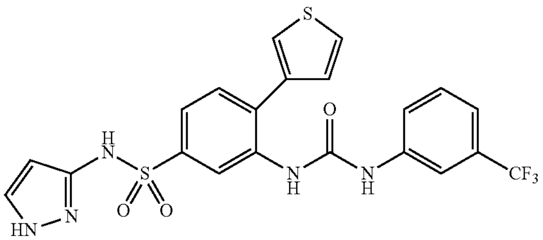 [SMILES: O=C(Nc1cccc(C(F)(F)F)c1)Nc1cc(S(=O)(=O)Nc2cc[nH]n2)ccc1-c1ccsc1] |

TABLE 2-continued
| Representative Compounds | |
|---|---|
| Cmpd # | Structure |
| 149 | 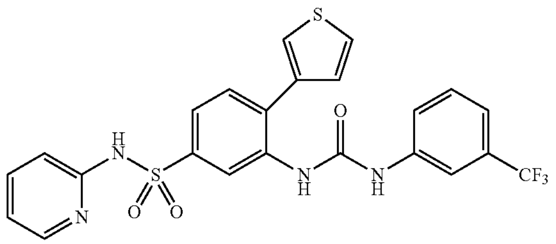 [SMILES: O=C(Nc1cccc(C(F)(F)F)c1)Nc1cc(S(=O)(=O)Nc2ccccn2)ccc1-c1ccsc1] |
| 150 | 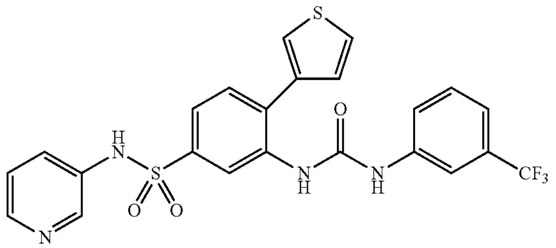 [SMILES: O=C(Nc1cccc(C(F)(F)F)c1)Nc1cc(S(=O)(=O)Nc2cccnc2)ccc1-c1ccsc1] |
| 151 | 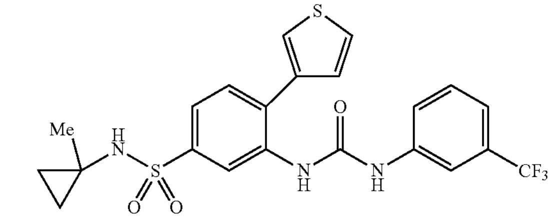 [SMILES: CC1(NS(=O)(=O)c2ccc(-c3ccsc3)c(NC(=O)Nc3cccc(C(F)(F)F)c3)c2)CC1] |
| 152 | 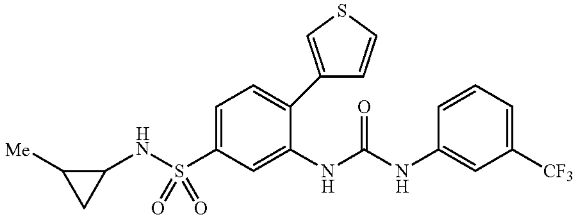 [SMILES: CC1CC1NS(=O)(=O)c1ccc(-c2ccsc2)c(NC(=O)Nc2cccc(C(F)(F)F)c2)c1] |
| 153 | 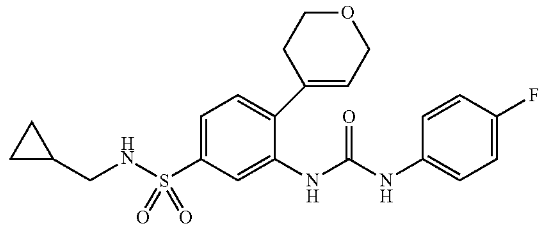 [SMILES: O=C(Nc1ccc(F)cc1)Nc1cc(S(=O)(=O)NCC2CC2)ccc1C1=CCOCC1] |
| 154 | 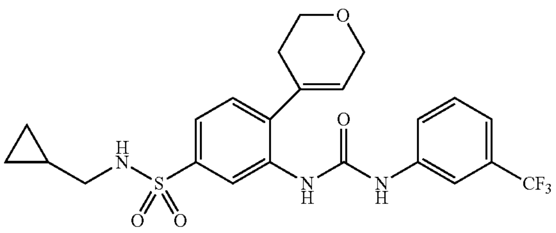 [SMILES: O=C(Nc1cccc(C(F)(F)F)c1)Nc1cc(S(=O)(=O)NCC2CC2)ccc1C1=CCOCC1] |

TABLE 2-continued
| Representative Compounds | |
|---|---|
| Cmpd # | Structure |
| 155 | 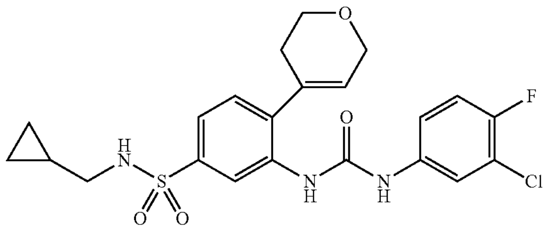 [SMILES: O=C(Nc1ccc(F)c(Cl)c1)Nc1cc(S(=O)(=O)NCC2CC2)ccc1C1=CCOCC1] |
| 156 | 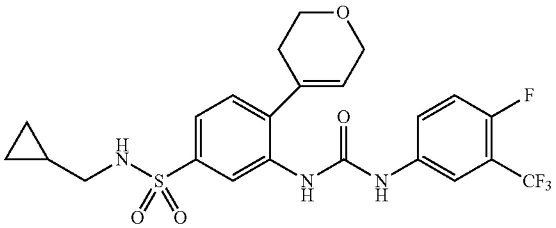 [SMILES: O=C(Nc1ccc(F)c(C(F)(F)F)c1)Nc1cc(S(=O)(=O)NCC2CC2)ccc1C1=CCOCC1] |
| 157 | 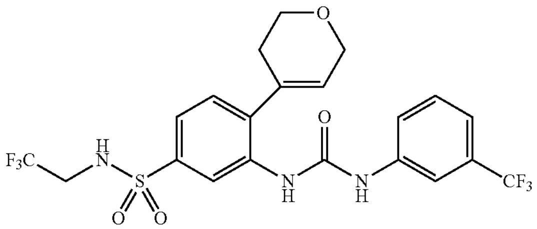 [SMILES: O=C(Nc1cccc(C(F)(F)F)c1)Nc1cc(S(=O)(=O)NCC(F)(F)F)ccc1C1=CCOCC1] |
| 158 | 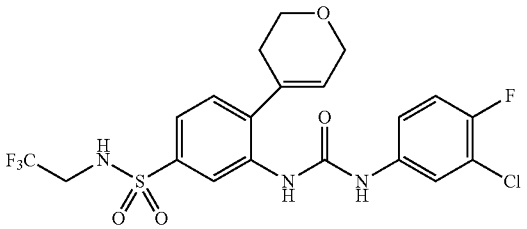 [SMILES: O=C(Nc1ccc(F)c(Cl)c1)Nc1cc(S(=O)(=O)NCC(F)(F)F)ccc1C1=CCOCC1] |
| 159 | 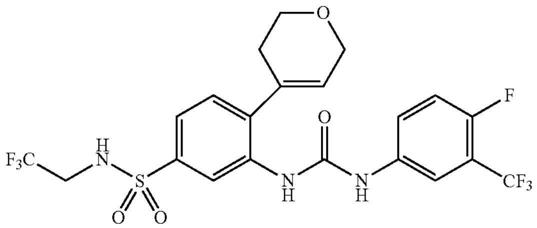 [SMILES: O=C(Nc1ccc(F)c(C(F)(F)F)c1)Nc1cc(S(=O)(=O)NCC(F)(F)F)ccc1C1=CCOCC1] |
| 160 | 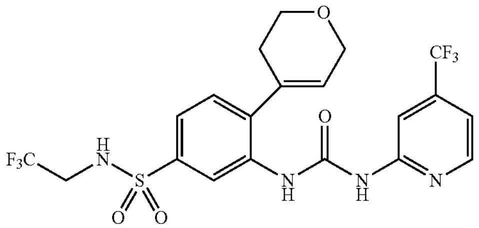 [SMILES: O=C(Nc1cc(C(F)(F)F)ccn1)Nc1cc(S(=O)(=O)NCC(F)(F)F)ccc1C1=CCOCC1] |

TABLE 2-continued
| Representative Compounds | |
|---|---|
| Cmpd # | Structure |
| 161 | 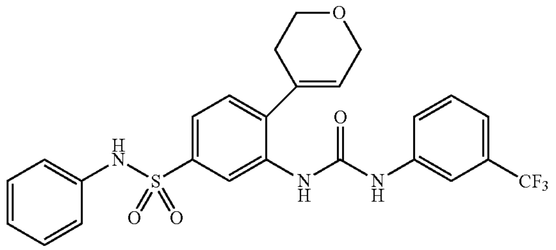 [SMILES: O=C(Nc1cccc(C(F)(F)F)c1)Nc1cc(S(=O)(=O)Nc2ccccc2)ccc1C1=CCOCC1] |
| 162 | 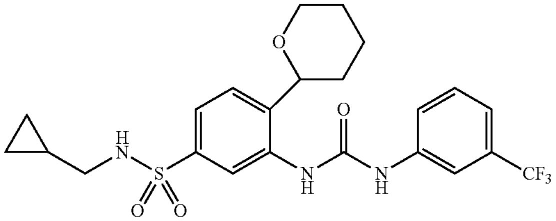 [SMILES: O=C(Nc1cccc(C(F)(F)F)c1)Nc1cc(S(=O)(=O)NCC2CC2)ccc1C1CCCCO1] |
| 163 | 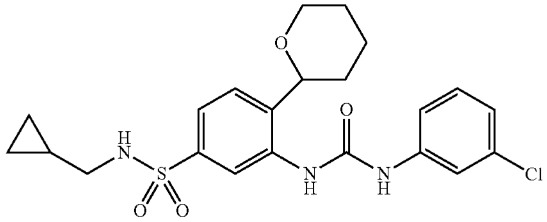 [SMILES: O=C(Nc1cccc(Cl)c1)Nc1cc(S(=O)(=O)NCC2CC2)ccc1C1CCCCO1] |
| 164 | 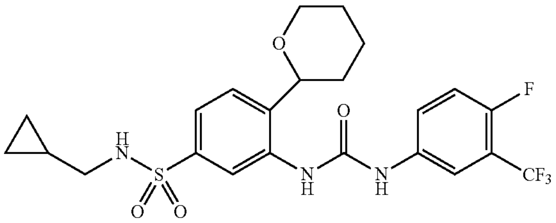 [SMILES: O=C(Nc1ccc(F)c(C(F)(F)F)c1)Nc1cc(S(=O)(=O)NCC2CC2)ccc1C1CCCCO1] |
| 165 | 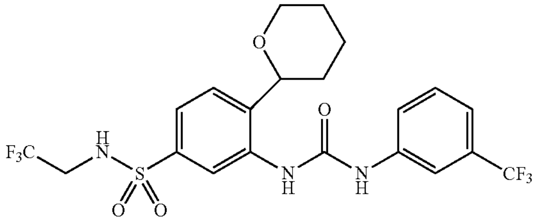 [SMILES: O=C(Nc1cccc(C(F)(F)F)c1)Nc1cc(S(=O)(=O)NCC(F)(F)F)ccc1C1CCCCO1] |
| 166 | 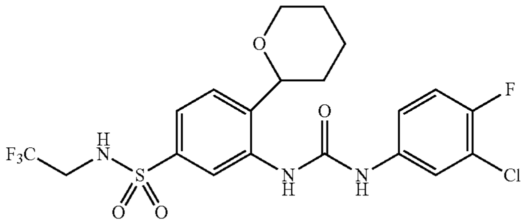 [SMILES: O=C(Nc1ccc(F)c(Cl)c1)Nc1cc(S(=O)(=O)NCC(F)(F)F)ccc1C1CCCCO1] |

TABLE 2-continued
| Representative Compounds | |
| --- | --- |
| Cmpd # | Structure |
| 167 | 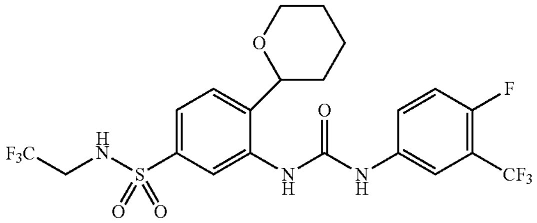 [SMILES: O=C(Nc1ccc(F)c(C(F)(F)F)c1)Nc1cc(S(=O)(=O)NCC(F)(F)F)ccc1C1CCCCO1] |
| 168 | 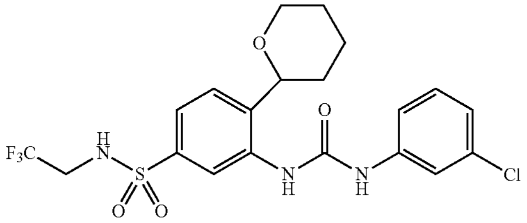 [SMILES: O=C(Nc1cccc(Cl)c1)Nc1cc(S(=O)(=O)NCC(F)(F)F)ccc1C1CCCCO1] |
| 169 | 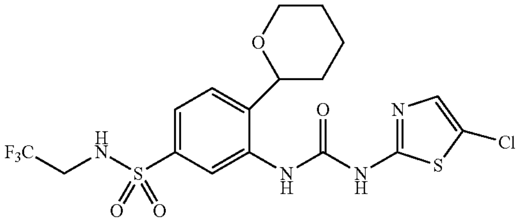 [SMILES: O=C(Nc1ncc(Cl)s1)Nc1cc(S(=O)(=O)NCC(F)(F)F)ccc1C1CCCCO1] |
| 170 | 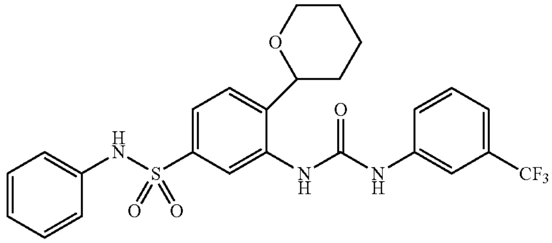 [SMILES: O=C(Nc1cccc(C(F)(F)F)c1)Nc1cc(S(=O)(=O)Nc2ccccc2)ccc1C1CCCCO1] |
| 171 | 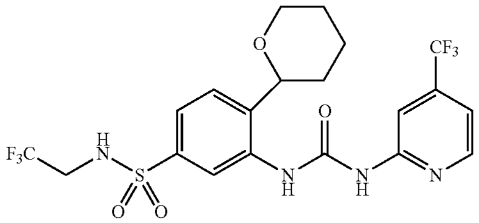 [SMILES: O=C(Nc1cc(C(F)(F)F)ccn1)Nc1cc(S(=O)(=O)NCC(F)(F)F)ccc1C1CCCCO1] |
| 172 | 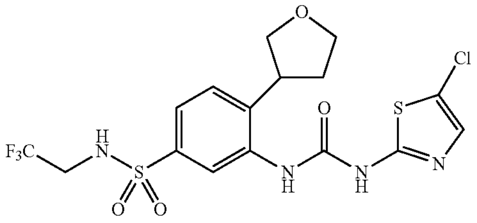 [SMILES: O=C(Nc1ncc(Cl)s1)Nc1cc(S(=O)(=O)NCC(F)(F)F)ccc1C1CCOC1] |

TABLE 2-continued
| Representative Compounds | |
|---|---|
| Cmpd # | Structure |
| 173 | 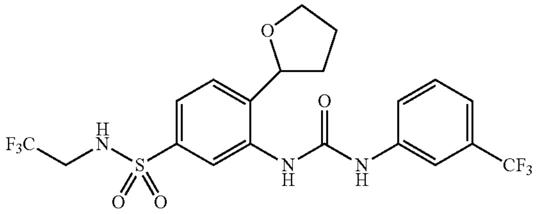 |
| 353 | 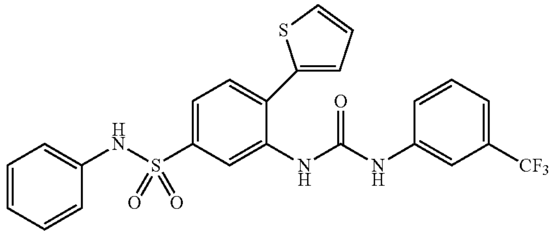 |
| 174 | 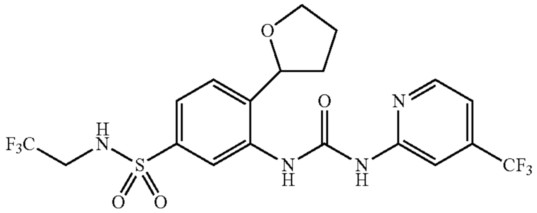 [SMILES: O=C(Nc1cc(C(F)(F)F)ccn1)Nc1cc(S(=O)(=O)NCC(F)(F)F)ccc1C1CCCO1] |
| 175 | 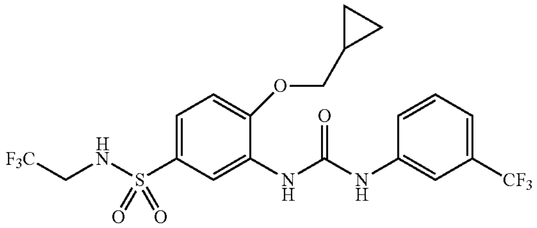 [SMILES: O=C(Nc1cccc(C(F)(F)F)c1)Nc1cc(S(=O)(=O)NCC(F)(F)F)ccc1OCC1CC1] |
| 176 | 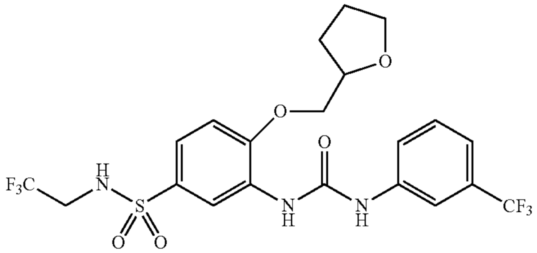 [SMILES: O=C(Nc1cccc(C(F)(F)F)c1)Nc1cc(S(=O)(=O)NCC(F)(F)F)ccc1OCC1CCCO1] |
| 177 | 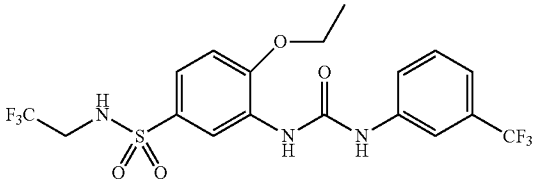 [SMILES: CCOc1ccc(S(=O)(=O)NCC(F)(F)F)cc1NC(=O)Nc1cccc(C(F)(F)F)c1] |

TABLE 2-continued
| Representative Compounds | |
|---|---|
| Cmpd # | Structure |
| 178 | 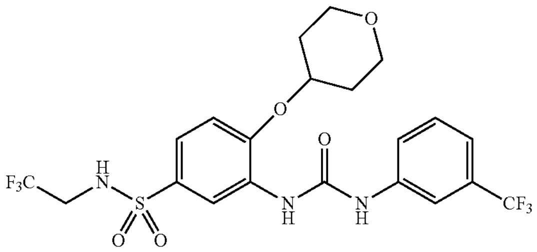 [SMILES: O=C(Nc1cccc(C(F)(F)F)c1)Nc1cc(S(=O)(=O)NCC(F)(F)F)ccc1OC1CCOCC1] |
| 179 | 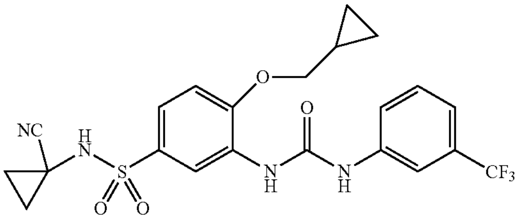 [SMILES: N#CC1(NS(=O)(=O)c2ccc(OCC3CC3)c(NC(=O)Nc3cccc(C(F)(F)F)c3)c2)CC1] |
| 180 | 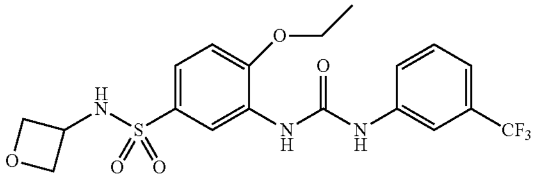 [SMILES: CCOc1ccc(S(=O)(=O)NC2COC2)cc1NC(=O)Nc1cccc(C(F)(F)F)c1] |
| 181 | 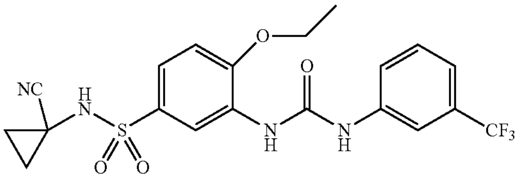 [SMILES: CCOc1ccc(S(=O)(=O)NC2(C#N)CC2)cc1NC(=O)Nc1cccc(C(F)(F)F)c1] |
| 183 | 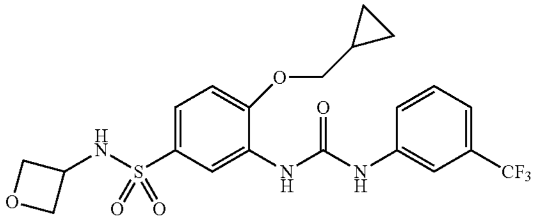 [SMILES: O=C(Nc1cccc(C(F)(F)F)c1)Nc1cc(S(=O)(=O)NC2COC2)ccc1OCC1CC1] |
| 184 | 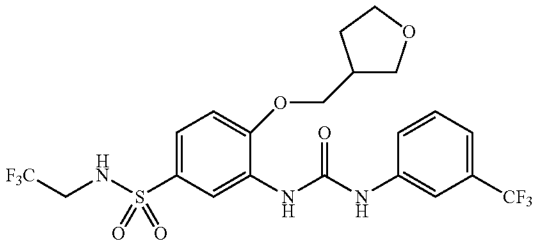 [SMILES: O=C(Nc1cccc(C(F)(F)F)c1)Nc1cc(S(=O)(=O)NCC(F)(F)F)ccc1OCC1CCOC1] |

TABLE 2-continued
| Representative Compounds | |
|---|---|
| Cmpd # | Structure |
| 185 | 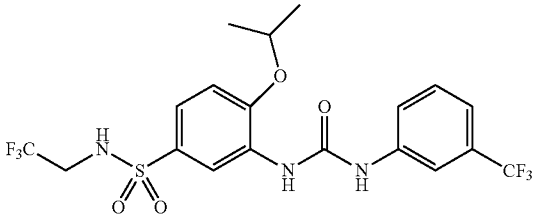 [SMILES: CC(C)Oc1ccc(S(=O)(=O)NCC(F)(F)F)cc1NC(=O)Nc1cccc(C(F)(F)F)c1] |
| 186 | 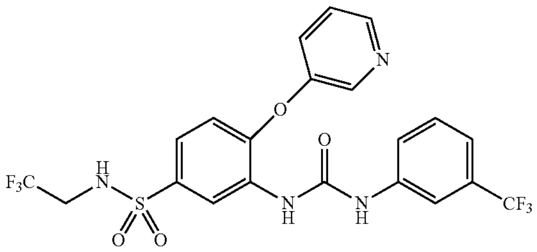 [SMILES: O=C(Nc1cccc(C(F)(F)F)c1)Nc1cc(S(=O)(=O)NCC(F)(F)F)ccc1Oc1cccnc1] |
| 187 | 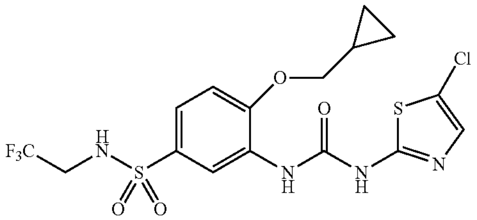 [SMILES: O=C(Nc1ncc(Cl)s1)Nc1cc(S(=O)(=O)NCC(F)(F)F)ccc1OCC1CC1] |
| 188 | 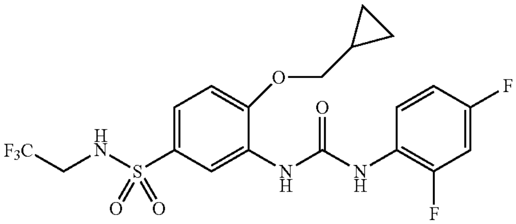 [SMILES: O=C(Nc1ccc(F)cc1F)Nc1cc(S(=O)(=O)NCC(F)(F)F)ccc1OCC1CC1] |
| 189 | 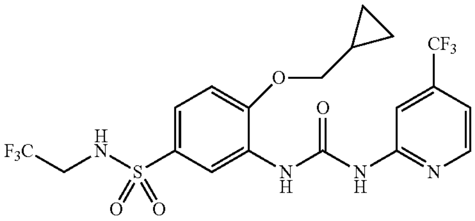 [SMILES: O=C(Nc1cc(C(F)(F)F)ccn1)Nc1cc(S(=O)(=O)NCC(F)(F)F)ccc1OCC1CC1] |
| 190 | 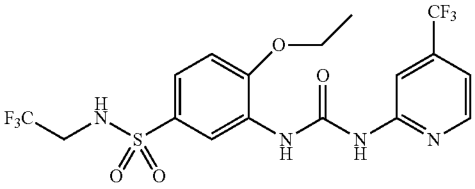 [SMILES: CCOc1ccc(S(=O)(=O)NCC(F)(F)F)cc1NC(=O)Nc1cc(C(F)(F)F)ccn1] |
| 191 | 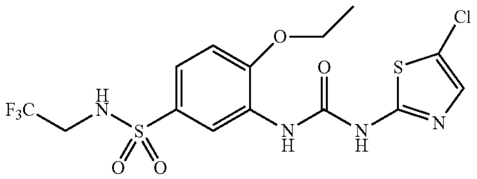 [SMILES: CCOc1ccc(S(=O)(=O)NCC(F)(F)F)cc1NC(=O)Nc1ncc(Cl)s1] |

TABLE 2-continued
| Cmpd # | Structure |
| --- | --- |
| 192 | 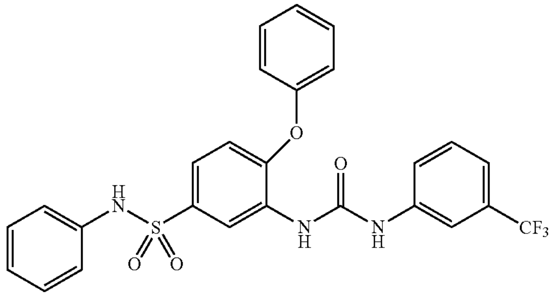 [SMILES: O=C(Nc1cccc(C(F)(F)F)c1)Nc1cc(S(=O)(=O)Nc2ccccc2)ccc1Oc1ccccc1] |
| 193 | 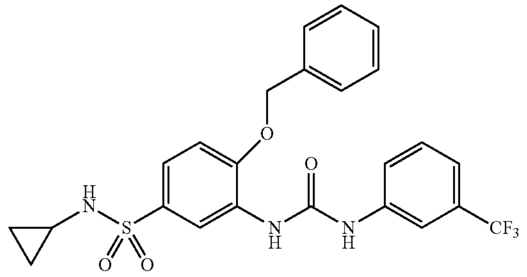 [SMILES: O=C(Nc1cccc(C(F)(F)F)c1)Nc1cc(S(=O)(=O)NC2CC2)ccc1OCc1ccccc1] |
| 194 | 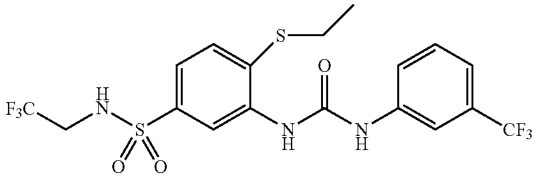 [SMILES: CCSc1ccc(S(=O)(=O)NCC(F)(F)F)cc1NC(=O)Nc1cccc(C(F)(F)F)c1] |
| 195 | 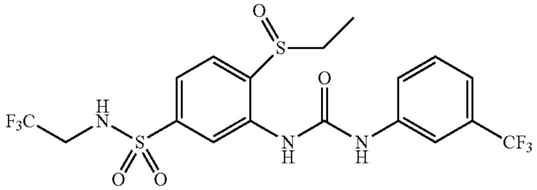 [SMILES: CCS(=O)c1ccc(S(=O)(=O)NCC(F)(F)F)cc1NC(=O)Nc1cccc(C(F)(F)F)c1] |
| 196 | 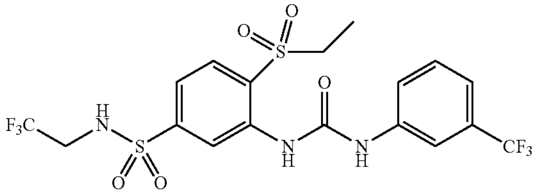 [SMILES: CCS(=O)(=O)c1ccc(S(=O)(=O)NCC(F)(F)F)cc1NC(=O)Nc1cccc(C(F)(F)F)c1] |
| 197 | 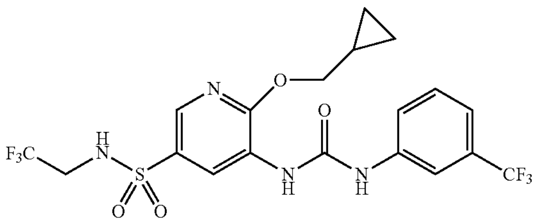 [SMILES: O=C(Nc1cccc(C(F)(F)F)c1)Nc1cc(S(=O)(=O)NCC(F)(F)F)cnc1OCC1CC1] |
Representative Compounds TABLE 2-continued
| Representative Compounds | |
|---|---|
| Cmpd # | Structure |
| 198 | 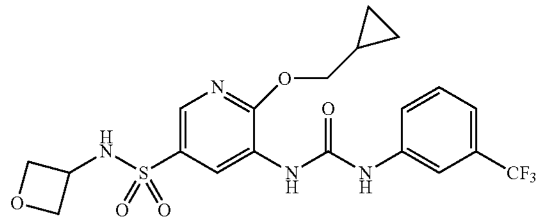 [SMILES: O=C(Nc1cccc(C(F)(F)F)c1)Nc1cc(S(=O)(=O)NC2COC2)cnc1OCC1CC1] |
| 199 | 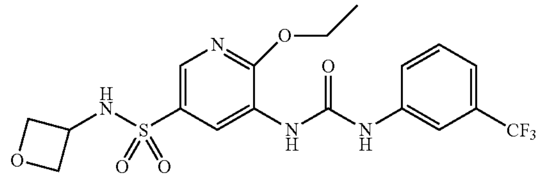 [SMILES: CCOc1ncc(S(=O)(=O)NC2COC2)cc1NC(=O)Nc1cccc(C(F)(F)F)c1] |
| 200 | 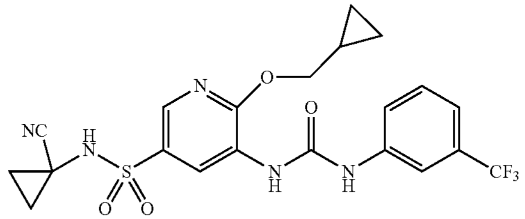 [SMILES: N#CC1(NS(=O)(=O)c2cnc(OCC3CC3)c(NC(=O)Nc3cccc(C(F)(F)F)c3)c2)CC1] |
| 201 | 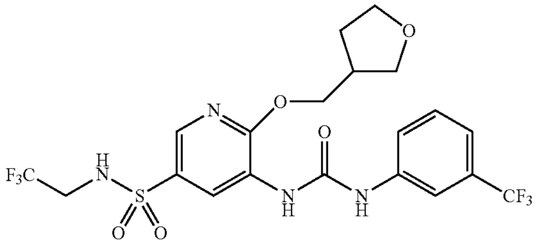 [SMILES: O=C(Nc1cccc(C(F)(F)F)c1)Nc1cc(S(=O)(=O)NCC(F)(F)F)cnc1OCC1CCOC1] |
| 202 | 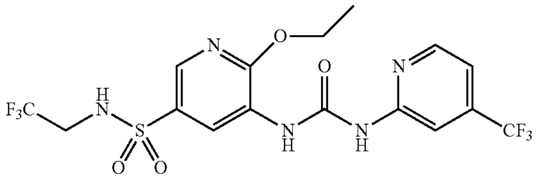 [SMILES: CCOc1ncc(S(=O)(=O)NCC(F)(F)F)cc1NC(=O)Nc1cc(C(F)(F)F)ccn1] |
| 203 | 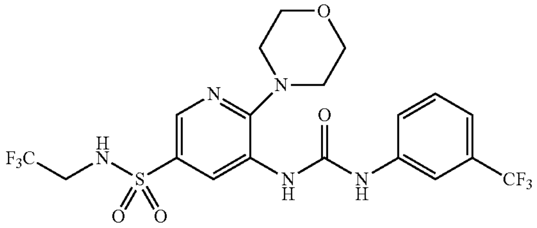 [SMILES: O=C(Nc1cccc(C(F)(F)F)c1)Nc1cc(S(=O)(=O)NCC(F)(F)F)cnc1N1CCOCC1] |
| 204 | 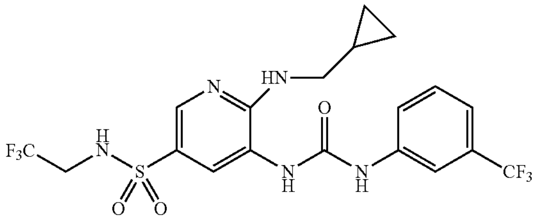 [SMILES: O=C(Nc1cccc(C(F)(F)F)c1)Nc1cc(S(=O)(=O)NCC(F)(F)F)cnc1NCC1CC1]

TABLE 2-continued
| Representative Compounds | |
|---|---|
| Cmpd # | Structure |
| 353 | 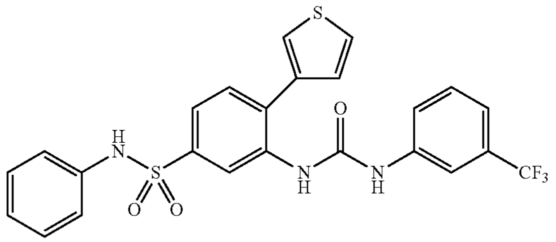 [SMILES: O=C(Nc1cccc(C(F)(F)F)c1)Nc1cc(S(=O)(=O)Nc2ccccc2)ccc1-c1ccsc1] |
| 354 | 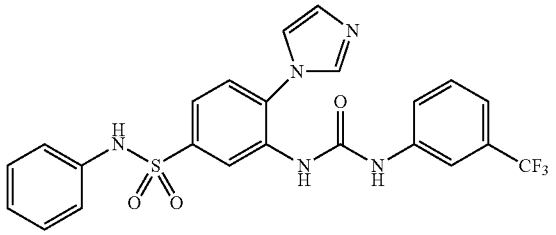 [SMILES: O=C(Nc1cccc(C(F)(F)F)c1)Nc1cc(S(=O)(=O)Nc2ccccc2)ccc1-n1ccnc1] |
| 355 | 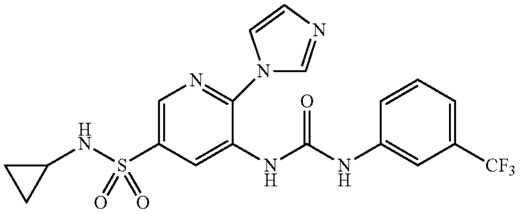 [SMILES: O=C(Nc1cccc(C(F)(F)F)c1)Nc1cc(S(=O)(=O)NC2CC2)cnc1-n1ccnc1] |
| 356 | 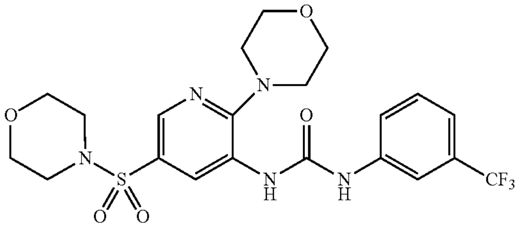 [SMILES: O=C(Nc1cccc(C(F)(F)F)c1)Nc1cc(S(=O)(=O)N2CCOCC2)cnc1N1CCOCC1] |
| 357 | 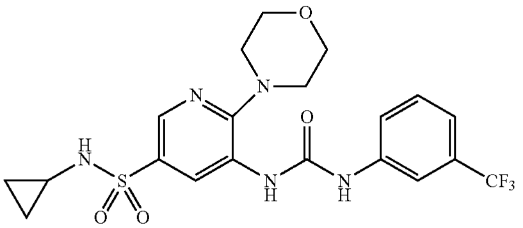 [SMILES: O=C(Nc1cccc(C(F)(F)F)c1)Nc1cc(S(=O)(=O)NC2CC2)cnc1N1CCOCC1] |
| 358 | 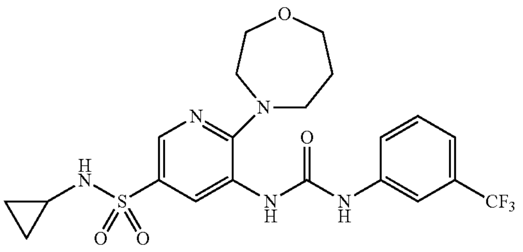 [SMILES: O=C(Nc1cccc(C(F)(F)F)c1)Nc1cc(S(=O)(=O)NC2CC2)cnc1N1CCCOCC1] |

TABLE 2-continued
| Representative Compounds | |
|---|---|
| Cmpd # | Structure |
| 359 | 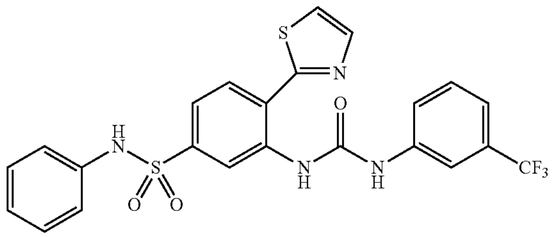 [SMILES: O=C(Nc1cccc(C(F)(F)F)c1)Nc1cc(S(=O)(=O)Nc2ccccc2)ccc1-c1nccs1] |
| 337 | 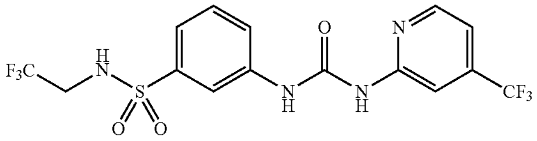 [SMILES: O=C(Nc1cccc(S(=O)(=O)NCC(F)(F)F)c1)Nc1cc(C(F)(F)F)ccn1] |
| 338 | 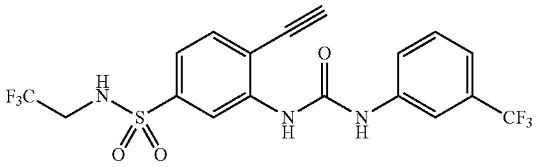 [SMILES: C#Cc1ccc(S(=O)(=O)NCC(F)(F)F)cc1NC(=O)Nc1cccc(C(F)(F)F)c1] |
| 339 | 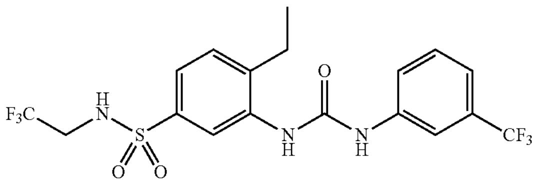 [SMILES: CCc1ccc(S(=O)(=O)NCC(F)(F)F)cc1NC(=O)Nc1cccc(C(F)(F)F)c1] |
| 340 | 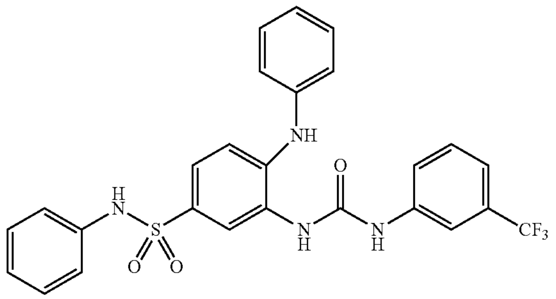 [SMILES: O=C(Nc1cccc(C(F)(F)F)c1)Nc1cc(S(=O)(=O)Nc2ccccc2)ccc1Nc1ccccc1] |
| 341 | 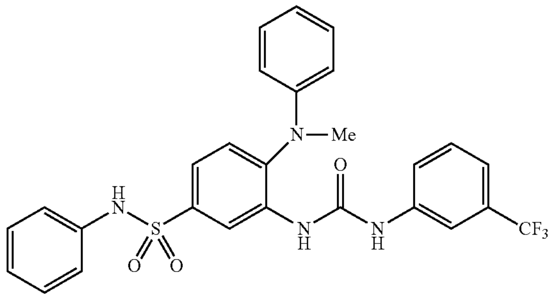 [SMILES: CN(c1ccccc1)c1ccc(S(=O)(=O)Nc2ccccc2)cc1NC(=O)Nc1cccc(C(F)(F)F)c1] |

TABLE 2-continued
| Representative Compounds | |
|---|---|
| Cmpd # | Structure |
| 342 | 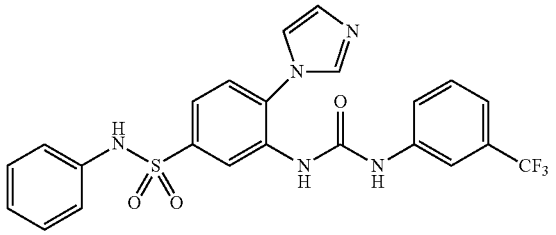 [SMILES: O=C(Nc1cccc(C(F)(F)F)c1)Nc1cc(S(=O)(=O)Nc2ccccc2)ccc1-n1ccnc1] |
| 343 | 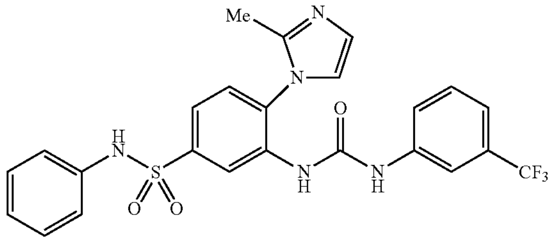 [SMILES: Cc1nccn1-c1ccc(S(=O)(=O)Nc2ccccc2)cc1NC(=O)Nc1cccc(C(F)(F)F)c1] |
| 344 | 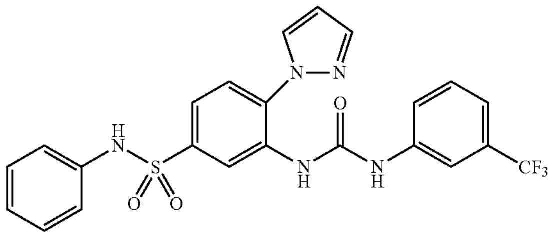 [SMILES: O=C(Nc1cccc(C(F)(F)F)c1)Nc1cc(S(=O)(=O)Nc2ccccc2)ccc1-n1cccn1] |
| 345 | 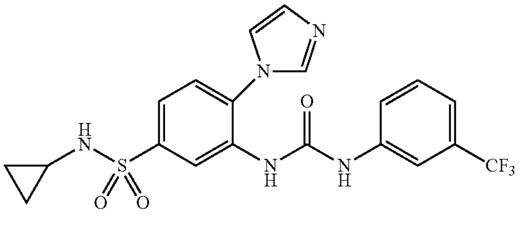 [SMILES: O=C(Nc1cccc(C(F)(F)F)c1)Nc1cc(S(=O)(=O)NC2CC2)ccc1-n1ccnc1] |
| 346 | 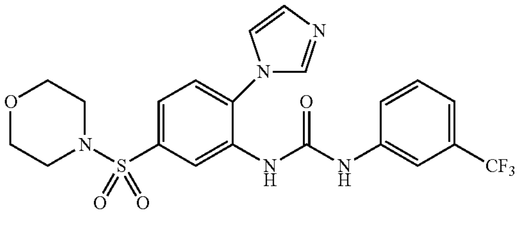 [SMILES: O=C(Nc1cccc(C(F)(F)F)c1)Nc1cc(S(=O)(=O)N2CCOCC2)ccc1-n1ccnc1] |
| 347 | 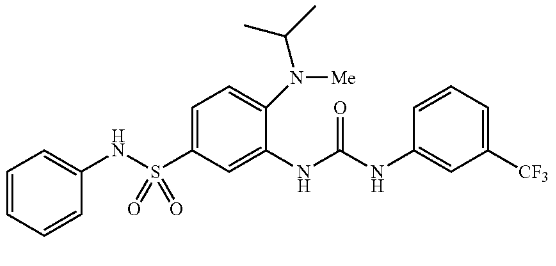 [SMILES: CC(C)N(C)c1ccc(S(=O)(=O)Nc2ccccc2)cc1NC(=O)Nc1cccc(C(F)(F)F)c1] |

TABLE 2-continued
| Representative Compounds | |
|---|---|
| Cmpd # | Structure |
| 348 | 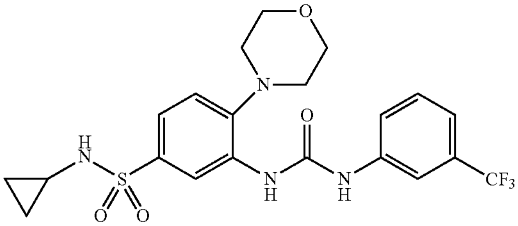 [SMILES: O=C(Nc1cccc(C(F)(F)F)c1)Nc1cc(S(=O)(=O)NC2CC2)ccc1N1CCOCC1] |
| 349 | 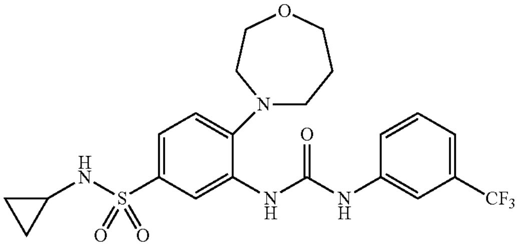 [SMILES: O=C(Nc1cccc(C(F)(F)F)c1)Nc1cc(S(=O)(=O)NC2CC2)ccc1N1CCCOCC1] |
| 350 | 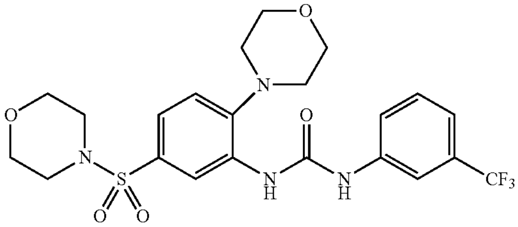 [SMILES: O=C(Nc1cccc(C(F)(F)F)c1)Nc1cc(S(=O)(=O)N2CCOCC2)ccc1N1CCOCC1] |
In some embodiments, the compound of formula (I), (II), (III) or (IV) is selected from compound number 1, 2, 3, 4, 5, 6, 7, 8, 9, 10, 11, 12, 25, 27, 28, 29, 30, 31, 32, 33, 34, 35, 36, 37, 38, 39, 40, 41, 42, 43, 44, 45, 46, 47, 48, 50, 66, 67, 68, 69, 70, 71, 72, 74, 76, 78, 79, 80, 81, 82, 83, 84, 85, 86, 87, 88, 89, 90, 91, 92, 93, 94, 97, 98, 99, 100, 101, 102, 103, 104, 105, 106, 107, 108, 111, 112, 113, 114, 115, 116, 117, 118, 119, 120, 121, 122, 123, 124, 125, 126, 127, 128, 129, 130, 131, 132, 133, 134, 135, 136, 138, 139, 146, 151, 152, 154, 155, 156, 157, 158, 159, 160, 161, 162, 163, 164, 165, 166, 167, 168, 169, 170, 171, 172, 173, 174, 175, 176, 177, 178, 179, 180, 181, 183, 184, 185, 186, 187, 188, 189, 190, 191, 194, 195, 196, 197, 198, 199, 200, 201, 202, 203, 204, 351, 337, 338, 339, 340, 341, 342, 345, 348, 349, 206, 207, 208, 221, 222, 225, 324, 304, 315, 316, and 320.
In some embodiments, the compound of formula (I), (II), (III) or (IV) is selected from the following:
31
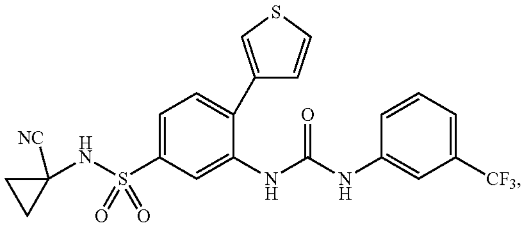
-continued
32
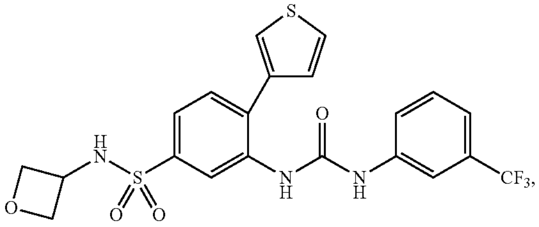
45
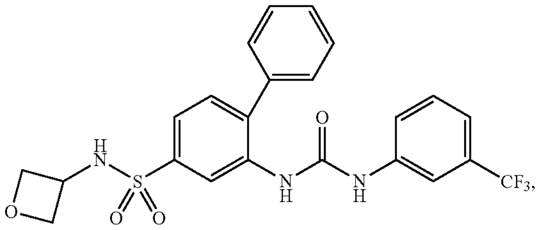
177
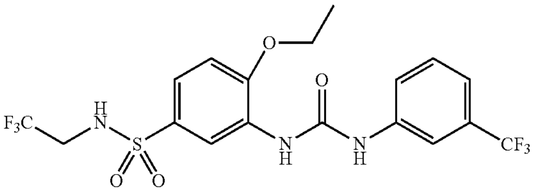

-continued

194

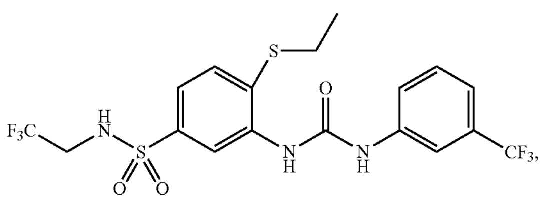

196

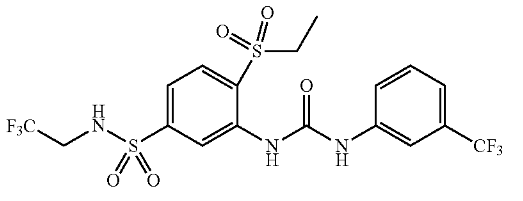

or

197

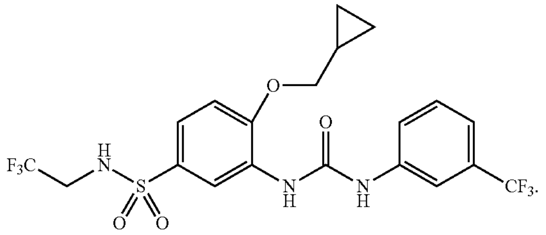

The compounds of one aspect of this invention may contain one or more asymmetric centers and thus occur as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

In certain embodiments, the compound of described herein is enriched for a structure or structures having a selected stereochemistry at one or more carbon atoms. For example, the compound is enriched in the specific stereoisomer by at least about 60%, 65%, 70%, 75%, 80%, 85%, 90%, 95%, 96%, 97%, 98%, or 99%.

The compounds described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; and the like.

Unless otherwise indicated when a disclosed compound is named or depicted by a structure without specifying the stereochemistry and has one or more chiral centers, it is understood to represent all possible stereoisomers of the compound.

The compounds of one aspect of this invention may also be represented in multiple tautomeric forms, in such instances, one aspect of the invention expressly includes all tautomeric forms of the compounds described herein, even though only a single tautomeric form may be represented (e.g., alkylation of a ring system may result in alkylation at multiple sites, one aspect of the invention expressly includes all such reaction products). All such isomeric forms of such compounds are expressly included herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R^{2+}$, $NHR^{3+}$, $NR^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Compositions and Routes of Administration

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of one aspect of this invention may be administered orally, parenterally, by inhalation spray, topically, rectally, nasally, buccally, vaginally or via an implanted reservoir, preferably by oral administration or administration by injection. The pharmaceutical compositions of one aspect of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of one aspect of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of one aspect of this invention may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of one aspect of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation. Topically-transdermal patches are also included in one aspect of this invention.

The pharmaceutical compositions of one aspect of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of one aspect of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of one aspect of this invention. Alternatively, those agents may be part of a single dosage form, mixed together with the compounds of one aspect of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of one aspect of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound described in any one of the embodiments herein, may further comprise another therapeutic agent useful for treating cancer.

Methods of Use

Provided is a method for inhibiting a mutant IDH1 or IDH2 activity comprising contacting a subject in need thereof a compound described in any one of the embodiments herein, or a pharmaceutically acceptable salt thereof. In one embodiment, the cancer to be treated is characterized by a mutant allele of IDH1 or IDH2 wherein the IDH1 or IDH2 mutation result in a new ability of the enzyme to catalyze the NADPH-dependent reduction of α-ketoglutarate to R(−)-2-hydroxyglutarate in a subject. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

Also provided are methods of treating a cancer characterized by the presence of a mutant allele of IDH1 comprising the step of administering to subject in need thereof (a) a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH1 wherein the IDH1 mutation result in a new ability of the enzyme to catalyze the NADPH-dependent reduction of α-ketoglutarate to R(−)-2-hydroxyglutarate in a patient. In one aspect of this embodiment, the IDH1 mutation is an R132X mutation. In another aspect of this embodiment, the R132X mutation is selected from R132H, R132C, R132L, R132V, R132S and R132G. In another aspect, the R132X mutation is R132 H or R132C. A cancer can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation result in a new ability of the enzyme to catalyze the NADPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds and methods of this invention are useful to treat any type of cancer that is characterized by the presence of a mutant allele of IDH1 imparting such activity and in particular an IDH1 R132H or R132C mutation.

In one aspect of this embodiment, the efficacy of cancer treatment is monitored by measuring the levels of 2HG in the subject. Typically levels of 2HG are measured prior to treatment, wherein an elevated level is indicative of the use of the compound described herein. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}C$-glutamine can be performed as described, e.g., in Munger et al. Nat Biotechnol 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

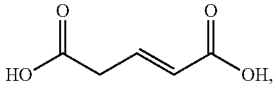,

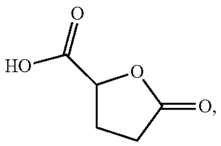,

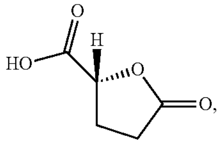, and

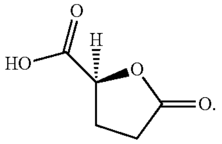.

In one embodiment the cancer is a tumor wherein at least 30, 40, 50, 60, 70, 80 or 90% of the tumor cells carry an IDH1 mutation, and in particular an IDH1 R132H or R132C mutation, at the time of diagnosis or treatment.

IDH1 R132X mutations are known to occur in certain types of cancers as indicated in Table 3, below.

TABLE 3

IDH mutations associated with certain cancers

| Cancer Type | IDH1 R132X Mutation | Tumor Type |
|---|---|---|
| brain tumors | R132H | primary tumor |
| | R132C | primary tumor |
| | R132S | primary tumor |
| | R132G | primary tumor |
| | R132L | primary tumor |
| | R132V | primary tumor |
| fibrosarcoma | R132C | HT1080 fibrosarcoma cell line |
| Acute Myeloid Leukemia (AML) | R132H | primary tumor |
| | R132G | primary tumor |
| | R132C | primary tumor |
| Prostate cancer | R132H | primary tumor |
| | R132C | primary tumor |
| Acute lymphoblastic leukemia (ALL) | R132C | primary tumor |
| paragangliomas | R132C | primary tumor |

IDH1 R132H mutations have been identified in glioblastoma, acute myelogenous leukemia, sarcoma, melanoma, non-small cell lung cancer, cholangiocarcinomas, chondrosarcoma, myelodysplastic syndromes (MDS), myeloproliferative neoplasm (MPN), colon cancer, and angio-immunoblastic non-Hodgkin's lymphoma (NHL). Accordingly, in one embodiment, the methods described herein are used to treat glioma (glioblastoma), acute myelogenous leukemia, sarcoma, melanoma, non-small cell lung cancer (NSCLC) or cholangiocarcinomas, chondrosarcoma, myelodysplastic syndromes (MDS), myeloproliferative neoplasm (MPN), colon cancer, or angio-immunoblastic non-Hodgkin's lymphoma (NHL) in a patient.

Accordingly in one embodiment, the cancer is a cancer selected from any one of the cancer types listed in Table 3, and the IDH R132X mutation is one or more of the IDH1 R132X mutations listed in Table 3 for that particular cancer type.

Treatment methods described herein can additionally comprise various evaluation steps prior to and/or following treatment with a compound described in any one of the embodiments described herein.

In one embodiment, prior to and/or after treatment with a compound described in any one of the embodiments described herein, the method further comprises the step of evaluating the growth, size, weight, invasiveness, stage and/or other phenotype of the cancer.

In one embodiment, prior to and/or after treatment with a compound described in any one of the embodiments described herein, the method further comprises the step of evaluating the IDH1 genotype of the cancer. This may be achieved by ordinary methods in the art, such as DNA sequencing, immuno analysis, and/or evaluation of the presence, distribution or level of 2HG.

In one embodiment, prior to and/or after treatment with a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

Provided is a method for inhibiting a mutant IDH2 activity comprising contacting a subject in need thereof a compound described in any one of the embodiments herein, or a pharmaceutically acceptable salt thereof. In one embodiment, the cancer to be treated is characterized by a mutant allele of IDH2 wherein the IDH2 mutation result in a new ability of the enzyme to catalyze the NADPH-dependent reduction of α-ketoglutarate to R(−)-2-hydroxyglutarate in a subject. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

Also provided are methods of treating a cancer characterized by the presence of a mutant allele of IDH2 comprising the step of administering to subject in need thereof (a) a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH2 wherein the IDH2 mutation result in a new ability of the enzyme to catalyze the NADPH-dependent reduction of α-ketoglutarate to R(−)-2-hydroxyglutarate in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation. A cancer can be analyzed by sequencing cell samples to determine the presence and specific nature of (e.g., the changed amino acid present at) a mutation at amino acid 140 and/or 172 of IDH2.

Without being bound by theory, applicants believe that mutant alleles of IDH2 wherein the IDH2 mutation result in a new ability of the enzyme to catalyze the NADPH-dependent reduction of α-ketoglutarate to R(−)-2-hydroxyglutarate, and in particular R140Q and/or R172K mutations of IDH2, characterize a subset of all types of cancers, without regard to their cellular nature or location in the body. Thus, the compounds and methods of one aspect of this invention are useful to treat any type of cancer that is characterized by the presence of a mutant allele of IDH2 imparting such activity and in particular an IDH2 R140Q and/or R172K mutation.

In one embodiment the cancer is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In another embodiment, one aspect of the invention provides a method of treating a cancer selected from glioblastoma (glioma), myelodysplastic syndrome (MDS), myeloproliferative neoplasm (MPN), acute myelogenous leukemia (AML), sarcoma, melanoma, non-small cell lung cancer, chondrosarcoma, cholangiocarcinomas or angioimmunoblastic lymphoma in a patient by administering to the patient a compound described herein in an amount effective to treat the cancer. In a more specific embodiment the cancer to be treated is glioma, myelodysplastic syndrome (MDS), myeloproliferative neoplasm (MPN), acute myelogenous leukemia (AML), melanoma, chondrosarcoma, or angioimmunoblastic non-Hodgkin's lymphoma (NHL).

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, J Neurooncol 91, 233-6 (2009); Kolker, S., Mayatepek, E. & Hoffmann, G. F. Neuropediatrics 33, 225-31 (2002); Wajner, M., Latini, A., Wyse, A. T. & Dutra-Filho, C. S. J Inherit Metab Dis 27, 427-48 (2004)). Furthermore, elevated brain levels of 2HG result in increased ROS levels (Kolker, S. et al. Eur J Neurosci 16, 21-8 (2002); Latini, A. et al. Eur J Neurosci 17, 2017-22 (2003)), potentially contributing to an increased risk of cancer. The ability of 2HG to act as an NMDA receptor agonist may contribute to this effect (Kolker, S. et al. Eur J Neurosci 16, 21-8 (2002)). 2HG may also be toxic to cells by competitively inhibiting glutamate and/or aKG utilizing enzymes. These include transaminases which allow utilization of glutamate nitrogen for amino and nucleic acid biosynthesis, and aKG-dependent prolyl hydroxylases such as those which regulate Hif1a levels.

Thus, according to another embodiment, one aspect of the invention provides a method of treating 2-hydroxyglutaric aciduria, particularly D-2-hydroxyglutaric aciduria, in a patient by administering to the patient a compound described herein.

Treatment methods described herein can additionally comprise various evaluation steps prior to and/or following treatment with a compound described in any one of the embodiments described herein.

In one embodiment, prior to and/or after treatment with a compound described in any one of the embodiments described herein, the method further comprises the step of evaluating the growth, size, weight, invasiveness, stage and/or other phenotype of the cancer.

In one embodiment, prior to and/or after treatment with a compound described in any one of the embodiments described herein, the method further comprises the step of evaluating the IDH2 genotype of the cancer. This may be achieved by ordinary methods in the art, such as DNA sequencing, immuno analysis, and/or evaluation of the presence, distribution or level of 2HG.

In one embodiment, prior to and/or after treatment with a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

Combination Therapies

In some embodiments, the methods described herein comprise the additional step of co-administering to a subject in need thereof a second therapy e.g., an additional cancer therapeutic agent or an additional cancer treatment. Exemplary additional cancer therapeutic agents include for example, chemotherapy, targeted therapy, antibody therapies, immunotherapy, and hormonal therapy. Additional cancer treatments include, for example: surgery, and radiation therapy. Examples of each of these treatments are provided below.

The term "co-administering" as used herein with respect to an additional cancer therapeutic agents means that the additional cancer therapeutic agent may be administered together with a compound of one aspect of this invention as part of a single dosage form (such as a composition of one aspect of this invention comprising a compound of one aspect of the invention and an second therapeutic agent as described above) or as separate, multiple dosage forms. Alternatively, the additional cancer therapeutic agent may be administered prior to, consecutively with, or following the administration of a compound of one aspect of this invention. In such combination therapy treatment, both the compounds of one aspect of this invention and the second therapeutic agent(s) are administered by conventional methods. The administration of a composition of one aspect of this invention, comprising both a compound of one aspect of the invention and a second therapeutic agent, to a subject does not preclude the separate administration of that same therapeutic agent, any other second therapeutic agent or any compound of one aspect of this invention to said subject at another time during a course of treatment. The term "co-administering" as used herein with respect to an additional cancer treatment means that the additional cancer treatment may occur prior to, consecutively with, concurrently with or following the administration of a compound of one aspect of this invention.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, over-expressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

EXAMPLES

| ABBREVIATIONS | |
|---|---|
| anhy.—anhydrous | $Et_2O$—diethyl ether |
| aq.—aqueous | EtOH—ethyl alcohol |
| min—minute(s) | EtOAc—ethyl acetate |

-continued

| ABBREVIATIONS |
|---|
| mL—milliliter |
| mmol—millimole(s) |
| mol—mole(s) |
| MS—mass spectrometry |
| NMR—nuclear magnetic resonance |
| TLC—thin layer chromatography |
| HPLC—high-performance liquid chromatography |
| Hz—hertz |
| δ—chemical shift |
| J—coupling constant |
| s—singlet |
| d—doublet |
| t—triplet |
| q—quartet |
| m—multiplet |
| br—broad |
| qd—quartet of doublets |
| dquin—doublet of quintets |
| dd—doublet of doublets |
| dt—doublet of triplets |
| $CHCl_3$—chloroform |
| DCM—dichloromethane |
| DMF—dimethylformamide |
| $NH_4OH$—ammonium hydroxide |
| EDCI—1-ethyl-3-(3-dimethyl-aminopropyl)carbodiimide |
| HOBt—1-hydroxybenzotriazole |
| HATU—O-(7-azabenzotriazol-1-yl)-N,N,N',N'-tetra-methyluronium |
| MeOH—methyl alcohol |
| MeCN—acetonitrile |
| PE—petroleum ether |
| THF—tetrahydrofuran |
| AcOH—acetic acid |
| HCl—hydrochloric acid |
| $H_2SO_4$—sulfuric acid |
| $NH_4Cl$—ammonium chloride |
| KOH—potassium hydroxide |
| NaOH—sodium hydroxide |
| $K_2CO_3$—potassium carbonate |
| $Na_2CO_3$—sodium carbonate |
| TFA—trifluoroacetic acid |
| $Na_2SO_4$—sodium sulfate |
| $NaBH_4$—sodium borohydride |
| $NaHCO_3$—sodium bicarbonate |
| LiHMDS—lithium hexamethyl-disilylamide |
| NaHMDS—sodium hexamethyl-disilylamide |
| LAH—lithium aluminum hydride |
| $NaBH_4$—sodium borohydride |
| LDA—lithium diisopropylamide |
| $Et_3N$—triethylamine |
| DMAP—4-(dimethylamino)pyridine |
| DIPEA—N,N-diisopropylethylamine |
| BINAP—2,2'-bis(diphenyl-phosphanyl)-1,1'-binaphthyl |

In the following examples, reagents were purchased from commercial sources (including Alfa, Acros, Sigma Aldrich, TCI and Shanghai Chemical Reagent Company), and used without further purification. Flash chromatography was performed on an Ez Purifier III using a column with silica gel particles of 200-300 mesh. Analytical and preparative thin layer chromatography plates (TLC) were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, 6) downfield from tetramethylsilane. Mass spectra were run with electrospray ionization (ESI) from a Waters LCT TOF Mass Spectrometer (Waters, USA). HPLC chromatographs were recorded on an Agilent 1200 Liquid Chromatography (Agilent, USA, column: Ultimate 4.6 mm×50 mm, 5 μm, mobile phase A: 0.1% formic acid in water; mobile phase B: acetonitrile). Microwave reactions were run on an Initiator 2.5 Microwave Synthesizer (Biotage, Sweden).

For exemplary compounds disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%.

Example 1: Preparation of Compounds

General Procedure for the Synthesis of Thiophene Sulfonamideureas

Scheme 1

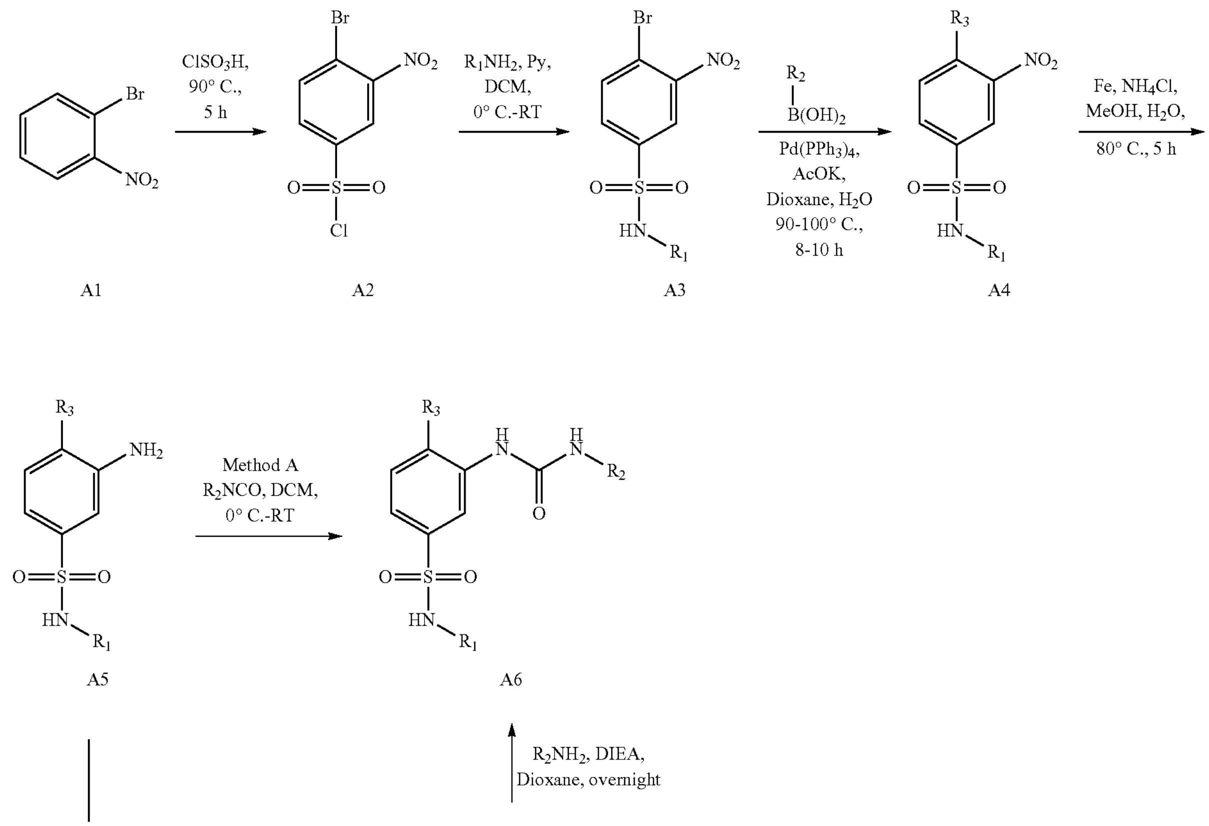

-continued

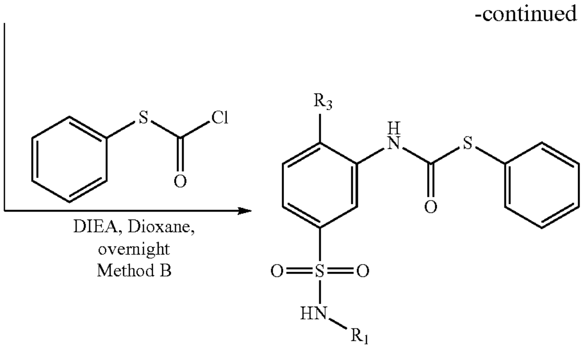

A7

4-bromo-3-nitro-N-phenylbenzenesulfonyl chloride (A2)

A round bottom flask containing chlorosulfonic acid (50 mL) was cooled to 0° C. and to which was added 1-bromo-2-nitrobenzene (5 g) in portions. The reaction mixture was then heated to 90° C. for 5 h and poured slowly into crushed ice. The product was then extracted with ethyl acetate, combined extracts were dried on anhydrous sodium sulfate and concentrated under vacuum. The residue obtained was then triturated with pentane, after decantation of pentane and drying yielded the sulfonyl chloride A2 which was used without further purification for the next step.

General Procedure for the Preparation of Sulfonamides A3

To a solution of amine (1 equiv.) and pyridine (3 equiv.) in dichloromethane was added sulfonyl chloride (A2) (1.2 equiv.) at 0° C. and stirred at room temperature for overnight. After completion of the reaction, the reaction mixture was diluted with dichloromethane, washed with dilute HCl and brine, dried over anhydrous sodium sulfate, filtered and concentrated under vacuum. The crude products were then purified by Silica gel column chromatography to afford sulfonamides (A3).

The following compounds were similarly prepared according to the above procedure:

4-bromo-3-nitro-N-phenylbenzenesulfonamide

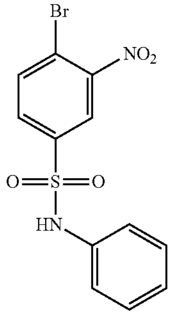 [SMILES: O=[N+]([O-])c1cc(S(=O)(=O)Nc2ccccc2)ccc1Br]

$^1$H NMR (400 MHz, DMSO-$d_3$) δ: 7.05-7.15 (m, 3H), 7.25-7.3 (m, 2H), 7.81 (d, 1H), 8.12 (d, 1H), 8.32 (s, 1H), 10.55 (s, 1H).

4-bromo-N-cyclopropyl-3-nitrobenzenesulfonamide

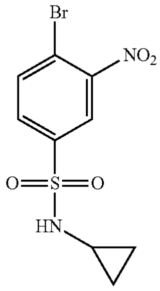 [SMILES: O=[N+]([O-])c1cc(S(=O)(=O)NC2CC2)ccc1Br]

$^1$H NMR (400 MHz, DMSO-$d_3$) δ: 0.35-0.4 (m, 2H), 0.45-0.55 (m, 2H), 2.15-2.25 (m, 1H), 7.93 (d, 1H), 8.2 (d, 1H), 8.26 (d, 1H), 8.39 (s, 1H).

4-bromo-N-(1-cyanocyclopropyl)-3-nitrobenzenesulfonamide

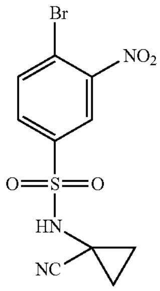 [SMILES: N#CC1(NS(=O)(=O)c2ccc(Br)c([N+](=O)[O-])c2)CC1]

$^1$H NMR (400 MHz, DMSO-$d_3$) δ: 1.3-1.35 (m, 2H), 1.45-1.52 (m, 2H), 8.0 (d, 1H), 8.22 (d, 1H), 8.42 (s, 1H), 9.52 (s, 1H).

4-bromo-3-nitro-N-(oxetan-3-yl)benzenesulfonamide

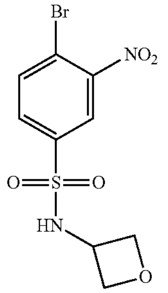 [SMILES: O=[N+]([O-])c1cc(S(=O)(=O)NC2COC2)ccc1Br]

$^1$H NMR (400 MHz, DMSO-$d_3$) δ: 4.25-4.35 (m, 2H), 4.4-4.5 (m, 1H), 4.52-4.6 (m, 2H), 7.92 (d, 1H), 7.15 (d, 1H), 8.38 (s, 1H), 8.92 (d, 1H).

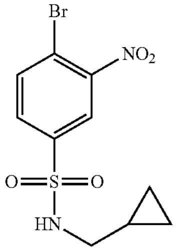 [SMILES: O=[N+]([O-])c1cc(S(=O)(=O)NCC2CC2)ccc1Br]

$^1$H NMR (400 MHz, $CD_3OD$) δ: 0.05-0.1 (m, 2H), 0.3-0.4 (m, 2H), 0.72-0.82 (m, 1H), 2.75 (t, 2H), 7.94 (d, 1H), 8.1-8.2 (m, 2H), 8.4 (s, 1H).

4-bromo-3-nitro-N-(2,2,2-trifluoroethyl)benzenesulfonamide

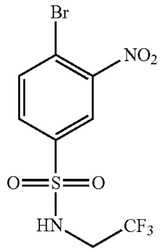 [SMILES: O=[N+]([O-])c1cc(S(=O)(=O)NCC(F)(F)F)ccc1Br]

$^1$H NMR (400 MHz, $CD_3OD$) δ: 3.7-3.82 (m, 2H), 7.95 (d, 1H), 8.18 (d, 1H), 8.4 (s, 1H), 9.0 (t, 1H).

4-bromo-3-nitro-N-(tetrahydro-2H-pyran-4-yl)benzenesulfonamide

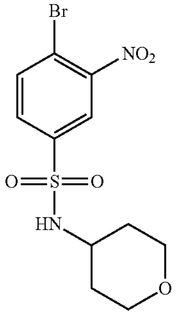 [SMILES: O=[N+]([O-])c1cc(S(=O)(=O)NC2CCOCC2)ccc1Br]

$^1$H NMR (400 MHz, DMSO-$d_6$) δ: 1.15 (t, 1H), 1.3-1.4 (m, 2H), 1.46-1.58 (m, 2H), 3.2-3.25 (m, 2H), 3.66-3.72 (m, 2H), 7.96 (d, 1H), 8.14-8.2 (m, 2H), 8.4 (s, 1H).

4-((4-bromo-3-nitrophenyl)sulfonyl)morpholine

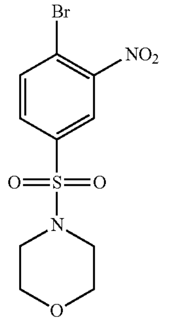 [SMILES: O=[N+]([O-])c1cc(S(=O)(=O)N2CCOCC2)ccc1Br]

$^1$H NMR (400 MHz, DMSO-$d_6$) δ: 2.93-3.0 (m, 4H), 3.6-3.64 (m, 4H), 7.87 (d, 1H), 8.2 (d, 1H), 8.32 (s, 1H).

4-ethyl-3-nitro-N-(2,2,2-trifluoroethyl)benzenesulfonamide

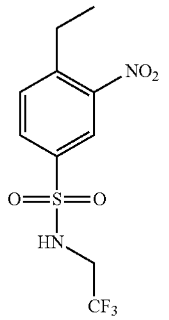

$^1$H NMR (400 MHz, DMSO-$d_6$) δ: 1.21 (t, 3H), 2.9 (q, 2H), 3.7-3.85 (m, 2H), 7.9 (d, 1H), 8.05 (d, 1H), 8.32 (s, 1H), 8.85 (t, 1H).

Representative Procedure for Cross Coupling to Yield A4:

A mixture of compound A3 (1.0 equiv.), boronic acid or boronate ester (1.5 equiv.), potassium acetate (3.0 equiv.) and tetrakis(triphenylphosphine)palladium(0) (0.1 equiv.) in mixture of dioxane-water (10:1) was stirred at 90-100° C. for 8-10 h. The reaction was cooled to room temperature and extracted in ethyl acetate. The organic extracts were subjected to an aqueous work-up, dried over anhydrous sodium sulfate, and concentrated under vacuum. The crude material was purified by column chromatography on silica gel (hexanes/ethyl acetate) to afford compound A4.

The following compounds were similarly prepared according to the above procedure using the appropriate boronic acid or boronate ester:

3-nitro-N-phenyl-4-(thiophen-3-yl)benzenesulfonamide

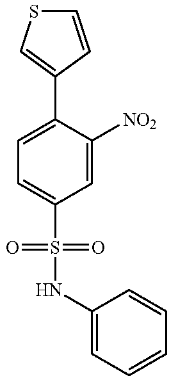 [SMILES: O=[N+]([O-])c1cc(S(=O)(=O)Nc2ccccc2)ccc1-c1ccsc1]

$^1$H NMR (400 MHz, $CDCl_3$) δ: 6.81 (s, 1H), 7.05 (d, 1H), 7.13 (d, 2H), 7.18-7.35 (m, 3H), 7.36-7.4 (m, 2H), 7.55 (d, 1H), 7.9 (d, 1H), 8.15 (s, 1H).

N-cyclopropyl-3-nitro-4-(thiophen-3-yl)benzenesulfonamide

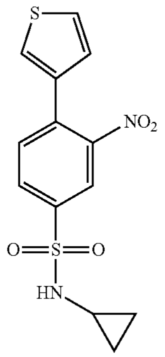 [SMILES: O=[N+]([O-])c1cc(S(=O)(=O)NC2CC2)ccc1-c1ccsc1]

$^1$H NMR (400 MHz, $CDCl_3$) δ: 0.6-0.75 (m, 4H), 2.3-2.4 (m, 1H), 5.05 (s, 1H), 7.1 (t, 1H), 7.42 (m, 2H), 7.7 (d, 1H), 8.1 (d, 1H), 8.28 (s, 1H).

N-(1-cyanocyclopropyl)-3-nitro-4-(thiophen-3-yl)benzenesulfonamide

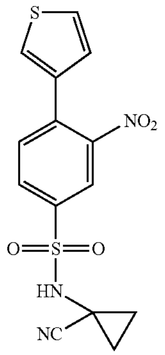 [SMILES: N#CC1(NS(=O)(=O)c2ccc(-c3ccsc3)c([N+](=O)[O-])c2)CC1]

$^1$H NMR (400 MHz, $CDCl_3$) δ: 1.3-1.36 (m, 2H), 1.45-1.5 (m, 2H), 7.2 (d, 1H), 7.7 (t, 1H), 7.82 (s, 1H), 7.95 (d, 1H), 8.15 (d, 1H), 8.36 (s, 1H), 9.45 (s, 1H).

3-nitro-N-(oxetan-3-yl)-4-(thiophen-3-yl)benzenesulfonamide

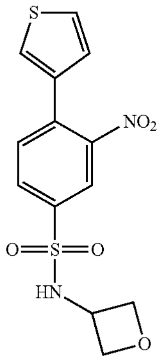 [SMILES: O=[N+]([O-])c1cc(S(=O)(=O)NC2COC2)ccc1-c1ccsc1]

$^1$H NMR (400 MHz, DMSO-$d_6$) δ: 4.3-4.38 (m, 2H), 4.42-4.55 (m, 1H), 4.56-4.6 (m, 2H), 7.2 (d, 1H), 7.7 (t, 1H), 7.8 (s, 1H), 7.85 (d, 1H), 8.05 (d, 1H), 8.3 (s, 1H), 8.9 (d, 1H). ESMS: Calculated: 340.32, Observed: 339.26 $(M-H)^-$.

2-nitro-N-(2,2,2-trifluoroethyl)-[1,1'-biphenyl]-4-sulfonamide

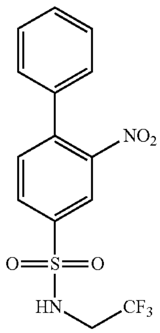 [SMILES: O=[N+]([O-])c1cc(S(=O)(=O)NCC(F)(F)F)ccc1-c1ccccc1]

$^1$H NMR (400 MHz, $CDCl_3$) δ: 3.8 (q, 2H), 5.1 (br s, 1H), 7.27-7.34 (m, 2H), 7.4-7.48 (m, 3H), 7.62 (d, 1H), 8.06 (d, 1H), 8.32 (s, 1H).

N-cyclopropyl-2-nitro-[1,1'-biphenyl]-4-sulfonamide

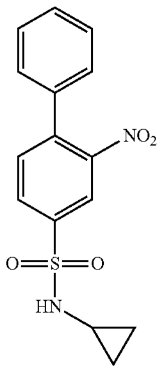 [SMILES: O=[N+]([O-])c1cc(S(=O)(=O)NC2CC2)ccc1-c1ccccc1]

$^1$H NMR (400 MHz, $CDCl_3$) δ: 0.65-0.72 (m, 4H), 2.32-2.4 (m, 1H), 5.01 (s, 1H), 7.28-7.34 (m, 2H), 7.45-7.5 (m, 3H), 7.62 (d, 1H), 8.12 (d, 1H), 8.35 (s, 1H). ESMS: Calculated: 318.35, Observed: 317.42 $(M-1)^-$.

2-nitro-N-(oxetan-3-yl)-[1,1'-biphenyl]-4-sulfonamide

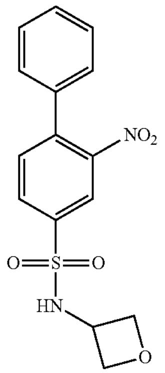 [SMILES: O=[N+]([O-])c1cc(S(=O)(=O)NC2COC2)ccc1-c1ccccc1]

$^1$H NMR (400 MHz, DMSO-$d_6$) δ: 4.32-4.4 (m, 2H), 4.45-4.62 (m, 3H), 7.4-7.6 (m, 5H), 7.82 (d, 1H), 8.12 (d, 1H), 8.35 (s, 1H), 8.93 (d, 1H).

N-(1-cyanocyclopropyl)-2-nitro-[1,1'-biphenyl]-4-sulfonamide

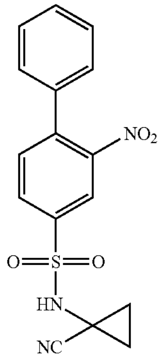 [SMILES: N#CC1(NS(=O)(=O)c2ccc(-c3ccccc3)c([N+](=O)[O-])c2)CC1]

$^1$H NMR (400 MHz, DMSO-$d_6$) δ: 1.32 (t, 2H), 1.46 (t, 2H), 7.34-7.5 (m, 5H), 7.85 (d, 1H), 8.17 (d, 1H), 8.4 (s, 1H), 9.46 (s, 1H). LCMS: Calculated: 343.36, Observed: 341.85 $(M-1)^-$.

N-cyclopropyl-3'-methyl-2-nitro-[1,1'-biphenyl]-4-sulfonamide

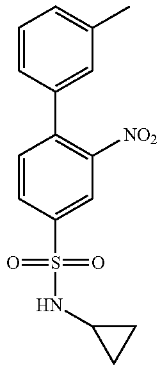 [SMILES: Cc1cccc(-c2ccc(S(=O)(=O)NC3CC3)cc2[N+](=O)[O-])c1]

$^1$H NMR (400 MHz, DMSO-$d_6$) δ: 0.42-0.57 (m, 4H), 2.12 (m, 1H), 2.33 (s, 3H), 7.15-7.4 (m, 4H), 7.8 (d, 1H), 8.1 (d, 1H), 8.25 (s, 1H), 8.31 (s, 1H).

3'-hydroxy-2-nitro-N-phenyl-[1,1'-biphenyl]-4-sulfonamide

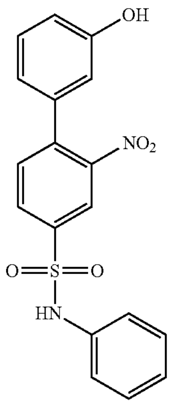 [SMILES: O=[N+]([O-])c1cc(S(=O)(=O)Nc2ccccc2)ccc1-c1cccc(O)c1]

$^1$H NMR (400 MHz, DMSO-$d_6$) δ: 6.66 (s, 1H), 6.73 (d, 1H), 6.82 (d, 1H), 7.06-7.5 (m, 6H), 7.72 (d, 1H), 8.0 (d, 1H), 8.24 (s, 1H), 9.72 (s, 1H), 10.56 (s, 1H).

For the following compounds of general formula A4, a similar cross-coupling procedure as described for Scheme 1, but replacing potassium acetate and palladium tetrakis-triphenylphosphine with equivalent amounts of cesium carbonate and $Pd(PPh3)_2Cl_2$, respectively:

N-(cyclopropylmethyl)-4-(3,6-dihydro-2H-pyran-4-yl)-3-nitrobenzenesulfonamide

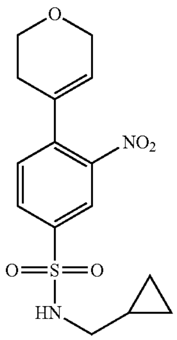 [SMILES: O=[N+]([O-])c1cc(S(=O)(=O)NCC2CC2)ccc1C1=CCOCC1]

$^1$H NMR (400 MHz, DMSO-$d_6$) δ: 0.05-0.12 (m, 2H), 0.3-0.4 (m, 2H), 0.75-0.85 (m, 1H), 2.26 (t, 2H), 2.72 (t, 2H), 3.8 (t, 2H), 4.18 (d, 2H), 5.82 (t, 1H), 7.7 (d, 1H), 8.0-8.06 (m, 2H), 8.3 (s, 1H).

4-(3,6-dihydro-2H-pyran-4-yl)-3-nitro-N-(2,2,2-trifluoroethyl)benzenesulfonamide

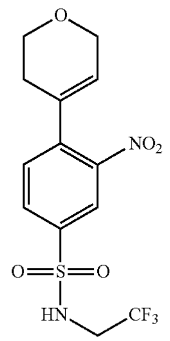 [SMILES: O=[N+]([O-])c1cc(S(=O)(=O)NCC(F)(F)F)ccc1C1=CCOCC1]

$^1$H NMR (400 MHz, $CD_3OD$) δ: 2.35 (t, 2H), 3.65-3.8 (m, 2H), 3.9 (t, 2H), 4.22 (d, 2H), 5.8 (t, 1H), 7.6 (d, 1H), 8.1 (d, 1H), 8.32 (s, 1H).

4-(3,6-dihydro-2H-pyran-4-yl)-3-nitro-N-phenylbenzenesulfonamide

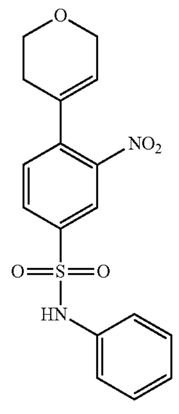 [SMILES: O=[N+]([O-])c1cc(S(=O)(=O)Nc2ccccc2)ccc1C1=CCOCC1]

$^1$H NMR (400 MHz, $CD_3OD$) δ: 2.21 (t, 2H), 3.75 (t, 2H), 4.12 (d, 2H), 5.8 (t, 1H), 7.05-7.15 (m, 3H), 7.22-7.3 (m, 2H), 7.64 (d, 1H), 7.98 (d, 1H), 8.22 (s, 1H), 10.55 (s, 1H). ESMS (neg): Calculated 360.38, Observed 359.48 $(M-H)^-$.

N-(cyclopropylmethyl)-4-(3,4-dihydro-2H-pyran-6-yl)-3-nitrobenzenesulfonamide (17a)

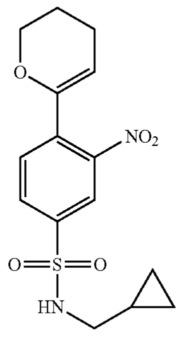 [SMILES: O=[N+]([O-])c1cc(S(=O)(=O)NCC2CC2)ccc1C1=CCCCO1]

$^1$H NMR (400 MHz, DMSO-$d_6$) δ: 0.05-0.1 (m, 2H), 0.3-0.4 (m, 2H), 0.7-0.82 (m, 1H), 1.75-1.85 (m, 2H), 2.15-2.2 (m, 2H), 2.72 (t, 2H), 3.95 (t, 2H), 5.4 (t, 1H), 7.8 (d, 1H), 8.0-8.1 (m, 2H), 8.15 (s, 1H).

4-(3,4-dihydro-2H-pyran-6-yl)-3-nitro-N-(2,2,2-trifluoroethyl)benzenesulfonamide (17b)

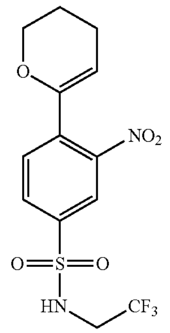 [SMILES: O=[N+]([O-])c1cc(S(=O)(=O)NCC(F)(F)F)ccc1C1=CCCCO1]

$^1$H NMR (400 MHz, DMSO-$d_6$) δ: 1.75-1.85 (m, 2H), 2.15-2.22 (m, 2H), 3.72-3.82 (m, 2H), 3.95 (t, 2H), 5.4 (t, 1H), 7.8 (d, 1H), 8.05 (d, 1H), 8.2 (s, 1H), 8.92 (s, 1H).

4-(3,4-dihydro-2H-pyran-6-yl)-3-nitro-N-phenylbenzenesulfonamide (17c)

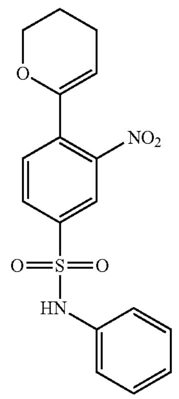 [SMILES: O=[N+]([O-])c1cc(S(=O)(=O)Nc2ccccc2)ccc1C1=CCCCO1]

$^1$H NMR (400 MHz, DMSO-$d_6$) δ: 1.7-1.8 (m, 2H), 2.1-2.2 (m, 2H), 3.9 (t, 2H), 5.4 (t, 1H), 7.05-7.11 (m, 3H), 7.22-7.3 (m, 2H), 7.75 (d, 1H), 7.9 (d, 1H), 8.1 (s, 1H), 10.5 (s, 1H).

4-(3,4-dihydro-2H-pyran-5-yl)-3-nitro-N-(2,2,2-trifluoroethyl)benzenesulfonamide

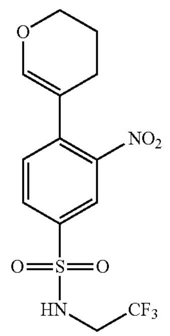 [SMILES: O=[N+]([O-])c1cc(S(=O)(=O)NCC(F)(F)F)ccc1C1=COCCC1]

$^1$H NMR (400 MHz, DMSO-$d_6$) δ: 1.9 (t, 2H), 2.1-2.2 (m, 2H), 3.72-3.85 (m, 2H), 4.0 (t, 2H), 6.64 (s, 1H), 7.7 (d, 1H), 8.0 (d, 1H), 8.25 (s, 1H), 8.85 (t, 1H); ESMS: Calculated; 366.31, Observed; 365.31 $(M-H)^-$.

4-(2,5-dihydrofuran-3-yl)-3-nitro-N-(2,2,2-trifluoroethyl)benzene sulfonamide

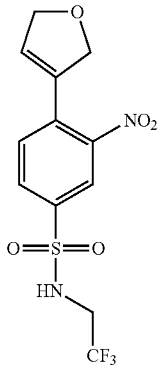 [SMILES: O=[N+]([O-])c1cc(S(=O)(=O)NCC(F)(F)F)ccc1C1=CCOC1]

A round bottom flask was charged with dry DMF and was purged using $N_2$ for 10 min., then to which 4-bromo-3-nitro-N-(2,2,2-trifluoroethyl)benzenesulfonamide (1 equiv.), 2,5-dihydrofuran (1.5 equiv.), (p-tolyl)$_3$P (0.1 equiv.) DIEA (3 equiv.) and Pd(OAc)$_2$ (0.1 equiv.) were added. The reaction mixture was then heated to 100° C. for 3 h. The reaction mixture was then diluted by the addition of ethyl acetate, filtered through a pad of celite, combined organic layers were washed with water, brine, dried over anhydrous sodium sulfate, filtered, and concentrated under vacuum. The crude product was then purified by silica gel column chromatography (35% ethyl acetate/hexane) to afford a residue which was used without further purification.

4-(4,5-dihydrofuran-2-yl)-3-nitro-N-(2,2,2-trifluoroethyl)benzene sulfonamide

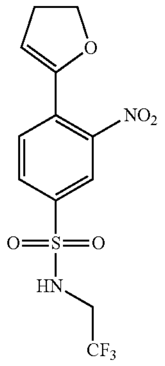 [SMILES: O=[N+]([O-])c1cc(S(=O)(=O)NCC(F)(F)F)ccc1C1=CCCO1]

4-(4,5-dihydrofuran-2-yl)-3-nitro-N-(2,2,2-trifluoroethyl)benzene sulfonamide was prepared from 2,3-dihydrofuran (1.5 equiv.) and the arylbromide by following the method as described for the preparation of 4-(2,5-dihydrofuran-3-yl)-3-nitro-N-(2,2,2-trifluoroethyl)benzene sulfonamide. $^1$H NMR (400 MHz, DMSO-$d_6$) δ: 2.4-2.45 (m, 1H), 3.2-3.5 (m, 1H), 3.7-3.82 (m, 2H), 5.0 (s, 1H), 6.05 (t, 1H), 6.7 (s, 1H), 7.82 (d, 1H), 8.2 (d, 1H), 8.46 (s, 1H), 8.95 (t, 1H); LCMS: Calculated; 352.29, Observed; 353.05 $(M+H)^+$.

General Procedure for the Preparation of Compounds A5:

To a solution of compound A4 (1 equiv.) in methanol-water (2:1) was added iron powder (5 equiv.) and ammonium chloride (3 equiv.). The reaction mixture was then stirred at 80° C. for 5 h and monitored by TLC. After completion of the reaction, the reaction mixture was filtered and the filtrate was concentrated. The residue was then dissolved in water and extracted with ethyl acetate, combined extracts were washed with brine, dried over anhydrous sodium sulfate, filtered and evaporated, triturated the residue with pentane and after decantation of pentane, the residue was dried to afford compound A5 and were used in the next step without further purification.

The following compounds were similarly prepared according to the above procedure:

3-amino-N-phenyl-4-(thiophen-3-yl)benzenesulfonamide

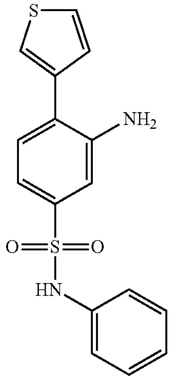 [SMILES: Nc1cc(S(=O)(=O)Nc2ccccc2)ccc1-c1ccsc1]

$^1$H NMR (400 MHz, $CDCl_3$) δ: 4.01 (br s, 2H), 6.66 (s, 1H), 7.08-7.2 (m, 5H), 7.2-7.3 (m, 4H), 7.4-7.45 (m, 2H).

3-amino-N-cyclopropyl-4-(thiophen-3-yl)benzenesulfonamide

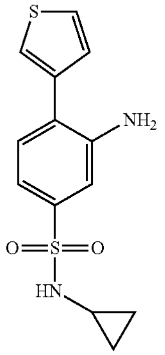

$^1$H NMR (400 MHz, $CD_3OD$) δ: 0.45-0.6 (m, 4H), 2.15-2.2 (m, 1H), 7.12-7.2 (d, 1H), 7.25-7.35 (m, 3H), 7.54-7.6 (m, 2H). LCMS: Calculated; 294.39, Observed; 295.00 $(M+H)^+$.

3-amino-N-(1-cyanocyclopropyl)-4-(thiophen-3-yl)benzenesulfonamide

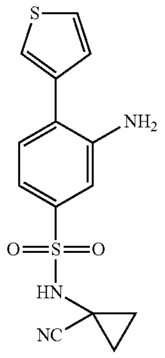

LCMS: Calculated; 319.40, Observed; 320.00 $(M+H)^+$.

3-amino-N-(oxetan-3-yl)-4-(thiophen-3-yl)benzenesulfonamide

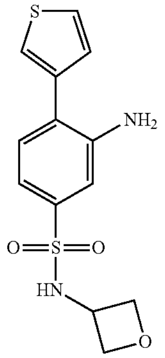 [SMILES: Nc1cc(S(=O)(=O)NC2COC2)ccc1-c1ccsc1]

LCMS: Calculated; 310.39, Observed; 311.10 $(M+H)^+$.

2-amino-N-(2,2,2-trifluoroethyl)-[1,1'-biphenyl]-4-sulfonamide

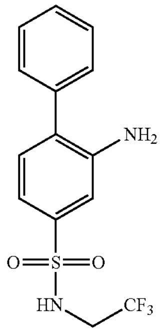 [SMILES: Nc1cc(S(=O)(=O)NCC(F)(F)F)ccc1-c1ccccc1]

$^1$H NMR (400 MHz, DMSO-$d_6$) δ: 3.6-3.7 (m, 2H), 5.25 (s, 2H), 7.02 (d, 1H), 7.14 (d, 1H), 7.2 (s, 1H), 7.35-7.5 (m, 5H), 8.45 (br s, 1H). LCMS: Calculated: 330.33, Observed: 331.10 $(M+H)^+$.

5-amino-N-(4-chlorophenyl)-2-methylbenzenesulfonamide

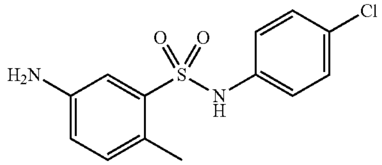 [SMILES: Cc1ccc(N)cc1S(=O)(=O)Nc1ccc(Cl)cc1]

$^1$H NMR (400 MHz, DMSO-$d_6$) δ: 2.34 (s, 3H), 5.32 (s, 2H), 6.62 (d, 1H), 6.94 (d, 1H), 7.03 (d, 2H), 7.13 (s, 1H), 7.26 (d, 2H), 10.34 (s, 1H). LCMS: Calculated; 296.77, Observed; 337.95 $(M+HCO2)^+$.

5-amino-N-(2-chlorophenyl)-2-methylbenzenesulfonamide

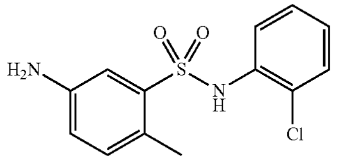 [SMILES: Cc1ccc(N)cc1S(=O)(=O)Nc1ccccc1Cl]

$^1$H NMR (400 MHz, DMSO-$D_6$) δ: 2.4 (s, 3H), 5.23 (s, 2H), 6.63 (d, 1H), 7.0 (m, 2H), 7.1-7.3 (m, 3H), 7.4 (d, 1H), 9.75 (s, 1H).

5-amino-N-(3-chlorophenyl)-2-methylbenzenesulfonamide

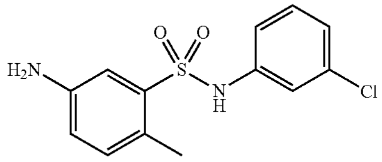

$^1$H NMR (400 MHz, DMSO-$D_6$) δ: 2.45 (s, 3H), 5.36 (s, 2H), 6.63 (d, 1H), 6.93-7.1 (m, 5H), 7.19-7.28 (m, 2H), 10.46 (s, 1H).

5-amino-N-(4-hydroxyphenyl)-2-methylbenzenesulfonamide

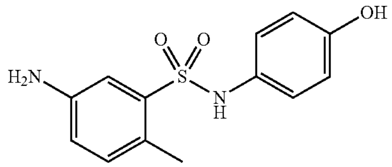

$^1$H NMR (400 MHz, DMSO-$D_6$) δ: 2.32 (s, 3H), 5.22 (s, 2H), 6.53-6.6 (m, 3H), 6.8 (d, 2H), 6.92 (d, 1H), 7.0 (s, 1H), 9.2 (s, 1H), 9.55 (s, 1H). LCMS: Calculated 278.33, Observed; 278.80 $(M+H)^+$.

3-amino-N-(4-chlorophenyl)benzenesulfonamide

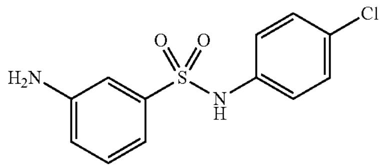 [SMILES: Nc1cccc(S(=O)(=O)Nc2ccc(Cl)cc2)c1]

LCMS: Calculated; 282.75, Observed; 283.50 $(M+H)^+$.

3-amino-4-ethyl-N-(2,2,2-trifluoroethyl)benzenesulfonamide

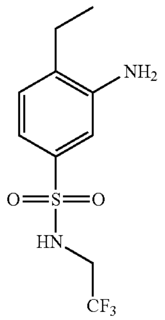 [SMILES: CCc1ccc(S(=O)(=O)NCC(F)(F)F)cc1N]

$^1$H NMR (400 MHz, DMSO-$d_6$) δ: 1.1 (t, 3H), 2.5 (q, 2H), 3.5-3.65 (m, 2H), 5.35 (s, 2H), 6.9 (d, 1H), 7.05 (s, 1H), 7.1 (d, 1H), 8.32 (t, 1H); ESMS: Calculated: 282.28, Observed: 283.15 $(M+H)^+$.

3-amino-4-ethynyl-N-(2,2,2-trifluoroethyl)benzenesulfonamide

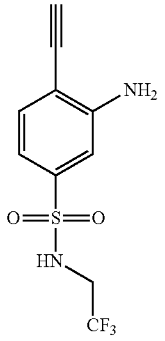 [SMILES: C#Cc1ccc(S(=O)(=O)NCC(F)(F)F)cc1N]

$^1$H NMR (400 MHz, $CDCl_3$) δ: 3.54 (s, 1H), 3.6-3.7 (m, 2H), 4.52 (br s, 2H), 4.8 (t, 1H), 7.12 (d, 1H), 71.6 (s, 1H), 7.45 (d, 1H). LCMS: Calculated; 278.25, Observed; 279.10 $(M+H)^+$.

2-amino-N-cyclopropyl-[1,1'-biphenyl]-4-sulfonamide

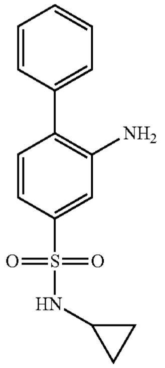

$^1$H NMR (400 MHz, DMSO-$d_6$) δ: 0.4-0.53 (m, 4H), 2.07-2.15 (m, 1H), 5.23 (s, 2H), 7.01 (d, 1H), 7.15 (d, 1H), 7.21 (s, 1H), 7.32-7.5 (m, 5H), 7.8 (s, 1H). LCMS: Calculated: 288.36, Observed: 289.15 $(M+H)^+$.

2-amino-N-(oxetan-3-yl)-[1,1'-biphenyl]-4-sulfonamide

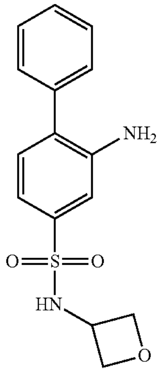

$^1$H NMR (400 MHz, DMSO-$d_6$) δ: 4.2-4.4 (m, 4H), 4.42-4.58 (m, 3H), 7.07 (d, 1H), 7.24 (s, 1H), 7.4-7.6 (m, 5H), 8.39 (d, 1H), 8.57 (d, 1H). LCMS: Calculated: 304.36, Observed: 305.10 $(M+H)^+$.

2-amino-N-(1-cyanocyclopropyl)-[1,1'-biphenyl]-4-sulfonamide

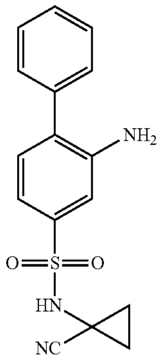 [SMILES: N#CC1(NS(=O)(=O)c2ccc(-c3ccccc3)c(N)c2)CC1]

$^1H$ NMR (400 MHz, DMSO-$d_6$) δ: 1.15 (t, 2H), 1.4 (t, 2H), 5.32 (s, 2H), 7.0-7.25 (m, 5H), 7.3-7.5 (m, 3H), 8.91 (s, 1H). LCMS: Calculated: 313.37, Observed: 314.15 $(M+H)^+$.

2-amino-3'-methyl-N-(tetrahydro-2H-pyran-4-yl)-[1,1'-biphenyl]-4-sulfonamide

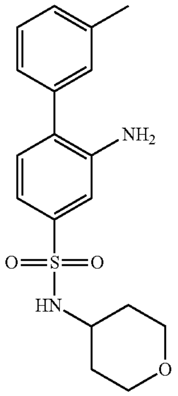 [SMILES: Cc1cccc(-c2ccc(S(=O)(=O)NC3CCOCC3)cc2N)c1]

LCMS: calculated: 346.44, Observed: 347.10 $(M+H)^+$.

2-amino-N-cyclopropyl-3'-methyl-[1,1'-biphenyl]-4-sulfonamide

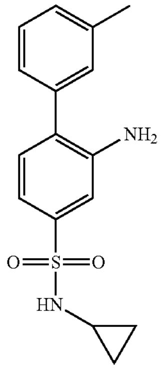

LCMS: calculated: 302.39, Observed: 303.15 $(M+H)^+$.

2-amino-3'-hydroxy-N-phenyl-[1,1'-biphenyl]-4-sulfonamide

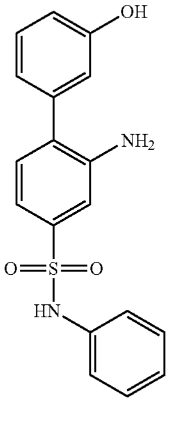 [SMILES: Nc1cc(S(=O)(=O)Nc2ccccc2)ccc1-c1cccc(O)c1]

$^1H$ NMR (400 MHz, DMSO-$d_6$) δ: 5.21 (s, 2H), 6.73 (t, 3H), 6.93-7.18 (m, 6H), 7.2-7.25 (m, 3H), 9.52 (s, 1H), 10.21 (s, 1H). LCMS: Calculated: 340.09, Observed: 341.10 $(M+H)^+$.

3-amino-N-(2,2,2-trifluoroethyl)benzenesulfonamide

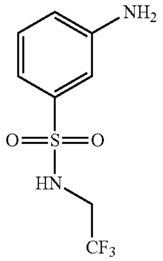 [SMILES: Nc1cccc(S(=O)(=O)NCC(F)(F)F)c1]

$^1H$ NMR (400 MHz, DMSO-$d_6$) δ: 3.6-3.72 (m, 2H), 7.1 (d, 1H), 7.2-7.35 (m, 2H), 7.4 (t, 1H), 8.6 (t, 1H). ESMS: Calculated; 254.23, Observed; 253.30 $(M-)^-$.

3-amino-N-(cyclopropylmethyl)-4-(3,6-dihydro-2H-pyran-4-yl)benzenesulfonamide

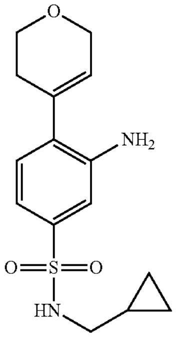 [SMILES: Nc1cc(S(=O)(=O)NCC2CC2)ccc1C1=CCOCC1]

$^1H$ NMR (400 MHz, DMSO-$d_6$) δ: 0.05-0.12 (m, 2H), 0.3-0.4 (m, 2H), 0.78-0.86 (m, 1H), 2.25 (t, 2H), 2.64 (t, 2H), 3.81 (t, 2H), 4.19 (d, 2H), 5.25 (br s, 2H), 5.8 (t, 1H), 6.9 (d, 1H), 7.02 (d, 1H), 7.08 (s, 1H), 7.5 (t, 1H).

3-amino-4-(3,6-dihydro-2H-pyran-4-yl)-N-(2,2,2-trifluoroethyl)benzenesulfonamide

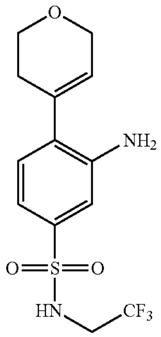 [SMILES: Nc1cc(S(=O)(=O)NCC(F)(F)F)ccc1C1=CCOCC1]

ESMS: Calculated; 336.33, Observed; 337.10 $(M+H)^+$.

Alternative Method for the Preparation of Compounds A5:

To a solution of compound A3 (1 equiv.) in methanol was added 20% palladium hydroxide (20% w/w) and the reaction mixture was stirred under hydrogen atmosphere for 24 h. After completion of the reaction, reaction mixture was filtered, evaporated the solvent under vacuum, residues was triturated with pentane, decanted the solvent and dried to afford compound A4 and was used in the next step without further purification. The following compounds were similarly prepared according to the alternative procedure for reduction of Compound A3 to Compound A4:

3-amino-N-(cyclopropylmethyl)-4-(tetrahydro-2H-pyran-2-yl)benzenesulfonamide

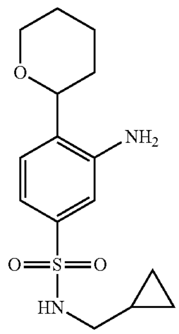 [SMILES: Nc1cc(S(=O)(=O)NCC2CC2)ccc1C1CCCCO1]

LCMS: Calculated: 310.41, Observed: 311.15 $(M+H)^+$.

3-amino-4-(tetrahydro-2H-pyran-2-yl)-N-(2,2,2-trifluoroethyl)benzenesulfonamide

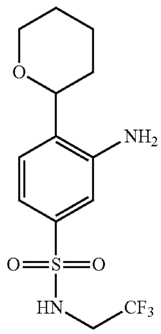 [SMILES: Nc1cc(S(=O)(=O)NCC(F)(F)F)ccc1C1CCCCO1]

LCMS: Calculated: 338.35, Observed: 339.10 $(M+H)^+$.

3-amino-N-phenyl-4-(tetrahydro-2H-pyran-2-yl)benzenesulfonamide

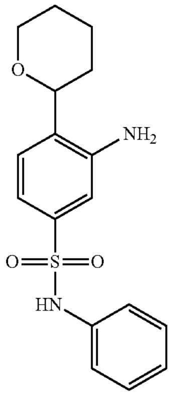 [SMILES: Nc1cc(S(=O)(=O)Nc2ccccc2)ccc1C1CCCCO1]

LCMS: Calculated: 332.42, Observed: 333.50 $(M+H)^+$.

3-amino-4-(tetrahydro-2H-pyran-3-yl)-N-(2,2,2-trifluoroethyl)benzenesulfonamide

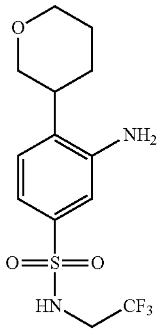 [SMILES: Nc1cc(S(=O)(=O)NCC(F)(F)F)ccc1C1CCCOC1]

ESMS: Calculated; 338.35, Observed; 337.33 $(M-H)^-$.

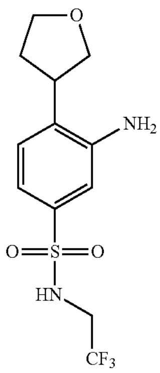 [SMILES: Nc1cc(S(=O)(=O)NCC(F)(F)F)ccc1C1CCOC1]

$^1H$ NMR (400 MHz, DMSO-$d_6$) δ: 1.8-1.9 (m, 1H), 2.2-2.3 (m, 1H), 3.4-3.48 (m, 1H), 3.52-3.62 (m, 3H), 3.7-3.8 (m, 1H), 3.85-3.92 (m, 1H), 3.98 (t, 1H), 5.5 (br s, 2H), 6.92 (d, 1H), 7.06 (s, 1H), 7.2 (d, 1H), 8.36 (t, 1H).

3-amino-4-(4,5-dihydrofuran-2-yl)-N-(2,2,2-trifluoroethyl)benzene sulfonamide

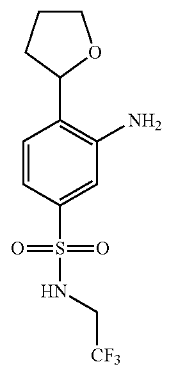 [SMILES: Nc1cc(S(=O)(=O)NCC(F)(F)F)ccc1C1CCCO1]

$^1$H NMR (400 MHz, DMSO-$d_6$) δ: 1.5-1.6 (m, 1H), 1.85-1.95 (m, 2H), 2.26-2.38 (m, 1H), 3.55-3.65 (m, 2H), 3.7-3.8 (m, 1H), 3.97-4.05 (m, 1H), 4.82 (t, 1H), 5.4 (br s, 2H), 6.94 (d, 1H), 7.08 (s, 1H), 7.25 (d, 1H), 8.35 (t, 1H).

3-amino-4-bromo-N-phenylbenzenesulfonamide

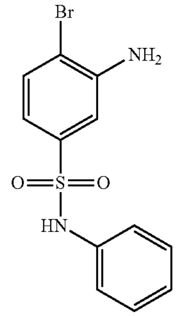 [SMILES: Nc1cc(S(=O)(=O)Nc2ccccc2)ccc1Br]

LCMS: Calculated: 327.20, Observed: 328.15 $(M+H)^+$.

General Procedure for the Preparation of Ureas A6

Method A:

The urea compounds were prepared by using either commercially available isocyanates or using isocyanates prepared via method described below from respective amines.

General Procedure for the Preparation of Isocyanates:

To a stirred solution of amine (1 equiv.) in dichloromethane was added triphosgene (0.35 equiv.) followed by triethyl amine (3 equiv.) at 0° C. The reaction mixture was stirred at room temperature and completion of the reaction was monitored by TLC. The reaction mixture was then dilute with dichloromethane, removed the precipitate by filtration and evaporated the filtrate to afford isocyanate.

General Procedure for the Preparation of Urea:

A solution of respective compound A5 (1 equiv.) in dichloromethane was cooled to 0° C. and to which a solution of respective isocyanate (1.1 equiv.) in dichloromethane was added. The reaction was brought to room temperature and stirred until completion of the reaction (monitored by TLC). The reaction mixture was then evaporated under vacuum and all the crude products were purified either by silica gel column chromatography or by preparative column chromatography to afford urea A6.

Method B:

To a solution of thiophenol (1 equivalent) in DCM was added triphosgene (0.6 equivalent) and pyridine (3 equivalents) at 0° C. The reaction mixture was brought to room temperature and stirred for a period of 5 h. After 5 h, the solvent was evaporated and the residue was dissolved in dioxane, the scaffold A5 (1 equivalent) was added and stirred for 12 h at room temperature. The reaction mixture was treated with water and extracted with ethyl acetate. The combined organic fractions were washed with brine, dried, concentrated and purified by column chromatography to obtain the thiocarbamates A7.

The thiocarbamate A7 (1 equivalent) was dissolved in dioxane to which respective amine (1 equivalent) and diisopropyl ethylamine (3 equivalents) were added and stirred at room temperature for overnight. After completion of the reaction as indicated by TLC, water was added to the reaction mixture and extracted with ethyl acetate. The organic layers were pooled, brine washed, dried, concentrated and purified by Reverse Phase Prep-HPLC to provide urea compounds A6.

S-phenyl (5-(N-phenylsulfamoyl)-2-(thiophen-3-yl)phenyl)carbamothioate

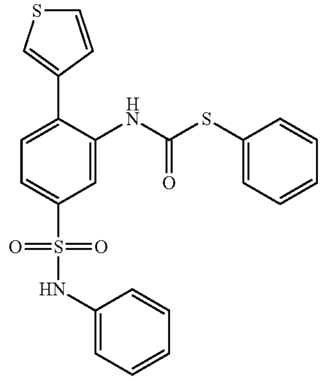 [SMILES: O=C(Nc1cc(S(=O)(=O)Nc2ccccc2)ccc1-c1ccsc1)Sc1ccccc1]

$^1$H NMR (400 MHz, $CD_3OD$) δ: 7.0-7.3 (m, 6H), 7.34-7.6 (9H), 8.1 (s, 1H).

S-phenyl (5-(N-cyclopropylsulfamoyl)-2-(thiophen-3-yl)phenyl)carbamothioate

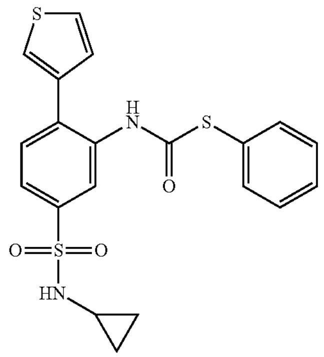 [SMILES: O=C(Nc1cc(S(=O)(=O)NC2CC2)ccc1-c1ccsc1)Sc1ccccc1]

$^1$H NMR (400 MHz, $CD_3OD$) δ: 0.45-0.6 (m, 4H), 2.16-2.25 (m, 1H), 7.25 (t, 1H), 7.4-7.6 (m, 8H), 7.72 (d, 1H), 8.15 (s, 1H).

S-phenyl (4-(N-(2,2,2-trifluoroethyl)sulfamoyl)-[1,1'-biphenyl]-2-yl)carbamothioate

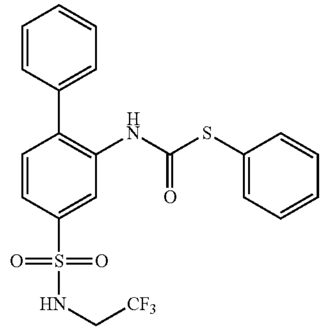 [SMILES: O=C(Nc1cc(S(=O)(=O)NCC(F)(F)F)ccc1-c1ccccc1)Sc1ccccc1]

$^1$H NMR (400 MHz, DMSO-$d_6$) δ: 3.66-3.8 (m, 2H), 7.33-7.6 (m, 11H), 7.75 (d, 1H), 7.92 (s, 1H), 8.72 (t, 1H), 10.07 (s, 1H).

The following compounds were similarly prepared according to Scheme 1, Method A:

N-phenyl-3-(3-phenylureido)-4-(thiophen-3-yl)benzenesulfonamide (1): (Method A)

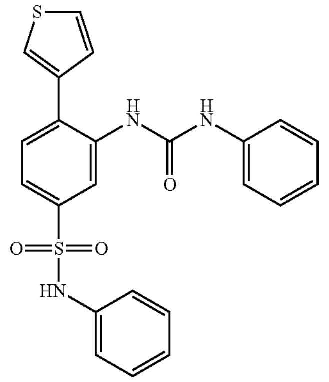 [SMILES: O=C(Nc1ccccc1)Nc1cc(S(=O)(=O)Nc2ccccc2)ccc1-c1ccsc1]

$^1$H NMR (400 MHz, $CD_3OD$) δ: 7.0-7.1 (m, 2H), 7.1-7.39 (m, 7H), 7.4-7.45 (m, 4H), 7.6 (s, 1H), 7.61 (d, 1H), 8.59 (s, 1H). LCMS: Calculated for $C_{23}H_{19}N_3O_3S_2$: 449.55, Observed: 450.15 $(M+H)^+$.

N-phenyl-4-(thiophen-3-yl)-3-(3-(o-tolyl)ureido)benzenesulfonamide (2): (Method A)

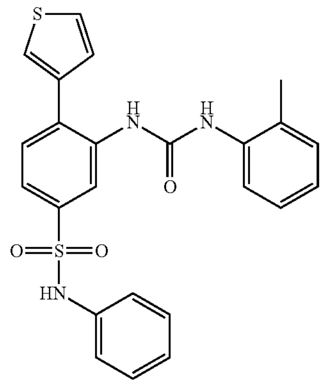 [SMILES: Cc1ccccc1NC(=O)Nc1cc(S(=O)(=O)Nc2ccccc2)ccc1-c1ccsc1]

$^1$H NMR (400 MHz, $CD_3OD$) δ: 2.00 (s, 3H), 7.0-7.3 (m, 9H), 7.31-7.6 (m, 5H), 8.43 (s, 1H). LCMS: Calculated for $C_{24}H_{21}N_3O_3S_2$: 463.57, Observed: 464.10 $(M+H)^+$.

N-phenyl-4-(thiophen-3-yl)-3-(3-(m-tolyl)ureido)benzenesulfonamide (3): (Method A)

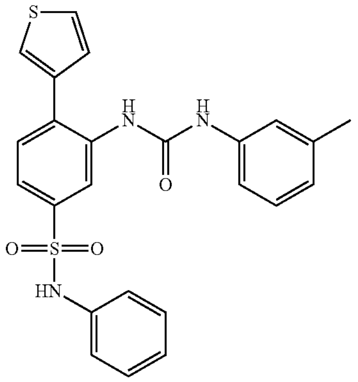 [SMILES: Cc1cccc(NC(=O)Nc2cc(S(=O)(=O)Nc3ccccc3)ccc2-c2ccsc2)c1]

$^1$H NMR (400 MHz, $CD_3OD$) δ: 2.3 (s, 3H), 6.81 (d, 1H), 7.0 (t, 1H), 7.05-7.21 (m, 8H), 7.39-7.41 (m, 2H), 7.59-7.6 (m, 2H), 8.58 (s, 1H). LCMS: Calculated for $C_{24}H_{21}N_3O_3S_2$: 463.57, Observed: 464.10 $(M+H)^+$.

3-(3-(2-fluorophenyl)ureido)-N-phenyl-4-(thiophen-3-yl)benzenesulfonamide (9): (Method A)

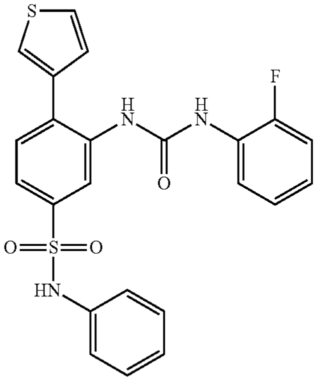 [SMILES: O=C(Nc1ccccc1F)Nc1cc(S(=O)(=O)Nc2ccccc2)ccc1-c1ccsc1]

$^1$H NMR (400 MHz, $CD_3OD$) δ: 7.0-7.3 (m, 7H), 7.38-7.4 (m, 3H), 7.5-7.6 (m, 3H), 8.1 (t, 1H), 8.5 (s, 1H). LCMS: Calculated for $C_{23}H_{18}FN_3O_3S_2$: 467.54, Observed: 468.10 $(M+H)^+$.

N-cyclopropyl-3-(3-(4-fluoro-2-(trifluoromethyl)phenyl)ureido)-4-(thiophen-3-yl)benzenesulfonamide (28): (Method A)

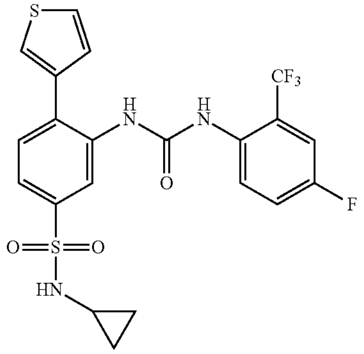 [SMILES: O=C(Nc1cc(S(=O)(=O)NC2CC2)ccc1-c1ccsc1)Nc1ccc(F)cc1C(F)(F)F]

$^1$H NMR (400 MHz, $CD_3OD$) δ: 0.5-0.6 (m, 4H), 2.2-2.3 (m, 1H), 7.25 (m, 2H), 7.3-7.7 (m, 5H), 7.71-7.8 (m, 1H), 8.4 (s, 1H). LCMS: Calculated for $C_{21}H_{17}F_4N_3O_3S_2$: 499.50, Observed: 500.05 $(M+H)^+$.

N-(1-cyanocyclopropyl)-4-(thiophen-3-yl)-3-(3-(3-(trifluoromethyl)phenyl)ureido)benzenesulfonamide (31): (Method A)

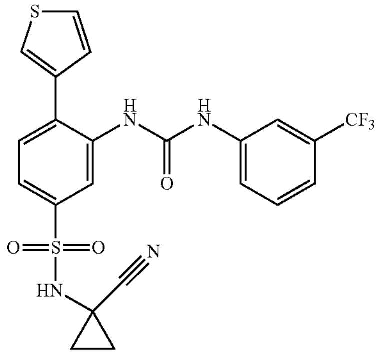 [SMILES: N#CC1(NS(=O)(=O)c2ccc(-c3ccsc3)c(NC(=O)Nc3cccc(C(F)(F)F)c3)c2)CC1]

$^1$H NMR (400 MHz, DMSO-$d_6$) δ: 1.2-1.3 (m, 2H), 1.4-1.5 (m, 2H), 7.3-7.4 (m, 2H), 7.5-7.6 (m, 4H), 7.78-7.8 (m, 2H), 8.0 (s, 1H), 8.19 (s, 1H), 8.6 (s, 1H), 9.2 (s, 1H), 9.6 (s, 1H). LCMS: Calculated for $C_{22}H_{17}F_3N_4O_3S_2$: 506.52, Observed: 507.10 $(M+H)^+$.

N-(oxetan-3-yl)-4-(thiophen-3-yl)-3-(3-(3-(trifluoromethyl)phenyl)ureido)benzenesulfonamide (32): (Method A)

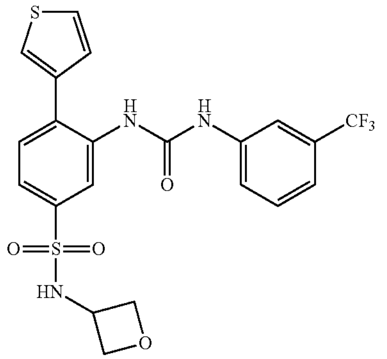

$^1$H NMR (400 MHz, DMSO-$d_6$) δ: 4.3-4.45 (m, 3H), 4.55 (m, 2H), 7.3-7.6 (m, 6H), 7.7-7.8 (m, 2H), 8.0 (s, 1H), 8.1 (s, 1H), 8.41 (s, 1H), 8.6 (d, 1H), 9.6 (s, 1H). LCMS: Calculated for $C_{21}H_{18}F_3N_3O_4S_2$: 497.51, Observed: 498.10 $(M+H)^+$.

N-(2,2,2-trifluoroethyl)-3-(3-(4-(trifluoromethyl)pyridin-2-yl)ureido)benzenesulfonamide (337): (Method A)

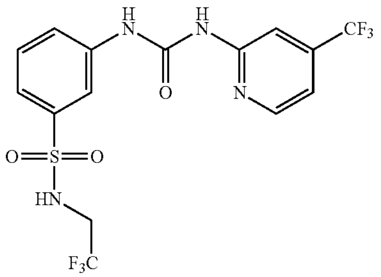 [SMILES: O=C(Nc1cccc(S(=O)(=O)NCC(F)(F)F)c1)Nc1cc(C(F)(F)F)ccn1]

$^1$H NMR (400 MHz, DMSO-$d_6$) δ: 3.7 (m, 2H), 7.4 (d, 1H), 7.5-7.6 (m, 2H), 7.61 (d, 1H), 8.08 (s, 1H), 8.15 (s, 1H), 8.58 (d, 1H), 8.65 (t, 1H), 9.75 (s, 1H), 10.0 (s, 1H). LCMS: Calculated for $C_{15}H_{12}F_6N_4O_3S$: 442.33, Observed: 443.20 $(M+H)^+$.

4-ethynyl-N-(2,2,2-trifluoroethyl)-3-(3-(3-(trifluoromethyl)phenyl) ureido)benzenesulfonamide (338): (Method A)

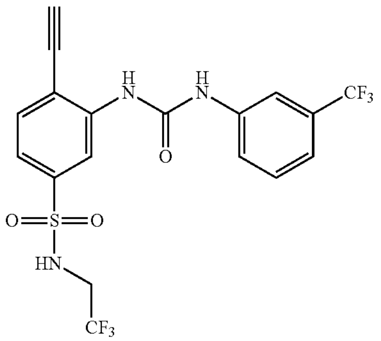 [SMILES: C#Cc1ccc(S(=O)(=O)NCC(F)(F)F)cc1NC(=O)Nc1cccc(C(F)(F)F)c1]

$^1$H NMR (400 MHz, $CDCl_3$+1 drop DMSO) δ: 2.6 (s, 1H), 3.55-3.62 (m, 3H), 7.2 (m, 1H), 7.4-7.6 (m, 3H), 7.7 (d, 1H), 7.8 (s, 1H), 8.19 (s, 1H), 8.81 (s, 1H), 9.2 (s, 1H). LCMS: Calculated for $C_{18}H_{13}F_6N_3O_3S$: 465.37, Observed: 466.05 $(M+H)^+$.

4-ethyl-N-(2,2,2-trifluoroethyl)-3-(3-(3-(trifluoromethyl)phenyl)ureido)benzenesulfonamide (339): (Method A)

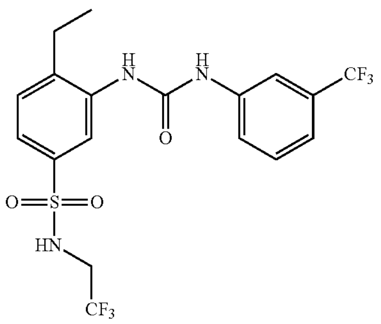 [SMILES: CCc1ccc(S(=O)(=O)NCC(F)(F)F)cc1NC(=O)Nc1cccc(C(F)(F)F)c1]

$^1$H NMR (400 MHz, DMSO-$d_6$) δ: 1.2 (t, 3H), 2.65 (q, 2H), 3.5 (m, 2H), 7.25-7.4 (m, 3H), 7.45-7.6 (m, 2H), 8.0 (s, 1H), 8.2 (s, 1H), 8.3 (s, 1H), 9.6 (s, 1H). LCMS: Calculated for $C_{18}H_{17}F_6N_3O_3S$: 469.40, Observed: 470.15 $(M+H)^+$.

2-(3-(2-fluorophenyl)ureido)-N-(2,2,2-trifluoro-ethyl)-[1,1'-biphenyl]-4-sulfonamide (33)

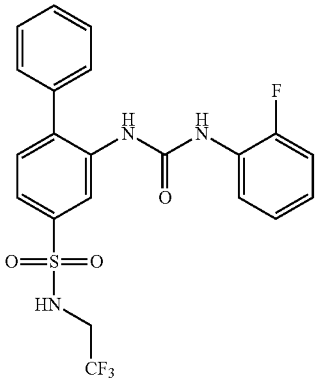

$^1$H NMR (400 MHz, DMSO-$d_6$) δ: 3.63-3.80 (m, 2H), 6.69-7.3 (m, 3H), 7.4-7.6 (m, 7H), 8.2 (t, 1H), 8.4 (s, 1H), 8.55 (s, 1H), 8.75 (br s, 1H), 9.04 (s, 1H). LCMS: Calculated for $C_{21}H_{17}F_4N_3O_3S$: 467.44, Observed: 468.10 $(M+H)^+$.

N-cyclopropyl-2-(3-phenylureido)-[1,1'-biphenyl]-4-sulfonamide (34)

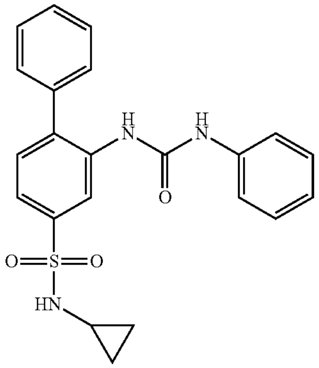 [SMILES: O=C(Nc1ccccc1)Nc1cc(S(=O)(=O)NC2CC2)ccc1-c1ccccc1]

$^1$H NMR (400 MHz, $CD_3OD$) δ: 0.54-0.62 (m, 4H), 2.22-2.32 (m, 1H), 7.0 (t, 1H), 7.25 (t, 2H), 7.30-7.60 (m, 8H), 7.64 (d, 1H), 8.58 (s, 1H). LCMS: Calculated for $C_{22}H_{21}N_3O_3S$: 407.49, Observed: 408.05 $(M+H)^+$.

N-cyclopropyl-2-(3-(2-fluorophenyl)ureido)-[1,1'-biphenyl]-4-sulfonamide (35)

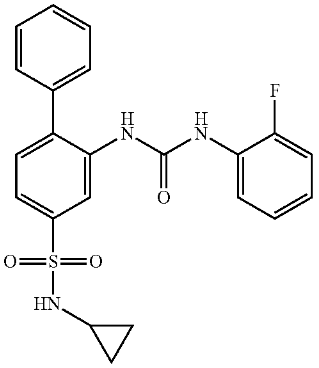 [SMILES: O=C(Nc1ccccc1F)Nc1cc(S(=O)(=O)NC2CC2)ccc1-c1ccccc1]

$^1$H NMR (400 MHz, $CD_3OD$) δ: 0.60 (t, 4H), 2.25-2.34 (m, 1H), 6.98-7.15 (m, 4H), 7.40-7.59 (m, 7H), 7.62 (d, 1H), 8.04 (t, 1H), 8.55 (s, 1H). LCMS: Calculated for $C_{22}H_{20}FN_3O_3S$: 425.48, Observed: 426.15 $(M+H)^+$.

N-cyclopropyl-2-(3-(3-(trifluoromethyl)phenyl)ureido)-[1,1'-biphenyl]-4-sulfonamide (36)

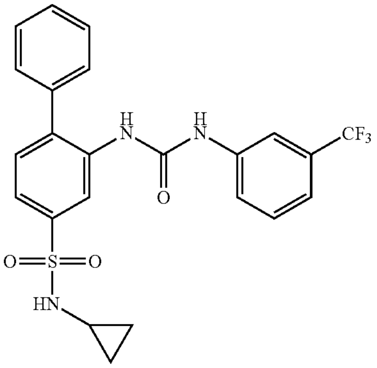 [SMILES: O=C(Nc1cccc(C(F)(F)F)c1)Nc1cc(S(=O)(=O)NC2CC2)ccc1-c1ccccc1]

$^1$H NMR (400 MHz, $CD_3OD$) δ: 0.50-0.70 (m, 4H), 2.20-2.30 (m, 1H), 7.30 (d, 1H), 7.40-7.60 (m, 8H), 7.65 (d, 1H), 7.85 (s, 1H), 8.60 (s, 1H). LCMS: Calculated for $C_{23}H_{20}F_3N_3O_3S$: 475.48, Observed: 476.20 $(M+H)^+$.

2-(3-(4-chlorophenyl)ureido)-N-(2,2,2-trifluoro-ethyl)-[1,1'-biphenyl]-4-sulfonamide (37)

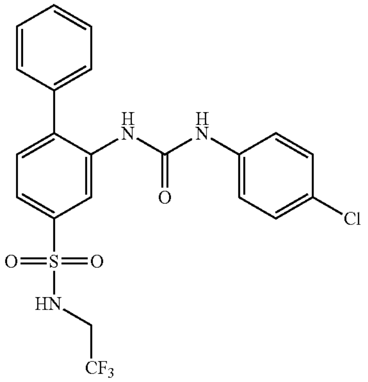 [SMILES: O=C(Nc1ccc(Cl)cc1)Nc1cc(S(=O)(=O)NCC(F)(F)F)ccc1-c1ccccc1]

$^1$H NMR (400 MHz, DMSO-d$_6$) δ: 3.62-3.8 (m, 2H), 7.30-7.60 (m, 11H), 7.90 (s, 1H), 8.55 (s, 1H), 8.70 (t, 1H), 9.30 (s, 1H). LCMS: Calculated for $C_{21}H_{17}ClF_3N_3O_3S$: 483.89, Observed: 505.95 (M+Na)$^+$.

2-(3-(2,5-difluorophenyl)ureido)-N-(2,2,2-trifluoroethyl)-[1,1'-biphenyl]-4-sulfonamide (38)

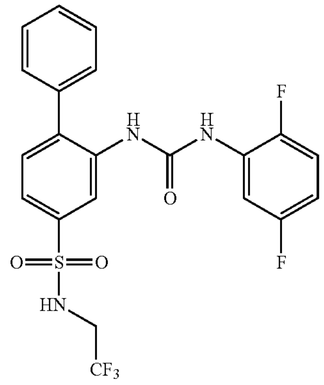

$^1$H NMR (400 MHz, DMSO-d$_6$) δ: 3.68-3.8 (m, 2H), 6.78-6.82 (m, 1H), 7.21-7.37 (m, 1H), 7.4-7.6 (m, 7H), 8.0-8.10 (m, 1H), 8.50 (d, 2H), 8.75 (br s, 1H), 9.22 (br s, 1H). LCMS: Calculated for $C_{21}H_{16}F5N_3O_3S$: 485.43, Observed: 486.10 (M+H)$^+$.

2-(3-(4-fluorophenyl)ureido)-N-(2,2,2-trifluoroethyl)-[1,1'-biphenyl]-4-sulfonamide (39)

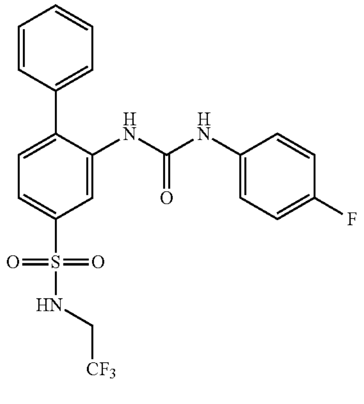 [SMILES: O=C(Nc1ccc(F)cc1)Nc1cc(S(=O)(=O)NCC(F)(F)F)ccc1-c1ccccc1]

$^1$H NMR (400 MHz, DMSO-d$_6$) δ: 3.65-3.79 (m, 2H), 7.10 (t, 2H), 7.4-7.6 (m, 9H), 7.84 (s, 1H), 8.58 (s, 1H), 8.70 (t, 1H), 9.20 (s, 1H). LCMS: Calculated for $C_{21}H_{17}F_4N_3O_3S$: 467.44, Observed: 489.90 (M+Na)$^+$.

2-(3-(3-chloro-4-fluorophenyl)ureido)-N-(2,2,2-trifluoroethyl)-[1,1'-biphenyl]-4-sulfonamide (40)

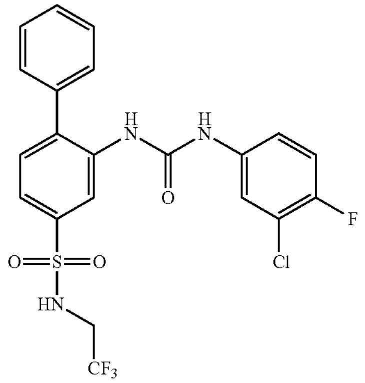 [SMILES: O=C(Nc1ccc(F)c(Cl)c1)Nc1cc(S(=O)(=O)NCC(F)(F)F)ccc1-c1ccccc1]

$^1$H NMR (400 MHz, DMSO-d$_6$) δ: 3.6-3.8 (m, 2H), 7.2 (br s, 1H), 7.35 (t, 1H), 7.40-7.60 (m, 7H), 7.78 (d, 1H), 7.95 (s, 1H), 8.52 (s, 1H), 8.70 (br s, 1H), 9.38 (br s, 1H). LCMS: Calculated for $C_{21}H_{16}ClF_4N_3O_3S$: 501.88, Observed: 502.00 (M+H)$^+$.

2-(3-(2,6-difluorophenyl)ureido)-N-(2,2,2-trifluoroethyl)-[1,1'-biphenyl]-4-sulfonamide (41)

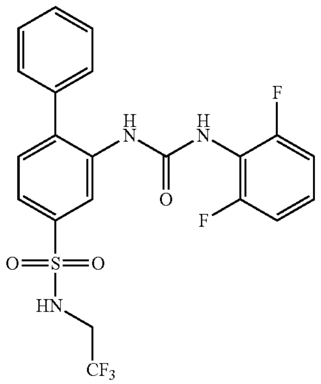 [SMILES: O=C(Nc1cc(S(=O)(=O)NCC(F)(F)F)ccc1-c1ccccc1)Nc1c(F)cccc1F]

$^1$H NMR (400 MHz, DMSO-d$_6$) δ: 3.6-3.78 (m, 2H), 7.12 (t, 2H), 7.21-7.38 (m, 1H), 7.40-7.60 (m, 7H), 8.10 (s, 1H), 8.55 (s, 1H), 8.64-8.75 (m, 2H). LCMS: Calculated for $C_{21}H_{16}F_5N_3O_3S$: 485.43, Observed: 508.10 (M+Na)$^+$.

2-(3-(2-chlorophenyl)ureido)-N-(2,2,2-trifluoroethyl)-[1,1'-biphenyl]-4-sulfonamide (42)

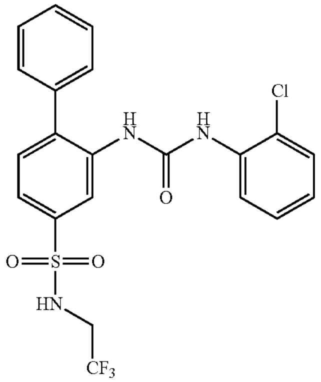 [SMILES: O=C(Nc1ccccc1Cl)Nc1cc(S(=O)(=O)NCC(F)(F)F)ccc1-c1ccccc1]

$^1H$ NMR (400 MHz, DMSO-$d_6$) δ: 3.62-3.79 (m, 2H), 7.08 (t, 1H), 7.32 (t, 1H), 7.41-7.62 (m, 8H), 8.10 (d, 1H), 8.40 (s, 1H), 8.64-8.78 (m, 3H). LCMS: Calculated for $C_{21}H_{17}ClF_3N_3O_3S$: 483.89, Observed: 484.05 $(M+H)^+$.

N-(2,2,2-trifluoroethyl)-2-(3-(2-(trifluoromethoxy)phenyl)ureido)-[1,1'-biphenyl]-4-sulfonamide (43)

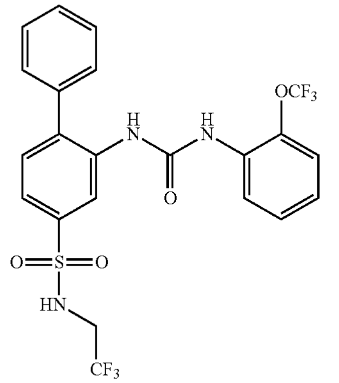 [SMILES: O=C(Nc1ccccc1OC(F)(F)F)Nc1cc(S(=O)(=O)NCC(F)(F)F)ccc1-c1ccccc1]

$^1H$ NMR (400 MHz, DMSO-$d_6$) δ: 3.65-3.8 (m, 2H), 7.10 (t, 1H), 7.3-7.61 (m, 9H), 8.18 (d, 1H), 8.38 (s, 1H), 8.6 (s, 1H), 8.70 (t, 1H), 8.84 (s, 1H). LCMS: Calculated for $C_{22}H_{17}F_6N_3O_4S$: 533.44, Observed: 534.00 $(M+H)^+$.

N-(2,2,2-trifluoroethyl)-2-(3-(3-(trifluoromethyl)phenyl)ureido)-[1,1'-biphenyl]-4-sulfonamide (44)

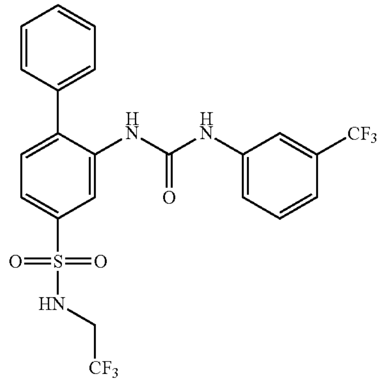

$^1H$ NMR (400 MHz, DMSO-$d_6$) δ: 3.70-3.82 (m, 2H), 7.30-7.65 (m, 10H), 8.02 (d, 2H), 8.60 (s, 1H), 8.80 (t, 1H), 9.58 (s, 1H). LCMS: Calculated for $C_{22}H_{17}F_6N_3O_3S$: 517.44, Observed: 518.15 $(M+H)^+$.

N-(oxetan-3-yl)-2-(3-(3-(trifluoromethyl)phenyl)ureido)-[1,1'-biphenyl]-4-sulfonamide (45)

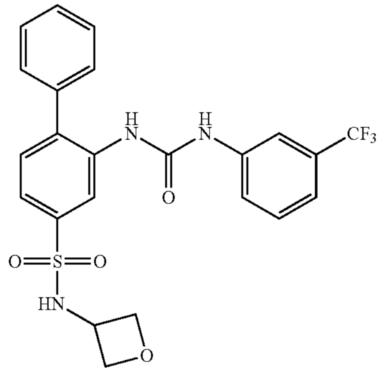 [SMILES: O=C(Nc1cccc(C(F)(F)F)c1)Nc1cc(S(=O)(=O)NC2COC2)ccc1-c1ccccc1]

$^1H$ NMR (400 MHz, DMSO-$d_6$) δ: 4.34 (t, 2H), 4.35-4.50 (m, 1H), 4.59 (t, 2H), 7.28-7.60 (m, 10H), 7.98 (d, 2H), 8.50 (s, 1H), 8.62 (d, 1H), 9.52 (s, 1H). LCMS: Calculated for $C_{23}H_{20}F_3N_3O_4S$: 491.48, Observed: 492.2 $(M+H)^+$.

N-(1-cyanocyclopropyl)-2-(3-(3-(trifluoromethyl)phenyl)ureido)-[1,1'-biphenyl]-4-sulfonamide (46)

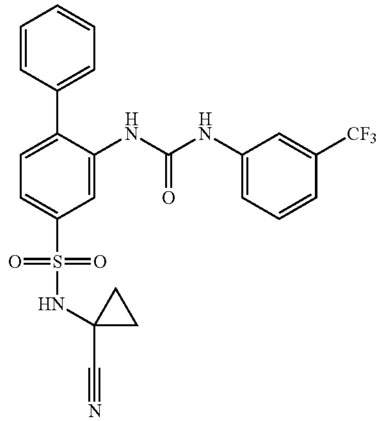 [SMILES: N#CC1(NS(=O)(=O)c2ccc(-c3ccccc3)c(NC(=O)Nc3cccc(C(F)(F)F)c3)c2)CC1]

$^1H$ NMR (400 MHz, DMSO-$d_6$) δ: 1.25 (t, 2H), 1.45 (t, 2H), 7.35 (br s, 1H), 7.40-7.62 (m, 9H), 8.0 (s, 2H), 8.62 (s, 1H), 9.18 (s, 1H), 9.55 (s, 1H). LCMS: Calculated for $C_{24}H_{19}F_3N_4O_3S$: 500.49, Observed: 501.2 $(M+H)^+$.

3'-methyl-N-(tetrahydro-2H-pyran-4-yl)-2-(3-(3-(trifluoromethyl)phenyl)ureido)-[1,1'-biphenyl]-4-sulfonamide (47)

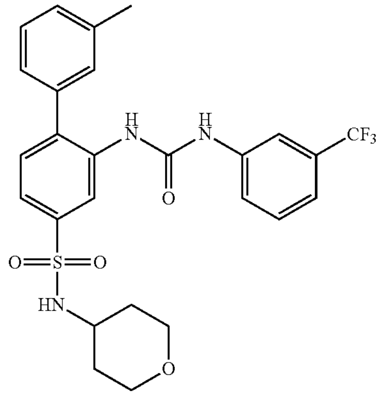

$^1$H NMR (400 MHz, DMSO-$d_6$) δ: 1.35-1.50 (m, 2H), 1.60-1.68 (m, 2H), 2.40 (s, 3H), 3.21-3.30 (m, 3H), 3.7-3.8 (m, 2H), 7.2-7.58 (m, 9H), 7.81 (d, 1H), 7.90 (s, 1H), 8.0 (s, 1H), 8.58 (s, 1H), 9.58 (s, 1H). LCMS: Calculated for $C_{26}H_{26}F_3N_3O_4S$: 533.56, Observed: 534.74 $(M+H)^+$.

N-cyclopropyl-3'-methyl-2-(3-(3-(trifluoromethyl) phenyl)ureido)-[1,1'-biphenyl]-4-sulfonamide (48)

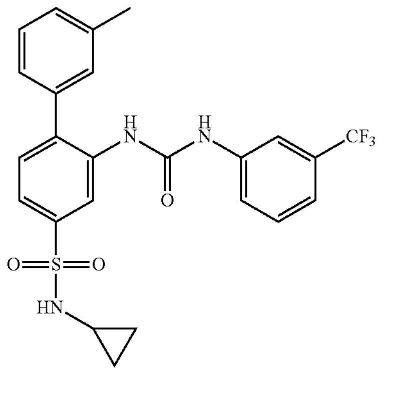 [SMILES: Cc1cccc(-c2ccc(S(=O)(=O)NC3CC3)cc2NC(=O)Nc2cccc(C(F)(F)F)c2)c1]

$^1$H NMR (400 MHz, DMSO-$d_6$) δ: 0.4-0.6 (m, 4H), 2.10-2.20 (m, 1H), 2.4 (s, 3H), 7.20-7.39 (m, 4H), 7.40-7.60 (m, 5H), 7.9 (s, 1H), 7.91-8.01 (m, 2H), 8.6 (s, 1H), 9.58 (s, 1H). LCMS: Calculated for $C_{24}H_{22}F_3N_3O_3S$: 489.51, Observed: 512.10 $(M+Na)^+$.

3'-methyl-N-morpholino-2-(3-(3-(trifluoromethyl) phenyl)ureido)-[1,1'-biphenyl]-4-sulfonamide (49)

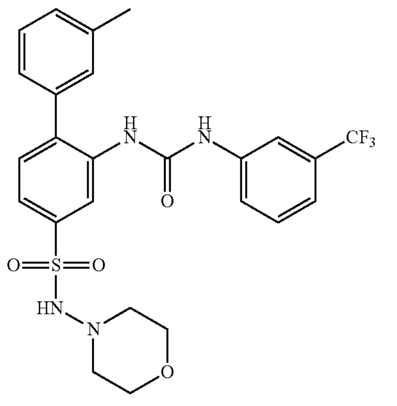 [SMILES: Cc1cccc(-c2ccc(S(=O)(=O)NN3CCOCC3)cc2NC(=O)Nc2cccc(C(F)(F)F)c2)c1]

$^1$H NMR (400 MHz, DMSO-$d_6$) δ: 2.40 (s, 3H), 2.95 (s, 4H), 3.64 (s, 4H), 7.2-7.38 (m, 4H), 7.40-7.60 (m, 5H), 7.90-8.0 (m, 2H), 8.50 (s, 1H), 9.60 (s, 1H). LCMS: Calculated for $C_{25}H_{25}F_3N_4O_4S$: 534.55, Observed: 536.99 $(M+2)^+$.

3'-hydroxy-N-phenyl-2-(3-(3-(trifluoromethyl)phenyl)ureido)-[1,1'-biphenyl]-4-sulfonamide (50)

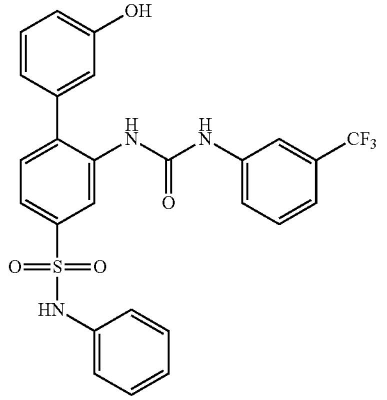 [SMILES: O=C(Nc1cccc(C(F)(F)F)c1)Nc1cc(S(=O)(=O)Nc2ccccc2)ccc1-c1cccc(O)c1]

$^1$H NMR (400 MHz, $CD_3OD$) δ: 6.75-6.90 (m, 3H), 7.05 (t, 1H), 7.15-7.35 (m, 8H), 7.40-7.55 (m, 3H), 7.90 (s, 1H), 8.62 (s, 1H). LCMS: Calculated for $C_{26}H_{20}F_3N_3O_4S$: 527.51, Observed: 528.63 $(M+H)^+$.

The following compounds were similarly prepared according to Method B in Scheme 1:

2-(3-cyclohexylureido)-N-(2,2,2-trifluoroethyl)-[1,1'-biphenyl]-4-sulfonamide (66)

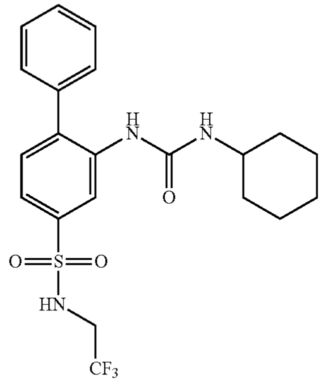 [SMILES: O=C(Nc1cc(S(=O)(=O)NCC(F)(F)F)ccc1-c1ccccc1)NC1CCCCC1]

$^1$H NMR (400 MHz, $CD_3OD$) δ: 1.10-1.42 (m, 5H), 1.58-1.75 (m, 3H), 1.85 (d, 2H), 3.45-3.60 (m, 1H), 3.6-3.70 (m, 2H), 7.35-7.6 (m, 8H), 8.42 (s, 1H). LCMS: Calculated for $C_{21}H_{24}F_3N_3O_3S$: 455.49, Observed: 456.20 $(M+H)^+$.

2-(3-(3-(methylsulfonyl)phenyl)ureido)-N-(2,2,2-trifluoroethyl)-[1,1'-biphenyl]-4-sulfonamide (67)

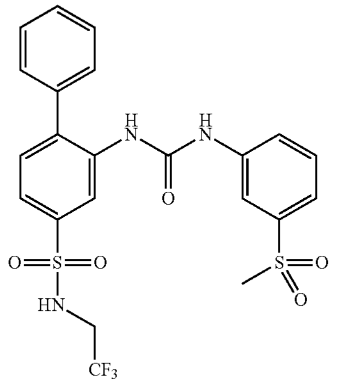 [SMILES: CS(=O)(=O)c1cccc(NC(=O)Nc2cc(S(=O)(=O)NCC(F)(F)F)ccc2-c2ccccc2)c1]

$^1H$ NMR (400 MHz, $CD_3OD$) δ: 3.10 (s, 3H), 3.60-3.75 (m, 2H), 7.40-7.70 (m, 10H), 8.16 (s, 1H), 8.58 (s, 1H). LCMS: Calculated for $C_{22}H_{20}F_3N_3O_5S_2$: 527.53, Observed: 528.30 $(M+H)^+$.

2-(3-(2,4-difluorophenyl)ureido)-N-(2,2,2-trifluoroethyl)-[1,1'-biphenyl]-4-sulfonamide (68)

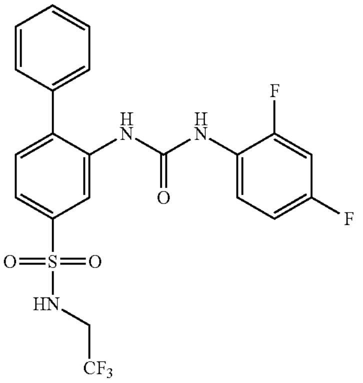 [SMILES: O=C(Nc1ccc(F)cc1F)Nc1cc(S(=O)(=O)NCC(F)(F)F)ccc1-c1ccccc1]

$^1H$ NMR (400 MHz, DMSO-$d_6$) δ: 3.62-3.80 (m, 2H), 7.02 (t, 1H), 7.28 (t, 1H), 7.39-7.62 (m, 7H), 8.04-8.28 (m, 1H), 8.38 (s, 1H), 8.52 (s, 1H), 8.70 (s, 1H), 9.01 (s, 1H). LCMS: Calculated for $C_{21}H_{16}F_5N_3O_3S$: 485.43, Observed: 486.05 $(M+H)^+$.

2-(3-(4-fluoro-3-(trifluoromethyl)phenyl)ureido)-N-(2,2,2-trifluoroethyl)-[1,1'-biphenyl]-4-sulfonamide (69)

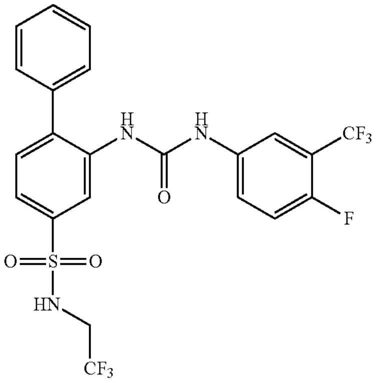 [SMILES: O=C(Nc1ccc(F)c(C(F)(F)F)c1)Nc1cc(S(=O)(=O)NCC(F)(F)F)ccc1-c1ccccc1]

$^1H$ NMR (400 MHz, DMSO-$d_6$) δ: 3.65-3.80 (m, 2H), 7.38-7.60 (m, 9H), 7.98 (s, 2H), 8.53 (s, 1H), 8.75 (br s, 1H), 9.50 (s, 1H). LCMS: Calculated for $C_{22}H_{16}F_7N_3O_3S$: 535.43, Observed: 536.10 $(M+H)^+$.

2-(3-(thiazol-2-yl)ureido)-N-(2,2,2-trifluoroethyl)-[1,1'-biphenyl]-4-sulfonamide (70)

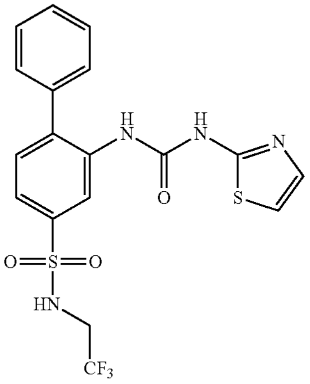 [SMILES: O=C(Nc1nccs1)Nc1cc(S(=O)(=O)NCC(F)(F)F)ccc1-c1ccccc1]

$^1H$ NMR (400 MHz, $CD_3OD$) δ: 3.61-3.77 (m, 2H), 6.95 (d, 1H), 7.16-7.20 (m, 2H), 7.38-7.59 (m, 5H), 7.62 (d, 1H), 8.65 (s, 1H). LCMS: Calculated for $C_{18}H_{15}F_3N_4O_3S_2$: 456.46, Observed: 457.00 $(M+H)^+$.

2-(3-(3-methylcyclohexyl)ureido)-N-(2,2,2-trifluoroethyl)-[1,1'-biphenyl]-4-sulfonamide (71)

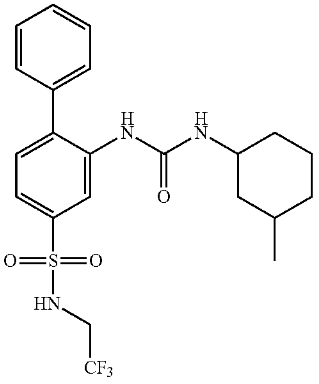 [SMILES: CC1CCCC(NC(=O)Nc2cc(S(=O)(=O)NCC(F)(F)F)ccc2-c2ccccc2)C1]

$^1H$ NMR (400 MHz, $CD_3OD$) δ: 0.65-1.03 (m, 6H), 1.21-1.95 (m, 7H), 3.41-3.58 (m, 1H), 3.61-3.72 (m, 1H), 7.38-7.59 (m, 7H), 8.42 (s, 1H). LCMS: Calculated for $C_{22}H_{26}F_3N_3O_3S$: 469.52, Observed: 470.05 $(M+H)^+$.

N-(2,2,2-trifluoroethyl)-2-(3-(3-(trifluoromethyl)cyclohexyl)ureido)-[1,1'-biphenyl]-4-sulfonamide (72)

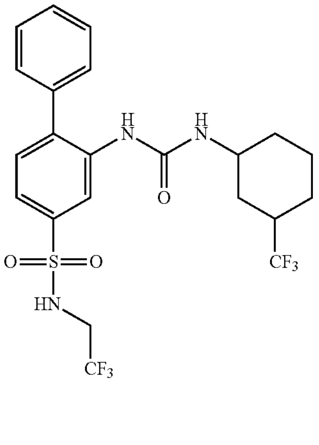 [SMILES: O=C(Nc1cc(S(=O)(=O)NCC(F)(F)F)ccc1-c1ccccc1)NC1CCCC(C(F)(F)F)C1]

$^1$H NMR (400 MHz, DMSO-$d_6$) δ: 0.98-1.65 (m, 4H), 1.70-1.90 (m, 2H), 2.05 (d, 1H), 2.31-2.49 (m, 2H), 3.42-3.58 (m, 1H), 3.62-3.78 (m, 2H), 6.81 (d, 1H), 7.31-7.61 (m, 7H), 8.39 (d, 1H), 8.52-8.68 (m, 2H). LCMS: Calculated for $C_{22}H_{23}F_6N_3O_3S$: 523.49, Observed: 546.10 $(M+Na)^+$.

N-(cyclopropylmethyl)-4-(3,6-dihydro-2H-pyran-4-yl)-3-(3-(3-(trifluoromethyl)phenyl)ureido)benzene sulfonamide (154)

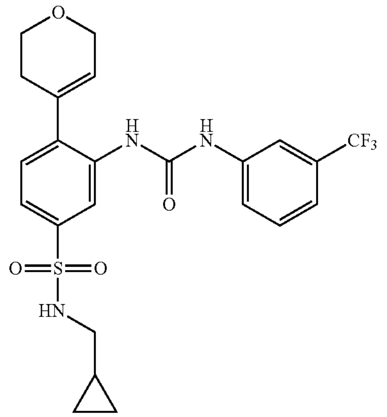 [SMILES: O=C(Nc1cccc(C(F)(F)F)c1)Nc1cc(S(=O)(=O)NCC2CC2)ccc1C1=CCOCC1]

$^1$H NMR (400 MHz, $CD_3OD$) δ: 0.1-0.2 (m, 2H), 0.4-0.5 (m, 2H), 0.9 (m, 1H), 2.4 (m, 2H), 2.8 (m, 2H), 3.95 (t, 2H), 4.3 (m, 2H), 5.9 (m, 1H), 7.3 (t, 1H), 7.4-7.62 (m, 4H), 8.0 (s, 1H), 8.42 (s, 1H). LCMS: Calculated for $C_{23}H_{24}F_3N_3O_4S$: 495.51, Observed: 518.10 $(M+Na)^+$.

3-(3-(3-chloro-4-fluorophenyl)ureido)-N-(cyclopropylmethyl)-4-(3,6-dihydro-2H-pyran-4-yl)benzene sulfonamide (155)

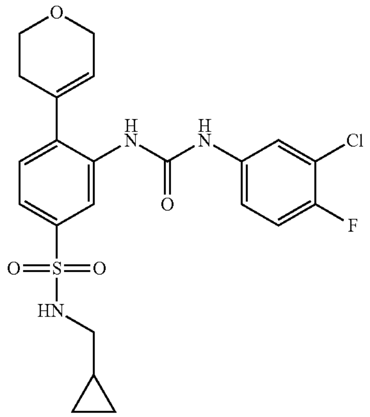 [SMILES: O=C(Nc1ccc(F)c(Cl)c1)Nc1cc(S(=O)(=O)NCC2CC2)ccc1C1=CCOCC1]

$^1$H NMR (400 MHz, $CD_3OD$) δ: 0.15 (m, 2H), 0.45 (m, 2H), 0.9 (m, 1H), 2.4 (m, 2H), 2.8 (d, 2H), 3.95 (t, 2H), 4.3 (m, 2H), 5.9 (m, 1H), 7.2 (t, 1H), 7.25-7.4 (m, 2H), 7.55 (d, 1H), 7.75 (d, 1H), 8.4 (s, 1H). LCMS: Calculated for $C_{22}H_{23}ClFN_3O_4S$: 479.95, Observed: 502.00 $(M+Na)^+$.

N-(cyclopropylmethyl)-4-(3,6-dihydro-2H-pyran-4-yl)-3-(3-(4-fluoro-3-(trifluoromethyl)phenyl)ureido) benzenesulfonamide (156)

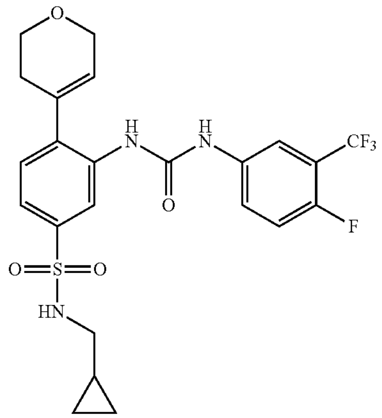 [SMILES: O=C(Nc1ccc(F)c(C(F)(F)F)c1)Nc1cc(S(=O)(=O)NCC2CC2)ccc1C1=CCOCC1]

$^1$H NMR (400 MHz, $CD_3OD$) δ: 0.1-0.2 (m, 2H), 0.4-0.5 (m, 2H), 0.9 (m, 1H), 2.4 (m, 2H), 2.8 (d, 2H), 3.95 (t, 2H), 4.35 (m, 2H), 5.9 (m, 1H), 7.25 (t, 1H), 7.35 (d, 1H), 7.52 (d, 1H), 7.62 (m, 1H), 7.9 (m, 1H), 8.45 (s, 1H). LCMS: Calculated for $C_{23}H_{23}F_4N_3O_4S$: 513.51, Observed: 514.10 $(M+H)^+$.

4-(3,6-dihydro-2H-pyran-4-yl)-N-(2,2,2-trifluoroethyl)-3-(3-(3-(trifluoromethyl)phenyl)ureido)benzene sulfonamide (157)

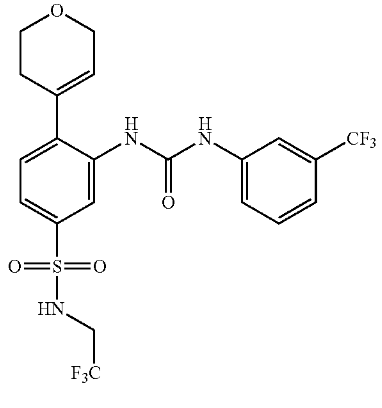 [SMILES: O=C(Nc1cccc(C(F)(F)F)c1)Nc1cc(S(=O)(=O)NCC(F)(F)F)ccc1C1=CCOCC1]

$^1$H NMR (400 MHz, DMSO-$d_6$) δ: 2.35 (m, 2H), 3.6-3.7 (m, 2H), 3.85 (t, 2H), 4.2-4.3 (m, 2H), 5.9 (m, 1H), 7.3-7.4 (m, 2H), 7.4-7.6 (m, 3H), 8.0 (s, 1H), 8.1 (s, 1H), 8.5 (s, 1H), 8.7 (t, 1H), 9.7 (s, 1H). LCMS: Calculated for $C_{21}H_{19}F_6N_3O_4S$: 523.45, Observed: 546.05 $(M+Na)^+$.

3-(3-(3-chloro-4-fluorophenyl)ureido)-4-(3,6-dihydro-2H-pyran-4-yl)-N-(2,2,2-trifluoroethyl)benzene sulfonamide (158)

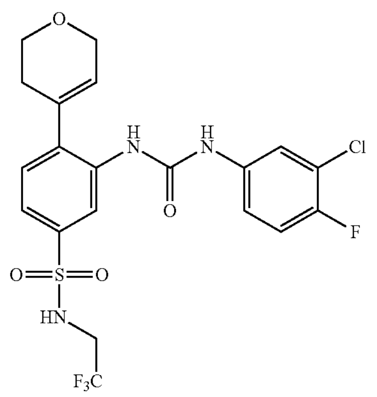 [SMILES: O=C(Nc1ccc(F)c(Cl)c1)Nc1cc(S(=O)(=O)NCC(F)(F)F)ccc1C1=CCOCC1]

$^1H$ NMR (400 MHz, $CD_3OD$) δ: 2.4 (s, 2H), 3.6-3.7 (m, 2H), 3.9 (t, 2H), 4.32 (s, 2H), 5.9 (m, 1H), 7.19 (t, 1H), 7.3 (m, 1H), 7.35 (d, 1H), 7.55 (d, 1H), 7.75 (d, 1H), 8.41 (s, 1H). LCMS: Calculated for $C_{20}H_{18}ClF_4N_3O_4S$: 507.89, Observed: 508.05 $(M+H)^+$.

4-(3,6-dihydro-2H-pyran-4-yl)-3-(3-(4-fluoro-3-(trifluoromethyl)phenyl)ureido)-N-(2,2,2-trifluoroethyl)benzenesulfonamide (159)

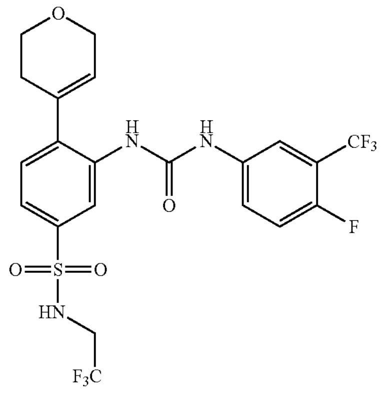 [SMILES: O=C(Nc1ccc(F)c(C(F)(F)F)c1)Nc1cc(S(=O)(=O)NCC(F)(F)F)ccc1C1=CCOCC1]

$^1H$ NMR (400 MHz, $CD_3OD$) δ: 2.4 (m, 2H), 3.6-3.7 (m, 2H), 3.95 (t, 2H), 4.35 (m, 2H), 5.9 (m, 1H), 7.25 (t, 1H), 7.35 (d, 1H), 7.55 (d, 1H), 7.65 (m, 1H), 7.9 (d, 1H), 8.45 (s, 1H). LCMS: Calculated for $C_{21}H_{18}F_7N_3O_4S$: 541.44, Observed: 542.15 $(M+H)^+$.

4-(3,6-dihydro-2H-pyran-4-yl)-N-(2,2,2-trifluoroethyl)-3-(3-(6-(trifluoromethyl)pyridin-2-yl)ureido) benzenesulfonamide (160)

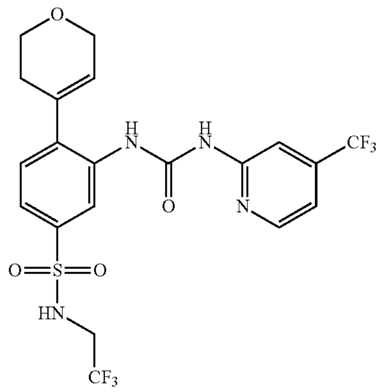 [SMILES: O=C(Nc1cc(C(F)(F)F)ccn1)Nc1cc(S(=O)(=O)NCC(F)(F)F)ccc1C1=CCOCC1]

$^1H$ NMR (400 MHz, DMSO-$d_6$) δ: 2.3 (m, 2H), 3.6-3.7 (m, 2H), 3.85 (t, 2H), 4.2 (m, 2H), 5.95 (m, 1H), 7.35-7.5 (m, 3H), 7.7 (d, 1H), 8.6 (d, 1H), 8.7-8.8 (m, 2H), 10.4 (s, 1H), 10.6 (br s, 1H). LCMS: Calculated for $C_{20}H_{18}F_6N_4O_4S$: 524.44, Observed: 525.2 $(M+H)^+$.

4-(3,6-dihydro-2H-pyran-4-yl)-N-phenyl-3-(3-(3-(trifluoromethyl)phenyl)ureido)benzene sulfonamide (161)

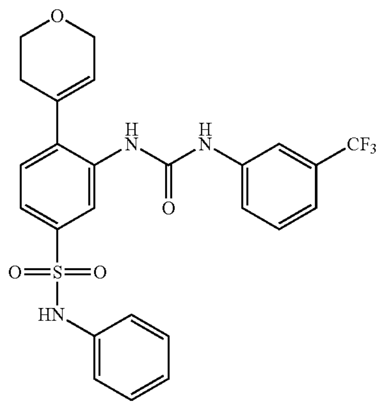 [SMILES: O=C(Nc1cccc(C(F)(F)F)c1)Nc1cc(S(=O)(=O)Nc2ccccc2)ccc1C1=CCOCC1]

$^1H$ NMR (400 MHz, $CD_3OD$) δ: 2.35 (m, 2H), 3.9 (t, 2H), 4.3 (m, 2H), 5.82 (m, 1H), 7.01 (t, 1H), 7.1-7.21 (m, 5H), 7.3 (d, 1H), 7.4 (d, 1H), 7.5 (t, 1H), 7.6 (d, 1H), 7.9 (s, 1H), 8.5 (s, 1H). LCMS: Calculated for $C_{25}H_{22}F_3N_3O_4S$: 517.72, Observed: 518.20 $(M+H)^+$.

N-(cyclopropylmethyl)-4-(tetrahydro-2H-pyran-2-yl)-3-(3-(3-(trifluoromethyl)phenyl)ureido)benzene sulfonamide (162)

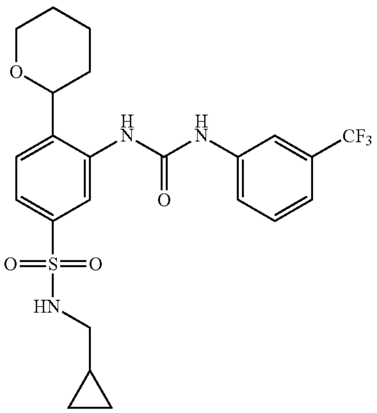 [SMILES: O=C(Nc1cccc(C(F)(F)F)c1)Nc1cc(S(=O)(=O)NCC2CC2)ccc1C1CCCCO1]

$^1$H NMR (400 MHz, $CD_3OD$) δ: 0.1-0.2 (m, 2H), 0.4-0.5 (m, 2H), 0.9 (m, 1H), 1.6-2.05 (m, 6H), 2.8 (d, 2H), 3.62 (t, 1H), 4.2 (d, 1H), 4.6 (m, 1H), 7.35 (d, 1H), 7.4-7.6 (m, 3H), 7.61 (d, 1H), 7.95 (s, 1H), 8.3 (s, 1H). LCMS: Calculated for $C_{23}H_{26}F_3N_3O_4S$: 497.53, Observed: 498.10 $(M+H)^+$.

3-(3-(3-chlorophenyl)ureido)-N-(cyclopropylmethyl)-4-(tetrahydro-2H-pyran-2-yl)benzenesulfonamide (163)

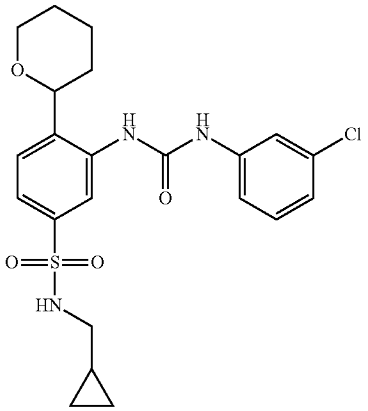 [SMILES: O=C(Nc1cccc(Cl)c1)Nc1cc(S(=O)(=O)NCC2CC2)ccc1C1CCCCO1]

$^1$H NMR (400 MHz, $CD_3OD$) δ: 0.1-0.2 (m, 2H), 0.4-0.5 (m, 2H), 0.8-1.0 (m, 1H), 1.6-2.0 (m, 6H), 2.8 (d, 2H), 3.61 (t, 1H), 4.2 (d, 1H), 4.6 (m, 1H), 7.0-7.1 (m, 1H), 7.2-7.4 (m, 2H), 7.5 (dd, 2H), 7.62 (s, 1H), 8.3 (s, 1H). LCMS: Calculated for $C_{22}H_{26}ClN_3O_4S$: 463.98, Observed: 464.00 $(M)^+$.

N-(cyclopropylmethyl)-3-(3-(4-fluoro-3-(trifluoromethyl)phenyl)ureido)-4-(tetrahydro-2H-pyran-2-yl) benzenesulfonamide (164)

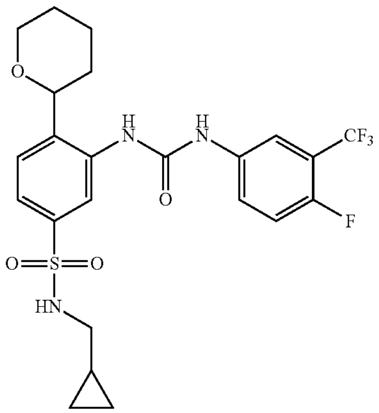 [SMILES: O=C(Nc1ccc(F)c(C(F)(F)F)c1)Nc1cc(S(=O)(=O)NCC2CC2)ccc1C1CCCCO1]

$^1$H NMR (400 MHz, $CD_3OD$) δ: 0.1-0.2 (m, 2H), 0.4-0.5 (m, 2H), 0.9 (m, 1H), 1.6-2.0 (m, 6H), 2.8 (d, 2H), 3.65 (t, 1H), 4.2 (d, 1H), 4.6 (m, 1H), 7.3 (t, 1H), 7.5 (dd, 2H), 7.7 (m, 1H), 7.9 (m, 1H), 8.3 (s, 1H). LCMS: Calculated for $C_{23}H_{25}F_4N_3O_4S$: 515.52, Observed: 516.10 $(M+H)^+$.

4-(tetrahydro-2H-pyran-2-yl)-N-(2,2,2-trifluoroethyl)-3-(3-(3-(trifluoromethyl)phenyl)ureido)benzene sulfonamide (165)

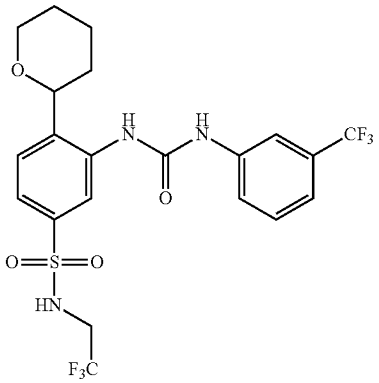 [SMILES: O=C(Nc1cccc(C(F)(F)F)c1)Nc1cc(S(=O)(=O)NCC(F)(F)F)ccc1C1CCCCO1]

$^1$H NMR (400 MHz, $CD_3OD$) δ: 1.59-1.82 (m, 5H), 1.9-2.0 (m, 1H), 3.59-3.8 (m, 3H), 4.2 (m, 1H), 4.6 (m, 1H), 7.3-7.31 (m, 1H), 7.4-7.6 (m, 3H), 7.61-7.62 (m, 1H), 7.9-7.91 (m, 1H), 8.39 (s, 1H). LCMS: Calculated for $C_{21}H_{21}F_6N_3O_4S$: 525.46, Observed: 548.05 (M+Na)+.

3-(3-(3-chloro-4-fluorophenyl)ureido)-4-(tetrahydro-2H-pyran-2-yl)-N-(2,2,2-trifluoroethyl)benzene sulfonamide (166)

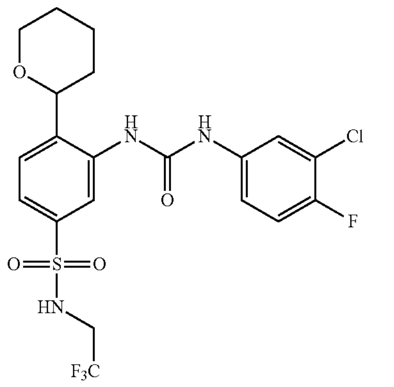 [SMILES: O=C(Nc1ccc(F)c(Cl)c1)Nc1cc(S(=O)(=O)NCC(F)(F)F)ccc1C1CCCCO1]

$^1$H NMR (400 MHz, $CD_3OD$) δ: 1.6-2.0 (m, 6H), 3.59-3.7 (m, 3H), 4.19 (d, 1H), 4.6 (d, 1H), 7.2 (t, 1H), 7.35-7.4 (m, 1H), 7.45 (d, 1H), 7.58 (d, 1H), 7.75 (m, 1H), 8.3 (s, 1H). LCMS: Calculated for $C_{20}H_{20}ClF_4N_3O_4S$: 509.90, Observed: 510.10 $(M+H)^+$.

3-(3-(4-fluoro-3-(trifluoromethyl)phenyl)ureido)-4-(tetrahydro-2H-pyran-2-yl)-N-(2,2,2-trifluoroethyl)benzenesulfonamide (167)

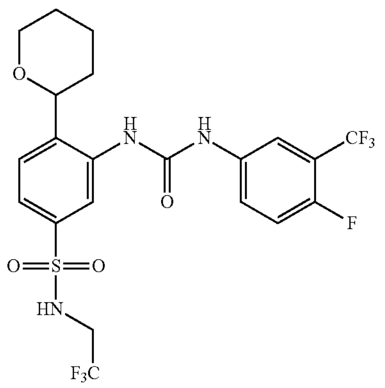 [SMILES: O=C(Nc1ccc(F)c(C(F)(F)F)c1)Nc1cc(S(=O)(=O)NCC(F)(F)F)ccc1C1CCCCO1]

$^1$H NMR (400 MHz, $CD_3OD$) δ: 1.6-2.0 (m, 6H), 3.59-3.8 (m, 3H), 4.2 (m, 1H), 4.6 (m, 1H), 7.3 (t, 1H), 7.5 (d, 1H), 7.59 (d, 1H), 7.7 (d, 1H), 7.9 (m, 1H), 8.35 (s, 1H). LCMS: Calculated for $C_{21}H_{20}F_7N_3O_4S$: 543.46, Observed: 566.0 $(M+Na)^+$.

3-(3-(3-chlorophenyl)ureido)-4-(tetrahydro-2H-pyran-2-yl)-N-(2,2,2-trifluoroethyl)benzenesulfonamide (168)

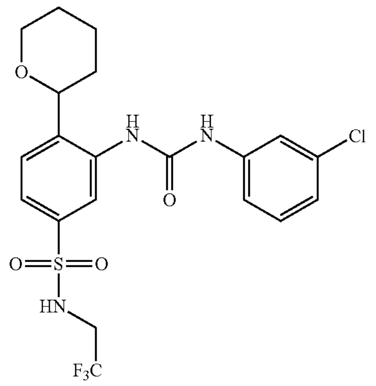 [SMILES: O=C(Nc1cccc(Cl)c1)Nc1cc(S(=O)(=O)NCC(F)(F)F)ccc1C1CCCCO1]

$^1$H NMR (400 MHz, $CD_3OD$) δ: 1.6-2.0 (m, 6H), 3.59-3.7 (m, 3H), 4.2 (d, 1H), 4.6 (m, 1H), 7.02 (d, 1H), 7.2-7.4 (m, 2H), 7.5 (dd, 2H), 7.61 (d, 1H), 8.3 (s, 1H). LCMS: Calculated for $C_{20}H_{21}ClF_3N_3O_4S$: 491.91, Observed: 509.00 $(M+NH_4)^+$.

3-(3-(5-chlorothiazol-2-yl)ureido)-4-(tetrahydro-2H-pyran-2-yl)-N-(2,2,2-trifluoroethyl)benzene sulfonamide (169)

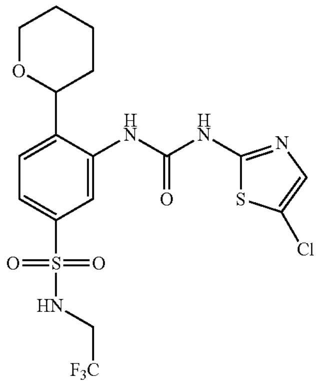 [SMILES: O=C(Nc1ncc(Cl)s1)Nc1cc(S(=O)(=O)NCC(F)(F)F)ccc1C1CCCCO1]

$^1$H NMR (400 MHz, $CD_3OD$) δ: 1.6-2.0 (m, 6H), 3.6-3.79 (m, 3H), 4.2 (d, 1H), 7.4 (d, 1H), 7.21 (s, 1H), 7.5 (d, 1H), 7.6 (d, 1H), 8.4 (s, 1H). LCMS: Calculated for $C_{17}H_{18}ClF_3N_4O_4S_2$: 498.93, Observed: 499.00 $(M)^+$.

N-phenyl-4-(tetrahydro-2H-pyran-2-yl)-3-(3-(3-(trifluoromethyl)phenyl)ureido)benzenesulfonamide (170)

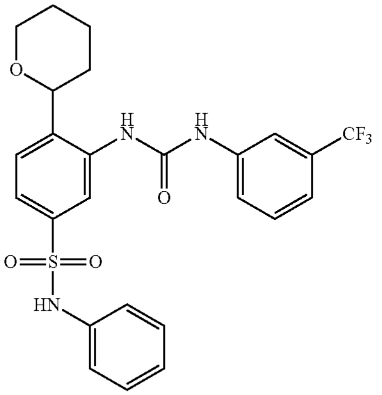 [SMILES: O=C(Nc1cccc(C(F)(F)F)c1)Nc1cc(S(=O)(=O)Nc2ccccc2)ccc1C1CCCCO1]

$^1$H NMR (400 MHz, $CD_3OD$) δ: 1.59-2.0 (m, 6H), 3.6-3.7 (m, 1H), 4.19 (m, 1H), 4.5 (m, 1H), 7.05 (t, 1H), 7.1 (m, 2H), 7.2 (m, 2H), 7.3-7.4 (m, 3H), 7.5 (t, 1H), 7.65 (d, 1H), 7.9 (s, 1H), 8.39 (s, 1H). LCMS: Calculated for $C_{25}H_{24}F_3N_3O_4S$: 519.54, Observed: 520.15 $(M+H)^+$.

4-(tetrahydro-2H-pyran-3-yl)-N-(2,2,2-trifluoroethyl)-3-(3-(6-(trifluoromethyl)pyridine-2-yl)ureido)benzenesulfonamide (171)

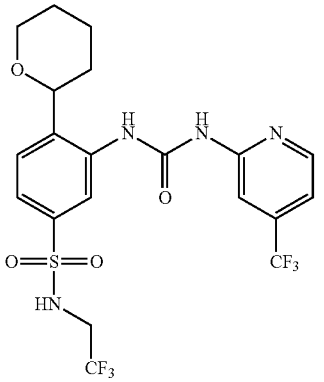 [SMILES: O=C(Nc1cc(C(F)(F)F)ccn1)Nc1cc(S(=O)(=O)NCC(F)(F)F)ccc1C1CCCCO1]

$^1$H NMR (400 MHz, $CDCl_3$) δ: 1.8-2.2 (m, 4H), 3.2 (m, 1H), 3.4 (t, 1H), 3.5-3.62 (m, 3H), 4.1 (t, 2H), 7.0 (s, 1H), 7.2 (d, 1H), 7.45 (d, 1H), 7.7 (d, 1H), 7.81 (br s, 1H), 8.6 (d, 1H), 8.7 (s, 1H), 8.9 (s, 1H), 12.3 (s, 1H). LCMS: Calculated for $C_{20}H_{20}F_6N_4O_4S$: 526.45, Observed: 527.12 $(M+H)^+$.

4-(tetrahydrofuran-2-yl)-N-(2,2,2-trifluoroethyl)-3-(3-(3-(trifluoro methyl)phenyl)ureido)benzene sulfonamide (173)

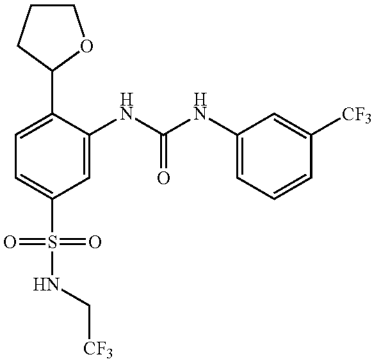

$^1$H NMR (400 MHz, DMSO-$d_6$) δ: 1.7 (m, 1H), 1.9-2.2 (m, 2H), 2.4 (m, 1H), 3.6-3.72 (m, 2H), 3.8-3.9 (m, 1H), 4.0-4.15 (m, 1H), 5.0 (t, 1H), 7.35 (d, 1H), 7.5-7.65 (m, 4H), 8.02 (s, 1H), 8.35 (m, 2H), 8.6 (s, 1H), 9.6 (s, 1H). LCMS: Calculated for $C_{20}H_{19}F_6N_3O_4S$: 511.44, Observed: 512.00 $(M+H)^+$.

The following compounds were similarly prepared according to Scheme 1, Method B:

3-(3-(2-ethylphenyl)ureido)-N-phenyl-4-(thiophen-3-yl)benzenesulfonamide (4): (Method B)

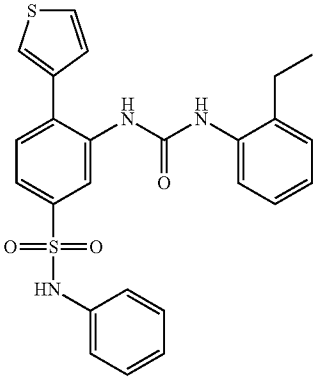 [SMILES: CCc1ccccc1NC(=O)Nc1cc(S(=O)(=O)Nc2ccccc2)ccc1-c1ccsc1]

$^1$H NMR (400 MHz, $CD_3OD$) δ: 1.3 (t, 3H), 2.6 (q, 2H), 7.0 (t, 1H), 7.1-7.3 (m, 8H), 7.4-7.6 (m, 5H), 8.5 (s, 1H). LCMS: Calculated for $C_{25}H_{23}N_3O_3S_2$: 477.60, Observed: 478.05 $(M+H)^+$.

3-(3-(3-ethylphenyl)ureido)-N-phenyl-4-(thiophen-3-yl)benzenesulfonamide (5): (Method B)

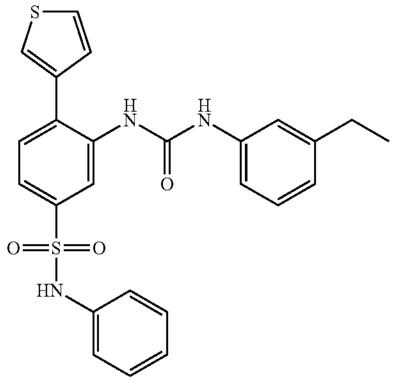 [SMILES: CCc1cccc(NC(=O)Nc2cc(S(=O)(=O)Nc3ccccc3)ccc2-c2ccsc2)c1]

$^1H$ NMR (400 MHz, $CD_3OD$) δ: 1.2 (t, 3H), 2.6 (q, 2H), 6.9 (d, 1H), 7.01 (t, 1H), 7.19-7.34 (m, 8H), 7.4 (dd, 2H), 7.6-7.61 (m, 2H), 8.6 (s, 1H). LCMS: Calculated for $C_{25}H_{23}N_3O_3S_2$: 477.60, Observed: 500.20 $(M+Na)^+$.

3-(3-(2-methoxyphenyl)ureido)-N-phenyl-4-(thiophen-3-yl)benzenesulfonamide (6): (Method B)

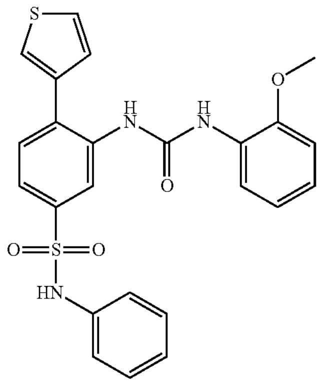 [SMILES: COc1ccccc1NC(=O)Nc1cc(S(=O)(=O)Nc2ccccc2)ccc1-c1ccsc1]

$^1H$ NMR (400 MHz, DMSO-$d_6$) δ: 3.8 (s, 3H), 6.8-7.0 (m, 4H), 7.01-7.3 (m, 5H), 7.4 (s, 2H), 7.6-7.8 (m, 3H), 8.1 (d, 1H), 8.4 (s, 1H), 8.7 (s, 1H), 10.4 (br s, 1H). LCMS: Calculated for $C_{24}H_{21}N_3O_4S_2$: 479.57, Observed: 480.05 $(M+H)^+$.

3-(3-(3-methoxyphenyl)ureido)-N-phenyl-4-(thiophen-3-yl)benzenesulfonamide (7): (Method B)

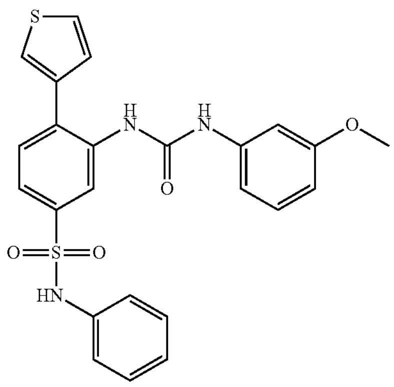 [SMILES: COc1cccc(NC(=O)Nc2cc(S(=O)(=O)Nc3ccccc3)ccc2-c2ccsc2)c1]

$^1H$ NMR (400 MHz, $CD_3OD$) δ: 3.8 (s, 3H), 6.6 (d, 1H), 6.8 (d, 1H), 7.0 (t, 1H), 7.1-7.3 (m, 7H), 7.35-7.45 (m, 2H), 7.59 (s, 1H), 7.61 (s, 1H), 8.6 (s, 1H). LCMS: Calculated for $C_{24}H_{21}N_3O_4S_2$: 479.57, Observed: 480.15 $(M+H)^+$.

3-(3-(3-chlorophenyl)ureido)-N-phenyl-4-(thiophen-3-yl)benzenesulfonamide (8): (Method B)

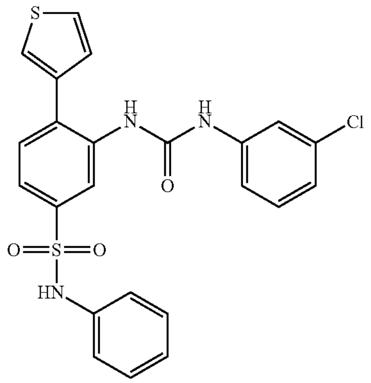 [SMILES: O=C(Nc1cccc(Cl)c1)Nc1cc(S(=O)(=O)Nc2ccccc2)ccc1-c1ccsc1]

$^1H$ NMR (400 MHz, DMSO-$d_6$) δ: 7.0-7.4 (m, 9H), 7.4-7.5 (m, 2H), 7.7-7.8 (m, 3H), 8.0 (s, 1H), 8.6 (s, 1H), 9.4 (s, 1H), 10.4 (s, 1H). LCMS: Calculated for $C_{23}H_{18}ClN_3O_3S_2$: 483.99, Observed: 484.00 $(M+H)^+$.

N-phenyl-4-(thiophen-3-yl)-3-(3-(2-(trifluoromethyl)phenyl)ureido)benzenesulfonamide (10) (Method B)

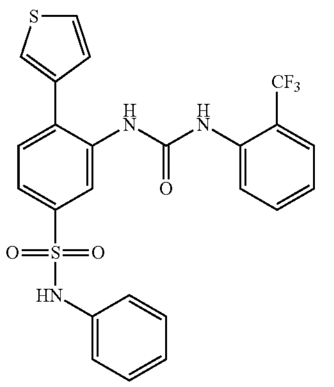 [SMILES: O=C(Nc1cc(S(=O)(=O)Nc2ccccc2)ccc1-c1ccsc1)Nc1ccccc1C(F)(F)F]

$^1H$ NMR (400 MHz, $CD_3OD$) δ: 7.05 (t, 1H), 7.05-7.21 (m, 4H), 7.3 (t, 1H), 7.41 (dd, 2H), 7.49-7.79 (m, 4H), 8.4 (s, 1H). LCMS: Calculated for $C_{19}H_{16}F_3N_3O_3S_2$: 517.54, Observed: 518.10 $(M+H)^+$.

3-(3-(2,5-dimethylphenyl)ureido)-N-phenyl-4-(thiophen-3-yl)benzenesulfonamide (11) (Method B)

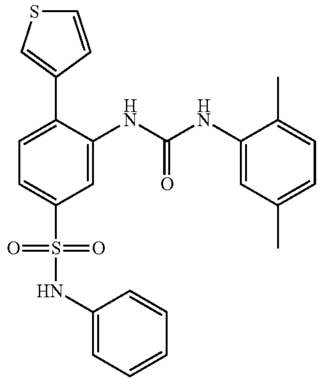 [SMILES: Cc1ccc(C)c(NC(=O)Nc2cc(S(=O)(=O)Nc3ccccc3)ccc2-c2ccsc2)c1]

$^1$H NMR (400 MHz, $CD_3OD$) δ: 2.2 (s, 3H), 2.3 (s, 3H), 6.9 (d, 1H), 7.0-7.05 (m, 2H), 7.1-7.6 (m, 10H), 8.5 (s, 1H). LCMS: Calculated for $C_{25}H_{23}N_3O_3S_2$: 477.62, Observed: 478.05 $(M+H)^+$.

3-(3-(2-fluoro-5-methylphenyl)ureido)-N-phenyl-4-(thiophen-3-yl)benzenesulfonamide (12) (Method B)

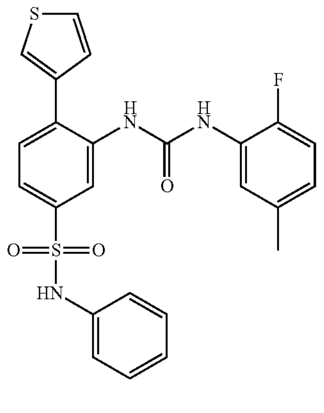 [SMILES: Cc1ccc(F)c(NC(=O)Nc2cc(S(=O)(=O)Nc3ccccc3)ccc2-c2ccsc2)c1]

$^1$H NMR (400 MHz, $CD_3OD$) δ: 2.3 (s, 3H), 6.8-7.1 (m, 3H), 7.11-7.38 (m, 5H), 7.4-7.6 (m, 4H), 7.9 (d, 1H), 8.5 (s, 1H). LCMS: Calculated for $C_{24}H_{20}FN_3O_3S_2$: 481.56, Observed: 482.05 $(M+H)^+$.

3-(3-(2-chlorophenyl)ureido)-N-cyclopropyl-4-(thiophen-3-yl)benzenesulfonamide (25) (Method B)

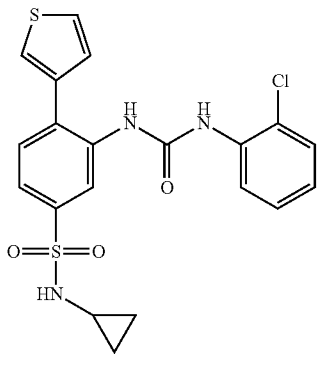 [SMILES: O=C(Nc1ccccc1Cl)Nc1cc(S(=O)(=O)NC2CC2)ccc1-c1ccsc1]

$^1$H NMR (400 MHz, $CD_3OD$) δ: 0.50-0.65 (m, 4H), 2.2-2.3 (m, 1H), 7.0-7.1 (m, 1H), 7.3 (m, 2H), 7.4 (m, 1H), 7.5-7.7 (m, 4H), 8.0 (d, 1H), 8.4 (s, 1H). LCMS: Calculated for $C_{20}H_{18}ClN_3O_3S_2$: 447.96, Observed: 448.05 $(M)^+$.

N-cyclopropyl-3-(3-(2,3-dichlorophenyl)ureido)-4-(thiophen-3-yl)benzenesulfonamide (27) (Method B)

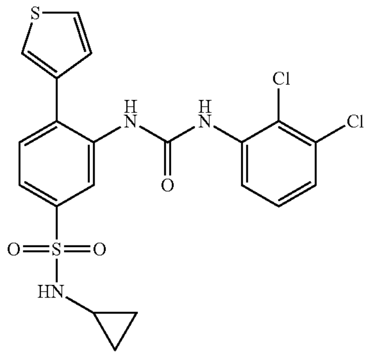 [SMILES: O=C(Nc1cc(S(=O)(=O)NC2CC2)ccc1-c1ccsc1)Nc1cccc(Cl)c1Cl]

$^1$H NMR (400 MHz, $CD_3OD$) δ: 0.5-0.6 (m, 4H), 2.2-2.30 (m, 1H), 7.2-7.3 (m, 3H), 7.5-7.7 (m, 4H), 8.0 (d, 1H), 8.4 (s, 1H). LCMS: Calculated for $C_{20}H_{17}Cl_2N_3O_3S_2$: 482.40, Observed: 505.40 $(M+Na)^+$.

N-cyclopropyl-3-(3-(5-methylpyridin-3-yl)ureido)-4-(thiophen-3-yl)benzenesulfonamide (29): (Method B)

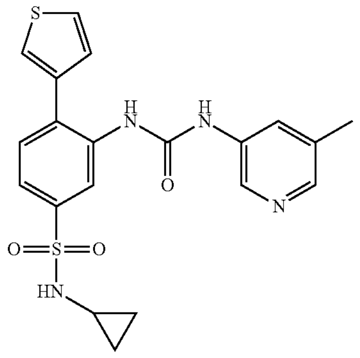 [SMILES: Cc1cncc(NC(=O)Nc2cc(S(=O)(=O)NC3CC3)ccc2-c2ccsc2)c1]

$^1$H NMR (400 MHz, DMSO-$d_6$) δ: 0.4-0.55 (m, 4H), 2.15 (m, 1H), 2.25 (s, 3H), 7.35 (d, 1H), 7.5-56 (m, 2H), 7.75-7.85 (m, 3H), 8.0-8.30 (m, 2H), 8.35 (s, 1H), 8.5 (s, 1H), 8.4 (br s, 1H. LCMS: Calculated for $C_{20}H_{20}N_4O_3S_2$: 428.53, Observed: 429.05 $(M+H)^+$.

N-cyclopropyl-3-(3-(6-methylpyridin-2-yl)ureido)-4-(thiophen-3-yl)benzenesulfonamide (30) (Method B)

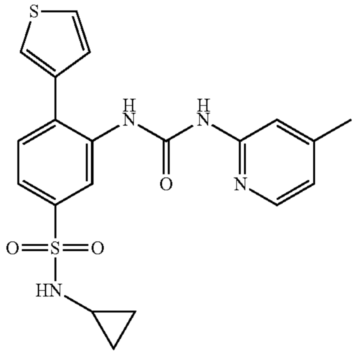 [SMILES: Cc1ccnc(NC(=O)Nc2cc(S(=O)(=O)NC3CC3)ccc2-c2ccsc2)c1]

$^1$H NMR (400 MHz, $CD_3OD$) δ: 0.58 (m, 4H), 2.2-2.3 (m, 1H), 2.28 (s, 3H), 6.7-6.8 (m, 2H), 7.2-7.3 (m, 1H), 7.5 (d, 1H), 7.59-7.62 (m, 4H), 8.9 (s, 1H). LCMS: Calculated for $C_{20}H_{20}N_4O_3S_2$: 428.53, Observed: 429.05 $(M+H)^+$.

Scheme 2:

Method C

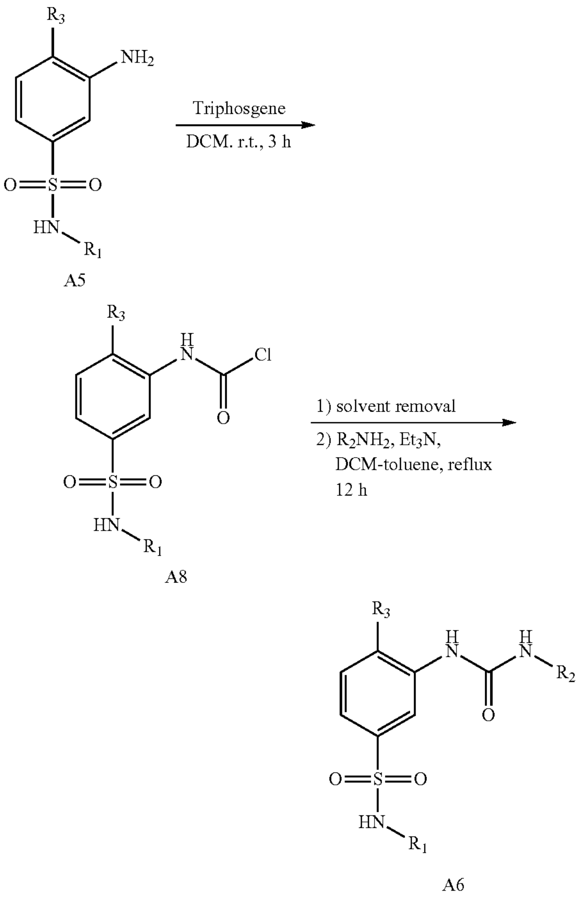

-continued

Method D

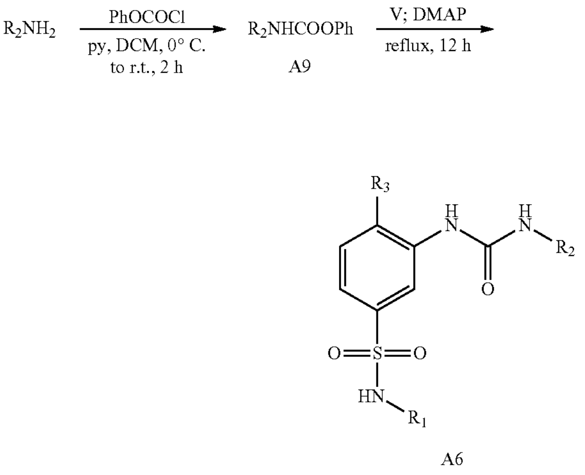

Method E

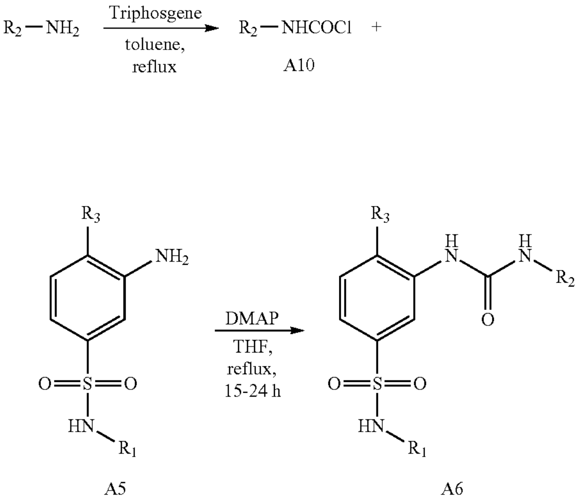

The methods in Scheme 2 were used to prepare desired urea compounds:

Method C (Scheme 2):

To a stirred solution of the scaffold A5 (1 equiv.) in dichloromethane was added triphosgene (0.6 equiv.) at 0° C. The reaction mixture was warmed to room temperature and stirring was continued for 3 h. After 3 h, the solvent was evaporated and the residue (carbamoyl chloride A8) was redissolved in DCM (in some cases in toluene) followed by the addition of the corresponding amine (1 equiv.) and triethyl amine (1 equiv.) and the reaction mass was refluxed for 12 h. After completion of the reaction, water was added to the reaction mixture and extracted with ethyl acetate. The organic layers were pooled, brine washed, dried, concentrated and purified by Reverse Phase Prep-HPLC to obtain compound A6.

The following compounds were similarly prepared according to Method C procedure:

2-(3-(5-chloro-2-fluorophenyl)ureido)-N-(2,2,2-trifluoroethyl)-[1,1'-biphenyl]-4-sulfonamide (74)

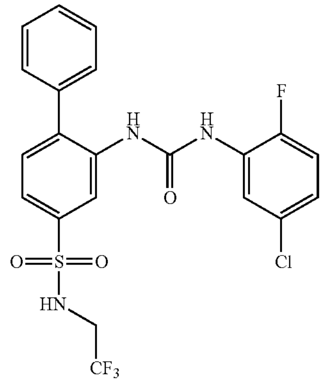 [SMILES: O=C(Nc1cc(Cl)ccc1F)Nc1cc(S(=O)(=O)NCC(F)(F)F)ccc1-c1ccccc1]

$^1H$ NMR (400 MHz, DMSO-$d_6$) δ: 3.65-3.8 (m, 2H), 7.15 (d, 1H), 7.25 (t, 1H), 7.40-7.61 (m, 7H), 8.25 (d, 1H), 8.55 (d, 2H), 8.75 (br s, 1H), 9.25 (br s, 1H). LCMS: Calculated for $C_{21}H_{16}ClF_4N_3O_3S$: 501.88, Observed: 502.00 $(M+H)^+$.

2-(3-(4-fluoro-2-(trifluoromethyl)phenyl)ureido)-N-(2,2,2-trifluoroethyl)-[1,1'-biphenyl]-4-sulfonamide (76)

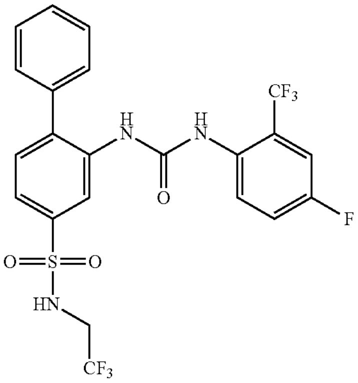 [SMILES: O=C(Nc1cc(S(=O)(=O)NCC(F)(F)F)ccc1-c1ccccc1)Nc1ccc(F)cc1C(F)(F)F]

$^1H$ NMR (400 MHz, DMSO-$d_6$) δ: 3.65-3.80 (m, 2H), 7.4-7.6 (m, 9H), 7.78 (t, 1H), 8.4 (s, 1H), 8.5 (s, 2H), 8.76 (t, 1H). LCMS: Calculated for $C_{22}H_{16}F_7N_3O_3S$: 535.43, Observed: 535.95 $(M+H)^+$.

2-(3-(1-methyl-1H-pyrazol-5-yl)ureido)-N-(2,2,2-trifluoroethyl)-[1,1'-biphenyl]-4-sulfonamide (77)

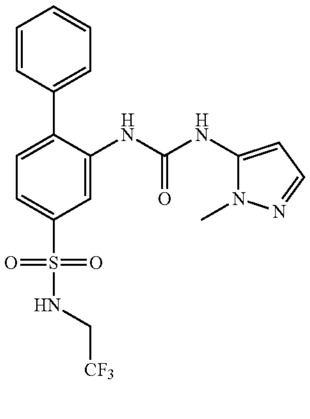 [SMILES: Cn1nccc1NC(=O)Nc1cc(S(=O)(=O)NCC(F)(F)F)ccc1-c1ccccc1]

$^1H$ NMR (400 MHz, $CD_3OD$) δ: 3.40-3.50 (m, 3H), 3.60-3.70 (m, 2H), 5.90 (br s, 1H), 7.30-7.65 (m, 8H), 8.70 (s, 1H). LCMS: Calculated for $C_{19}H_{18}F_3N_5O_3S$: 453.44, Observed: 454.10 $(M+H)^+$.

N-(2,2,2-trifluoroethyl)-2-(3-(3-(trifluoromethyl)pyridin-4-yl)ureido)-[1,1'-biphenyl]-4-sulfonamide (78)

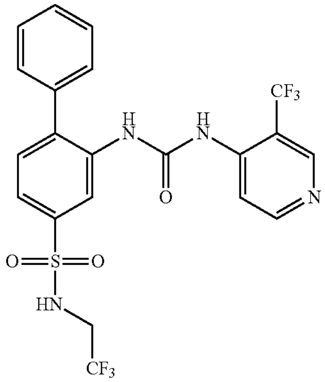 [SMILES: O=C(Nc1cc(S(=O)(=O)NCC(F)(F)F)ccc1-c1ccccc1)Nc1ccncc1C(F)(F)F]

$^1H$ NMR (400 MHz, $CD_3OD$) δ: 3.60-3.75 (m, 2H), 7.40-7.58 (m, 6H), 7.75 (d, 1H), 8.42 (s, 1H), 8.66 (d, 1H), 8.79 (d, 1H), 8.85 (s, 1H). LCMS: Calculated for $C_{21}H_{16}F_6N_4O_3S$: 518.43, Observed: 519.00 $(M+H)^+$.

2-(3-(6-chloropyridin-2-yl)ureido)-N-(2,2,2-trifluoroethyl)-[1,1'-biphenyl]-4-sulfonamide (79)

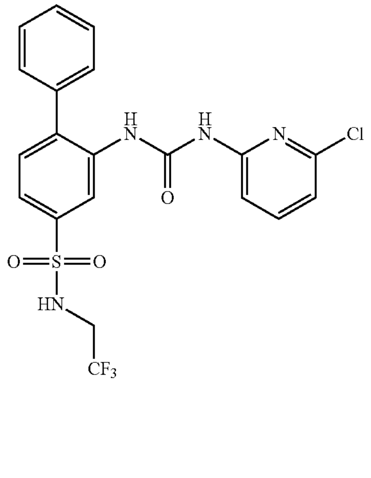 [SMILES: O=C(Nc1cccc(Cl)n1)Nc1cc(S(=O)(=O)NCC(F)(F)F)ccc1-c1ccccc1]

$^1H$ NMR (400 MHz, DMSO-$d_6$) δ: 3.62-3.80 (m, 2H), 7.02 (d, 1H), 7.40-7.82 (m, 9H), 8.56 (s, 1H), 8.75 (s, 1H), 8.90 (s, 1H), 10.10 (s, 1H). LCMS: Calculated for $C_{20}H_{16}ClF_3N_4O_3S$: 484.88, Observed: 485.2 $(M+H)^+$.

2-(3-(3-(hydroxymethyl)phenyl)ureido)-N-(2,2,2-trifluoroethyl)-[1,1'-biphenyl]-4-sulfonamide (80)

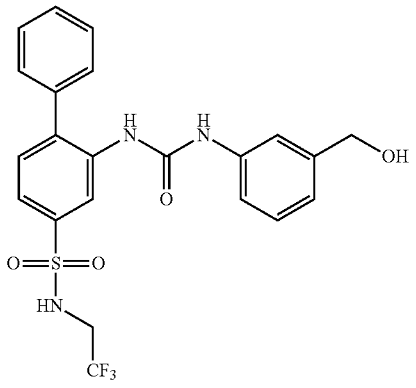 [SMILES: O=C(Nc1cccc(CO)c1)Nc1cc(S(=O)(=O)NCC(F)(F)F)ccc1-c1ccccc1]

$^1$H NMR (400 MHz, DMSO-$d_6$) δ: 3.65-3.80 (m, 2H), 4.45 (d, 2H), 5.18 (t, 1H), 6.90 (d, 1H), 7.19-7.35 (m, 2H), 7.38-7.62 (m, 8H), 7.85 (s, 1H), 8.60 (s, 1H), 8.70 (t, 1H), 9.20 (s, 1H). LCMS: Calculated for $C_{22}H_{20}F_3N_3O_4S$: 479.11, Observed: 480.05 $(M+H)^+$.

2-(3-(3-hydroxyphenyl)ureido)-N-(2,2,2-trifluoroethyl)-[1,1'-biphenyl]-4-sulfonamide (81)

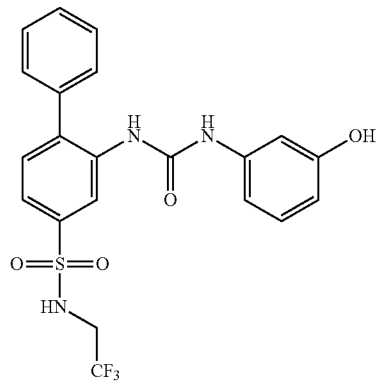 [SMILES: O=C(Nc1cccc(O)c1)Nc1cc(S(=O)(=O)NCC(F)(F)F)ccc1-c1ccccc1]

$^1$H NMR (400 MHz, DMSO-$d_6$) δ: 3.44 (br s, 1H), 3.60-3.80 (m, 2H), 6.38 (d, 1H), 6.72 (d, 1H), 7.0-7.16 (m, 2H), 7.38-7.60 (m, 6H), 7.95 (s, 1H), 8.58 (s, 1H), 8.70 (t, 1H), 9.05 (s, 1H), 9.35 (br s, 1H). LCMS: Calculated for $C_{21}H_{18}F_3N_3O_4S$: 465.44, Observed: 466.05 $(M+H)^+$.

2-(3-(4-chloropyridin-2-yl)ureido)-N-(2,2,2-trifluoroethyl)-[1,1'-biphenyl]-4-sulfonamide (82)

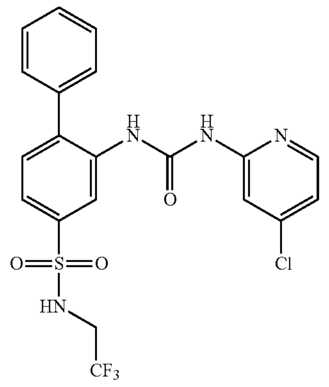

$^1$H NMR (400 MHz, DMSO-$d_6$) δ: 3.60-3.80 (m, 2H), 7.0 (d, 1H), 7.22 (d, 1H), 7.40-7.62 (m, 8H), 8.75 (t, 1H), 8.84 (s, 1H), 10.04 (s, 1H), 10.95 (br s, 1H). LCMS: Calculated for $C_{20}H_{16}ClF_3N_4O_3S$: 484.88, Observed: 485.00 $(M+H)^+$.

2-(3-(3-(methylsulfinyl)phenyl)ureido)-N-(2,2,2-trifluoroethyl)-[1,1'-biphenyl]-4-sulfonamide (83)

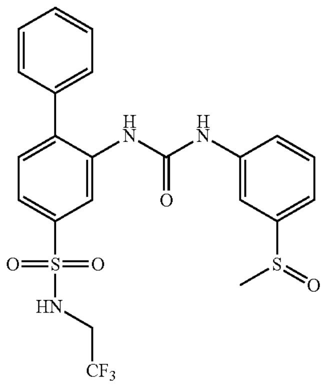 [SMILES: CS(=O)c1cccc(NC(=O)Nc2cc(S(=O)(=O)NCC(F)(F)F)ccc2-c2ccccc2)c1]

$^1$H NMR (400 MHz, DMSO-$d_6$) δ: 2.72 (s, 3H), 3.65-3.80 (m, 2H), 7.22 (s, 1H), 7.40-7.60 (m, 9H), 7.84 (s, 1H), 7.95 (s, 1H), 8.58 (s, 1H), 8.75 (t, 1H), 9.50 (s, 1H). LCMS: Calculated for $C_{22}H_{20}F_3N_3O_4S_2$: 511.54, Observed: 512.10 $(M+H)^+$.

N-(2,2,2-trifluoroethyl)-2-(3-(4-(trifluoromethyl)pyridin-3-yl)ureido)-[1,1'-biphenyl]-4-sulfonamide (84)

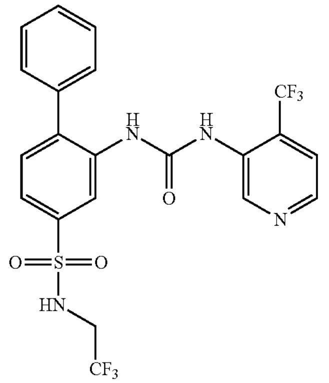 [SMILES: O=C(Nc1cc(S(=O)(=O)NCC(F)(F)F)ccc1-c1ccccc1)Nc1cnccc1C(F)(F)F]

$^1$H NMR (400 MHz, $CD_3OD$) δ: 3.60-3.75 (m, 2H), 7.38-7.60 (m, 6H), 7.60-7.75 (m, 2H), 8.40 (s, 1H), 8.52 (d, 1H), 9.10 (s, 1H). LCMS: Calculated for $C_{21}H_{16}F_6N_4O_3S$: 518.43, Observed: 519.15 $(M+H)^+$.

2-(3-(4-chloropyridin-3-yl)ureido)-N-(2,2,2-trifluoroethyl)-[1,1'-biphenyl]-4-sulfonamide (85)

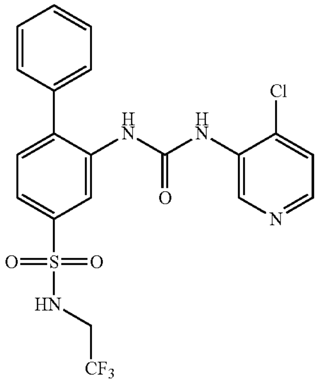 [SMILES: O=C(Nc1cnccc1Cl)Nc1cc(S(=O)(=O)NCC(F)(F)F)ccc1-c1ccccc1]

$^1$H NMR (400 MHz, $CD_3OD$) δ: 3.60-3.75 (m, 2H), 7.40-7.58 (m, 6H), 7.65-7.75 (m, 2H), 8.25 (br s, 1H), 8.50 (s, 1H), 9.42 (br s, 1H). LCMS: Calculated for $C_{20}H_{16}ClF_3N_4O_3S$: 484.88, Observed: 485.00 $(M+H)^+$.

2-(3-(6-fluoropyridin-2-yl)ureido)-N-(2,2,2-trifluoroethyl)-[1,1'-biphenyl]-4-sulfonamide (86)

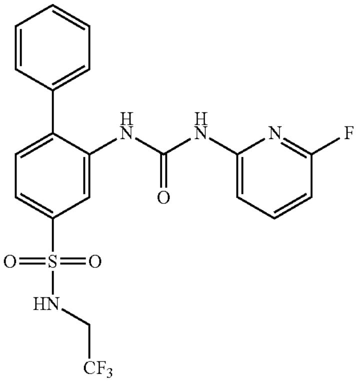 [SMILES: O=C(Nc1cccc(F)n1)Nc1cc(S(=O)(=O)NCC(F)(F)F)ccc1-c1ccccc1]

$^1$H NMR (400 MHz, DMSO-$d_6$) δ: 3.65-3.80 (m, 2H), 6.68 (d, 1H), 7.40-7.62 (m, 8H), 7.80-7.95 (m, 1H), 8.60 (s, 1H), 8.75 (t, 1H), 8.98 (s, 1H), 9.98 (s, 1H). LCMS: Calculated for $C_{20}H_{16}F_4N_4O_3S$: 468.42, Observed: 469.05 $(M+H)^+$.

N-(2,2,2-trifluoroethyl)-2-(3-(4-(trifluoromethyl)pyridin-2-yl)ureido)-[1,1'-biphenyl]-4-sulfonamide (87)

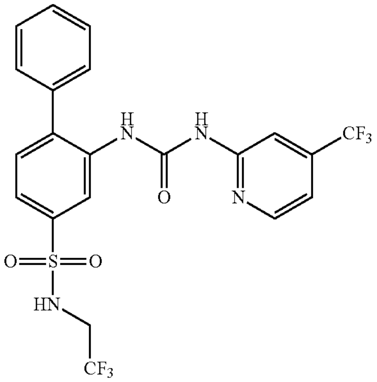 [SMILES: O=C(Nc1cc(C(F)(F)F)ccn1)Nc1cc(S(=O)(=O)NCC(F)(F)F)ccc1-c1ccccc1]

$^1$H NMR (400 MHz, DMSO-$d_6$) δ: 3.62-3.79 (m, 2H), 7.21 (d, 1H), 7.41-7.61 (m, 8H), 7.82 (s, 1H), 8.78 (s, 1H), 8.8 (s, 1H), 10.2 (s, 1H), 10.60 (br s, 1H). LCMS: Calculated for $C_{21}H_{16}F_6N_4O_3S$: 518.43, Observed: 519.00 $(M+H)^+$.

2-(3-(3-chlorophenyl)ureido)-N-(2,2,2-trifluoroethyl)-[1,1'-biphenyl]-4-sulfonamide (88)

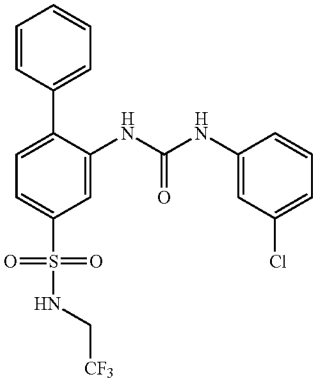 [SMILES: O=C(Nc1cccc(Cl)c1)Nc1cc(S(=O)(=O)NCC(F)(F)F)ccc1-c1ccccc1]

$^1$H NMR (400 MHz, DMSO-$d_6$) δ: 3.6-3.8 (m, 2H), 7.0 (d, 1H), 7.18 (d, 1H), 7.30 (t, 1H), 7.4-7.6 (m, 7H), 7.68 (s, 1H), 7.98 (s, 1H), 8.55 (s, 1H), 8.73 (t, 1H), 9.38 (s, 1H). LCMS: Calculated for $C_{21}H_{17}ClF_3N_3O_3S$: 483.89, Observed: 484.00 $(M+H)^+$.

2-(3-(3,5-difluorophenyl)ureido)-N-(2,2,2-trifluoroethyl)-[1,1'-biphenyl]-4-sulfonamide (89)

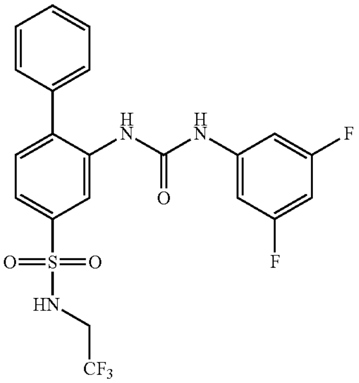 [SMILES: O=C(Nc1cc(F)cc(F)c1)Nc1cc(S(=O)(=O)NCC(F)(F)F)ccc1-c1ccccc1]

$^1$H NMR (400 MHz, DMSO-$d_6$) δ: 3.67-3.81 (m, 2H), 6.80 (t, 1H), 7.18 (d, 2H), 7.40-7.61 (m, 7H), 8.08 (s, 1H), 8.50 (s, 1H), 8.75 (t, 1H), 9.57 (s, 1H). LCMS: Calculated for $C_{21}H_{16}F_5N_3O_3S$: 485.43, Observed: 486.00 $(M+H)^+$.

2-(3-(2-chloro-5-fluorophenyl)ureido)-N-(2,2,2-trifluoroethyl)-[1,1'-biphenyl]-4-sulfonamide (90)

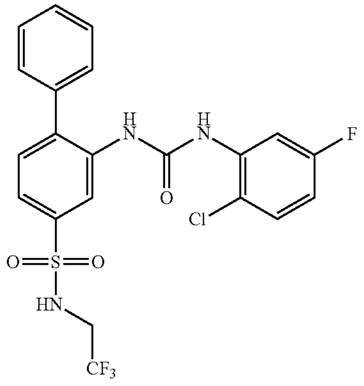 [SMILES: O=C(Nc1cc(F)ccc1Cl)Nc1cc(S(=O)(=O)NCC(F)(F)F)ccc1-c1ccccc1]

$^1$H NMR (400 MHz, DMSO-$d_6$) δ: 3.62-3.78 (m, 2H), 6.90 (t, 1H), 7.4-7.61 (m, 8H), 8.02 (d, 1H), 8.35-8.42 (m, 1H), 8.75 (s, 1H), 8.90 (d, 2H). LCMS: Calculated for $C_{21}H_{16}ClF_4N_3O_3S$: 501.88, Observed: 502.00 $(M+H)^+$.

2-(3-(1,5-dimethyl-1H-pyrazol-3-yl)ureido)-N-(2,2,2-trifluoroethyl)-[1,1'-biphenyl]-4-sulfonamide (91)

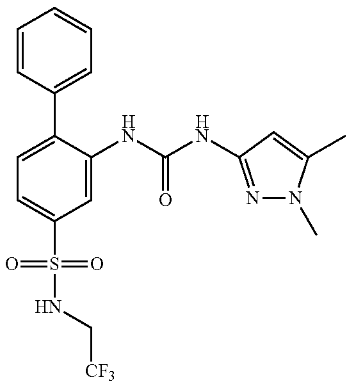 [SMILES: Cc1cc(NC(=O)Nc2cc(S(=O)(=O)NCC(F)(F)F)ccc2-c2ccccc2)nn1C]

$^1$H NMR (400 MHz, $CDCl_3$) δ: 2.10 (s, 3H), 3.15 (s, 3H), 3.60-3.75 (m, 2H), 5.50 (s, 1H), 7.0-7.10 (m, 1H), 7.39 (d, 1H), 7.40-7.59 (m, 6H), 7.62 (d, 1H), 8.95 (s, 1H), 10.20 (br s, 1H). LCMS: Calculated for $C_{20}H_{20}F_3N_5O_3S$: 467.46, Observed: 468.10 $(M+H)^+$.

2-(3-(1-isopropyl-1H-pyrazol-3-yl)ureido)-N-(2,2,2-trifluoroethyl)-[1,1'-biphenyl]-4-sulfonamide (92)

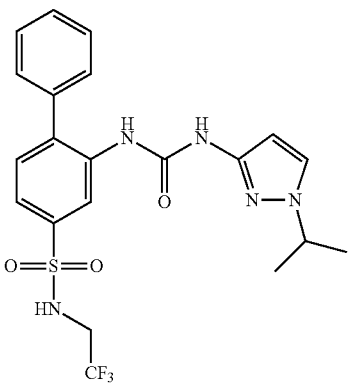 [SMILES: CC(C)n1ccc(NC(=O)Nc2cc(S(=O)(=O)NCC(F)(F)F)ccc2-c2ccccc2)n1]

$^1$H NMR (400 MHz, $CD_3OD$) δ: 1.2 (d, 6H), 3.6-3.72 (m, 2H), 4.0 (m, 1H), 5.9 (br s, 1H), 7.4-7.6 (m, 7H), 7.62 (d, 1H), 8.6 (s, 1H). LCMS: Calculated for $C_{21}H_{22}F_3N_5O_3S$: 481.49, Observed: 482.00 $(M+H)^+$.

2-(3-(1-ethyl-1H-pyrazol-3-yl)ureido)-N-(2,2,2-trifluoroethyl)-[1,1'-biphenyl]-4-sulfonamide (93)

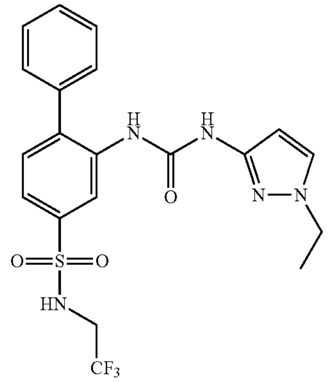 [SMILES: CCn1ccc(NC(=O)Nc2cc(S(=O)(=O)NCC(F)(F)F)ccc2-c2ccccc2)n1]

$^1$H NMR (400 MHz, $CD_3OD$) δ: 1.18 (t, 3H), 3.60-3.75 (m, 4H), 5.90 (br s, 1H), 7.35-7.55 (m, 7H), 7.60 (d, 1H), 8.64 (s, 1H). LCMS: Calculated for $C_{20}H_{20}F_3N_5O_3S$: 467.46, Observed: 468.05 $(M+H)^+$.

N-(2,2,2-trifluoroethyl)-2-(3-(5-(trifluoromethyl)pyridin-3-yl)ureido)-[1,1'-biphenyl]-4-sulfonamide (94)

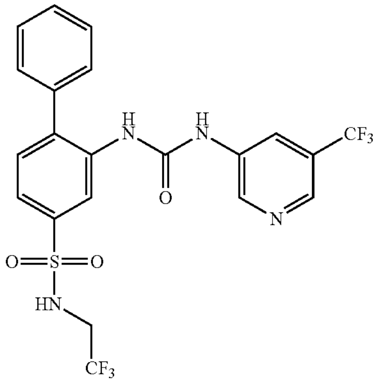 [SMILES: O=C(Nc1cncc(C(F)(F)F)c1)Nc1cc(S(=O)(=O)NCC(F)(F)F)ccc1-c1ccccc1]

$^1$H NMR (400 MHz, DMSO-$d_6$) δ: 3.65-3.80 (m, 2H), 7.40-7.62 (m, 7H), 8.18 (s, 1H), 8.42 (s, 1H), 8.56 (d, 2H), 8.65 (s, 1H), 8.75 (t, 1H), 9.70 (s, 1H). LCMS: Calculated for $C_{21}H_{16}F_6N_4O_3S$: 518.43, Observed: 519.3 $(M+H)^+$.

Method D (Scheme 2):

To a solution of the corresponding amines (1 equiv.) in dichloromethane was added pyridine (1 equiv.) and phenyl chloroformate (1 equiv.) at 0° C. Stirring was continued for 2 h followed by the addition of the scaffold amine (1 equiv.) and DMAP (0.2 equiv.). The reaction mixture was refluxed overnight. After cooling, water was added and extracted with dichloromethane. The pooled organic fractions were brine washed, dried, concentrated and purified by Reverse Phase Prep-HPLC to provide compounds A6.

The following compounds were similarly prepared according to the Method D procedure:

2-(3-(2-fluoropyridin-3-yl)ureido)-N-(2,2,2-trifluoroethyl)-[1,1'-biphenyl]-4-sulfonamide (97)

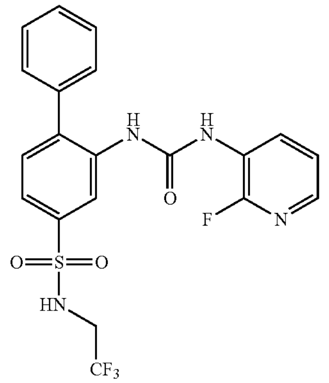 [SMILES: O=C(Nc1cc(S(=O)(=O)NCC(F)(F)F)ccc1-c1ccccc1)Nc1cccnc1F]

$^1$H NMR (400 MHz, DMSO-d$_6$) δ: 3.60-3.80 (m, 2H), 7.25-7.35 (m, 1H), 7.40-7.62 (m, 7H), 7.80 (s, 1H), 8.50 (d, 2H), 8.60 (t, 1H), 8.74 (s, 1H), 9.23 (s, 1H). LCMS: Calculated for $C_{20}H_{16}F_4N_4O_3S$: 468.42, Observed: 512.81 $(M+HCO2)^+$.

2-(3-(5-fluoropyridin-3-yl)ureido)-N-(2,2,2-trifluoroethyl)-[1,1'-biphenyl]-4-sulfonamide (98)

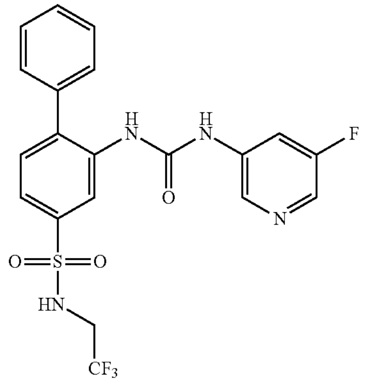 [SMILES: O=C(Nc1cncc(F)c1)Nc1cc(S(=O)(=O)NCC(F)(F)F)ccc1-c1ccccc1]

$^1$H NMR (400 MHz, DMSO-d$_6$) δ: 3.60-3.80 (m, 2H), 7.40-7.60 (m, 7H), 7.98 (d, 1H), 8.12 (s, 1H), 8.20 (s, 1H), 8.30 (s, 1H), 8.52 (s, 1H), 8.72 (s, 1H), 9.60 (s, 1H). LCMS: Calculated for $C_{20}H_{16}F_4N_4O_3S$: 468.42, Observed: 469.09 $(M+H)^+$.

2-(3-(3-fluoropyridin-2-yl)ureido)-N-(2,2,2-trifluoroethyl)-[1,1'-biphenyl]-4-sulfonamide (99)

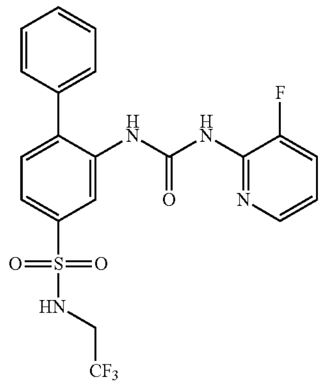 [SMILES: O=C(Nc1cc(S(=O)(=O)NCC(F)(F)F)ccc1-c1ccccc1)Nc1ncccc1F]

$^1$H NMR (400 MHz, DMSO-d$_6$) δ: 3.65-3.80 (m, 2H), 6.90-7.0 (m, 1H), 7.10 (d, 1H), 7.40-7.70 (m, 8H), 8.75 (s, 1H), 8.92 (s, 1H), 9.72 (s, 1H), 11.60 (s, 1H). LCMS: Calculated for $C_{20}H_{16}F_4N_4O_3S$: 468.42, Observed: 469.13 $(M+H)^+$.

Method E (Scheme 2):

To a stirred solution of triphosgene (2.8 equiv.) in toluene at room temperature was added the amine (1 equiv.) and refluxed until the amine was consumed completely as indicated by TLC. The solvent was evaporated in vacuo and the crude reaction mixture was dissolved in dry THF to which the scaffold amine A5 (1 equiv.) and DMAP (0.2 equiv.) were added. The same was heated at 60 to 70° C. for 15 to 24 h. After completion of the reaction, the solvent was evaporated and the product was purified by column chromatography to obtain compound A6.

The following compounds were similarly prepared according to the Method E procedure: 2-(3-(5-chlorothiazol-2-yl)ureido)-N-(2,2,2-trifluoroethyl)-[1,1'-biphenyl]-4-sulfonamide (100):

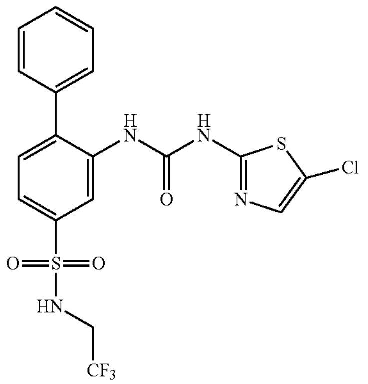 [SMILES: O=C(Nc1ncc(Cl)s1)Nc1cc(S(=O)(=O)NCC(F)(F)F)ccc1-c1ccccc1]

$^1$H NMR (400 MHz, $CD_3OD$) δ: 3.62-3.75 (m, 2H), 7.15 (s, 1H), 7.41-7.58 (m, 6H), 7.65 (d, 1H), 8.6 (s, 1H). LCMS: Calculated for $C_{18}H_{14}ClF_3N_4O_3S_2$: 490.90, Observed: 490.95 $(M^+)$.

2-(3-(5-chloro-4-methylthiazol-2-yl)ureido)-N-(2,2,2-trifluoroethyl)-[1,1'-biphenyl]-4-sulfonamide (101)

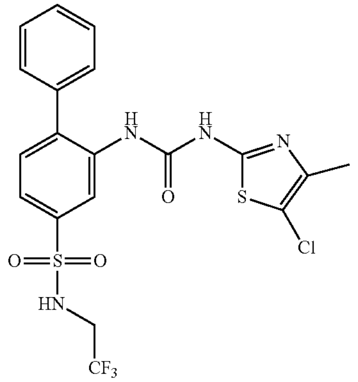 [SMILES: Cc1nc(NC(=O)Nc2cc(S(=O)(=O)NCC(F)(F)F)ccc2-c2ccccc2)sc1Cl]

$^1$H NMR (400 MHz, $CD_3OD$) δ: 2.18 (s, 3H), 3.62-3.74 (m, 2H), 7.40-7.59 (m, 6H), 7.65 (d, 1H), 8.59 (s, 1H). LCMS: Calculated for $C_{19}H_{16}ClF_3N_4O_3S_2$: 504.93, Observed: 505.05 ($M^+$).

3-(3-(5-chlorothiazol-2-yl)ureido)-4-(tetrahydrofuran-3-yl)-N-(2,2,2-trifluoroethyl)benzene sulfonamide (172)

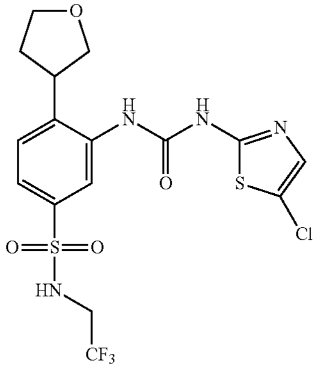 [SMILES: O=C(Nc1ncc(Cl)s1)Nc1cc(S(=O)(=O)NCC(F)(F)F)ccc1C1CCOC1]

$^1$H NMR (400 MHz, $CD_3OD$) δ: 2.0 (m, 1H), 2.45 (m, 1H), 3.6-3.7 (m, 3H), 3.8-4.0 (m, 2H), 4.0-4.2 (m, 2H), 7.21 (s, 1H), 7.6 (d, 1H), 7.7 (d, 1H), 8.2 (s, 1H). LCMS: Calculated for $C_{16}H_{16}ClF_3N_4O_4S_2$: 484.90, Observed: 484.95 $(M+H)^+$.

2-(3-(4-methyloxazol-2-yl)ureido)-N-(2,2,2-trifluoroethyl)-[1,1'-biphenyl]-4-sulfonamide (102)

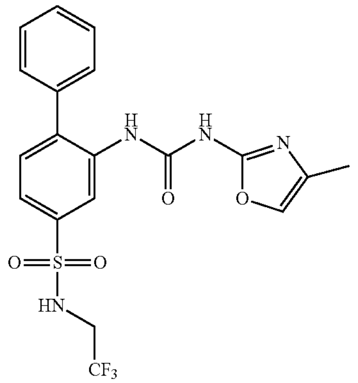 [SMILES: Cc1coc(NC(=O)Nc2cc(S(=O)(=O)NCC(F)(F)F)ccc2-c2ccccc2)n1]

$^1$H NMR (400 MHz, $CD_3OD$) δ: 1.75 (s, 3H), 3.60-3.70 (q, 2H), 7.10 (s, 1H), 7.39-7.55 (m, 6H), 7.64 (d, 1H), 8.78 (s, 1H). LCMS: Calculated for $C_{19}H_{17}F_3N_4O_4S$: 454.42, Observed: 455.05 $(M+H)^+$.

N-(2,2,2-trifluoroethyl)-2-(3-(4-(trifluoromethyl)thiazol-2-yl)ureido)-[1,1'-biphenyl]-4-sulfonamide (103)

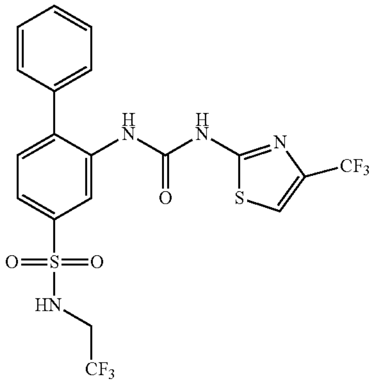 [SMILES: O=C(Nc1nc(C(F)(F)F)cs1)Nc1cc(S(=O)(=O)NCC(F)(F)F)ccc1-c1ccccc1]

$^1$H NMR (400 MHz, $CD_3OD$) δ: 3.60-3.70 (m, 2H), 7.38-7.60 (m, 7H), 7.70 (d, 1H), 8.60 (s, 1H). LCMS: Calculated for $C_{19}H_{14}F_6N_4O_3S_2$: 524.46, Observed: 525.00 $(M+H)^+$.

N-(2,2,2-trifluoroethyl)-2-(3-(3-(trifluoromethyl)pyridin-2-yl)ureido)-[1,1'-biphenyl]-4-sulfonamide (104)

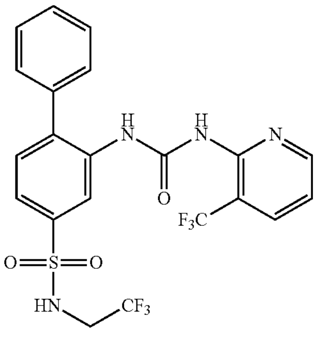 [SMILES: O=C(Nc1cc(S(=O)(=O)NCC(F)(F)F)ccc1-c1ccccc1)Nc1ncccc1C(F)(F)F]

$^1$H NMR (400 MHz, $CD_3OD$) δ: 3.60-3.75 (m, 2H), 7.05 (t, 1H), 7.40-7.70 (m, 8H), 8.03 (d, 1H), 8.90 (s, 1H). LCMS: Calculated for $C_{21}H_{16}F_6N_4O_3S$: 518.43, Observed: 519.0 $(M+H)^+$.

4-(tetrahydrofuran-2-yl)-N-(2,2,2-trifluoroethyl)-3-(3-(4-(trifluoro methyl)pyridin-2-yl)ureido)benzene sulfonamide (174)

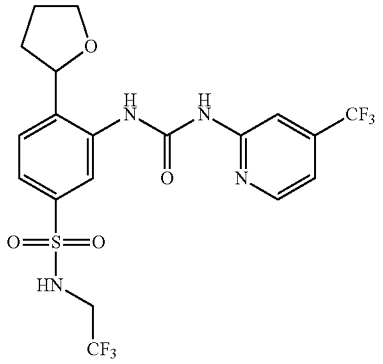 [SMILES: O=C(Nc1cc(C(F)(F)F)ccn1)Nc1cc(S(=O)(=O)NCC(F)(F)F)ccc1C1CCCO1]

$^1$H NMR (400 MHz, $CD_3OD$) δ: 1.8-1.9 (m, 1H), 2.0-2.2 (m, 2H), 2.5 (m, 1H), 3.59-3.62 (m, 2H), 3.9-4.0 (m, 1H), 4.15-4.21 (m, 1H), 5.15 (t, 1H), 7.30 (d, 1H), 7.55 (s, 1H), 7.6-7.7 (m, 2H), 8.4 (s, 1H), 8.59 (d, 1H). LCMS: Calculated for $C_{19}H_{18}F_6N_4O_4S$: 512.43, Observed: 513.10 $(M+H)^+$.

Method F (Scheme 3): Urea Formation Via Buchwald Coupling on the Scaffold Urea Derivative:

Scheme 3:

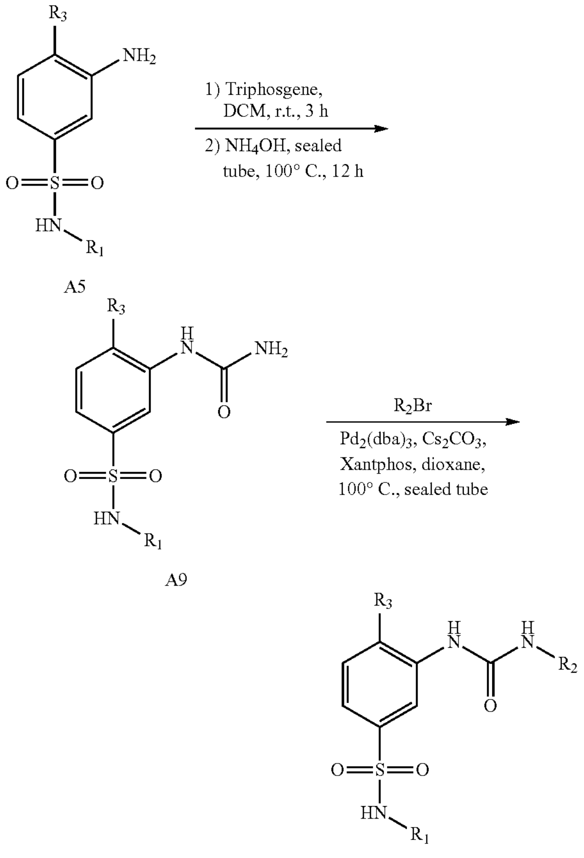

A5 A9 A6

General Procedure for the Synthesis of Pyrimidine Ureas:

To a stirred solution of compound A5 (1 equiv.) in dichloromethane was added triphosgene (0.6 equiv.) at 0° C. and stirred for 3 h. The solvent was evaporated and anhydrous THF was added to the residue. The residue was transferred to a sealed tube and $NH_4OH$ was added and heated overnight at 100° C. TLC indicated the formation of a new spot. Ethyl acetate was added to the reaction mass and extracted. The combined organic layers were washed with brine, dried, concentrated and purified by column chromatography to obtain compound A11.

To a solution of compound A11 (1 equiv.) and an aryl-bromide (1 equiv.) in dioxane was added cesium carbonate (1.5 equiv.) and the mixture was purged with nitrogen for 5 minutes. To this Xantphos (0.15 equiv.) and $Pd_2(dba)_3$ (0.1 equiv.) were added and the reaction mixture was further purged with nitrogen for 10 minutes in a sealed tube. This was then heated to 100° C. for overnight. The reaction mixture was brought to room temperature, water was added and extracted with ethyl acetate twice. The organic fractions were pooled, washed with brine, dried, concentrated and purified by Reverse Phase Prep HPLC., affording product A6.

The following compounds were similarly prepared according to the Scheme 3 procedure:

2-(3-(4-chloropyrimidin-2-yl)ureido)-N-(2,2,2-trifluoroethyl)-[1,1'-biphenyl]-4-sulfonamide (105)

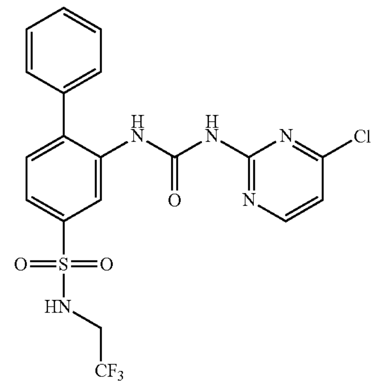 [SMILES: O=C(Nc1nccc(Cl)n1)Nc1cc(S(=O)(=O)NCC(F)(F)F)ccc1-c1ccccc1]

$^1$H NMR (400 MHz, DMSO-$d_6$) δ: 3.65-3.80 (m, 2H), 7.15 (d, 1H), 7.40-7.75 (m, 8H), 8.75 (t, 1H), 8.85 (s, 1H), 10.62 (s, 1H), 11.25 (s, 1H). LCMS: Calculated for $C_{19}H_{15}ClF_3N_5O_3S$: 485.87, Observed: 486.05 $(M+H)^+$.

N-(2,2,2-trifluoroethyl)-2-(3-(4-(trifluoromethyl)pyrimidin-2-yl)ureido)-[1,1'-biphenyl]-4-sulfonamide (106)

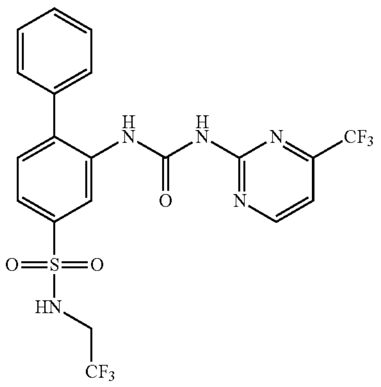

$^1$H NMR (400 MHz, DMSO-$d_6$) δ: 3.65-3.81 (m, 2H), 7.40-7.65 (m, 8H), 8.15 (d, 1H), 8.78 (t, 1H), 8.82 (s, 1H), 10.80 (s, 1H), 11.10 (s, 1H). LCMS: Calculated for $C_{20}H_{15}F_6N_5O_3S$: 519.42, Observed: 520.10 $(M+H)^+$.

2-(3-(4-methylpyrimidin-2-yl)ureido)-N-(2,2,2-trifluoroethyl)-[1,1'-biphenyl]-4-sulfonamide (107)

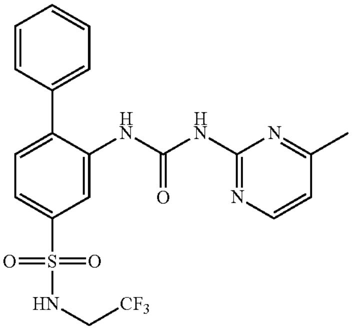 [SMILES: Cc1ccnc(NC(=O)Nc2cc(S(=O)(=O)NCC(F)(F)F)ccc2-c2ccccc2)n1]

$^1$H NMR (400 MHz, DMSO-$d_6$) δ: 2.05 (s, 3H), 3.70-3.80 (m, 2H), 6.85 (d, 1H), 7.40-7.65 (m, 7H), 7.85 (d, 1H), 8.74 (t, 1H), 8.82 (s, 1H), 10.10 (s, 1H), 11.62 (s, 1H). LCMS: Calculated for $C_{20}H_{18}F_3N_5O_3S$: 465.45, Observed: 466.05 $(M+H)^+$.

Method G: Procedure for the Synthesis of N-(4-(N-(2,2,2-trifluoroethyl)sulfamoyl)-[1,1'-biphenyl]-2-yl)-1H-indole-1-carboxamide (108)

Scheme 4

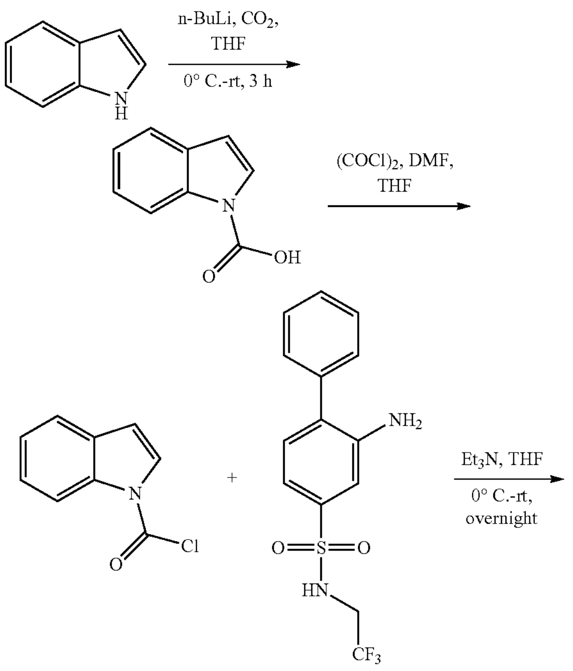

A5

-continued

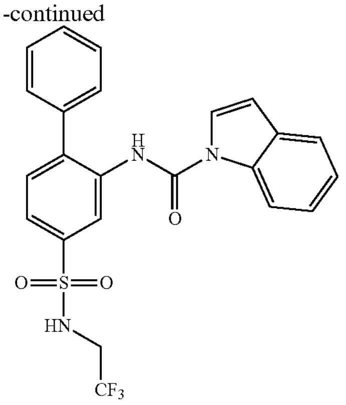

108

A solution of n-BuLi in hexane (1 equiv.) was added to a solution of indole (1 equiv.) in dry THF at 0° C. and was stirred for 30 min at 0° C. Then $CO_2$ gas purged into the reaction mixture using dry ice for 2 h at room temperature and monitored by TLC. After completion of the reaction, the reaction mixture was quenched with water. The reaction mixture was then washed with ethyl acetate, acidified the aqueous phase with 1 N HCl to pH 1 and extracted with ethyl acetate. Combined organic extracts were dried over $Na_2SO_4$, filtered and evaporated the solvent to dryness under vacuo to afford indole-1-carboxylic acid as off-white solid.

To a solution of indole-1-carboxylic acid (1 equiv.) as obtained above and DMF (catalytic) in THF, oxalyl chloride (2 equiv.) was added at 0° C. and stirred for 2 h at room temperature. Then a solution of compound A5 (1 equiv.) and triethyl amine (2 equiv.) in dry THF was added to the reaction mixture at 0° C. and stirred overnight at room temperature. Reaction mixture was then quenched with water and extracted with ethyl acetate. Combined organic extracts were dried over $Na_2SO_4$, filtered and evaporated the solvent under vacuo. The crude product was then purified by column chromatography (Silica gel 60-120, 15% ethyl acetate in hexane as eluent) to afford compound the title compound.

$^1$H NMR (400 MHz, DMSO-$d_6$) δ: 3.78-3.85 (m, 2H), 6.72 (s, 1H), 7.15-7.29 (m, 2H), 7.30-7.42 (m, 3H), 7.50-7.70 (m, 4H), 7.75-7.86 (m, 2H), 8.0-8.10 (m, 2H), 8.80 (t, 1H), 9.98 (s, 1H). LCMS: Calculated for $C_{23}H_{18}F_3N_3O_3S$: 473.47, Observed: 472.23 $(M-H)^-$.

4-bromo-N-phenyl-3-(3-(3-(trifluoromethyl)phenyl)ureido)benzenesulfonamide

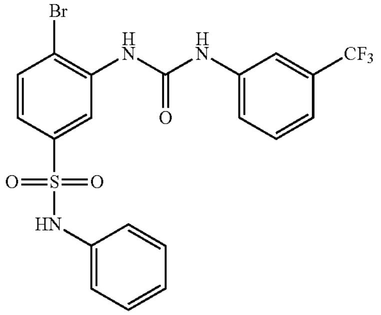 [SMILES: O=C(Nc1cccc(C(F)(F)F)c1)Nc1cc(S(=O)(=O)Nc2ccccc2)ccc1Br]

4-bromo-N-phenyl-3-(3-(3-(trifluoromethyl)phenyl)ureido)benzenesulfonamide was prepared by adopted the general procedure as described for the urea formation by Method A (Scheme 1).

$^1$H NMR (400 MHz, $CD_3OD$) δ: 7.03-7.26 (m, 6H), 7.31 (d, 1H), 7.46 (t, 1H), 7.6 (d, 1H), 7.65 (d, 1H), 7.96 (s, 1H), 8.72 (s, 1H).

N-phenyl-4-(thiophen-3-yl)-3-(3-(3-(trifluoromethyl)phenyl)ureido)benzenesulfonamide (351)

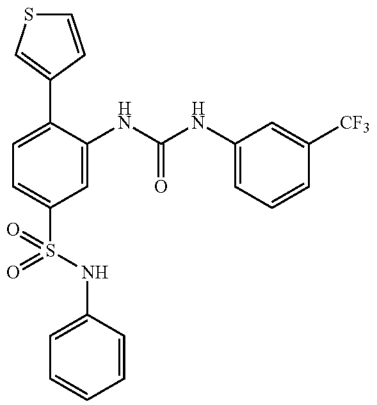 [SMILES: O=C(Nc1cccc(C(F)(F)F)c1)Nc1cc(S(=O)(=O)Nc2ccccc2)ccc1-c1ccsc1]

N-phenyl-4-(thiophen-3-yl)-3-(3-(3-(trifluoromethyl)phenyl)ureido)benzenesulfonamide was prepared by using the general cross-coupling procedure as described for the general synthesis of compound A4 (Scheme 1). $^1$H NMR (400 MHz, $CD_3OD$) δ: 7.0-7.08 (m, 1H), 7.1-7.3 (m, 7H), 7.4-7.5 (m, 3H), 7.52-7.6 (m, 2H), 7.9 (s, 1H), 8.05 (s, 1H), 8.45 (s, 1H), 9.6 (s, 1H). LCMS: Calculated for $C_{24}H_{18}F_3N_3O_3S_2$: 517.54, Observed: 518.38 $(M+H)^+$.

General Procedure for the Synthesis of Thiophene Sulfonamideurea Derivatives (R1 Variations):

Scheme 5

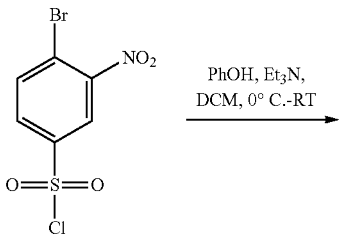

A2

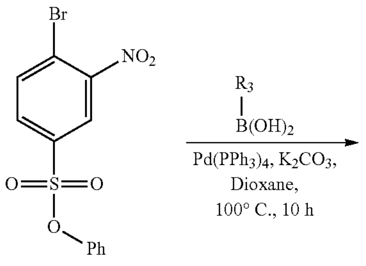

A15

-continued

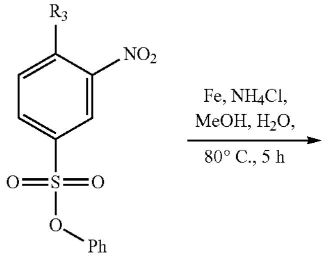

A16

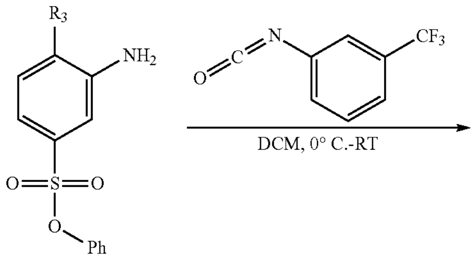

A17

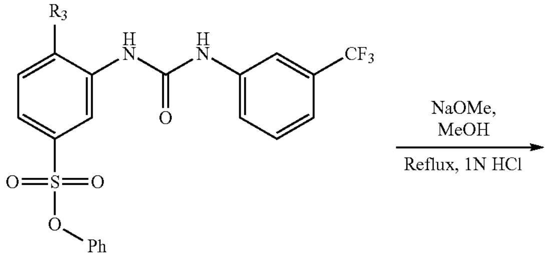

A18

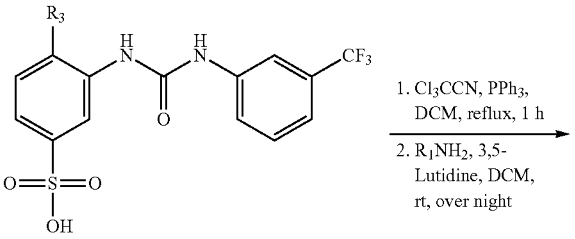

A19

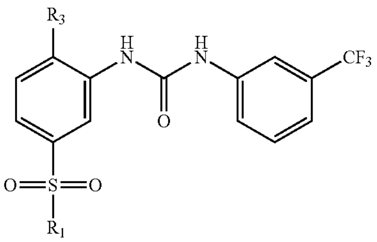

A20

Phenyl 4-bromo-3-nitrobenzenesulfonate (7)

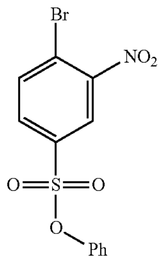 [SMILES: O=[N+]([O-])c1cc(S(=O)(=O)Oc2ccccc2)ccc1Br]

To a solution of phenol (1 equiv.) and triethyl amine (3 equiv.) in dichloromethane was added sulfonyl chloride (A2) (1.2 equiv.) at 0° C. and stirred at room temperature for overnight. After completion of the reaction, the reaction mixture was diluted with dichloromethane, washed with water and brine, dried over anhydrous sodium sulfate, filtered and concentrated under vacuum. The crude product was then purified by Silica gel column chromatography (25% ethyl acetate-hexane) to afford phenyl sulfonate (A15).

$^1$H NMR (400 MHz, $CDCl_3$) δ: 7.0-7.01 (m, 2H), 7.25-7.4 (m, 3H), 7.8-7.9 (d, 1H), 7.9-8.00 (d, 1H), 8.25 (s, 1H).

Phenyl 3-nitro-4-(thiophen-3-yl)benzenesulfonate (A15)

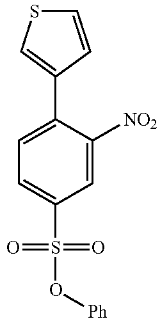 [SMILES: O=[N+]([O-])c1cc(S(=O)(=O)Oc2ccccc2)ccc1-c1ccsc1]

Phenyl 3-nitro-4-(thiophen-3-yl)benzenesulfonate has been prepared using compound A15 (1 equiv.) and thiophene-3-boronic acid (1.5 equiv.), and following the method described for the synthesis of compound A4 excluding water. $^1$H NMR (400 MHz, DMSO-$d_6$) δ: 7.1-7.2 (m, 3H), 7.35-7.45 (m, 3H), 7.73 (t, 1H), 7.88 (s, 1H), 7.95 (d, 1H), 8.15 (d, 1H), 8.45 (s, 1H).

Phenyl 3-amino-4-(thiophen-3-yl)benzenesulfonate

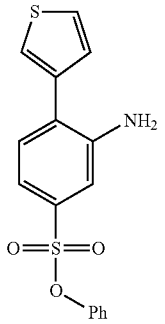

Phenyl 3-amino-4-(thiophen-3-yl)benzenesulfonate was prepared by nitro reduction of compound A16 by following the method described for the preparation of compound A5 (Scheme 1). LCMS: Calculated; 331.41, Observed; 331.95 $(M+H)^+$.

Phenyl 4-(thiophen-3-yl)-3-(3-(3-(trifluoromethyl) phenyl)ureido)benzenesulfonate

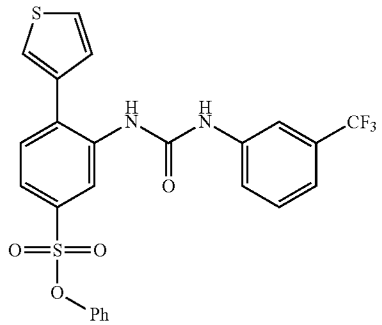 [SMILES: O=C(Nc1cccc(C(F)(F)F)c1)Nc1cc(S(=O)(=O)Oc2ccccc2)ccc1-c1ccsc1]

Phenyl 4-(thiophen-3-yl)-3-(3-(3-(trifluoromethyl)phenyl)ureido)benzenesulfonate was prepared from compound A17 (1 equiv.) using 3-(trifluoromethyl)phenylisocyanate (1 equiv.) in dichloromethane by following the method described for the preparation of compound A6. $^1$H NMR (400 MHz, DMSO-$d_6$) δ: 7.15 (d, 2H), 7.3-7.6 (m, 9H), 7.8 (d, 1H), 7.9 (s, 1H), 7.98 (s, 1H), 8.2 (s, 1H), 8.61 (s, 1H), 9.61 (s, 1H). LCMS: Calculated; 518.53, Observed; 540.90 $(M+Na)^+$.

4-(thiophen-3-yl)-3-(3-(3-(trifluoromethyl)phenyl) ureido)benzenesulfonic acid

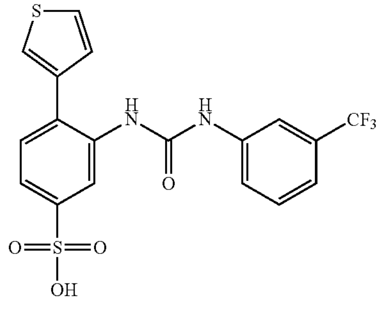 [SMILES: O=C(Nc1cccc(C(F)(F)F)c1)Nc1cc(S(=O)(=O)O)ccc1-c1ccsc1]

To a solution of compound A18 (1 equiv.) in methanol was added sodium methoxide (5 equiv.) in one portion and allowed stir at room temperature for 15 min. Then the reaction mixture was heated to reflux for 12 h and monitored by TLC. After completion of the reaction, reaction was cooled to room temperature and acidified to pH 2 using 1N HCl. The reaction mixture was then concentrated under vacuum, residue was extracted with ethyl acetate, filtered, dried the filtrate over anhydrous sodium sulfate and evaporated the solvent to afford compound A19.

$^1$H NMR (400 MHz, DMSO-$d_6$) δ: 7.25-7.35 (m, 4H), 7.45-7.56 (m, 3H), 7.65-7.7 (m, 2H), 7.9 (s, 1H), 7.98 (s, 1H), 8.12 (s, 1H), 9.4 (s, 1H). LCMS: Calculated; 442.43, Observed; 442.95 $(M+H)^+$.

General Procedure for the Preparation of Sulfonamides A20:

A solution of triphenylphosphine (3 equiv.) in dichloromethane was added to a mixture of benzene sulfonic acid A19 (1 equiv.) and trichloroacetonitrile (3 equiv.) in dichloromethane at reflux. The mixture was stirred for approximately 1 h. A mixture of respective amine (3 equiv.) and 3,5-lutidine (9 equiv.) was added to the above mixture. The reaction mixture was then allowed to stir at room temperature and monitored by TLC. When the reaction was complete, the organic layer was washed with 1 N HCl and saturated aqueous sodium bicarbonate solution, dried over anhydrous sodium sulfate and evaporated in vacuum. The crude materials were then purified by preparative HPLC purification to afford sulfonamides A20.

The following compounds were similarly prepared according to the Scheme 7 procedures:

N-methyl-4-(thiophen-3-yl)-3-(3-(3-(trifluoromethyl)phenyl)ureido)benzenesulfonamide (111)

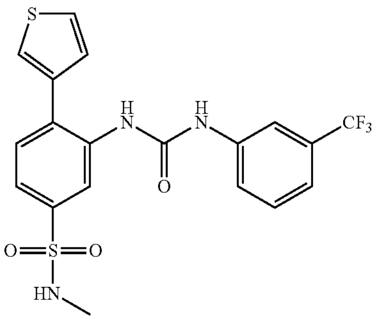 [SMILES: CNS(=O)(=O)c1ccc(-c2ccsc2)c(NC(=O)Nc2cccc(C(F)(F)F)c2)c1]

$^1$H NMR (400 MHz, DMSO-$d_6$) δ: 2.5 (d, 3H), 7.3-7.35 (m, 2H), 7.45-7.6 (m, 5H), 7.75-7.85 (m, 2H), 8.0 (s, 1H), 8.1 (s, 1H), 8.41 (s, 1H), 9.6 (s, 1H). LCMS: Calculated for $C_{19}H_{16}F_3N_3O_3S_2$: 455.47, Observed: 456.05 $(M+H)^+$.

N-ethyl-4-(thiophen-3-yl)-3-(3-(3-(trifluoromethyl)phenyl)ureido)benzenesulfonamide (112)

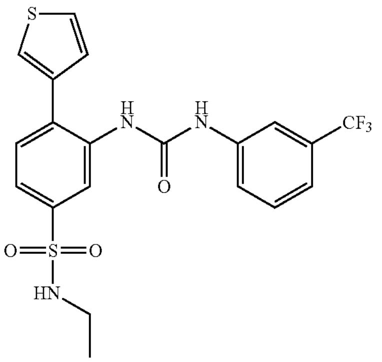 [SMILES: CCNS(=O)(=O)c1ccc(-c2ccsc2)c(NC(=O)Nc2cccc(C(F)(F)F)c2)c1]

$^1$H NMR (400 MHz, DMSO-$d_6$) δ: 1.0 (t, 3H), 2.8 (m, 2H), 7.3-7.4 (m, 2H), 7.45-7.59 (m, 4H), 7.6 (t, 1H), 7.8 (d, 1H), 7.81 (s, 1H), 8.0 (s, 1H), 8.05 (s, 1H), 8.42 (s, 1H), 9.6 (s, 1H). LCMS: Calculated for $C_{20}H_{18}F_3N_3O_3S_2$: 469.50, Observed: 470.15 $(M+H)^+$.

N-propyl-4-(thiophen-3-yl)-3-(3-(3-(trifluoromethyl)phenyl)ureido)benzenesulfonamide (113)

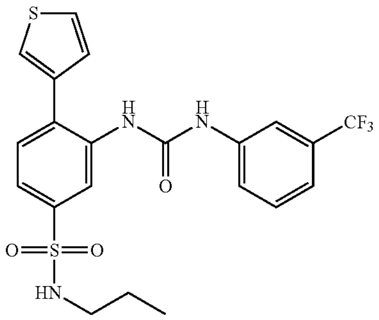 [SMILES: CCCNS(=O)(=O)c1ccc(-c2ccsc2)c(NC(=O)Nc2cccc(C(F)(F)F)c2)c1]

$^1$H NMR (400 MHz, DMSO-$d_6$) δ: 0.8 (t, 3H), 1.4-1.45 (m, 2H), 2.7-2.8 (m, 2H), 7.35 (m, 2H), 7.45-7.55 (m, 3H), 7.58-7.7 (m, 2H), 7.75-7.85 (m, 2H), 8.0 (s, 1H), 8.1 (s, 1H), 8.45 (s, 1H), 9.6 (s, 1H). LCMS: Calculated for $C_{21}H_{20}F_3N_3O_3S_2$: 483.53, Observed: 506.10 $(M+Na)^+$.

N-butyl-4-(thiophen-3-yl)-3-(3-(3-(trifluoromethyl)phenyl)ureido)benzenesulfonamide (114)

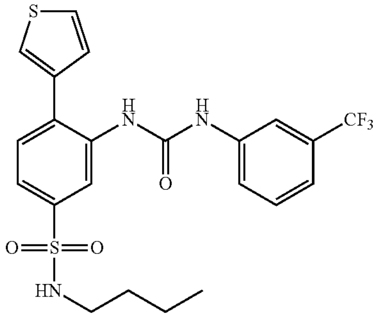 [SMILES: CCCCNS(=O)(=O)c1ccc(-c2ccsc2)c(NC(=O)Nc2cccc(C(F)(F)F)c2)c1]

$^1$H NMR (400 MHz, DMSO-$d_6$) δ: 0.8 (t, 3H), 1.2-1.45 (m, 4H), 2.79-2.8 (m, 2H), 7.3-7.4 (m, 2H), 7.41-7.6 (m, 4H), 7.6 (t, 1H), 7.79-7.8 (t, 1H), 7.81 (s, 1H), 8.0 (s, 1H), 8.01 (s, 1H), 8.41 (s, 1H), 9.6 (s, 1H). LCMS: Calculated for $C_{22}H_{22}F_3N_3O_3S_2$: 497.55, Observed: 520.10 $(M+Na)^+$.

N-isopropyl-4-(thiophen-3-yl)-3-(3-(3-(trifluoromethyl)phenyl)ureido)benzenesulfonamide (115)

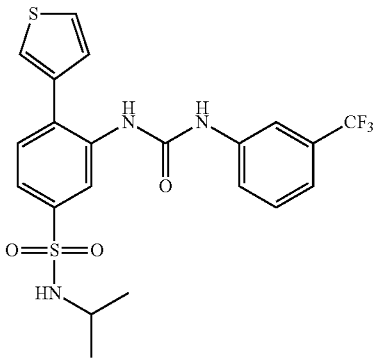 [SMILES: CC(C)NS(=O)(=O)c1ccc(-c2ccsc2)c(NC(=O)Nc2cccc(C(F)(F)F)c2)c1]

$^{1}H$ NMR (400 MHz, DMSO-$d_6$) δ: 1.0 (d, 6H), 3.2-3.4 (m, 1H), 7.35-7.4 (m, 2H), 7.5-7.6 (m, 4H), 7.62 (d, 1H), 7.78-7.82 (m, 2H), 8.0 (s, 1H), 8.1 (s, 1H), 8.5 (s, 1H), 9.6 (s, 1H). LCMS: Calculated for $C_{21}H_{20}F_3N_3O_3S_2$: 483.53, Observed: 506.10 $(M+Na)^+$.

N-isobutyl-4-(thiophen-3-yl)-3-(3-(3-(trifluoromethyl)phenyl)ureido)benzenesulfonamide (116)

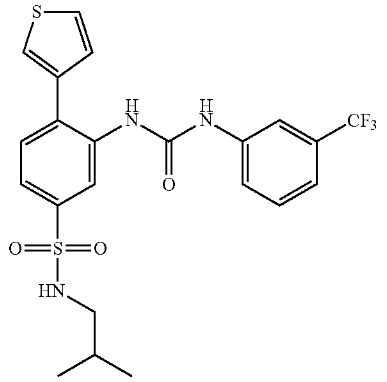 [SMILES: CC(C)CNS(=O)(=O)c1ccc(-c2ccsc2)c(NC(=O)Nc2cccc(C(F)(F)F)c2)c1]

$^{1}H$ NMR (400 MHz, DMSO-$d_6$) δ: 0.85 (d, 6H), 1.6-1.7 (m, 1H), 2.6 (m, 2H), 7.21-7.4 (m, 2H), 7.43-7.6 (m, 4H), 7.7 (t, 1H), 7.8 (d, 1H), 7.81 (d, 2H), 8.41 (s, 1H), 9.6 (s, 1H), 10.0 (s, 1H). LCMS: Calculated for $C_{22}H_{22}F_3N_3O_3S_2$: 497.55, Observed: 520.05 $(M+Na)^+$.

N-(sec-butyl)-4-(thiophen-3-yl)-3-(3-(3-(trifluoromethyl)phenyl)ureido)benzenesulfonamide (117)

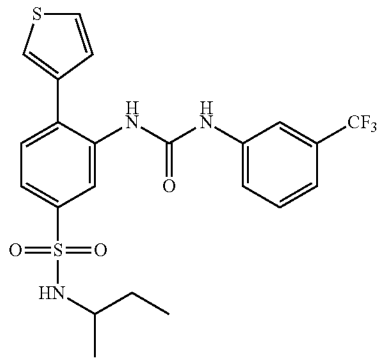 [SMILES: CCC(C)NS(=O)(=O)c1ccc(-c2ccsc2)c(NC(=O)Nc2cccc(C(F)(F)F)c2)c1]

$^{1}H$ NMR (400 MHz, DMSO-$d_6$) δ: 0.78 (t, 3H), 0.98 (d, 3H), 1.3-1.4 (m, 2H), 3.0-3.15 (m, 1H), 7.3-7.4 (m, 2H), 7.58-7.1 (m, 5H), 7.8 (d, 1H), 7.81 (d, 1H), 8.0 (s, 1H), 8.05 (s, 1H), 8.5 (s, 1H), 9.6 (s, 1H). LCMS: Calculated for $C_{22}H_{22}F_3N_3O_3S_2$: 497.55, Observed: 520.10 $(M+Na)^+$.

N-(tert-butyl)-4-(thiophen-3-yl)-3-(3-(3-(trifluoromethyl)phenyl)ureido)benzenesulfonamide (118)

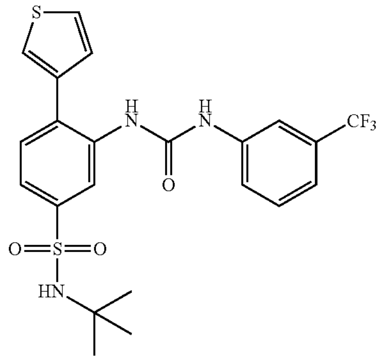 [SMILES: CC(C)(C)NS(=O)(=O)c1ccc(-c2ccsc2)c(NC(=O)Nc2cccc(C(F)(F)F)c2)c1]

$^{1}H$ NMR (400 MHz, DMSO-$d_6$) δ: 1.2 (s, 9H), 7.39-7.4 (m, 2H), 7.5-7.6 (m, 7H), 7.8 (d, 1H), 8.05 (s, 1H), 8.5 (s, 1H), 9.6 (s, 1H). LCMS: Calculated for $C_{22}H_{22}F_3N_3O_3S_2$: 497.55, Observed: 520.00 $(M+Na)^+$.

N-allyl-4-(thiophen-3-yl)-3-(3-(3-(trifluoromethyl)phenyl)ureido)benzenesulfonamide (119)

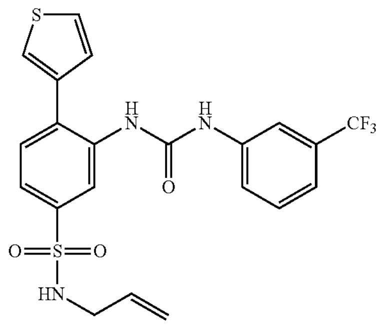 [SMILES: C=CCNS(=O)(=O)c1ccc(-c2ccsc2)c(NC(=O)Nc2cccc(C(F)(F)F)c2)c1]

$^{1}H$ NMR (400 MHz, DMSO-$d_6$) δ: 3.5 (m, 2H), 5.05 (d, 1H), 5.2 (d, 1H), 5.65-5.8 (m, 1H), 7.2-7.4 (m, 2H), 7.4-7.62 (m, 4H), 7.7-7.89 (m, 3H), 8.0 (s, 1H), 8.1 (s, 1H), 8.5 (s, 1H), 9.6 (s, 1H).

LCMS: Calculated for $C_{21}H_{18}F_3N_3O_3S_2$: 481.51, Observed: 504.10 $(M+Na)^+$.

N-(2-hydroxyethyl)-4-(thiophen-3-yl)-3-(3-(3-(trifluoromethyl)phenyl)ureido)benzenesulfonamide (120)

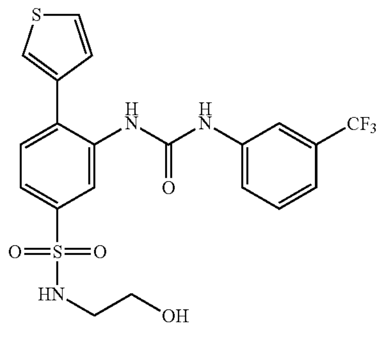 [SMILES: O=C(Nc1cccc(C(F)(F)F)c1)Nc1cc(S(=O)(=O)NCCO)ccc1-c1ccsc1]

$^1$H NMR (400 MHz, DMSO-$d_6$) δ: 2.8 (m, 2H), 3.4 (m, 2H), 4.7 (t, 1H), 7.21-7.4 (m, 2H), 7.5-7.6 (m, 5H), 7.61 (t, 1H), 7.8-7.81 (m, 2H), 8.0 (s, 1H), 8.41 (s, 1H), 9.6 (s, 1H). LCMS: Calculated for $C_{20}H_{18}F_3N_3O_4S_2$: 485.50, Observed: 508.15 $(M+Na)^+$.

N-(2-methoxyethyl)-4-(thiophen-3-yl)-3-(3-(3-(trifluoromethyl)phenyl)ureido)benzenesulfonamide (121)

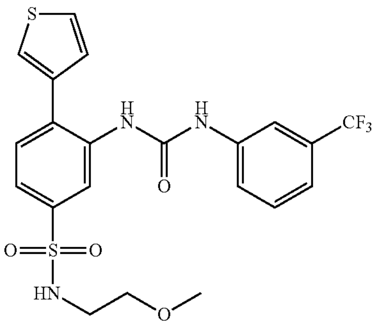 [SMILES: COCCNS(=O)(=O)c1ccc(-c2ccsc2)c(NC(=O)Nc2cccc(C(F)(F)F)c2)c1]

$^1$H NMR (400 MHz, DMSO-$d_6$) δ: 2.9 (m, 2H), 3.18 (s, 3H), 3.3 (t, 2H), 7.39-7.4 (m, 2H), 7.41-7.61 (m, 4H), 7.7-7.82 (m, 3H), 8.0 (s, 1H), 8.1 (s, 1H), 8.41 (s, 1H), 9.6 (s, 1H). LCMS: Calculated for $C_{21}H_{20}F_3N_3O_4S_2$: 499.53, Observed: 500.05 $(M+H)^+$.

N-(3-methoxypropyl)-4-(thiophen-3-yl)-3-(3-(3-(trifluoromethyl)phenyl)ureido)benzenesulfonamide (122)

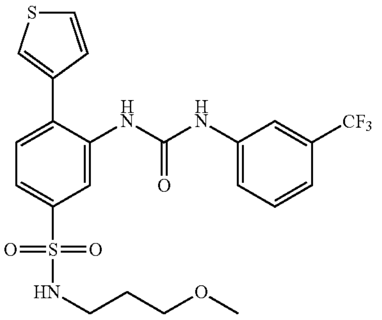 [SMILES: COCCCNS(=O)(=O)c1ccc(-c2ccsc2)c(NC(=O)Nc2cccc(C(F)(F)F)c2)c1]

$^1$H NMR (400 MHz, DMSO-$d_6$) δ: 1.6 (m, 2H), 2.8 (m, 2H), 3.18 (s, 3H), 3.21 (m, 2H), 7.2-7.4 (m, 2H), 7.4-7.82 (m, 7H), 8.0 (s, 1H), 8.01 (s, 1H), 8.5 (s, 1H), 9.6 (s, 1H). LCMS: Calculated for $C_{22}H_{22}F_3N_3O_4S_2$: 513.55, Observed: 514.10 $(M+H)^+$.

N-(1-hydroxy-3-methylbutan-2-yl)-4-(thiophen-3-yl)-3-(3-(3-(trifluoromethyl)phenyl)ureido)benzene sulfonamide (123)

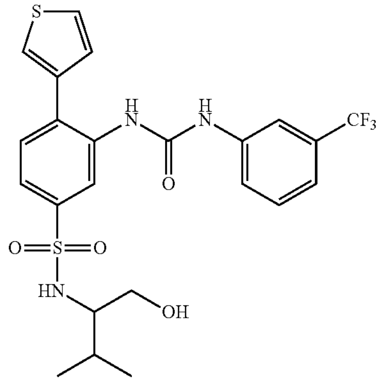 [SMILES: CC(C)C(CO)NS(=O)(=O)c1ccc(-c2ccsc2)c(NC(=O)Nc2cccc(C(F)(F)F)c2)c1]

$^1$H NMR (400 MHz, DMSO-$d_6$) δ: 0.7-0.8 (2d, 6H), 1.9 (m, 1H), 3.0 (br s, 1H), 3.2 (m, 2H), 4.5 (m, 1H), 7.38-7.81 (m, 9H), 8.0 (s, 1H), 8.1 (s, 1H), 8.5 (s, 1H), 9.6 (s, 1H). LCMS: Calculated for $C_{23}H_{24}F_3N_3O_4S_2$: 527.58, Observed: 550.10 $(M+Na)^+$.

N-cyclopropyl-4-(thiophen-3-yl)-3-(3-(3-(trifluoromethyl)phenyl)ureido)benzenesulfonamide (124)

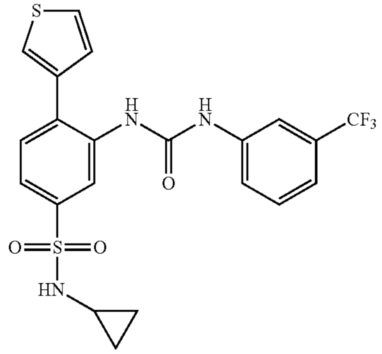 [SMILES: O=C(Nc1cccc(C(F)(F)F)c1)Nc1cc(S(=O)(=O)NC2CC2)ccc1-c1ccsc1]

$^1$H NMR (400 MHz, DMSO-$d_6$) δ: 0.4-0.6 (m, 2H), 0.8-0.9 (m, 2H), 2.1-2.2 (m, 1H), 7.3-7.4 (m, 2H), 7.5-7.6 (m, 4H), 7.8-7.81 (m, 2H), 8.0-8.1 (m, 2H), 8.1 (s, 1H), 8.5 (s, 1H), 9.6 (s, 1H). LCMS: Calculated for $C_{21}H_{18}F_3N_3O_3S_2$: 481.51, Observed: 482.70 $(M+H)^+$.

N-cyclobutyl-4-(thiophen-3-yl)-3-(3-(3-(trifluoromethyl)phenyl)ureido)benzenesulfonamide (125)

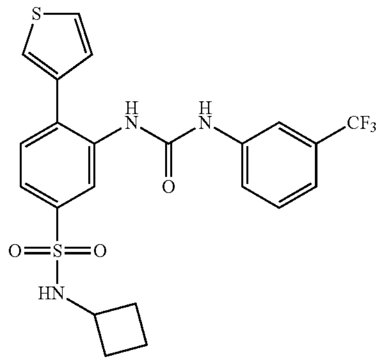 [SMILES: O=C(Nc1cccc(C(F)(F)F)c1)Nc1cc(S(=O)(=O)NC2CCC2)ccc1-c1ccsc1]

$^1$H NMR (400 MHz, DMSO-$d_6$) δ: 1.4-1.6 (m, 2H), 1.72-2.1 (m, 4H), 3.6-3.7 (m, 1H), 7.39-7.4 (m, 3H), 7.41-7.7 (m, 5H), 7.79 (m, 2H), 7.81 (s, 1H), 8.41 (s, 1H), 9.6 (s, 1H). LCMS: Calculated for $C_{22}H_{20}F_3N_3O_3S_2$: 495.54, Observed: 518.05 $(M+Na)^+$.

N-cyclopentyl-4-(thiophen-3-yl)-3-(3-(3-(trifluoromethyl)phenyl)ureido)benzenesulfonamide (126)

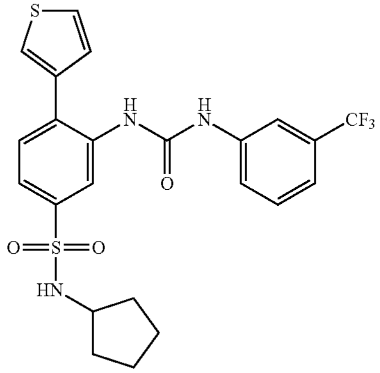 [SMILES: O=C(Nc1cccc(C(F)(F)F)c1)Nc1cc(S(=O)(=O)NC2CCCC2)ccc1-c1ccsc1]

$^1$H NMR (400 MHz, DMSO-$d_6$) δ: 1.3-1.45 (m, 4H), 1.5-1.7 (m, 4H), 3.4-3.5 (m, 1H), 7.3-7.4 (m, 2H), 7.41-7.69 (m, 4H), 7.7 (d, 1H), 7.8-7.81 (m, 1H), 7.87 (s, 1H), 8.0 (s, 1H), 8.01 (s, 1H), 8.5 (s, 1H), 9.6 (s, 1H). LCMS: Calculated for $C_{23}H_{22}F_3N_3O_3S_2$: 509.56, Observed: 510.10 $(M+H)^+$.

N-(cyclopropylmethyl)-4-(thiophen-3-yl)-3-(3-(3-(trifluoromethyl)phenyl)ureido)benzenesulfonamide (127)

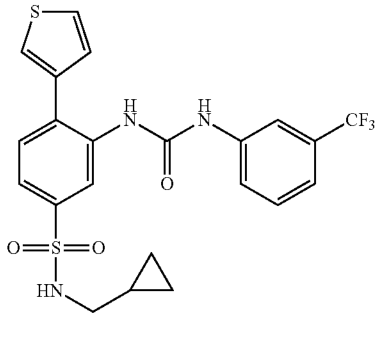 [SMILES: O=C(Nc1cccc(C(F)(F)F)c1)Nc1cc(S(=O)(=O)NCC2CC2)ccc1-c1ccsc1]

$^1$H NMR (400 MHz, DMSO-$d_6$) δ: 0.1 (m, 2H), 0.4 (m, 2H), 0.85 (m, 1H), 2.7 (m, 2H), 7.3-7.4 (m, 2H), 7.41-7.7 (m, 4H), 7.7-7.8 (m, 3H), 8.0 (s, 1H), 8.01 (s, 1H), 8.4 (s, 1H), 9.6 (s, 1H). LCMS: Calculated for $C_{22}H_{20}F_3N_3O_3S_2$: 495.54, Observed: 518.10 $(M+Na)^+$.

N-(cyclobutylmethyl)-4-(thiophen-3-yl)-3-(3-(3-(trifluoromethyl)phenyl)ureido)benzenesulfonamide (128)

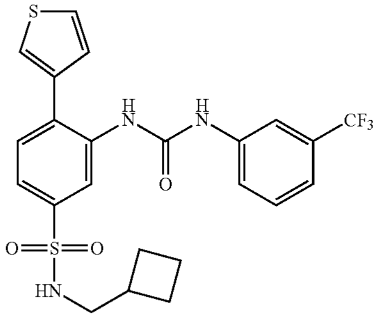 [SMILES: O=C(Nc1cccc(C(F)(F)F)c1)Nc1cc(S(=O)(=O)NCC2CCC2)ccc1-c1ccsc1]

$^1$H NMR (400 MHz, DMSO-$d_6$) δ: 1.55-1.70 (m, 2H), 1.7-1.8 (m, 2H), 1.9-2.0 (m, 2H), 2.3-2.4 (m, 1H), 2.8 (m, 2H), 7.35 (m, 2H), 7.45-7.55 (m, 4H), 7.65 (t, 1H), 7.75 (d, 1H), 7.81 (s, 1H), 8.05 (s, 1H), 8.09 (s, 1H), 8.45 (s, 1H), 9.6 (s, 1H). LCMS: Calculated for $C_{23}H_{22}F_3N_3O_3S_2$: 509.56, Observed: 510.10 $(M+Na)^+$.

N-(cyclopentylmethyl)-4-(thiophen-3-yl)-3-(3-(3-(trifluoromethyl)phenyl)ureido)benzenesulfonamide (129)

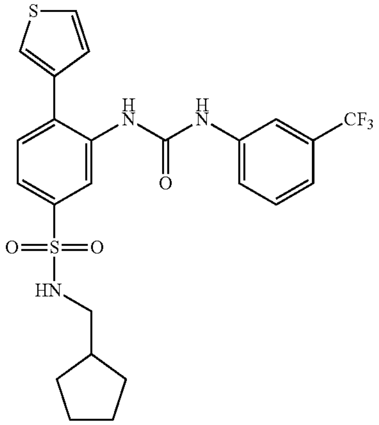 [SMILES: O=C(Nc1cccc(C(F)(F)F)c1)Nc1cc(S(=O)(=O)NCC2CCCC2)ccc1-c1ccsc1]

$^1$H NMR (400 MHz, DMSO-$d_6$) δ: 1.1-1.2 (m, 2H), 1.4-1.59 (m, 4H), 1.6-1.7 (m, 2H), 1.9-2.0 (m, 1H), 2.7 (m, 2H), 7.38-7.82 (m, 7H), 8.05 (d, 1H), 8.15 (d, 1H), 8.2-8.5 (m, 3H), 9.58 (s, 1H). LCMS: Calculated for $C_{24}H_{24}F_3N_3O_3S_2$: 523.59, Observed: 546.05 $(M+Na)^+$.

4-(thiophen-3-yl)-N-(2,2,2-trifluoroethyl)-3-(3-(3-(trifluoromethyl)phenyl)ureido)benzenesulfonamide (130)

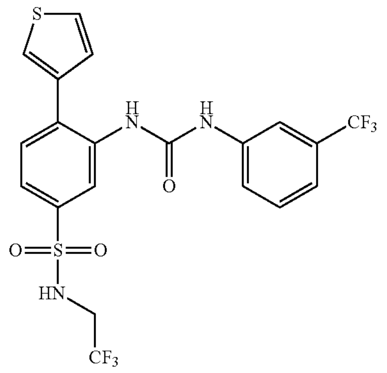 [SMILES: O=C(Nc1cccc(C(F)(F)F)c1)Nc1cc(S(=O)(=O)NCC(F)(F)F)ccc1-c1ccsc1]

$^1$H NMR (400 MHz, DMSO-$d_6$) δ: 3.6-3.7 (m, 2H), 7.3-7.4 (m, 2H), 7.5-7.62 (m, 4H), 7.79-7.8 (m, 1H), 7.81 (s, 1H), 8.02 (s, 1H), 8.1 (s, 1H), 8.5 (s, 1H), 8.7 (t, 1H), 9.6 (s, 1H). LCMS: Calculated for $C_{20}H_{15}F_6N_3O_3S_2$: 523.47, Observed: 546.05 $(M+Na)^+$.

1-(5-(morpholinosulfonyl)-2-(thiophen-3-yl)phenyl)-3-(3-(trifluoromethyl)phenyl)urea (131)

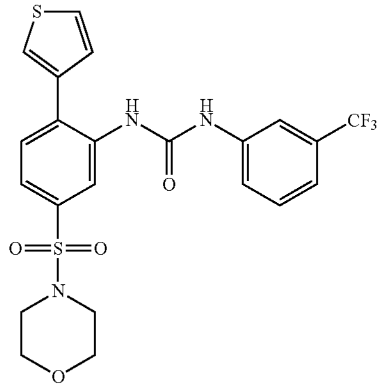 [SMILES: O=C(Nc1cccc(C(F)(F)F)c1)Nc1cc(S(=O)(=O)N2CCOCC2)ccc1-c1ccsc1]

$^1$H NMR (400 MHz, DMSO-$d_6$) δ: 2.9-3.0 (m, 4H), 3.6-3.7 (m, 4H), 7.3-7.6 (m, 5H), 7.61-7.8 (m, 2H), 7.86 (s, 1H), 8.0 (s, 1H), 8.19 (s, 1H), 8.4 (s, 1H), 9.6 (s, 1H). LCMS: Calculated for $C_{22}H_{20}F_3N_3O_4S_2$: 511.54, Observed: 512.55 $(M+H)^+$.

N-(tetrahydro-2H-pyran-4-yl)-4-(thiophen-3-yl)-3-(3-(3-(trifluoromethyl)phenyl)ureido)benzene sulfonamide (132)

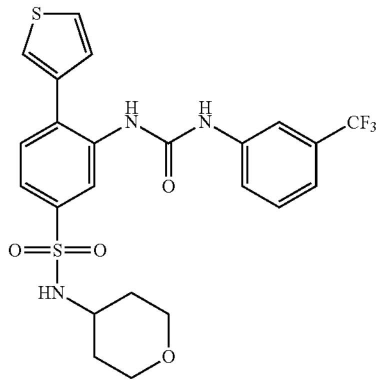 [SMILES: O=C(Nc1cccc(C(F)(F)F)c1)Nc1cc(S(=O)(=O)NC2CCOCC2)ccc1-c1ccsc1]

$^1$H NMR (400 MHz, DMSO-$d_6$) δ: 1.3-1.45 (m, 2H), 1.5-1.7 (m, 2H), 3.2-3.4 (m, 2H), 3.7-3.8 (m, 2H), 7.3-7.39 (m, 2H), 7.5-7.6 (m, 4H), 7.7-7.9 (m, 4H), 8.05 (s, 1H), 8.1 (s, 1H), 8.5 (s, 1H), 9.6 (s, 1H). LCMS: Calculated for $C_{23}H_{22}F_3N_3O_4S_2$: 525.56, Observed: 548.15 $(M+Na)^+$.

N-((tetrahydro-2H-pyran-4-yl)methyl)-4-(thiophen-3-yl)-3-(3-(3-(trifluoromethyl)phenyl)ureido)benzene sulfonamide (133)

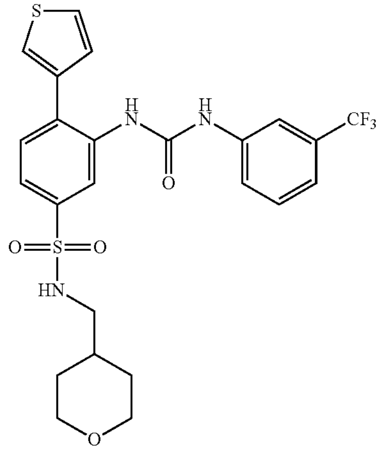 [SMILES: O=C(Nc1cccc(C(F)(F)F)c1)Nc1cc(S(=O)(=O)NCC2CCOCC2)ccc1-c1ccsc1]

$^1$H NMR (400 MHz, DMSO-$d_6$) δ: 1.0-1.21 (m, 2H), 1.58-1.65 (m, 3H), 2.65 (m, 2H), 3.2-3.21 (m, 2H), 3.8 (m, 2H), 7.38-7.4 (m, 2H), 7.5-7.62 (m, 5H), 7.7 (t, 1H), 7.8 (d, 1H), 7.8 (d, 1H), 8.0 (s, 1H), 8.01 (s, 1H), 8.42 (s, 1H). LCMS: Calculated for $C_{24}H_{24}F_3N_3O_4S_2$: 539.59, Observed: 562.10 $(M+Na)^+$.

N-(tetrahydro-2H-thiopyran-4-yl)-4-(thiophen-3-yl)-3-(3-(3-(trifluoromethyl)phenyl)ureido)benzene sulfonamide (134)

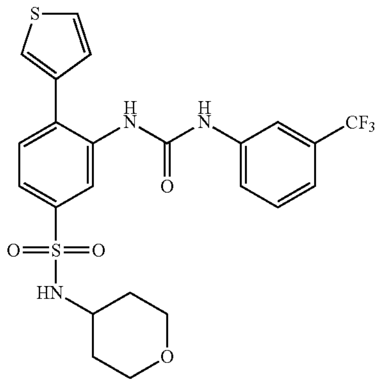 [SMILES: O=C(Nc1cccc(C(F)(F)F)c1)Nc1cc(S(=O)(=O)NC2CCOCC2)ccc1-c1ccsc1]

$^1$H NMR (400 MHz, DMSO-$d_6$) δ: 1.4-1.6 (m, 2H), 1.9-2.0 (m, 2H), 2.4-2.6 (m, 4H), 3.0-3.2 (m, 1H), 7.2-7.4 (m, 2H), 7.5-7.6 (m, 4H), 7.78-7.79 (m, 3H), 8.0 (s, 1H), 8.1 (s, 1H), 8.5 (s, 1H), 9.6 (s, 1H). LCMS: Calculated for $C_{23}H_{22}F_3N_3O_3S_3$: 541.63, Observed: 541.70 $(M+H)^+$.

1-(5-((1,1-dioxidothiomorpholino)sulfonyl)-2-(thiophen-3-yl)phenyl)-3-(3-(trifluoromethyl)phenyl)urea (135)

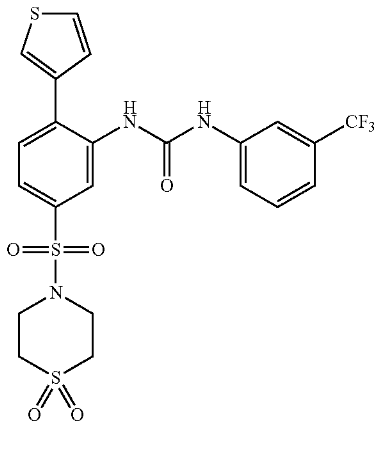 [SMILES: O=C(Nc1cccc(C(F)(F)F)c1)Nc1cc(S(=O)(=O)N2CCS(=O)(=O)CC2)ccc1-c1ccsc1]

$^1$H NMR (400 MHz, $CD_3OD$) δ: 3.3 (m, 4H), 3.5 (m, 4H), 7.3-7.4 (m, 2H), 7.4-7.61 (m, 4H), 7.8 (d, 1H), 7.9 (s, 1H), 8.0 (s, 1H), 8.2 (s, 1H), 8.5 (s, 1H), 9.6 (s, 1H). LCMS: Calculated for $C_{22}H_{20}F_3N_3O_5S_3$: 559.60, Observed: 560.05 $(M+H)^+$.

N-benzyl-4-(thiophen-3-yl)-3-(3-(3-(trifluoromethyl)phenyl)ureido)benzenesulfonamide (136)

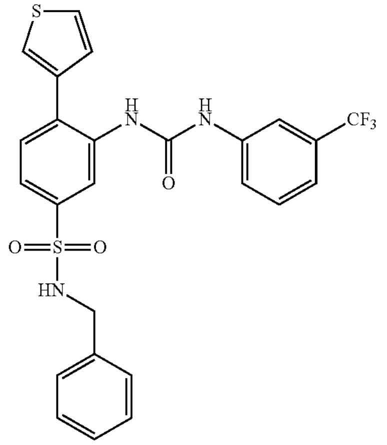 [SMILES: O=C(Nc1cccc(C(F)(F)F)c1)Nc1cc(S(=O)(=O)NCc2ccccc2)ccc1-c1ccsc1]

$^1$H NMR (400 MHz, DMSO-$d_6$) δ: 4.0 (d, 2H), 7.2-7.4 (m, 8H), 7.5-7.6 (m, 5H), 7.79-7.82 (m, 2H), 8.21 (t, 1H), 8.5 (s, 1H), 9.6 (s, 1H). LCMS: Calculated for $C_{25}H_{20}F_3N_3O_3S_2$: 531.57, Observed: 554.10 $(M+Na)^+$.

N-methoxy-4-(thiophen-3-yl)-3-(3-(3-(trifluoromethyl)phenyl)ureido)benzenesulfonamide (138)

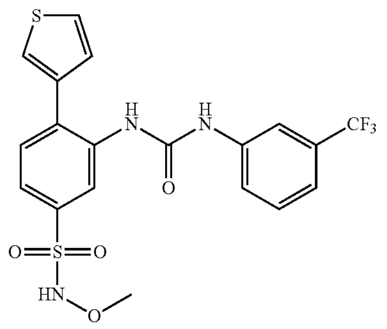 [SMILES: CONS(=O)(=O)c1ccc(-c2ccsc2)c(NC(=O)Nc2cccc(C(F)(F)F)c2)c1]

$^1$H NMR (400 MHz, DMSO-$d_6$) δ: 3.65 (s, 3H), 7.3-7.4 (m, 2H), 7.5-7.6 (m, 4H), 7.78 (t, 1H), 7.85 (s, 1H), 8.02 (s, 1H), 8.12 (s, 1H), 8.52 (s, 1H), 9.6 (s, 1H), 10.6 (s, 1H). LCMS: Calculated for $C_{19}H_{16}F_3N_3O_4S_2$: 471.47, Observed: 472.05 $(M+H)^+$.

N-ethoxy-4-(thiophen-3-yl)-3-(3-(3-(trifluoromethyl)phenyl)ureido)benzenesulfonamide (139)

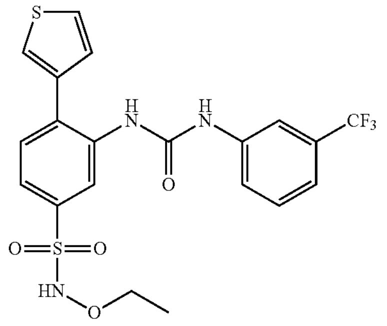 [SMILES: CCONS(=O)(=O)c1ccc(-c2ccsc2)c(NC(=O)Nc2cccc(C(F)(F)F)c2)c1]

$^1$H NMR (400 MHz, DMSO-$d_6$) δ: 1.06 (t, 3H), 3.95 (q, 2H), 7.3-7.4 (m, 2H), 7.5-7.6 (m, 4H), 7.78 (t, 1H), 7.85 (s, 1H), 8.02 (s, 1H), 8.12 (s, 1H), 8.52 (s, 1H), 9.6 (s, 1H), 10.3 (br s, 1H). LCMS: Calculated for $C_{20}H_{18}F_3N_3O_4S_2$: 485.50, Observed: 486.05 $(M+H)^+$.

N-(4-hydroxyphenyl)-4-(thiophen-3-yl)-3-(3-(3-(trifluoromethyl)phenyl)ureido)benzenesulfonamide (146)

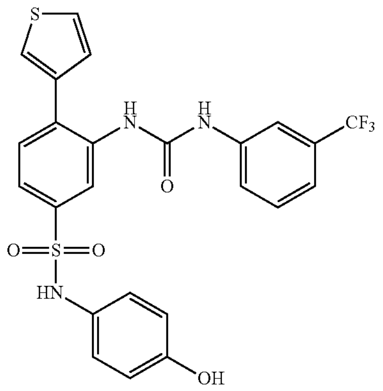 [SMILES: O=C(Nc1cccc(C(F)(F)F)c1)Nc1cc(S(=O)(=O)Nc2ccc(O)cc2)ccc1-c1ccsc1]

$^1$H NMR (400 MHz, DMSO-$d_6$) δ: 6.6 (d, 1H), 7.95 (d, 1H), 7.26-7.4 (m, 2H), 7.65-7.6 (m, 8H), 7.7-7.8 (m, 2H), 8.02 (d, 1H), 8.45 (s, 1H), 9.55 (s, 1H), 9.88 (s, 1H). ESMS Calculated for $C_{24}H_{18}F_3N_3O_4S_2$: 533.54, Observed: 556.15 $(M+Na)^+$.

N-(1-methylcyclopropyl)-4-(thiophen-3-yl)-3-(3-(3-(trifluoromethyl)phenyl)ureido)benzenesulfonamide (151)

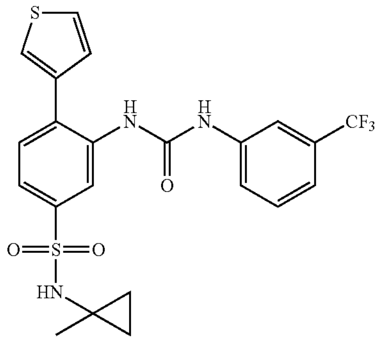 [SMILES: CC1(NS(=O)(=O)c2ccc(-c3ccsc3)c(NC(=O)Nc3cccc(C(F)(F)F)c3)c2)CC1]

$^1$H NMR (400 MHz, DMSO-$d_6$) δ: 0.4 (m, 2H), 0.65 (m, 2H), 1.15 (s, 3H), 7.39-7.4 (m, 2H), 7.41-7.6 (m, 4H), 7.79-7.8 (m, 2H), 8.0 (s, 1H), 8.01 (s, 1H), 8.05 (s, 1H), 8.5 (s, 1H), 9.6 (s, 1H). LCMS: Calculated for $C_{22}H_{20}F_3N_3O_3S_2$: 495.54, Observed: 518.15 $(M+Na)^+$.

N-(2-methylcyclopropyl)-4-(thiophen-3-yl)-3-(3-(3-(trifluoromethyl)phenyl)ureido)benzenesulfonamide (152)

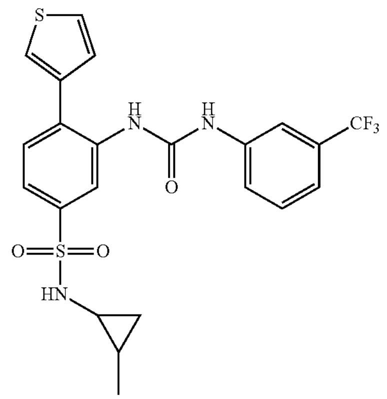 [SMILES: CC1CC1NS(=O)(=O)c1ccc(-c2ccsc2)c(NC(=O)Nc2cccc(C(F)(F)F)c2)c1]

$^1$H NMR (400 MHz, DMSO-$d_6$) δ: 0.3 (m, 1H), 0.6 (m, 1H), 0.7-0.8 (m, 1H), 0.9 (d, 3H), 1.84 (m, 1H), 7.35 (m, 2H), 7.4-7.6 (m, 4H), 7.75-7.95 (m, 3H), 8.0 (s, 1H), 8.1 (s, 1H), 8.5 (s, 1H), 9.6 (s, 1H). LCMS: Calculated for $C_{22}H_{20}F_3N_3O_3S_2$: 495.54, Observed: 496.00 $(M+H)^+$.

Ether Series: Urea Sulfonamides; General Synthetic Scheme for the Ether Series:

Scheme 6

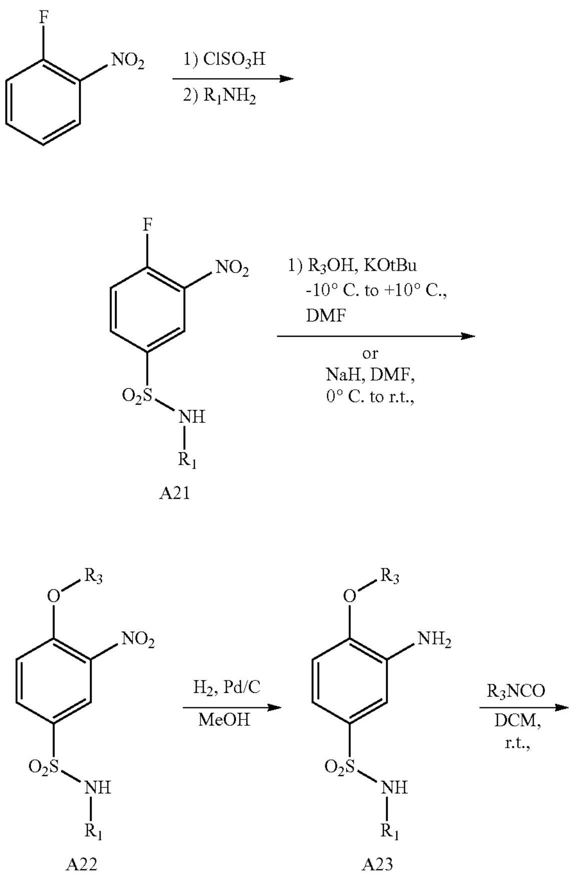

-continued

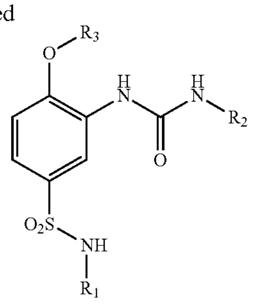

A24

General Procedure for the Synthesis of 3-Nitro-4-Fluoro Benzene Sulfonamides (A21):

To a ice-cooled solution of chlorosulfonic acid (10 ml) at 0° C. was added 1-fluoro-2-nitrobenzene 1 (1 g). The reaction mixture was brought to room temperature and heated to 90° C. for 5 h. After completion of the reaction, it was brought to room temperature and poured into crushed ice and extracted with ethyl acetate. The combined organic layers were washed with brine, dried over $MgSO_4$, concentrated and purified by column chromatography to obtain the 4-fluoro-3-nitrobenzenesulfonyl chloride.

To a stirred solution of the respective amines (1 equiv.) in dichloromethane was added pyridine (3 equiv.) at 0° C. and stirred for 0.5 h, followed by the addition of the 4-fluoro-3-nitrobenzenesulfonyl chloride and stirred at room temperature for 12 h. The reaction mixture was concentrated in vacuo and the residue was dissolved in ethyl acetate, washed with 1N HCl, brine, dried, concentrated and purified by column chromatography to obtain 3-nitro-4-fluoro benzene sulfonamides A21.

The following compounds were prepared using the general procedure for compounds A21:

4-fluoro-3-nitro-N-(2,2,2-trifluoroethyl)benzenesulfonamide

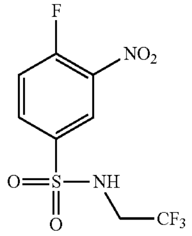 [SMILES: O=[N+]([O-])c1cc(S(=O)(=O)NCC(F)(F)F)ccc1F]

$^{1}H$ NMR (400 MHz, $CDCl_3$) δ: 3.8 (q, 2H), 5.21 (br s, 1H), 7.5 (t, 1H), 8.1-8.2 (m, 1H), 8.6 (d, 1H).

N-(1-cyanocyclopropyl)-4-fluoro-3-nitrobenzenesulfonamide

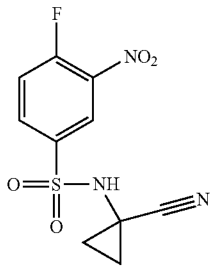 [SMILES: N#CC1(NS(=O)(=O)c2ccc(F)c([N+](=O)[O-])c2)CC1]

$^{1}H$ NMR (400 MHz, DMSO-$d_6$) δ: 1.3-1.39 (m, 2H), 1.45-1.51 (m, 2H), 7.92 (t, 1H), 8.25 (d, 1H), 8.58 (d, 1H), 9.5 (s, 1H).

4-fluoro-3-nitro-N-(oxetan-3-yl)benzenesulfonamide

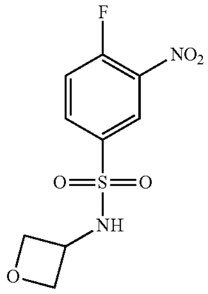 [SMILES: O=[N+]([O-])c1cc(S(=O)(=O)NC2COC2)ccc1F]

$^{1}H$ NMR (400 MHz, DMSO-$d_6$) δ: 4.23 (q, 1H), 4.38-4.58 (m, 4), 7.8 (t, 1H), 8.18 (d, 1H), 8.42 (d, 1), 8.9 (d, 1H); ESMS: Calculated: 276.24, Observed: 279.24 $(M+3H)^+$.

General Procedure for the Synthesis of Ethers A22:

The alcohol (4 equiv.) was dissolved in dimethyl formamide and maintained at −10° C. To this KOtBu (4 equiv.) was added and stirred for 2 h at the same temperature. After 2 h, 3-nitro-4-fluoro benzene sulfonamides 2a-e was added and stirred at −10° C. for an additional 2 h. The reaction mixture mass was brought to room temperature and stirred overnight. After completion of the reaction as indicated by TLC, water was added and extracted with ethyl acetate. The combined organic fractions were washed with brine, dried, concentrated and purified by column chromatography to obtain the respective ethers A22.

The following compounds were prepared using the general procedure for compounds A21:

4-(cyclopropylmethoxy)-3-nitro-N-(2,2,2-trifluoroethyl)benzenesulfonamide

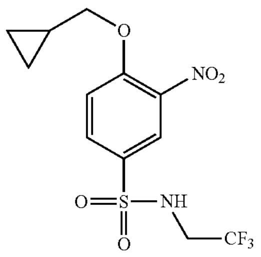 [SMILES: O=[N+]([O-])c1cc(S(=O)(=O)NCC(F)(F)F)ccc1OCC1CC1]

$^1H$ NMR (400 MHz, $CDCl_3$) δ: 0.41 (d, 2H), 0.7 (d, 2H), 1.3-1.38 (m, 1H), 3.56 (q, 2H), 4.05 (d, 2H), 5.01 (t, 1H), 7.18 (d, 1H), 7.9 (d, 1H), 8.51 (s, 1H); ESMS: Calculated: 354.05, Observed: 355.00 $(M+H)^+$.

4-ethoxy-3-nitro-N-(2,2,2-trifluoroethyl)benzenesulfonamide

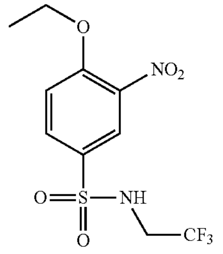 [SMILES: CCOc1ccc(S(=O)(=O)NCC(F)(F)F)cc1[N+](=O)[O-]]

$^1H$ NMR (400 MHz, DMSO) δ: 1.36 (t, 3H), 3.78 (q, 2H), 4.3 (q, 2H), 7.58 (d, 1H), 8.02 (d, 1H), 8.29 (s, 1H), 8.74 (br s, 1H). ESMS: Calculated: 328.26, Observed: 327.29 $(M-H)^-$.

3-nitro-4-((tetrahydro-2H-pyran-4-yl)oxy)-N-(2,2,2-trifluoroethyl)benzenesulfonamide

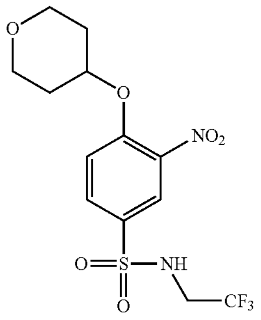 [SMILES: O=[N+]([O-])c1cc(S(=O)(=O)NCC(F)(F)F)ccc1OC1CCOCC1]

$^1H$ NMR (400 MHz, DMSO-$d_6$) δ: 1.6-1.7 (m, 2H), 1.95-2.04 (m, 2H), 3.51 (q, 2H), 3.7-3.85 (m, 4H), 5.0 (m, 1H), 7.68 (d, 1H), 8.0 (d, 1H), 8.3 (s, 1H), 8.71 (t, 1H). ESMS: Calculated: 384.33, Observed: 383.32 $(M-)^-$.

N-(1-cyanocyclopropyl)-4-(cyclopropylmethoxy)-3-nitrobenzenesulfonamide

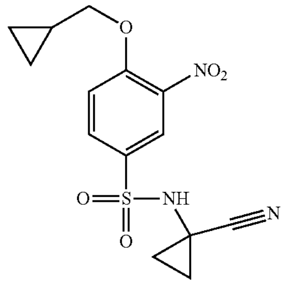 [SMILES: N#CC1(NS(=O)(=O)c2ccc(OCC3CC3)c([N+](=O)[O-])c2)CC1]

$^1H$ NMR (400 MHz, DMSO-$d_6$) δ: 0.3-0.4 (m, 2H), 0.59-0.63 (m, 2H), 1.2-1.37 (m, 3H), 1.4-1.49 (m, 2H), 4.19 (d, 2H), 7.59 (d, 1H), 8.03 (d, 1H), 8.29 (s, 1H), 9.23 (s, 1H). LCMS: Calculated: 337.07, Observed: 338.05 $(M+H)^+$.

4-ethoxy-3-nitro-N-(oxetan-3-yl)benzenesulfonamide

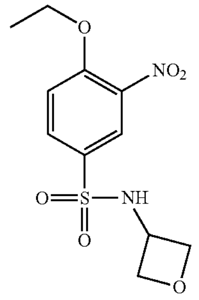

LCMS: Calculated; 302.30, Observed; 301.15 $(M-H)^-$.

N-(1-cyanocyclopropyl)-4-ethoxy-3-nitrobenzenesulfonamide

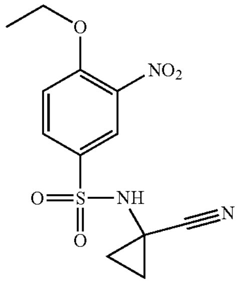 [SMILES: CCOc1ccc(S(=O)(=O)NC2(C#N)CC2)cc1[N+](=O)[O-]]

$^1H$ NMR (400 MHz, DMSO-$d_6$) δ: 1.2-1.5 (m, 7H), 4.32 (d, 2H), 7.6 (d, 1H), 8.01 (d, 1H), 8.3 (s, 1H), 9.22 (s, 1H). LCMS: Calculated: 311.06, Observed: 311.10 $(M^+)$.

4-(cyclopropylmethoxy)-3-nitro-N-(oxetan-3-yl)benzenesulfonamide

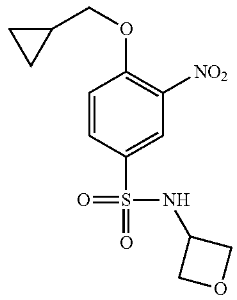 [SMILES: O=[N+]([O-])c1cc(S(=O)(=O)NC2COC2)ccc1OCC1CC1]

$^{1}$H NMR (400 MHz, DMSO-$d_6$) δ: 039 (d, 2H), 0.6 (d, 2H), 1.2-1.32 (m, 1H), 4.18 (d, 2H), 4.2-4.6 (m, 5H), 7.25 (d, 1H), 7.5 (d, 1H), 7.73 (d, 1H), 8.1 (s, 1H).

3-nitro-4-((tetrahydrofuran-3-yl)methoxy)-N-(2,2,2-trifluoroethyl)benzenesulfonamide

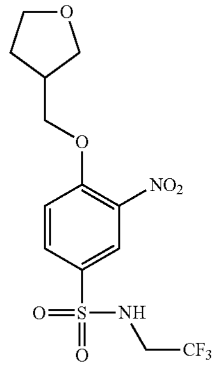

$^{1}$H NMR (400 MHz, DMSO-$d_6$) δ: 1.52-1.59 (m, 1H), 1.99-2.1 (m, 1H), 2.61-2.79 (m, 1H), 3.5-3.8 (m, 6), 4.19-4.3 (m, 2H), 7.6 (d, 1H), 8.02 (d, 1H), 8.3 (s, 1H), 8.78 (br s 1H).

4-isopropoxy-3-nitro-N-(2,2,2-trifluoroethyl)benzenesulfonamide

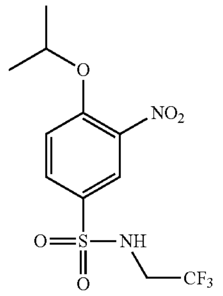

$^{1}$H NMR (400 MHz, DMSO-$d_6$) δ: 1.3 (d, 6H), 3.69-3.7 (m, 2H), 4.9-5.0 (m, 1H), 7.6 (d, 1H), 8.0 (d, 1H), 8.24 (s, 1H), 8.7 (s, 1H).

3-nitro-4-(pyridin-3-yloxy)-N-(2,2,2-trifluoroethyl)benzenesulfonamide

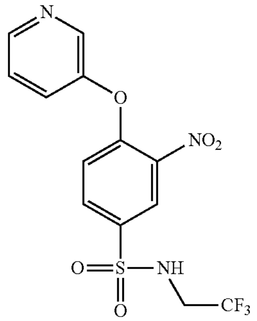 [SMILES: O=[N+]([O-])c1cc(S(=O)(=O)NCC(F)(F)F)ccc1Oc1cccnc1]

$^{1}$H NMR (400 MHz, $CDCl_3$) δ: 3.75 (q, 2H), 6.3 (t, 1H), 7.08 (d, 1H), 7.4-7.5 (m, 1H), 7.99-8.04 (m, 4H), 8.6 (s, 1H); ESMS: Calculated: 377.30, Observed: 378.00 $(M+H)^+$.

3-nitro-4-phenoxy-N-phenylbenzenesulfonamide

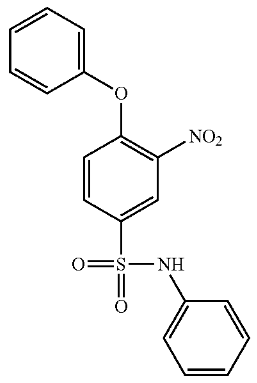 [SMILES: O=[N+]([O-])c1cc(S(=O)(=O)Nc2ccccc2)ccc1Oc1ccccc1]

ESMS: Calculated: 370.38, Observed: 369.43 $(M-H)^-$.

General Procedure for the Synthesis of Amines A23:

The ether compound A22 (100 mg) was dissolved in methanol, 10% Pd/C (10 mg) was added and the reaction mixture was stirred under $H_2$ atmosphere for 12 h. After completion of the reaction as indicated by TLC, it was filtered through a pad of celite and concentrated. The crude residue was washed with pentane and decanted and the residue was concentrated to obtain a colorless solid.

The following compounds were prepared using the general procedure for compounds A23:

3-amino-4-(cyclopropylmethoxy)-N-(2,2,2-trifluoroethyl)benzenesulfonamide

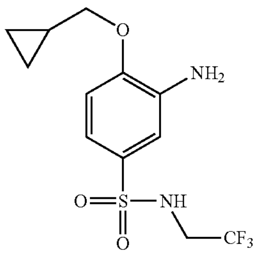

$^1$H NMR (400 MHz, $CDCl_3$) δ: 0.39 (d, 2H), 0.68 (d, 2H), 1.3-1.38 (m, 1H), 3.6 (q, 2H), 3.92 (d, 2H), 4.1 (br s 2H), 4.58 (t, 1H), 6.79 (d. 1H), 7.19 (s, 1H), 7.22 (d, 1H); ESMS: Calculated: 324.32, Observed: 325.00 $(M+H)^+$.

3-amino-4-((tetrahydrofuran-2-yl)methoxy)-N-(2,2,2-trifluoroethyl)benzenesulfonamide

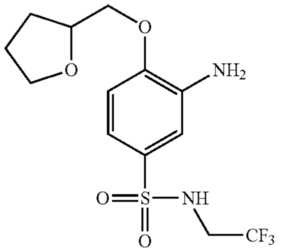 [SMILES: Nc1cc(S(=O)(=O)NCC(F)(F)F)ccc1OCC1CCCO1]

ESMS: Calculated; 354.35, Observed; 353.33 $(M-)^-$.

3-amino-4-ethoxy-N-(2,2,2-trifluoroethyl)benzenesulfonamide

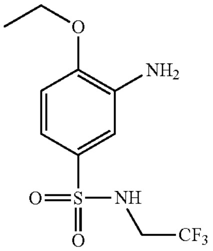 [SMILES: CCOc1ccc(S(=O)(=O)NCC(F)(F)F)cc1N]

$^1$H NMR (400 MHz, DMSO) δ: 1.38 (t, 3H), 3.58 (q, 2H), 4.05 (q, 2H), 5.16 (s, 2H), 6.88 (d, 1H), 6.98 (d, 1H), 7.02 (s, 1H), 8.23 (s, 1H); ESMS: Calculated: 298.28, Observed: 297.31 $(M-H)^-$.

3-amino-4-((tetrahydro-2H-pyran-4-yl)oxy)-N-(2,2,2-trifluoroethyl)benzenesulfonamide

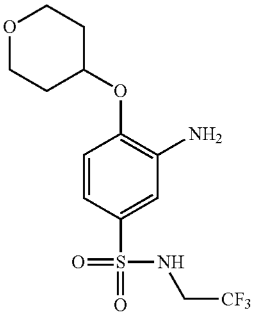 [SMILES: Nc1cc(S(=O)(=O)NCC(F)(F)F)ccc1OC1CCOCC1]

$^1$H NMR (400 MHz, DMSO-$d_6$) δ: 1.55-1.7 (m, 2H), 1.9-2.0 (m, 2H), 3.4-3.61 (m. 5H), 3.8-3.91 (m, 2H), 4.61 (br s, 2H), 6.92-7.01 (m, 2H), 7.03 (s, 1H), 8.24 (t, 1H); ESMS: Calculated: 354.35, Observed: 353.33 $(M-)^-$.

3-amino-N-(1-cyanocyclopropyl)-4-(cyclopropylmethoxy)benzenesulfonamide

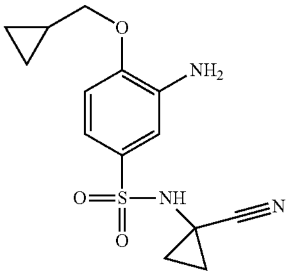 [SMILES: N#CC1(NS(=O)(=O)c2ccc(OCC3CC3)c(N)c2)CC1]

$^1$H NMR (400 MHz, DMSO-$d_6$) δ: 0.3-0.4 (m, 2H), 0.59-0.63 (m, 2H), 1.05-1.3 (m, 3H), 1.31-1.4 (m, 2H), 3.9 (d, 2H), 5.19 (s, 2H), 6.97 (d, 1H), 6.99 (d, 1H), 7.02 (s, 1H), 8.7 (s, 1H). LCMS: Calculated: 307.1, Observed: 308.20 $(M+H)^+$.

3-amino-4-ethoxy-N-(oxetan-3-yl)benzenesulfonamide

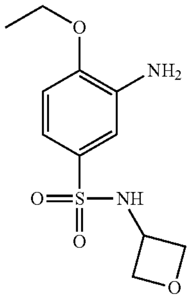 [SMILES: CCOc1ccc(S(=O)(=O)NC2COC2)cc1N]

$^1$H NMR (400 MHz, DMSO-$d_6$) δ: 1.34 (t, 3H), 4.1 (q, 2H), 4.2-4.3 (m, 3H), 4.4-4.51 (m, 2H), 5.17 (s, 2H), 6.82 (s, 1H), 6.9-7.01 (m, 2H), 8.17 (br s, 1H).

3-amino-N-(1-cyanocyclopropyl)-4-ethoxybenzenesulfonamide

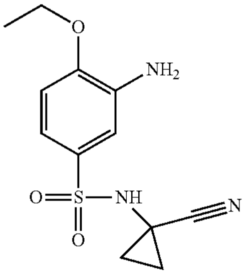 [SMILES: CCOc1ccc(S(=O)(=O)NC2(C#N)CC2)cc1N]

$^1$H NMR (400 MHz, DMSO-$d_6$) δ: 1.1-1.4 (m, 7H), 4.03 (d, 2H), 5.18 (s, 2H), 6.7 (d, 1H), 6.9 (d, 1H), 7.01 (s, 1H), 8.68 (s, 1H).

3-amino-4-(cyclopropylmethoxy)-N-(oxetan-3-yl)benzenesulfonamide

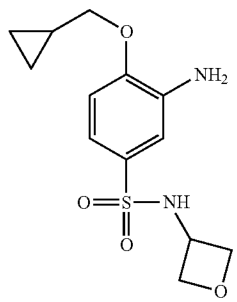

$^1$H NMR (400 MHz, $CDCl_3$) δ: 0.39 (q, 2H), 0.63 (q, 2H), 1.2-1.38 (m, 1H), 3.9 (d, 2H), 4.1 (br s, 2H), 4.34 (t, 2H), 4.43-4.52 (m, 1H), 4.7 (t, 2H), 4.98 (d, 1H), 6.78 (d, 1H), 7.12 (s, 1H), 7.18 (d, 1H).

3-amino-4-((tetrahydrofuran-3-yl)methoxy)-N-(2,2,2-trifluoroethyl)benzenesulfonamide

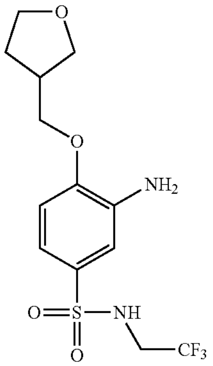

$^1$H NMR (400 MHz, DMSO-$d_6$) δ: 1.4-1.5 (m, 1H), 1.98-2.5 (m, 1H), 2.6-2.77 (m, 1H), 3.45-4.0 (m, 8H), 5.15 (br s, 2H), 6.91-7.0 (m, 2H)), 7.02 (s, 1H), 8.23 (s, 1H).

3-amino-4-isopropoxy-N-(2,2,2-trifluoroethyl)benzenesulfonamide

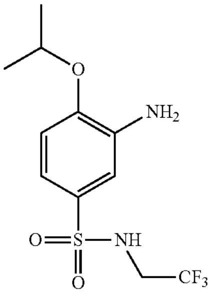 [SMILES: CC(C)Oc1ccc(S(=O)(=O)NCC(F)(F)F)cc1N]

$^1$H NMR (400 MHz, DMSO-$d_6$) δ: 1.3 (d, 6H), 3.55 (t, 2H), 4.6 (t, 1H), 5.1 (s, 2H), 6.91 (d, 2H), 7.01 (s, 1H), 8.12 (br s, 1H). ESMS: Calculated: 312.08, Observed: 313.05 $(M+H)^+$.

3-amino-4-(pyridin-3-yloxy)-N-(2,2,2-trifluoroethyl)benzenesulfonamide

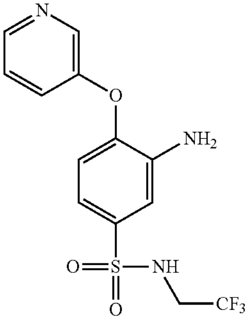 [SMILES: Nc1cc(S(=O)(=O)NCC(F)(F)F)ccc1Oc1cccnc1]

ESMS: Calculated: 347.31, Observed: 348.00 $(M+H)^+$.

3-amino-4-phenoxy-N-phenylbenzenesulfonamide

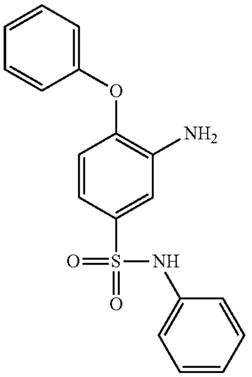

LCMS: Calculated: 340.40, Observed: 341.07 $(M+H)^+$.

General Procedure for the Synthesis of Ureas A24:

To a stirred solution of the amine (1 equiv.) in dichloromethane was added 1.3 equiv. of isocyanate (either commercially available or prepared by the general procedure described for the synthesis of isocyanates) and stirred overnight at room temperature. The reaction mass was then concentrated and washed with ether to remove the undesired dimer impurity. The residue was evaporated in vacuo and purified by Reverse Phase Prep-HPLC to yield the desired compounds.

The following compounds were prepared using the general procedure for compounds A24:

4-(cyclopropylmethoxy)-N-(2,2,2-trifluoroethyl)-3-(3-(3-(trifluoromethyl)phenyl)ureido)benzenesulfonamide (175)

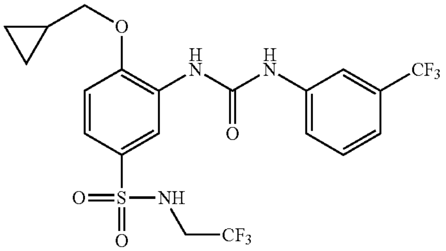 [SMILES: O=C(Nc1cccc(C(F)(F)F)c1)Nc1cc(S(=O)(=O)NCC(F)(F)F)ccc1OCC1CC1]

$^1$H NMR (400 MHz, DMSO-$d_6$) δ: 0.39-0.41 (m, 2H), 0.6-0.62 (m, 2H), 1.2-1.4 (m, 1H), 3.6 (s, 2H), 4.12 (d, 2H), 7.2 (d, 1H), 7.39 (d, 1H), 7.42 (d, 1H), 7.58-7.6 (m, 2H), 8.14 (s, 1H), 8.4 (s, 1H), 8.42 (t, 1H), 8.7 (s, 1H), 9.89 (s, 1H). LCMS: Calculated for $C_{20}H_{19}F_6N_3O_4S$: 511.44, Observed: 512.25 $(M+H)^+$.

4-((tetrahydrofuran-2-yl)methoxy)-N-(2,2,2-trifluoroethyl)-3-(3-(3-(trifluoromethyl)phenyl)ureido) benzenesulfonamide (176)

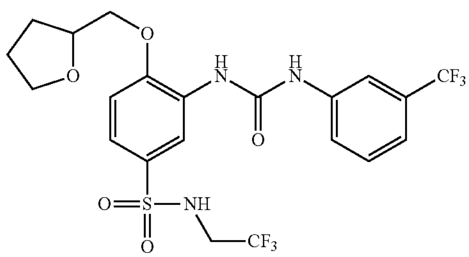 [SMILES: O=C(Nc1cccc(C(F)(F)F)c1)Nc1cc(S(=O)(=O)NCC(F)(F)F)ccc1OCC1CCCO1]

$^1$H NMR (400 MHz, DMSO-$d_6$) δ: 1.60-2.15 (m, 4H), 3.55-3.85 (m, 4H), 4.10-4.40 (m, 3H), 7.20-7.50 (m, 3H), 7.50-7.60 (m, 2H), 8.05 (s, 1H), 8.35 (s, 1H), 8.50 (br s, 1H), 8.65 (s, 1H), 9.95 (s, 1H). LCMS: Calculated for $C_{21}H_{21}F_6N_3O_5S$: 541.46, Observed: 542.15 $(M+H)^+$.

4-ethoxy-N-(2,2,2-trifluoroethyl)-3-(3-(3-(trifluoromethyl)phenyl)ureido)benzenesulfonamide (177)

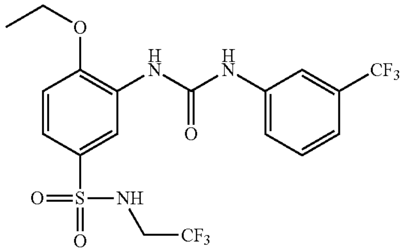 [SMILES: CCOc1ccc(S(=O)(=O)NCC(F)(F)F)cc1NC(=O)Nc1cccc(C(F)(F)F)c1]

$^1$H NMR (400 MHz, DMSO-$d_6$ in 0.03% TMS) δ: 1.44 (t, 3H), 3.50-3.60 m, 2H), 4.20-4.30 (q, 2H), 7.20 (d, 1H), 7.30-7.48 (m, 2H), 7.55 (s, 2H), 8.05 (s, 1H), 8.40 (s, 1H), 8.50 (t, 1H), 8.70 (s, 1H), 9.85 (s, 1H). LCMS: Calculated for $C_{18}H_{17}F_6N_3O_4S$: 485.40, Observed: 486.00 $(M+H)^+$.

4-((tetrahydro-2H-pyran-4-yl)oxy)-N-(2,2,2-trifluoroethyl)-3-(3-(3-(trifluoromethyl)phenyl)ureido) benzenesulfonamide (178)

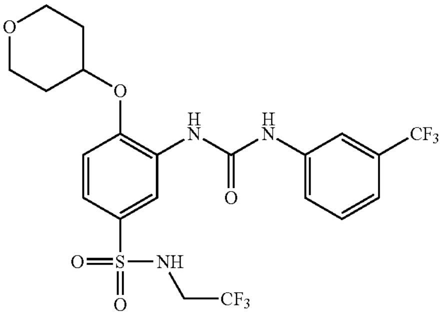 [SMILES: O=C(Nc1cccc(C(F)(F)F)c1)Nc1cc(S(=O)(=O)NCC(F)(F)F)ccc1OC1CCOCC1]

$^1$H NMR (400 MHz, DMSO-$d_6$) δ: 1.6-1.8 (m, 2H), 2.0-2.1 (m, 2H), 3.41 (t, 2H), 3.62 (t, 2H), 3.9-4.0 (s, 2H), 4.8-0.81 (m, 1H), 7.22-7.6 (m, 5H), 8.05 (m, 1H), 8.21 (s, 1H), 8.5 (t, 1H), 8.68 (s, 1H), 9.9 (s, 1H). LCMS: Calculated for $C_{21}H_{21}F_6N_3O_5S$:541.46, Observed: 542.05 $(M+H)^+$.

N-(1-cyanocyclopropyl)-4-(cyclopropylmethoxy)-3-(3-(3-(trifluoromethyl)phenyl)ureido)benzene sulfonamide (179)

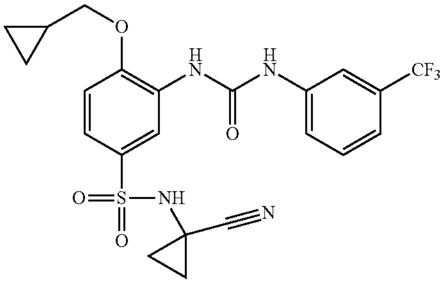 [SMILES: N#CC1(NS(=O)(=O)c2ccc(OCC3CC3)c(NC(=O)Nc3cccc(C(F)(F)F)c3)c2)CC1]

$^1$H NMR (400 MHz, DMSO-$d_6$) δ: 0.4-0.41 (m, 2H), 0.6-0.61 (m, 2H), 1.2-1.4 (m, 5H), 4.01 (s, 2H), 7.2-7.6 (m, 5H), 8.1 (s, 1H), 8.4 (s, 1H), 8.79 (s, 1H), 9.9 (s, 1H), 10.0 (s, 1H). LCMS: Calculated for $C_{22}H_{21}F_3N_4O_4S$ 494.48, Observed: 495.35 $(M+H)^+$.

4-ethoxy-N-(oxetan-3-yl)-3-(3-(3-(trifluoromethyl) phenyl)ureido)benzenesulfonamide (180)

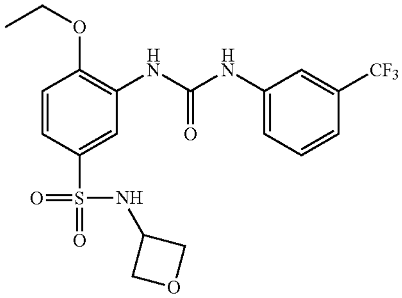 [SMILES: CCOc1ccc(S(=O)(=O)NC2COC2)cc1NC(=O)Nc1cccc(C(F)(F)F)c1]

$^1$H NMR (400 MHz, DMSO-$d_6$ $D_2O$ exchange) δ: 1.42 (t, 3H), 4.20-4.40 (m, 5H), 4.50 (t, 2H), 7.19 (d, 1H), 7.30-7.42 (m, 2H), 7.55 (s, 2H), 8.02 (s, 1H), 8.60 (s, 1H). LCMS: Calculated for $C_{19}H_{20}F_3N_3O_5S$: 459.43, Observed: 460.3 $(M+H)^+$.

N-(1-cyanocyclopropyl)-4-ethoxy-3-(3-(3-(trifluoromethyl)phenyl)ureido)benzenesulfonamide (181)

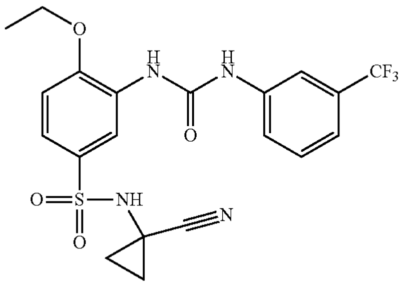 [SMILES: CCOc1ccc(S(=O)(=O)NC2(C#N)CC2)cc1NC(=O)Nc1cccc(C(F)(F)F)c1]

$^1$H NMR (400 MHz, DMSO-$d_6$) δ: 1.22 (s, 3H), 1.30-1.50 (m, 4H), 4.20-4.30 (m, 2H), 7.20-7.60 (m, 5H), 8.05 (s, 1H), 8.40 (s, 1H), 8.75 (s, 1H), 8.95 (s, 1H), 9.90 (s, 1H). LCMS: Calculated for $C_{20}H_{19}F_3N_4O_4S$: 468.44, Observed: 468.15 ($M^+$).

4-(cyclopropylmethoxy)-N-(oxetan-3-yl)-3-(3-(3-(trifluoromethyl)phenyl)ureido)benzenesulfonamide (183)

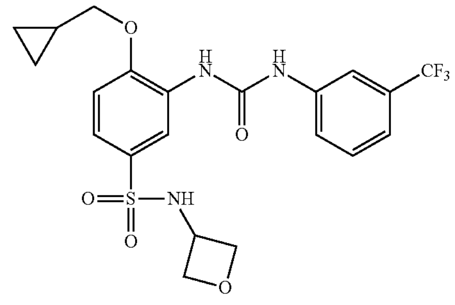 [SMILES: O=C(Nc1cccc(C(F)(F)F)c1)Nc1cc(S(=O)(=O)NC2COC2)ccc1OCC1CC1]

$^1$H NMR (400 MHz, DMSO-$d_6$) δ: 0.40 (d, 2H), 0.64 (d, 2H), 1.30-1.40 (m, 1H), 4.02 (s, 2H), 4.20-4.40 (m, 3H), 4.50 (t, 2H), 7.20 (d, 1H), 7.30-7.40 (m, 2H), 7.50-7.60 (m, 2H), 8.01 (s, 1H), 8.38-8.45 (m, 2H), 8.62 (s, 1H), 9.95 (s, 1H). LCMS: Calculated for $C_{21}H_{22}F_3N_3O_5S$: 485.47, Observed: 486.30 $(M+H)^+$.

4-((tetrahydrofuran-3-yl)methoxy)-N-(2,2,2-trifluoroethyl)-3-(3-(3-(trifluoromethyl)phenyl)ureido) benzenesulfonamide (184)

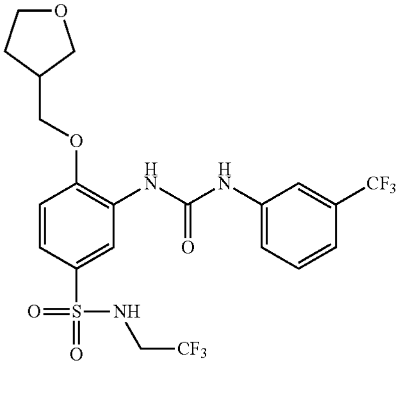 [SMILES: O=C(Nc1cccc(C(F)(F)F)c1)Nc1cc(S(=O)(=O)NCC(F)(F)F)ccc1OCC1CCOC1]

$^1$H NMR (400 MHz, DMSO-$d_6$) δ: 1.60-1.75 (m, 1H), 2.05-2.20 (m, 1H), 2.70-2.82 (m, 1H), 3.52-3.95 (m, 6H), 4.05-4.22 (m, 2H), 7.20-7.62 (m, 5H), 8.05 (s, 1H), 8.25 (s, 1H), 8.52 (t, 1H), 8.66 (s, 1H), 9.85 (s, 1H). LCMS: Calculated for $C_{21}H_{21}F_6N_3O_5S$: 541.46, Observed: 542.20 $(M+H)^+$.

4-isopropoxy-N-(2,2,2-trifluoroethyl)-3-(3-(3-(trifluoromethyl)phenyl)ureido)benzenesulfonamide (185)

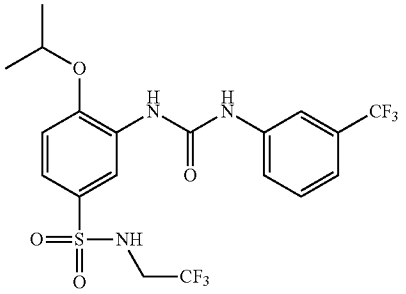 [SMILES: CC(C)Oc1ccc(S(=O)(=O)NCC(F)(F)F)cc1NC(=O)Nc1cccc(C(F)(F)F)c1]

$^1$H NMR (400 MHz, DMSO-$d_6$) δ: 1.40 (d, 6H), 3.50-3.60 (m, 2H), 4.80-4.90 (m, 1H), 7.20-7.60 (m, 5H), 8.05 (s, 1H), 8.25 (s, 1H), 8.50 (t, 1H), 8.70 (s, 1H), 9.9 (s, 1H). LCMS: Calculated for $C_{19}H_{19}F_6N_3O_4S$: 499.4, Observed: 500.30 $(M+H)^+$.

4-(pyridin-3-yloxy)-N-(2,2,2-trifluoroethyl)-3-(3-(3-(trifluoromethyl)phenyl)ureido)benzenesulfonamide (186)

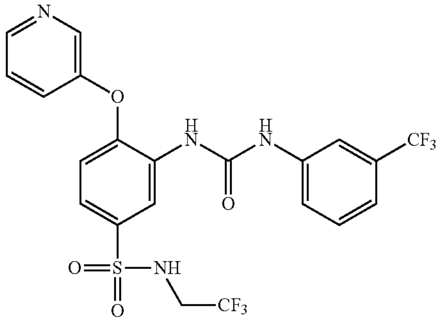 [SMILES: O=C(Nc1cccc(C(F)(F)F)c1)Nc1cc(S(=O)(=O)NCC(F)(F)F)ccc1Oc1cccnc1]

$^1$H NMR (400 MHz, $CD_3OD$) δ: 3.62-3.72 (q, 2H), 7.10 (d, 1H), 7.32 (d, 1H), 7.45-7.70 (m, 4H), 7.78 (d, 1H), 7.92 (s, 1H), 8.45-8.60 (m, 1H), 8.88 (s, 1H), 9.25 (s, 1H). LCMS: Calculated for $C_{21}H_{16}F_6N_4O_4S$: 534.43, Observed: 534.08 ($M^+$).

3-(3-(5-chlorothiazol-2-yl)ureido)-4-(cyclopropylmethoxy)-N-(2,2,2-trifluoroethyl)benzenesulfonamide (187)

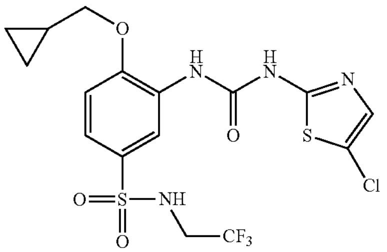 [SMILES: O=C(Nc1ncc(Cl)s1)Nc1cc(S(=O)(=O)NCC(F)(F)F)ccc1OCC1CC1]

$^1$H NMR (400 MHz, DMSO-$d_6$) δ: 0.40 (d, 2H), 0.60-0.66 (m, 2H), 1.30-1.40 (m, 1H), 3.52-3.65 (m, 2H), 4.02 (d, 2H), 7.22 (d, 1H), 7.40-7.50 (m, 2H), 8.55 (t, 1H), 8.64 (s, 1H), 8.80 (br s, 1H), 11.62 (br s, 1H). LCMS: Calculated for $C_{16}H_{16}ClF_3N_4O_4S_2$: 484.90, Observed: 485.00 ($M^+$).

4-(cyclopropylmethoxy)-3-(3-(2,4-difluorophenyl)ureido)-N-(2,2,2-trifluoroethyl)benzenesulfonamide (188)

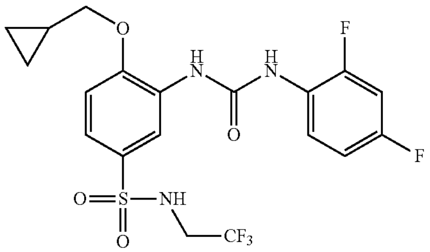 [SMILES: O=C(Nc1ccc(F)cc1F)Nc1cc(S(=O)(=O)NCC(F)(F)F)ccc1OCC1CC1]

$^1$H NMR (400 MHz, DMSO-$d_6$) δ: 0.40 (d, 2H), 0.62 (d, 2H), 1.30-1.40 (m, 1H), 3.50-3.65 (q, 2H), 4.04 (d, 2H), 7.05 (t, 1H), 7.2 (d, 1H), 7.35 (t, 1H), 7.42 (d, 1H), 8.05-8.15 (q, 1H), 8.45 (s, 1H), 8.65 (s, 1H), 8.8 (s, 1H), 9.42 (s, 1H). LCMS: Calculated for $C_{19}H_{18}F_5N_3O_4S$: 479.42, Observed: 480.05 $(M+H)^+$.

4-(cyclopropylmethoxy)-N-(2,2,2-trifluoroethyl)-3-(3-(4-(trifluoromethyl)pyridin-2-yl)ureido)benzene sulfonamide (189)

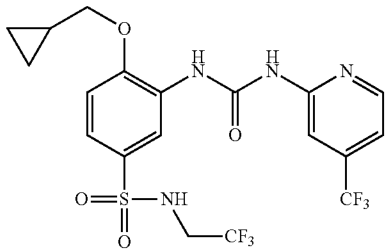 [SMILES: O=C(Nc1cc(C(F)(F)F)ccn1)Nc1cc(S(=O)(=O)NCC(F)(F)F)ccc1OCC1CC1]

$^1$H NMR (400 MHz, DMSO-$d_6$) δ: 0.40 (d, 2H), 0.65 (d, 2H), 1.35-1.45 (m, 1H), 3.50-3.65 (q, 2H), 4.02 (d, 2H), 7.2 (d, 1H), 7.39-7.50 (m, 2H), 7.70 (br s, 1H), 8.45-8.60 (m, 2H), 8.80 (s, 1H), 10.45 (br s, 1H), 11.04 (br s, 1H). LCMS: Calculated for $C_{19}H_{18}F_6N_4O_4S$: 512.43, Observed: 513.05 $(M+H)^+$.

4-ethoxy-N-(2,2,2-trifluoroethyl)-3-(3-(4-(trifluoromethyl)pyridin-2-yl)ureido)benzenesulfonamide (190)

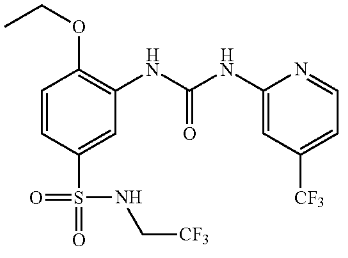 [SMILES: CCOc1ccc(S(=O)(=O)NCC(F)(F)F)cc1NC(=O)Nc1cc(C(F)(F)F)ccn1]

$^1$H NMR (400 MHz, DMSO-$d_6$) δ: 1.50 (t, 3H), 3.50-3.70 (q, 2H), 4.20-4.30 (q, 2H), 7.2 (d, 1H), 7.4 (d, 1H), 7.48 (d, 1H), 7.78 (s, 1H), 8.54 (t, 2H), 8.78 (s, 1H), 10.44 (s, 1H), 10.75 (br s, 1H). LCMS: Calculated for $C_{17}H_{16}F_6N_4O_4S$: 486.39, Observed: 487.10 $(M+H)^+$.

3-(3-(5-chlorothiazol-2-yl)ureido)-4-ethoxy-N-(2,2,2-trifluoroethyl)benzenesulfonamide (191)

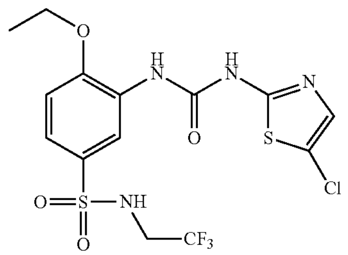 [SMILES: CCOc1ccc(S(=O)(=O)NCC(F)(F)F)cc1NC(=O)Nc1ncc(Cl)s1]

$^1$H NMR (400 MHz, DMSO-$d_6$) δ: 1.42 (t, 3H), 3.50-3.60 (m, 2H), 4.18-4.30 (q, 2H), 7.22 (d, 1H), 7.40-7.50 (m, 2H), 8.50-8.80 (m, 3H), 11.58 (s, 1H). LCMS: Calculated for $C_{14}H_{14}ClF_3N_4O_4S$ 458.86, Observed: 458.95 ($M^+$).

4-phenoxy-N-phenyl-3-(3-(3-(trifluoromethyl)phenyl)ureido)benzenesulfonamide (192)

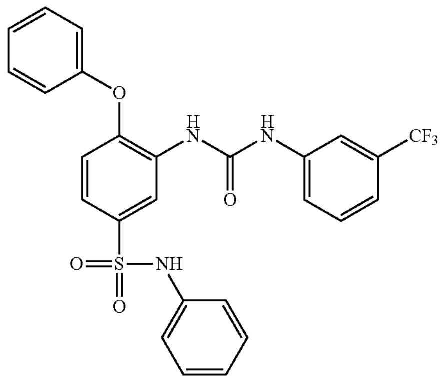 [SMILES: O=C(Nc1cccc(C(F)(F)F)c1)Nc1cc(S(=O)(=O)Nc2ccccc2)ccc1Oc1ccccc1]

$^1$H NMR (400 MHz, $CD_3OD$) δ: 6.75 (d, 1H), 6.98-7.39 (m, 10H), 7.40-7.5 (m, 3H), 7.60 (d, 1H), 7.95 (s, 1H), 8.85 (s, 1H). LCMS: Calculated for $C_{26}H_{20}F_3N_3O_4S$: 527.51, Observed: 528.47 $(M+H)^+$.

Scheme 7

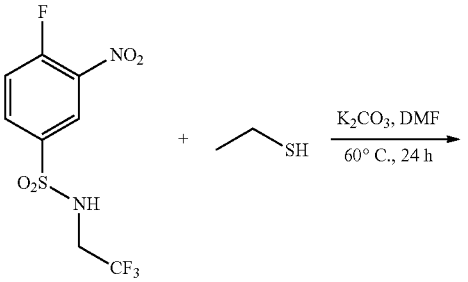

-continued

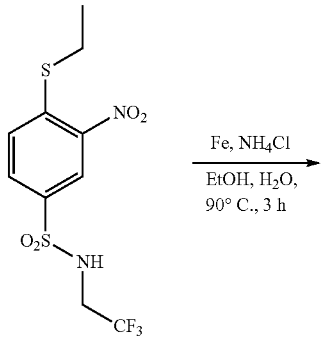

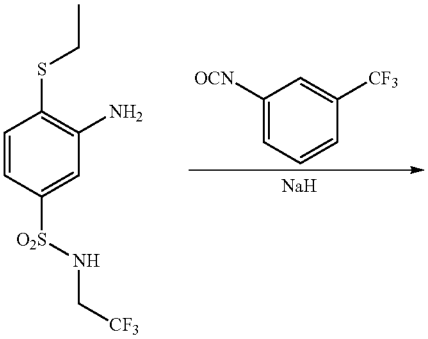

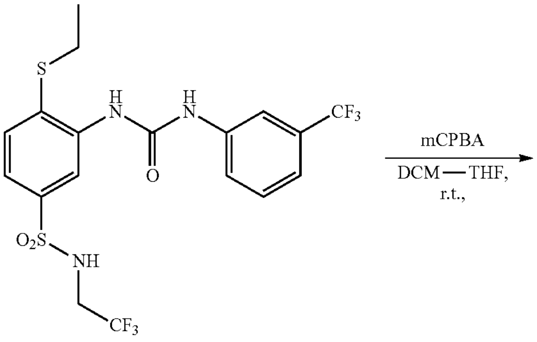

194

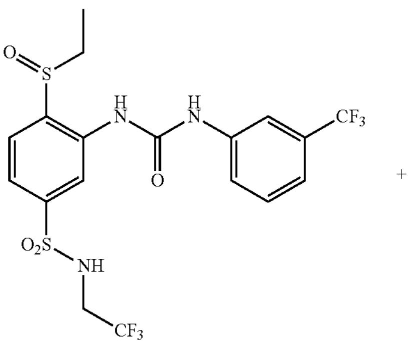

+

195

-continued

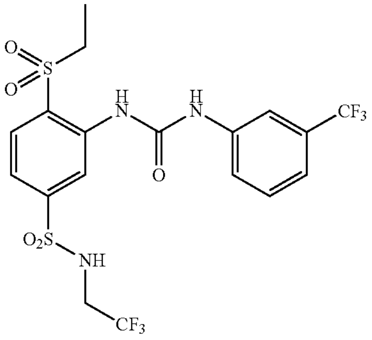

196

4-(ethylthio)-3-nitro-N-(2,2,2-trifluoroethyl)benzenesulfonamide

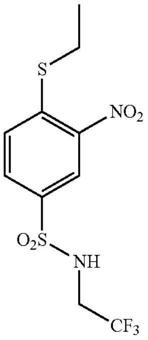

To a stirred solution of compound 4-fluoro-3-nitro-N-(2,2,2-trifluoroethyl)benzenesulfonamide (1 equiv.) in dimethyl formamide was added anhydrous $K_2CO_3$ (3 equiv.) and ethanethiol (1.2 equiv.). The mixture was heated at 60° C. for 24 h. This was cooled to room temperature and water was added and extracted with ethyl acetate. The ethyl acetate layer was washed with brine, dried over anh. $Na_2SO_4$ and concentrated to obtain the title compound as a colorless solid. $^1H$ NMR (400 MHz, DMSO-$d_6$) δ: 1.32 (t, 3H), 3.18 (q, 2H), 3.78 (q, 2H), 7.8 (d, 1H), 8.02 (d, 1H), 8.57 (s, 1H), 8.9 (br s, 1H).

3-amino-4-(ethylthio)-N-(2,2,2-trifluoroethyl)benzenesulfonamide

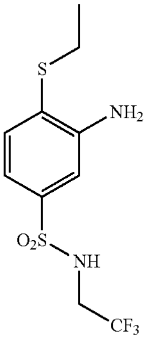

To 4-(ethylthio)-3-nitro-N-(2,2,2-trifluoroethyl)benzenesulfonamide (1 equiv.) in a single neck round bottom flask in ethanol:$H_2O$ (2:1) was added Fe (3 equiv.) and $NH_4Cl$ (3 equiv.). The reaction mixture was heated at 90° C. for 3 h, brought to room temperature and filtered through a pad of celite. The residue was washed with methanol, and the filtrate was evaporated and diluted with ethyl acetate, washed with water and brine, dried and concentrated to obtain the title compound. $^1H$ NMR (400 MHz, DMSO-$d_6$) δ: 1.2 (t, 3H), 2.9 (q, 2H), 3.6 (q, 2H), 5.6 (s, 2H), 6.92 (d, 1H), 7.1 (s, 1H), 7.39 (d, 1H), 8.43 (t, 1H).

4-(ethylthio)-N-(2,2,2-trifluoroethyl)-3-(3-(3-(trifluoromethyl)phenyl)ureido)benzenesulfonamide (194)

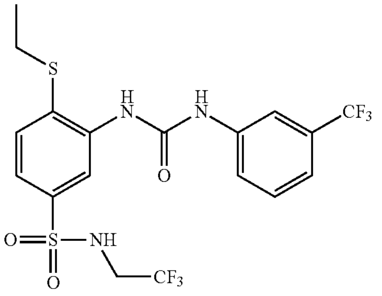 [SMILES: CCSc1ccc(S(=O)(=O)NCC(F)(F)F)cc1NC(=O)Nc1cccc(C(F)(F)F)c1]

To a stirred solution of 3-amino-4-(ethylthio)-N-(2,2,2-trifluoroethyl)benzenesulfonamide (1 equiv.) in dichloromethane was added 1.3 equiv. of isocyanate (commercially available m-trifluoromethyl phenyl isocyanate) and stirred overnight at room temperature. The reaction mass was then concentrated and washed with ether to remove the undesired dimer impurity. The residue was evaporated in vacuo and purified by Reverse Phase Prep-HPLC to yield the title compound.

$^1H$ NMR (400 MHz, DMSO-$d_6$) δ: 1.22 (t, 3H), 3.0-3.10 (m, 2H), 3.60-3.74 (q, 2H), 7.30-7.70 (m, 5H), 8.05 (s, 1H), 8.38-8.70 (m, 3H), 9.90 (s, 1H). LCMS: Calculated for $C_{18}H_{17}F_6N_3O_3S_2$ 501.46, Observed: 502.80 $(M+H)^+$.

4-(ethylsulfinyl)-N-(2,2,2-trifluoroethyl)-3-(3-(3-(trifluoromethyl)phenyl)ureido)benzenesulfonamide (195)

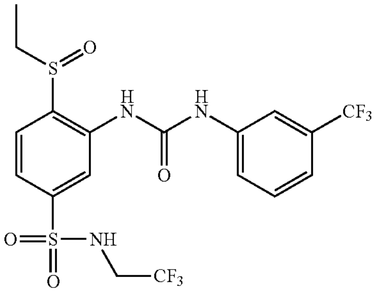 [SMILES: CCS(=O)c1ccc(S(=O)(=O)NCC(F)(F)F)cc1NC(=O)Nc1cccc(C(F)(F)F)c1]

Compound 194 (1 equiv.) was dissolved in THF at room temperature to which m-chloroperoxy benzoic acid (1 equiv.) was added and stirred overnight. The solvent was evaporated and the residue was diluted in dichloromethane and washed with satd. sodium thiosulfate, satd. $NaHCO_3$ followed by water and brine. The organic layer was dried over $Na_2SO_4$, concentrated and purified by column chromatography to obtain the title compound. $^1H$ NMR (400 MHz, DMSO-$d_6$) δ: 1.14 (t, 3H), 2.90-3.10 (m, 2H), 3.70-3.80 (q, 2H), 7.35 (d, 1H), 7.45-7.90 (m, 4H), 8.02 (s, 1H), 8.46 (s, 1H), 8.85 (s, 1H), 9.10 (s, 1H), 9.82 (s, 1H). LCMS: Calculated for $C_{18}H_{17}F_6N_3O_4S_2$: 517.46, Observed: 518.20 $(M+H)^+$.

4-(ethylsulfonyl)-N-(2,2,2-trifluoroethyl)-3-(3-(3-(trifluoromethyl)phenyl)ureido)benzenesulfonamide (196)

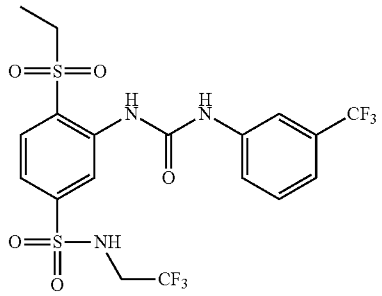 [SMILES: CCS(=O)(=O)c1ccc(S(=O)(=O)NCC(F)(F)F)cc1NC(=O)Nc1cccc(C(F)(F)F)c1]

Compound 196 was prepared by adopted a similar procedure as described for the synthesis of compound 195, while 3 equiv. of mCPBA was used for the sulfone formation and compound 196 was obtained.

$^1H$ NMR (400 MHz, DMSO-$d_6$) δ: 1.18 (t, 3H), 3.40-3.50 (q, 2H), 3.70-3.82 (q, 2H), 7.30-7.74 (m, 4H), 8.0-8.10 (m, 2H), 8.70-9.02 (m, 3H), 10.40 (s, 1H). LCMS: Calculated for $C_{18}H_{17}F_6N_3O_5S_2$ 533.46, Observed: 534.15 $(M+H)^+$.

General Procedure for the Synthesis of Sulfonamide Urea Derivatives; Central Pyridyl Ring Scheme 7

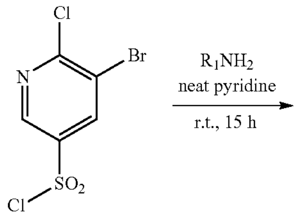

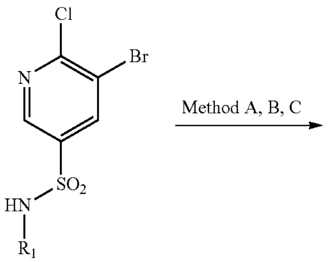

A25

-continued

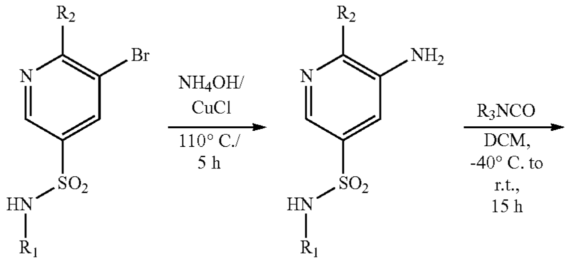

A26

A27

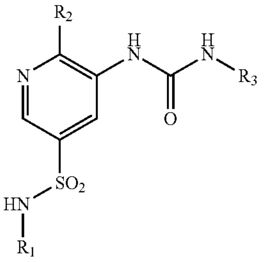

A28

General Procedure for the Synthesis of Sulfonamides

To a stirred solution of respective amines (1 equiv.) in pyridine was added 3-bromo-2-chloro pyridine-5-sulfonyl chloride (1 equiv.) at room temperature and stirred for over a period of 12 h. The completion of the reaction was monitored by TLC and the reaction mass was evaporated to dryness and dichloromethane was added to the residue, washed with 1N HCl and with water and extracted with DCM. The organic fractions were pooled, washed with brine, dried, concentrated and purified by column chromatography to obtain the sulfonamide compounds.

The following compounds were similarly prepared according to the above procedure:

5-bromo-6-chloro-N-(2,2,2-trifluoroethyl)pyridine-3-sulfonamide

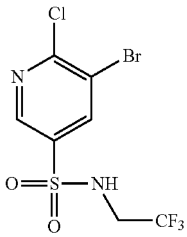 [SMILES: O=S(=O)(NCC(F)(F)F)c1cnc(Cl)c(Br)c1]

$^1$H NMR (400 MHz, DMSO-$d_6$) δ: 3.85 (q, 2H), 8.59 (s, 1H), 8.8 (s, 1H), 9.03 (s, 1H).

5-bromo-6-chloro-N-(oxetan-3-yl)pyridine-3-sulfonamide

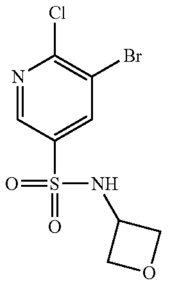 [SMILES: O=S(=O)(NC1COC1)c1cnc(Cl)c(Br)c1]

$^1$H NMR (400 MHz, DMSO-$d_6$+$D_2O$) δ: 4.25-4.32 (m, 2H), 4.42-4.6 (m, 3H), 8.5 (s, 1H), 8.72 (s, 1H).

5-bromo-6-chloro-N-(1-cyanocyclopropyl)pyridine-3-sulfonamide

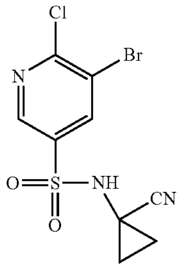 [SMILES: N#CC1(NS(=O)(=O)c2cnc(Cl)c(Br)c2)CC1]

$^1$H NMR (400 MHz, DMSO-$d_6$) δ: 1.34 (t, 2H), 1.47 (t, 2H), 8.53 (s, 1H), 8.82 (S, 1H), 9.52 (s, 1H).

General Procedure for the Synthesis of Sulfonamide Ethers (Method A):

To a stirred solution of respective alcohol (1.5 equiv.) in DMF was added KOtBu (2 equiv.) and stirred at room temperature for 30 min. The sulfonamide compound A25 (1 equiv.) was added to the reaction mixture and stirred at room temperature for 12 h. The completion of the reaction was monitored by TLC, water was added and extracted with ethyl acetate. The combined organic fractions were washed with brine, dried, concentrated and purified by column chromatography to obtain the ether compounds.

The following compounds were similarly prepared according to the above procedure:

5-bromo-6-(cyclopropylmethoxy)-N-(2,2,2-trifluoroethyl)pyridine-3-sulfonamide

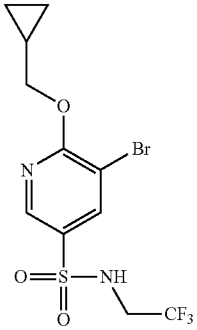 [SMILES: O=S(=O)(NCC(F)(F)F)c1cnc(OCC2CC2)c(Br)c1]

$^1$H NMR (400 MHz, DMSO-$d_6$) δ: 0.38 (d, 2H), 0.58 (d, 2H), 1.2-1.3 (m, 1H), 3.8 (q, 2H), 4.28 (d, 2H), 8.38 (s, 1H), 8.47 (s, 1H), 8.75 (s, 1H).

5-bromo-6-(cyclopropylmethoxy)-N-(oxetan-3-yl)pyridine-3-sulfonamide

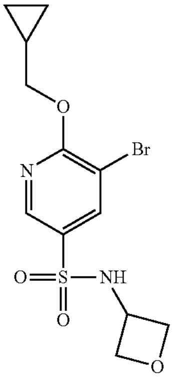 [SMILES: O=S(=O)(NC1COC1)c1cnc(OCC2CC2)c(Br)c1]

$^1$H NMR (400 MHz, DMSO-$d_6$) δ: 0.38 (d, 2H), 0.59 (d, 2H), 1.2-1.32 (m, 1H), 4.2-4.35 (m, 2H), 4.39-4.49 (m, 2H), 4.52-4.6 (m, 3H), 8.29 (s, 1H), 8.45 (s, 1H), 8.68 (d, 1H). ESMS: Calculated; 363.23, Observed; 362.48 $(M-H)^-$.

5-bromo-6-ethoxy-N-(oxetan-3-yl)pyridine-3-sulfonamide

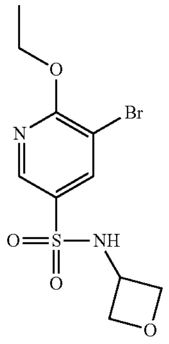 [SMILES: CCOc1ncc(S(=O)(=O)NC2COC2)cc1Br]

$^1$H NMR (400 MHz, DMSO-$d_6$) δ: 1.34 (t, 3H), 4.24-4.46 (m, 7H), 8.27 (s, 1H), 8.5 (s, 1H), 8.62 (s, 1H).

5-bromo-N-(1-cyanocyclopropyl)-6-(cyclopropylmethoxy)pyridine-3-sulfonamide

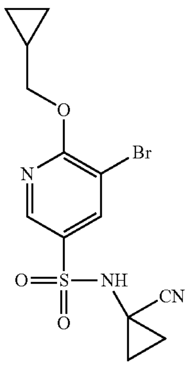 [SMILES: N#CC1(NS(=O)(=O)c2cnc(OCC3CC3)c(Br)c2)CC1]

$^1$H NMR (400 MHz, DMSO-$d_6$) δ: 0.3-0.35 (m, 2H), 0.5-0.6 (m, 2H), 1.2-1.5 (m, 5H), 4.26 (d, 2H), 8.5 (s, 1H), 8.58 (s, 1H), 8.6 (s, 1H).

5-bromo-6-((tetrahydrofuran-3-yl)methoxy)-N-(2,2,2-trifluoroethyl)pyridine-3-sulfonamide

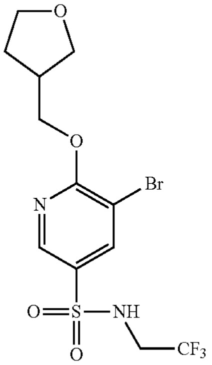 [SMILES: O=S(=O)(NCC(F)(F)F)c1cnc(OCC2CCOC2)c(Br)c1]

$^1$H NMR (400 MHz, DMSO-$d_6$) δ: 1.63-1.72 (m, 1H), 1.95-1.25 (m, 1H), 2.64-2.74 (m, 1H), 3.5-3.6 (m, 1H), 3.62-3.7 (m, 1H), 3.7-3.82 (m, 4H), 4.28-4.41 (m, 2H), 8.35 (s, 1H), 8.55 (s, 1H), 8.73 (t, 1H).

5-bromo-6-ethoxy-N-(2,2,2-trifluoroethyl)pyridine-3-sulfonamide

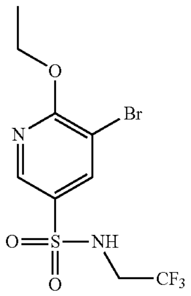 [SMILES: CCOc1ncc(S(=O)(=O)NCC(F)(F)F)cc1Br]

$^1$H NMR (400 MHz, DMSO-$d_6$) δ: 1.34 (t, 3H), 3.78 (q, 2H), 4.45 (q, 2H), 8.32 (s, 1H), 8.54 (s, 1H), 8.72 (br s, 1H); ESMS: Calculated; 363.15, Observed; 383.21 $(M+H+H_2O)^+$.

Procedure for the Displacement of Chloro Group with Morpholine (Method B):

5-bromo-6-morpholino-N-(2,2,2-trifluoroethyl)pyridine-3-sulfonamide

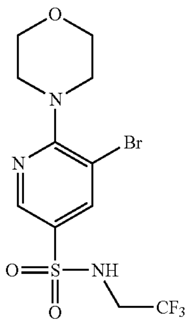 [SMILES: O=S(=O)(NCC(F)(F)F)c1cnc(N2CCOCC2)c(Br)c1]

To a stirred solution of morpholine (1.1 equiv.) in DMF was added $K_2CO_3$ (3 equiv.) and sulfonamide compound A25 (1 equiv.) at room temperature and the reaction mixture was stirred under heating at 120° C. for a period of 16 h. After the completion of the reaction, as indicated by TLC, the reaction mass was treated with water and extracted with ethyl acetate. The pooled organic fractions were washed with brine, dried, concentrated and purified by column chromatography to obtain the title compound A26 is 60% yield. $^1$H NMR (400 MHz, DMSO-$d_6$) δ: 3.4-3.46 (m, 4H), 3.7-3.82 (m, 6H), 8.22 (s, 1H), 8.58 (s, 1H), 8.66 (t, 1H). LCMS: Calculated; 404.20, Observed; 403.95 ($M^+$).

Procedure for the Displacement of Chloro with Cyclopropylmethylamine (Method C):

5-bromo-6-((cyclopropylmethyl)amino)-N-(2,2,2-trifluoroethyl)pyridine-3-sulfonamide

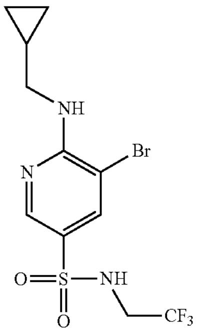 [SMILES: O=S(=O)(NCC(F)(F)F)c1cnc(NCC2CC2)c(Br)c1]

To the sulfonamide compound A25 (1 equiv.) in DMSO in a sealed tube was added $Et_3N$ (2.1 equiv.) followed by cyclopropylmethyl amine (1.1 equiv.) and heated at 150° C. for a period of 2 h. The reaction mass was brought to room temperature and stirred for a period of 12 h at room temperature. The reaction mass was diluted with ethyl acetate washed with satd. $NaHCO_3$ followed by water and brine, and extracted with ethyl acetate. The pooled organic fractions were dried, concentrated and purified by column chromatography to obtain the amine compound A27 in 80% yield.

$^1$H NMR (400 MHz, DMSO-$d_6$) δ: 0.2-0.26 (m, 2H), 0.15-0.21 (m, 2H), 1.5-1.15 (m, 1H), 3.25-3.3 (m, 2H), 3.7 (q, 2H), 7.3 (t, 1H), 8.0 (s, 1H), 8.35 (s, 1H), 8.4 (br s, 1H). LCMS: Calculated; 388.20, Observed; 390.10 $(M+2H)^+$.

General Procedure for the Displacement of Bromo with Ammonia

Compound A27 (1 equiv.) was taken in a sealed tube and was treated with aq. $NH_4OH$ (10 volumes) and CuCl (0.5 equiv.) at room temperature. The reaction mixture was stirred at 110° C. for 5 h. The completion of the reaction was monitored by TLC, and the reaction mass was concentrated to remove $NH_3$. The residue was treated with ethyl acetate and washed with water, brine, dried, concentrated and purified by column chromatography to obtain the amines.

The following compounds were similarly prepared according to the above procedure:

5-amino-6-(cyclopropylmethoxy)-N-(2,2,2-trifluoroethyl)pyridine-3-sulfonamide

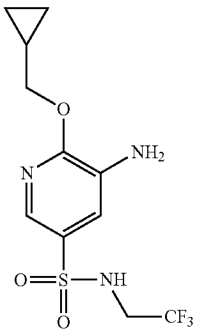 [SMILES: Nc1cc(S(=O)(=O)NCC(F)(F)F)cnc1OCC1CC1]

$^1$H NMR (400 MHz, DMSO-$d_6$) δ: 0.38 (d, 2H), 0.57 (d, 2H), 1.21-1.3 (m, 1H), 3.63 (q, 2H), 4.19 (d, 2H), 5.42 (s, 2H), 7.19 (s, 1H), 7.73 (s, 1H), 8.5 (t, 1H). LCMS: Calculated: 325.31, Observed: 326.00 $(M+H)^+$.

5-amino-6-(cyclopropylmethoxy)-N-(oxetan-3-yl) pyridine-3-sulfonamide

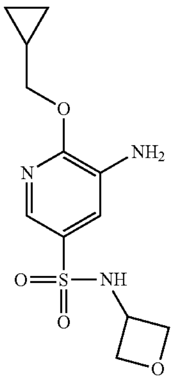 [SMILES: Nc1cc(S(=O)(=O)NC2COC2)cnc1OCC1CC1]

Crude product was used in the next step without further purification.

5-amino-6-ethoxy-N-(oxetan-3-yl)pyridine-3-sulfonamide

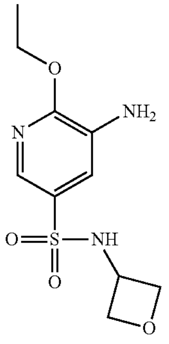 [SMILES: CCOc1ncc(S(=O)(=O)NC2COC2)cc1N]

Crude product was used in the next step without further purification.

5-amino-N-(1-cyanocyclopropyl)-6-(cyclopropylmethoxy)pyridine-3-sulfonamide

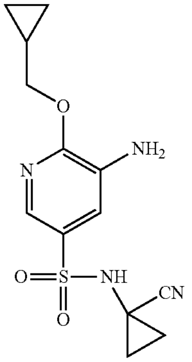 [SMILES: N#CC1(NS(=O)(=O)c2cnc(OCC3CC3)c(N)c2)CC1]

$^1$H NMR (400 MHz, DMSO-$d_6$+$D_2O$) δ: 0.3-0.35 (m, 2H), 0.5-0.5 (m, 2H), 1.2-1.3 (m, 5H), 4.2 (d, 2H), 7.2 (s, 1H), 7.8 (s, 1H).

5-amino-6-((tetrahydrofuran-3-yl)methoxy)-N-(2,2,2-trifluoroethyl)pyridine-3-sulfonamide

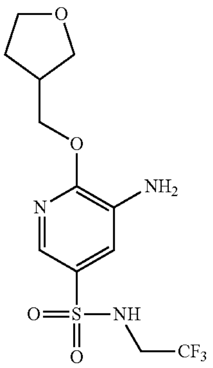 [SMILES: Nc1cc(S(=O)(=O)NCC(F)(F)F)cnc1OCC1CCOC1]

$^1$H NMR (400 MHz, DMSO-$d_6$) δ: 1.6-1.7 (m, 1H), 1.95-2.05 (m, 1H), 2.6-2.7 (m, 1H), 3.5-3.8 (m, 6H), 4.14-4.35 (m, 2H), 5.5 (s, 2H), 7.18 (s, 1H), 7.72 (s, 1H), 8.5 (t, 1H); ESMS: Calculated; 355.33, Observed; 354.30 $(M-)^-$.

5-amino-6-ethoxy-N-(2,2,2-trifluoroethyl)pyridine-3-sulfonamide

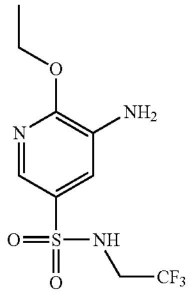 [SMILES: CCOc1ncc(S(=O)(=O)NCC(F)(F)F)cc1N]

$^1$H NMR (400 MHz, DMSO-$d_6$) δ: 1.32 (t, 3H), 3.62 (q, 2H), 4.35 (q, 2H), 5.42 (s, 2H), 7.12 (s, 1H), 7.72 (s, 1H), 8.46 (t, 1H); ESMS: Calculated; 299.27, Observed; 298.23 $(M-)^-$.

5-amino-6-morpholino-N-(2,2,2-trifluoroethyl)pyridine-3-sulfonamide

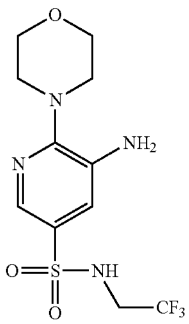 [SMILES: Nc1cc(S(=O)(=O)NCC(F)(F)F)cnc1N1CCOCC1]

$^1$H NMR (400 MHz, DMSO-$d_6$) δ: 4.06 (m, 4H), 3.6-3.7 (m, 2H), 4.73 (m, 4H), 5.3 (s, 2H), 7.26 (s, 1H), 7.92 (s, 1H), 8.5 (t, 1H). LCMS: Calculated; 340.32, Observed; 341.22 $(M+H)^+$.

5-amino-6-((cyclopropylmethyl)amino)-N-(2,2,2-trifluoroethyl)pyridine-3-sulfonamide

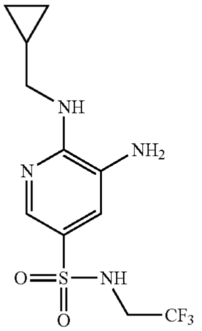 [SMILES: Nc1cc(S(=O)(=O)NCC(F)(F)F)cnc1NCC1CC1]

$^1$H NMR (400 MHz, DMSO-$d_6$) δ: 0.2 (m, 2H), 0.42 (m, 2H), 1.04-1.12 (m, 1H), 3.24 (t, 2H), 3.46-3.6 (m, 2H), 5.2 (s, 2H), 6.45 (t, 1H), 6.91 (s, 1H), 7.75 (s, 1H), 8.16 (t, 1H). LCMS: Calculated; 324.32, Observed; 325.10 $(M+H)^+$.

The following compounds were similarly prepared according to the general procedure in Method A (Scheme 1):

6-(cyclopropylmethoxy)-N-(2,2,2-trifluoroethyl)-5-(3-(3-(trifluoromethyl)phenyl)ureido)pyridine-3-sulfonamide (197)

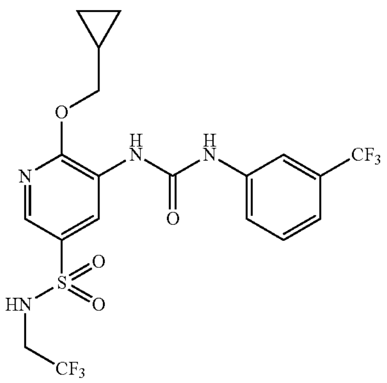 [SMILES: O=C(Nc1cccc(C(F)(F)F)c1)Nc1cc(S(=O)(=O)NCC(F)(F)F)cnc1OCC1CC1]

$^1$H NMR (400 MHz, DMSO-$d_6$) δ: 0.42 (d, 2H), 0.62 (d, 2H), 1.35-1.40 (m, 1H), 3.65-3.80 (m, 2H), 4.35 (d, 2H), 7.38 (s, 1H), 7.56 (s, 2H), 8.10 (s, 1H), 8.20 (s, 1H), 8.61 (s, 1H), 8.78 (t, 1H), 8.88 (s, 1H), 9.95 (s, 1H). LCMS: Calculated for $C_{19}H_{18}F_6N_4O_4S$: 512.43, Observed: 513.10 $(M+H)^+$.

6-(cyclopropylmethoxy)-N-(oxetan-3-yl)-5-(3-(3-(trifluoromethyl)phenyl)ureido)pyridine-3-sulfonamide (198)

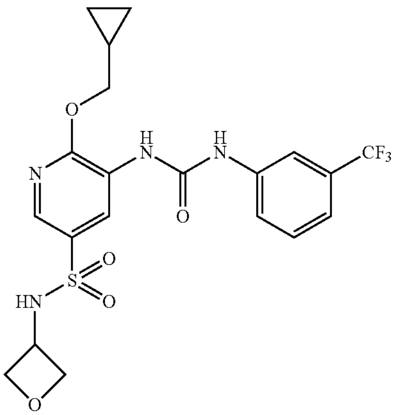 [SMILES: O=C(Nc1cccc(C(F)(F)F)c1)Nc1cc(S(=O)(=O)NC2COC2)cnc1OCC1CC1]

$^1$H NMR (400 MHz, DMSO-$d_6$) δ: 0.40 (d, 2H), 0.60 (d, 2H), 1.30-1.42 (br s, 1H), 4.20-4.60 (m, 7H), 7.38 (s, 1H), 7.60 (s, 2H), 8.10 (d, 2H), 8.50-8.80 (m, 3H), 9.92 (s, 1H). LCMS: Calculated for $C_{20}H_{21}F_3N_4O_5S$: 486.46, Observed: 487.3 $(M+H)^+$.

6-ethoxy-N-(oxetan-3-yl)-5-(3-(3-(trifluoromethyl)phenyl)ureido)pyridine-3-sulfonamide (199)

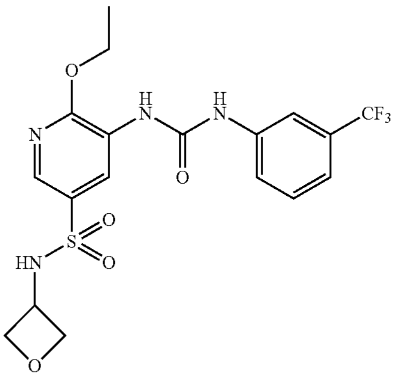 [SMILES: CCOc1ncc(S(=O)(=O)NC2COC2)cc1NC(=O)Nc1cccc(C(F)(F)F)c1]

$^1$H NMR (400 MHz, DMSO-$d_6$) δ: 1.42 (t, 3H), 4.20-4.62 (m, 7H), 7.36 (s, 1H), 7.55 (s, 2H), 8.0-8.20 (m, 2H), 8.50-8.85 (m, 3H), 9.90 (s, 1H). LCMS: Calculated for $C_{18}H_{19}F_3N_4O_5S$: 460.43, Observed: 461.25 $(M+H)^+$.

N-(1-cyanocyclopropyl)-6-(cyclopropylmethoxy)-5-(3-(3-(trifluoromethyl)phenyl)ureido)pyridine-3-sulfonamide (200)

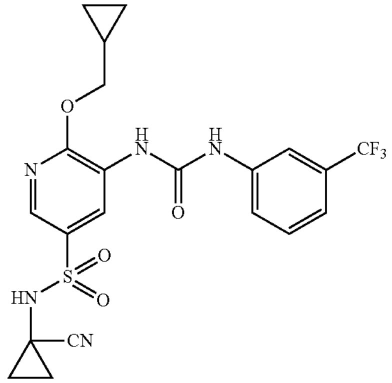 [SMILES: N#CC1(NS(=O)(=O)c2cnc(OCC3CC3)c(NC(=O)Nc3cccc(C(F)(F)F)c3)c2)CC1]

$^1$H NMR (400 MHz, DMSO-$d_6$) δ: 0.40 (d, 2H), 0.60 (d, 2H), 1.20-1.35 (m, 4H), 1.42 (s, 1H), 4.39 (d, 2H), 7.42 (s, 1H), 7.58 (s, 2H), 8.10 (s, 1H), 8.22 (s, 1H), 8.64 (s, 1H), 8.90 (s, 1H), 9.22 (s, 1H), 9.95 (s, 1H). LCMS: Calculated for $C_{21}H_{20}F_3N_5O_4S$: 495.47, Observed: 496.35 $(M+H)^+$.

6-((tetrahydrofuran-3-yl)methoxy)-N-(2,2,2-trifluoroethyl)-5-(3-(3-(trifluoromethyl)phenyl)ureido)pyridine-3-sulfonamide (201)

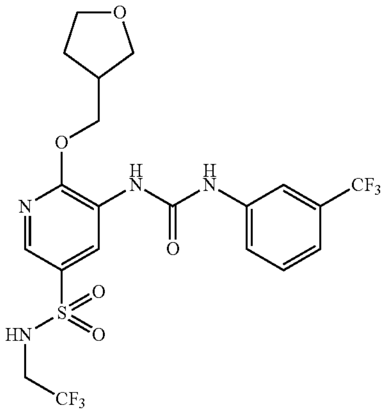 [SMILES: O=C(Nc1cccc(C(F)(F)F)c1)Nc1cc(S(=O)(=O)NCC(F)(F)F)cnc1OCC1CCOC1]

$^1$H NMR (400 MHz, DMSO-$d_6$) δ: 1.62-1.80 (m, 1H), 2.0-2.15 (m, 1H), 2.70-2.82 (m, 1H), 3.60-3.74 (m, 4H), 3.75-3.90 (m, 2H), 4.35 (t, 1H), 4.50 (t, 1H), 7.38 (s, 1H), 7.58 (s, 2H), 8.05 (s, 1H), 8.20 (s, 1H), 8.45 (s, 1H), 8.75 (s, 1H), 8.85 (s, 1H), 9.90 (s, 1H). LCMS: Calculated for $C_{20}H_{20}F_6N_4O_5S$: 542.45, Observed: 543.30 $(M+H)^+$.

6-ethoxy-N-(2,2,2-trifluoroethyl)-5-(3-(4-(trifluoromethyl)pyridine-2-yl)ureido)pyridine-3-sulfonamide (202)

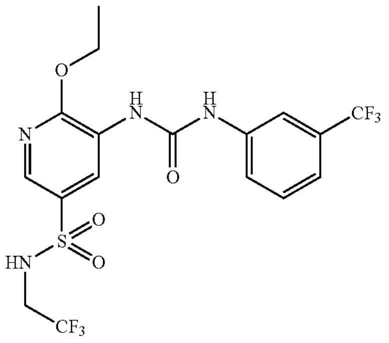 [SMILES: CCOc1ncc(S(=O)(=O)NCC(F)(F)F)cc1NC(=O)Nc1cccc(C(F)(F)F)c1]

$^1$H NMR (400 MHz, DMSO-$d_6$) δ: 1.26 (t, 3H), 3.62-3.75 (m, 2H), 4.45-4.60 (m, 2H), 7.10 (d, 1H), 7.40 (d, 1H), 7.82 (br s, 1H), 8.24 (s, 1H), 8.55 (d, 1H), 8.78 (t, 1H), 8.90 (s, 1H), 10.54 (s, 1H). LCMS: Calculated for $C_{16}H_{15}F_6N_5O_4S$: 487.39, Observed: 487.95 $(M^+)$.

6-morpholino-N-(2,2,2-trifluoroethyl)-5-(3-(3-(trifluoromethyl)phenyl)ureido)pyridine-3-sulfonamide (203)

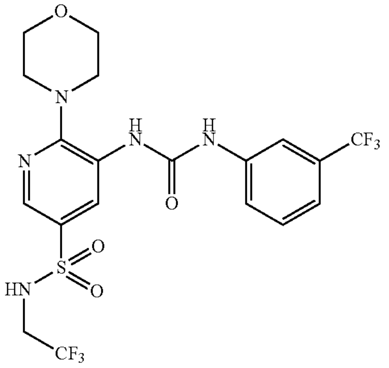 [SMILES: O=C(Nc1cccc(C(F)(F)F)c1)Nc1cc(S(=O)(=O)NCC(F)(F)F)cnc1N1CCOCC1]

$^1$H NMR (400 MHz, DMSO-$d_6$) δ: 3.15-3.25 (br s, 4H), 3.65-3.90 (m, 6H), 7.36 (d, 1H), 7.50-7.62 (br s, 2H), 8.05 (s, 1H), 8.20 (s, 1H), 8.38 (s, 1H), 8.65 (s, 1H), 8.80 (br s, 1H), 9.82 (s, 1H). LCMS: Calculated for $C_{19}H_{19}F_6N_5O_4S$: 527.44, Observed: 528.15 $(M+H)^+$.

6-((cyclopropylmethyl)amino)-N-(2,2,2-trifluoroethyl)-5-(3-(3-(trifluoromethyl)phenyl)ureido)pyridine-3-sulfonamide (204)

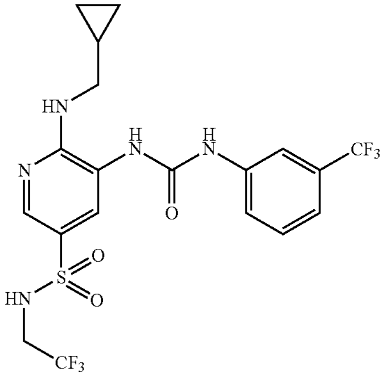 [SMILES: O=C(Nc1cccc(C(F)(F)F)c1)Nc1cc(S(=O)(=O)NCC(F)(F)F)cnc1NCC1CC1]

$^1$H NMR (400 MHz, DMSO-$d_6$) δ: 0.25 (d, 2H), 0.45 (d, 2H), 1.10-1.20 (m, 1H), 3.20-3.30 (m, 2H), 3.55-3.70 (m, 2H), 6.98 (t, 1H), 7.32 (d, 1H), 7.50-7.65 (m, 2H), 7.95 (s, 1H), 8.05 (s, 1H), 8.22 (d, 2H), 8.40 (t, 1H), 9.25 (s, 1H). LCMS: Calculated for $C_{19}H_{19}F_6N_5O_3S$: 511.44, Observed: 512.30 $(M+H)^+$.

General Procedure for the Synthesis of Urea Sulfonamides)

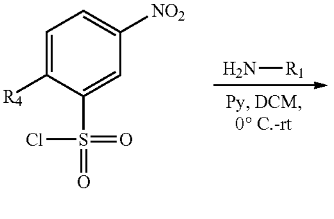

-continued

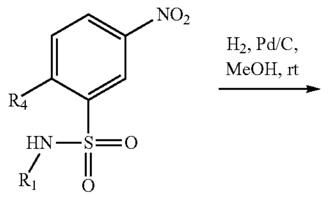

A29

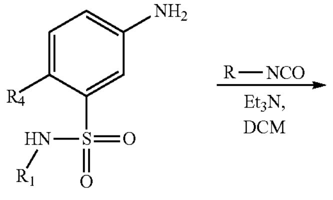

A30

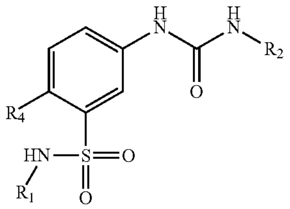

A31

The following compounds were prepared similar to the sequence for synthesis of compounds A2 in Scheme 1, using the appropriate sulfonyl chloride and amine.

2-methyl-5-nitro-N-phenylbenzenesulfonamide

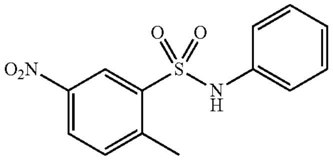 [SMILES: Cc1ccc([N+](=O)[O-])cc1S(=O)(=O)Nc1ccccc1]

$^{1}$H NMR (400 MHz, DMSO-d$_6$) δ: 2.65 (s, 3H), 7.0-7.16 (m, 3H), 7.2-7.3 (m, 2H), 7.66 (d, 1H), 8.32 (d, 1H), 8.55 (s, 1H), 10.7 (s, 1H).

N-(4-chlorophenyl)-2-methyl-5-nitrobenzenesulfonamide

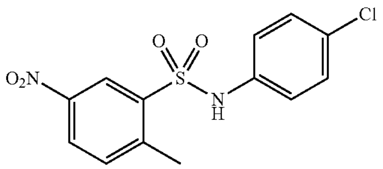

LCMS: Calculated; 326.76, Observed; 325.10 (M−)$^-$.

N-(2-chlorophenyl)-2-methyl-5-nitrobenzenesulfonamide

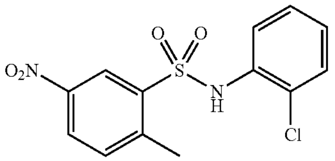 [SMILES: Cc1ccc([N+](=O)[O-])cc1S(=O)(=O)Nc1ccccc1Cl]

$^{1}$H NMR (400 MHz, DMSO-D$_6$) δ: 2.66 (s, 3H), 7.2-7.34 (m, 3H), 7.4 (d, 1H), 7.72 (d, 1H), 8.18 (m, 2H), 10.47 (s, 1H).

N-(3-chlorophenyl)-2-methyl-5-nitrobenzenesulfonamide

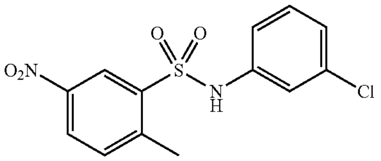 [SMILES: Cc1ccc([N+](=O)[O-])cc1S(=O)(=O)Nc1cccc(Cl)c1]

$^{1}$H NMR (400 MHz, DMSO-D$_6$) δ: 2.66 (s, 3H), 7.02-7.12 (m, 3H), 7.25 (t, 1H), 7.72 (d, 1H), 8.36 (d, 1H), 8.57 (s, 1H), 11.0 (s, 1H).

N-(4-hydroxyphenyl)-2-methyl-5-nitrobenzenesulfonamide

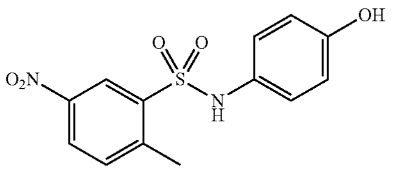 [SMILES: Cc1ccc([N+](=O)[O-])cc1S(=O)(=O)Nc1ccc(O)cc1]

$^{1}$H NMR (400 MHz, $CD_3OD$) δ: 2.63 (s, 3H), 6.6 (d, 2H), 6.83 (d, 2H), 7.54 (d, 1H), 8.22 (d, 1H), 8.53 (s, 1H).

General Procedure for Catalytic Reduction of Aryl-Nitro Compounds:

A thoroughly de-aerated and $N_2$-purged solution of sulfonamide (1 equiv.), 5% Pd/C (10% w/w) in MeOH was hydrogenated with hydrogen (1 atm). After stirring for overnight at room temperature, the reaction mixture was filtered through a pad of celite, and the pad was further washed with MeOH. The filtrate was concentrated and the residue was purified by column chromatography (silica gel, 60-120 mesh, 5:5, EtOAc-hexane) to afford the aniline product.

5-amino-2-methyl-N-phenylbenzenesulfonamide

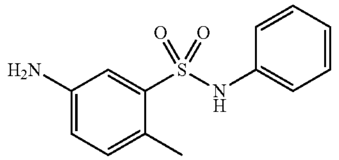

$^1$H NMR (400 MHz, DMSO-$d_6$) δ: 2.36 (s, 3H), 5.32 (s, 2H), 6.5 (d, 1H), 6.92-7.08 (m, 4H), 7.16-7.23 (m, 3H), 10.12 (br s, 1H). LCMS: Calculated; 262.33, Observed; 263.00 $(M+H)^+$.

3-amino-N-phenylbenzenesulfonamide

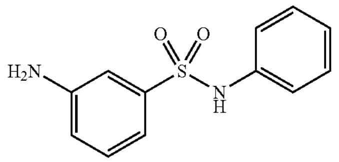 [SMILES: Nc1cccc(S(=O)(=O)Nc2ccccc2)c1]

LCMS: Calculated; 248.30, Observed; 249.15 $(M^++1)$.

2-methyl-N-phenyl-5-(3-(3-(trifluoromethyl)phenyl) ureido)benzenesulfonamide (206)

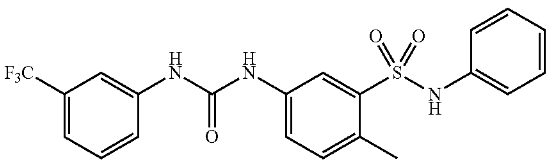 [SMILES: Cc1ccc(NC(=O)Nc2cccc(C(F)(F)F)c2)cc1S(=O)(=O)Nc1ccccc1]

$^1$H NMR (400 MHz, DMSO-$d_6$) δ: 2.23 (s, 3H), 6.98 (t, 1H), 7.01 (d, 2H), 7.14-7.34 (m, 4H), 7.44-7.60 (m, 3H), 7.92 (s, 1H), 8.12 (s, 1H), 9.00 (d, 2H), 10.30 (s, 1H). LCMS: Calculated for $C_{21}H_{18}F_3N_3O_3S$: 449.45, Observed 472.25 $(M+Na)^+$.

2-methyl-N-phenyl-5-(3-(4-(trifluoromethyl)phenyl) ureido)benzenesulfonamide (207)

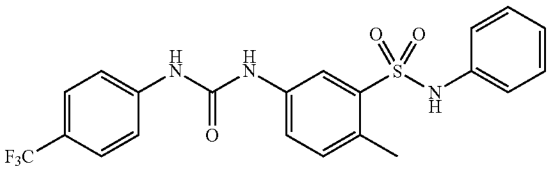 [SMILES: Cc1ccc(NC(=O)Nc2ccc(C(F)(F)F)cc2)cc1S(=O)(=O)Nc1ccccc1]

$^1$H NMR (400 MHz, DMSO-$d_6$) δ: 6.98 (t, 1H), 7.01 (d, 2H), 7.18-7.26 (m, 3H), 7.52 (d, 1H), 7.59-7.65 (m, 4H), 8.12 (s, 1H), 9.04 (s, 1H), 10.39 (s, 1H). LCMS: Calculated for $C_{21}H_{18}F_3N_3O_3S$: 449.45, Observed 472.30 $(M+Na)^+$.

N-phenyl-3-(3-(4-(trifluoromethoxy)phenyl)ureido) benzenesulfonamide (208)

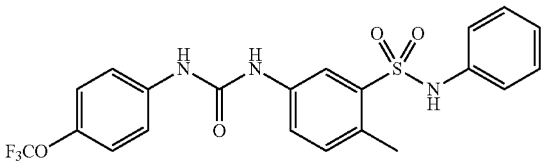 [SMILES: Cc1ccc(NC(=O)Nc2ccc(OC(F)(F)F)cc2)cc1S(=O)(=O)Nc1ccccc1]

$^1$H NMR (400 MHz, DMSO-$d_6$) δ: 2.42 (s, 3H), 6.98 (t, 1H), 7.15-7.31 (m, 5H), 7.52-7.58 (m, 3H), 8.05 (s, 1H), 8.82 (s, 1H), 8.98 (s, 1H), 10.39 (s, 1H). LCMS: Calculated for $C_{21}H_{18}F_3N_3O_4S$: 465.45, Observed 466.30 $(M+H)^+$.

The following compounds were prepared similar to the procedure in Method A (Scheme 1) for the synthesis of 6:

N-(4-chlorophenyl)-2-methyl-5-(3-(3(trifluoromethyl)phenyl)ureido)benzenesulfonamide (221)

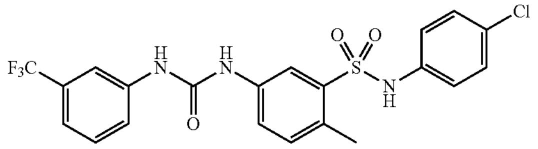 [SMILES: Cc1ccc(NC(=O)Nc2cccc(C(F)(F)F)c2)cc1S(=O)(=O)Nc1ccc(Cl)cc1]

$^1$H NMR (400 MHz, $CD_3OD$) δ: 2.5 (s, 3H), 7.00-7.14 (m, 2H), 7.15-7.39 (m, 4H), 7.4-7.5 (m, 1H), 7.5-7.7 (m, 2H), 7.85-7.9 (m, 1H), 8.0-8.1 (m, 1H). LCMS: Calculated for $C_{21}H_{17}ClF_3N_3O_3S$: 483.89, Observed: 484.05 $(M+H)^+$.

N-(4-chlorophenyl)-2-methyl-5-(3-(4-(trifluoromethyl)phenyl)ureido)benzenesulfonamide (222)

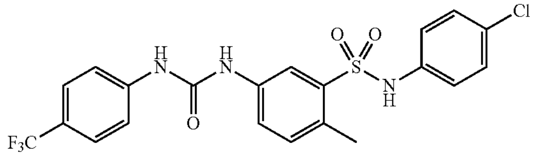 [SMILES: Cc1ccc(NC(=O)Nc2ccc(C(F)(F)F)cc2)cc1S(=O)(=O)Nc1ccc(Cl)cc1]

$^1$H NMR (400 MHz, $CD_3OD$) δ: 2.6 (s, 3H), 7.0-7.3 (m, 5H), 7.5-7.7 (m, 5H), 8.1 (d, 1H). LCMS: Calculated for $C_{21}H_{17}ClF_3N_3O_3S$: 483.89, Observed: 506.25 $(M+Na)^+$.

N-(4-chlorophenyl)-2-methyl-5-(3-(4-(trifluoromethoxy)phenyl)ureido)benzenesulfonamide (225)

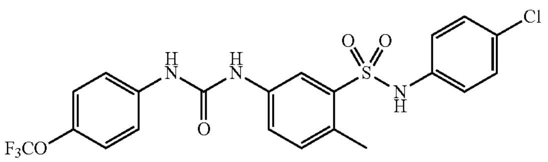 [SMILES: Cc1ccc(NC(=O)Nc2ccc(OC(F)(F)F)cc2)cc1S(=O)(=O)Nc1ccc(Cl)cc1]

$^{1}H$ NMR (400 MHz, $CD_3OD$) δ: 2.59 (s, 3H), 7.1 (d, 2H), 7.19-7.28 (m, 5H), 7.5-7.6 (m, 3H), 8.07 (s, 1H). LCMS: Calculated for $C_{21}H_{17}ClF_3N_3O_4S$: 499.89, Observed: 550.25 $(M+H)^+$.

N-(4-hydroxyphenyl)-2-methyl-5-(3-(3-(trifluoromethyl)phenyl)ureido)benzenesulfonamide (304)

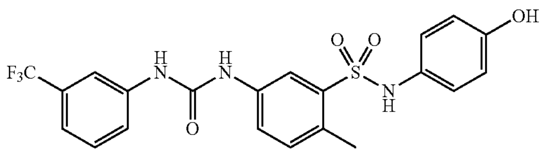 [SMILES: Cc1ccc(NC(=O)Nc2cccc(C(F)(F)F)c2)cc1S(=O)(=O)Nc1ccc(O)cc1]

$^{1}H$ NMR (400 MHz, $CD_3OD$) δ: 2.5 (s, 3H), 7.6 (d, 2H), 7.89 (d, 2H), 7.2-7.35 (m, 2H), 7.48 (t, 1H), 7.59-7.65 (m, 2H), 7.8-7.9 (m, 2H); HPLC purity: 96.41%, LCMS: Calculated for $C_{21}H_{18}F_3N_3O_4S$: 465.45, Observed: 487.95 $(M+Na)^+$.

N-(2,3-dihydrobenzo[b][1,4]dioxin-6-yl)-2-methyl-5-(3-(3(trifluoromethyl)phenyl)ureido)benzenesulfonamide (315)

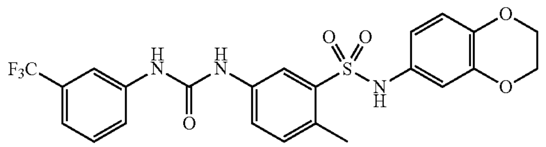 [SMILES: Cc1ccc(NC(=O)Nc2cccc(C(F)(F)F)c2)cc1S(=O)(=O)Nc1ccc2c(c1)OCCO2]

$^{1}H$ NMR (400 MHz, $CD_3OD$) δ: 2.51 (s, 3H), 4.16 (s, 4H), 6.50-6.65 (m, 3H), 7.20-7.38 (m, 2H), 7.44 (t, 1H), 7.57-7.65 (m, 2H), 7.84 (d, 2H). LCMS: Calculated for $C_{23}H_{20}F_3N_3O_5S$: 507.48, Observed: 508 $(M+H)^+$.

N-(1H-indol-6-yl)-2-methyl-5-(3-(3-(trifluoromethyl)phenyl)ureido)benzenesulfonamide (316)

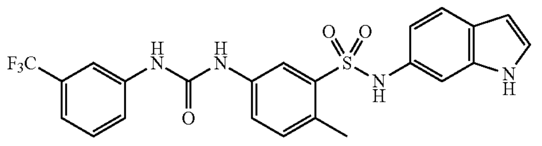 [SMILES: Cc1ccc(NC(=O)Nc2cccc(C(F)(F)F)c2)cc1S(=O)(=O)Nc1ccc2cc[nH]c2c1]

$^{1}H$ NMR (400 MHz, $CD_3OD$) δ: 2.58 (s, 3H), 6.31 (s, 1H), 6.7 (d, 1H), 7.1-7.4 (m, 5H), 7.48 (t, 1H), 7.6 (d, 2H), 7.89 (s, 1H), 7.98 (s, 1H). LCMS: Calculated for $C_{23}H_{19}F_3N_4O_3S$: 488.48, Observed: 511.25 $(M+Na)^+$.

N-(1H-indol-7-yl)-2-methyl-5-(3-(3-(trifluoromethyl)phenyl)ureido)benzenesulfonamide (317)

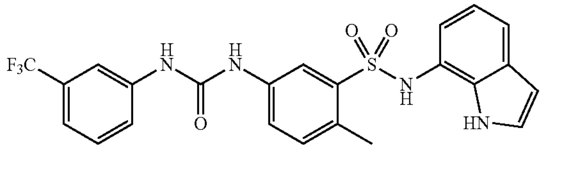 [SMILES: Cc1ccc(NC(=O)Nc2cccc(C(F)(F)F)c2)cc1S(=O)(=O)Nc1cccc2cc[nH]c12]

$^{1}H$ NMR (400 MHz, $CD_3OD$) δ: 2.5 (s, 3H), 6.32 (s, 1H), 6.8 (d, 1H), 7.17-7.3 (m, 5H), 7.43 (t, 1H), 7.56 (d, 1H), 7.84 (d, 1H), 7.8 (s, 1H), 7.85 (s, 1H). LCMS: Calculated for $C_{23}H_{19}F_3N_4O_3S$: 488.48, Observed: 511.00 $(M+Na)^+$.

N-(1H-benzo[d]imidazol-7-yl)-2-methyl-5-(3-(3-(trifluoromethyl)phenyl)ureido)benzenesulfonamide (319)

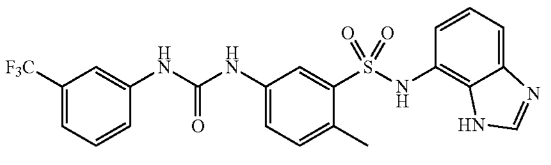 [SMILES: Cc1ccc(NC(=O)Nc2cccc(C(F)(F)F)c2)cc1S(=O)(=O)Nc1cccc2nc[nH]c12]

$^{1}H$ NMR (400 MHz, $CD_3OD$) δ: 2.6 (s, 3H), 7.22-7.4 (m, 4H), 7.45 (t, 1H), 7.52-7.66 (m, 3H), 7.87 (s, 1H), 8.3 (s, 1H), 9.1 (s, 1H). LCMS: Calculated for $C_{22}H_{18}F_3N_5O_3S$: 489.47, Observed: 490.25 $(M+H)^+$.

2-methyl-N-(1-methyl-1H-benzo[d]imidazol-5-yl)-5-(3-(3-(trifluoromethyl)phenyl)ureido)benzene sulfonamide (320)

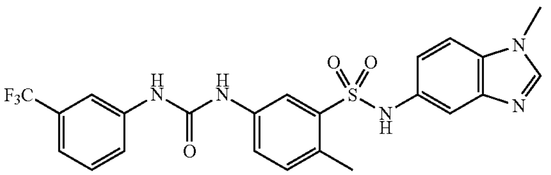 [SMILES: Cc1ccc(NC(=O)Nc2cccc(C(F)(F)F)c2)cc1S(=O)(=O)Nc1ccc2c(c1)ncn2C]

LCMS: Calculated for $C_{23}H_{20}F_3N_5O_3S$: 503.50, Observed: 504.05 $(M+H)^+$.

N-(3-hydroxyphenyl)-2-methyl-5-(3-(4-(trifluoromethyl)phenyl)ureido)benzenesulfonamide (324)

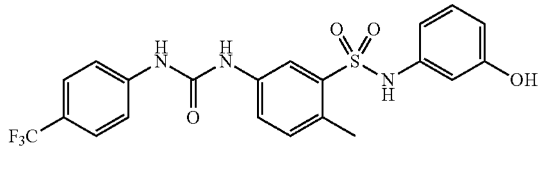 [SMILES: Cc1ccc(NC(=O)Nc2ccc(C(F)(F)F)cc2)cc1S(=O)(=O)Nc1cccc(O)c1]

$^{1}H$ NMR (400 MHz, $CD_3OD$) δ: 2.59 (s, 3H), 6.56 (d, 1H), 6.6 (s, 1H), 6.99 (t, 1H), 7.08 (d, 1H), 7.52-7.68 (m, 6H), 8.08 (s, 1H). LCMS: Calculated for $C_{21}H_{18}F_3N_3O_4S$: 465.45, Observed: 466.35 $(M+H)^+$.

Scheme 8

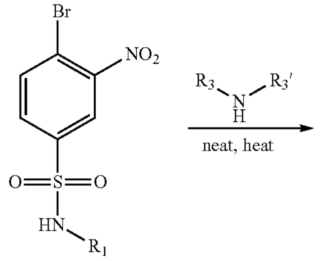

A2

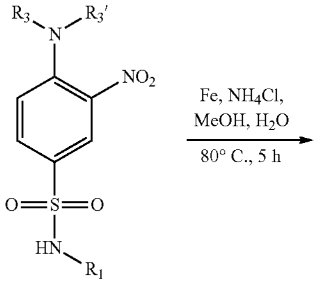

A32

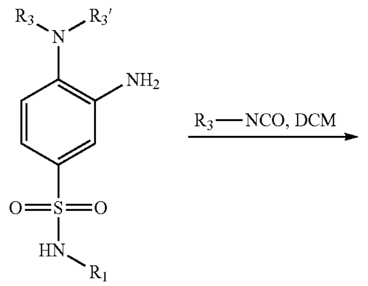

A33

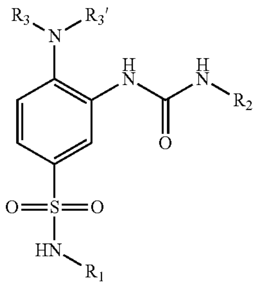

A34

General Procedure for the Preparation of Compounds A32:

A round bottom flask was charged with compound A2 (1 equiv.) and an amine (2 equiv.). The resultant mixture was heated neat to 90° C. and monitored by TLC. After completion of the reaction, the mixture was adsorbed on silica gel and purified by column chromatography to afford compound A32.

The following compounds were similarly prepared according to the above procedure:

3-nitro-N-phenyl-4-(phenylamino)benzenesulfonamide

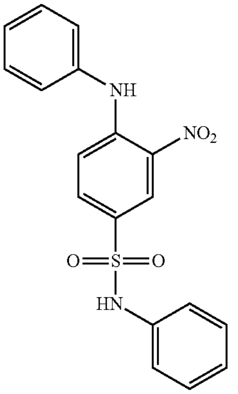 [SMILES: O=[N+]([O-])c1cc(S(=O)(=O)Nc2ccccc2)ccc1Nc1ccccc1]

ESMS: Calculated: 369.39, Observed: 368.15 $(M-)^-$.

4-(methyl(phenyl)amino)-3-nitro-N-phenylbenzenesulfonamide

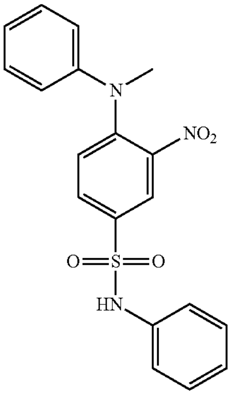 [SMILES: CN(c1ccccc1)c1ccc(S(=O)(=O)Nc2ccccc2)cc1[N+](=O)[O-]]

ESMS: Calculated: 383.42, Observed: 384.10 $(M+H)^+$.

4-(1H-imidazol-1-yl)-3-nitro-N-phenylbenzenesulfonamide

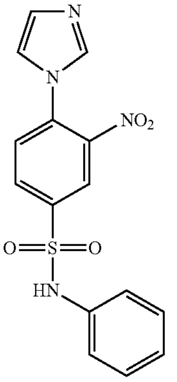 [SMILES: O=[N+]([O-])c1cc(S(=O)(=O)Nc2ccccc2)ccc1-n1ccnc1]

$^1$H NMR (400 MHz, DMSO-$d_6$) δ: 7.06-7.2 (m, 4H), 7.25-7.3 (m, 2H), 7.46 (s, 1H), 7.86 (d, 1H), 7.96 (s, 1H), 8.15 (d, 1H), 8.48 (s, 1H), 10.68 (br s, 1H). LCMS: Calculated: 344.35, Observed: 345.10 $(M+H)^+$.

N-cyclopropyl-4-(1H-imidazol-1-yl)-3-nitrobenzenesulfonamide

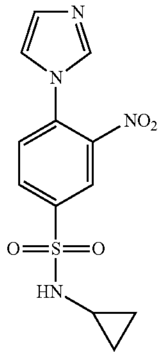 [SMILES: O=[N+]([O-])c1cc(S(=O)(=O)NC2CC2)ccc1-n1ccnc1]

$^1$H NMR (400 MHz, $CDCl_3$) δ: 0.35-0.4 (m, 2H), 0.45-0.55 (m, 2H), 2.15-2.25 (m, 1H), 5.52 (br s, 1H), 7.10 (s, 1H), 7.65 (d, 1H), 7.7 (s, 1H), 8.22 (d, 1H), 8.5 (s, 1H).

N-cyclopropyl-4-morpholino-3-nitrobenzenesulfonamide

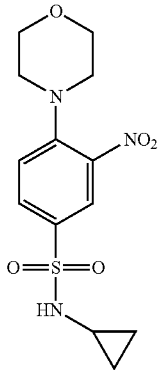 [SMILES: O=[N+]([O-])c1cc(S(=O)(=O)NC2CC2)ccc1N1CCOCC1]

$^1$H NMR (400 MHz, DMSO-$d_6$) δ: 0.34-0.4 (m, 2H), 0.45-0.51 (m, 2H), 2.08-2.15 (m, 1H), 3.11-3.2 (m, 4H), 3.66-3.75 (m, 4H), 7.43 (d, 1H), 7.85 (d, 1H), 7.95 (s, 1H), 8.2 (s, 1H).

N-cyclopropyl-3-nitro-4-(1,4-oxazepan-4-yl)benzenesulfonamide

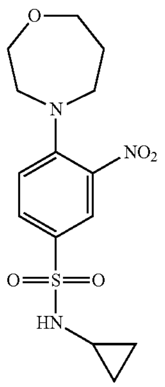 [SMILES: O=[N+]([O-])c1cc(S(=O)(=O)NC2CC2)ccc1N1CCCOCC1]

ESMS: Calculated: 341.38, Observed: 342.20 $(M+H)^+$.

The following compounds were similarly prepared according to the procedure for synthesis of Intermediate 4 in Scheme 1:

3-amino-N-phenyl-4-(phenylamino)benzenesulfonamide

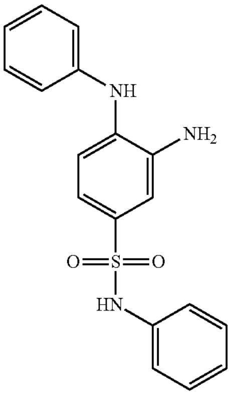

LCMS: Calculated: 339.41, Observed: 340.50 $(M+H)^+$.

3-amino-4-(methyl(phenyl)amino)-N-phenylbenzenesulfonamide

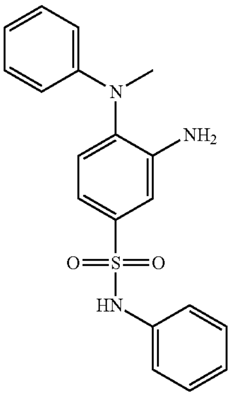

LCMS: Calculated: 353.44, Observed: 354.20 $(M+H)^+$.

3-amino-4-(1H-imidazol-1-yl)-N-phenylbenzenesulfonamide

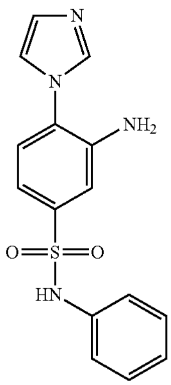 [SMILES: Nc1cc(S(=O)(=O)Nc2ccccc2)ccc1-n1ccnc1]

LCMS: Calculated: 314.36, Observed: 315.50

3-amino-N-cyclopropyl-4-(1H-imidazol-1-yl)benzenesulfonamide

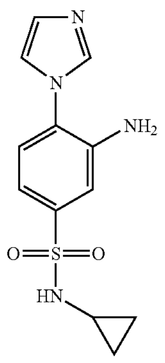 [SMILES: Nc1cc(S(=O)(=O)NC2CC2)ccc1-n1ccnc1]

LCMS: Calculated: 278.33, Observed: 279.15 ($M^{+}$+1).

3-amino-N-cyclopropyl-4-morpholinobenzenesulfonamide

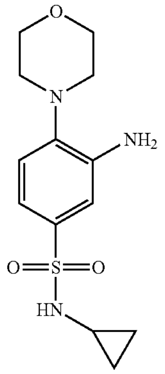 [SMILES: Nc1cc(S(=O)(=O)NC2CC2)ccc1N1CCOCC1]

$^{1}$H NMR (400 MHz, DMSO-$d_6$) δ: 0.35-0.48 (m, 4H), 2.0-2.08 (m, 1H), 2.8-2.88 (m, 4H), 3.72-3.8 (m, 4H), 5.2 (s, 2H), 6.95-7.05 (m, 2H), 7.12 (s, 1H), 7.62 (br s, 1H).

3-amino-N-cyclopropyl-4-(1,4-oxazepan-4-yl)benzenesulfonamide

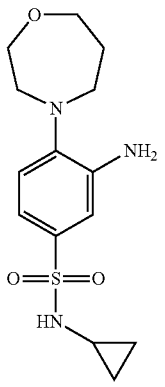 [SMILES: Nc1cc(S(=O)(=O)NC2CC2)ccc1N1CCCOCC1]

LCMS: Calculated: 311.40, Observed: 312.50 $(M+H)^{+}$.

The following compounds were similarly prepared as compounds A6 according to Method A in Scheme 1:

N-phenyl-4-(phenylamino)-3-(3-(3-(trifluoromethyl)phenyl)ureido)benzenesulfonamide (340)

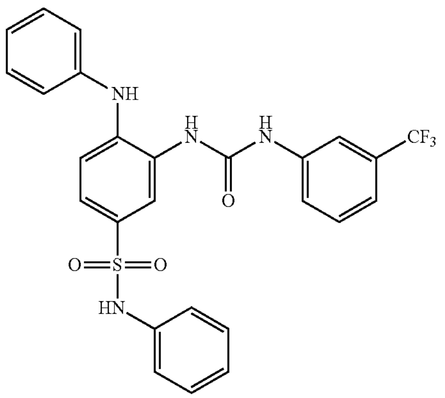 [SMILES: O=C(Nc1cccc(C(F)(F)F)c1)Nc1cc(S(=O)(=O)Nc2ccccc2)ccc1Nc1ccccc1]

$^{1}$H NMR (400 MHz, $CD_3OD$) δ: 6.9-7.05 (m, 5H), 7.1-7.4 (m, 9H), 7.45 (t, 1H), 7.59 (d, 1H), 7.9 (s, 1H), 8.2 (s, 1H). ESMS Calculated for $C_{26}H_{21}F_3N_4O_3S$: 526.53, Observed: 527.44 ($M^{+}$+1).

4-(methyl(phenyl)amino)-N-phenyl-3-(3-(3-(trifluoromethyl)phenyl)ureido)benzenesulfonamide (341)

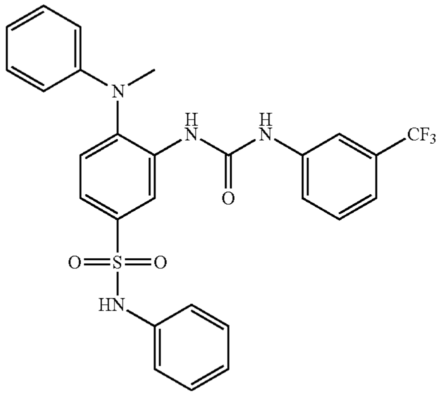 [SMILES: CN(c1ccccc1)c1ccc(S(=O)(=O)Nc2ccccc2)cc1NC(=O)Nc1cccc(C(F)(F)F)c1]

$^{1}$H NMR (400 MHz, $CD_3OD$) δ: 3.13 (s, 3H), 6.62 (d, 2H), 6.8 (t, 1H), 7.02 (t, 1H), 7.1-7.3 (m, 8H), 7.32-7.52 (m, 3H), 7.83 (s, 1H), 8.8 (s, 1H). ESMS Calculated for $C_{27}H_{23}F_3N_4O_3S$: 540.56, Observed: 541.84 $(M+H)^{+}$.

4-(1H-imidazol-1-yl)-N-phenyl-3-(3-(3-(trifluoromethyl)phenyl)ureido)benzenesulfonamide (342)

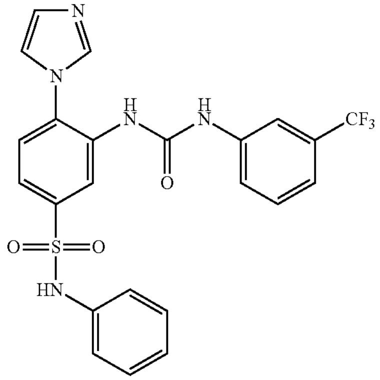 [SMILES: O=C(Nc1cccc(C(F)(F)F)c1)Nc1cc(S(=O)(=O)Nc2ccccc2)ccc1-n1ccnc1]

$^1$H NMR (400 MHz, $CD_3OD$) δ: 7.1 (t, 1H), 7.15-7.61 (m, 10H), 7.85 (s, 1H), 7.9 (s, 1H), 8.2 (s, 1H), 8.6 (s, 1H). LCMS: Calculated for $C_{23}H_{18}F_3N_5O_3S$: 501.48, Observed: 502.3 $(M+H)^+$.

N-cyclopropyl-4-(1H-imidazol-1-yl)-3-(3-(3-(trifluoromethyl)phenyl)ureido)benzenesulfonamide (345)

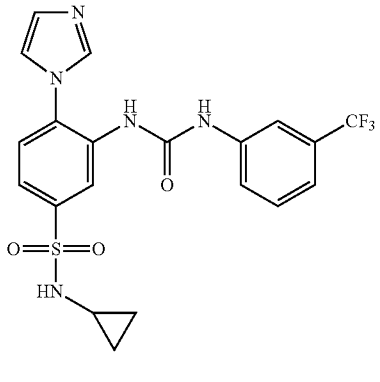 [SMILES: O=C(Nc1cccc(C(F)(F)F)c1)Nc1cc(S(=O)(=O)NC2CC2)ccc1-n1ccnc1]

$^1$H NMR (400 MHz, DMSO-$d_6$) δ: 0.4-0.6 (m, 4H), 2.1-2.2 (m, 1H), 7.2 (s, 1H), 7.3 (d, 1H), 7.4-7.6 (m, 5H), 7.79-8.0 (m, 2H), 8.15 (m, 2H), 8.61 (s, 1H), 9.6 (s, 1H). LCMS: Calculated for $C_{20}H_{18}F_3N_5O_3S$: 465.45, Observed: 465.96 $(M+H)^+$.

N-cyclopropyl-4-morpholino-3-(3-(3-(trifluoromethyl)phenyl)ureido)benzenesulfonamide (348)

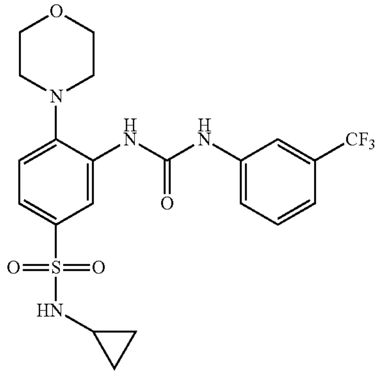 [SMILES: O=C(Nc1cccc(C(F)(F)F)c1)Nc1cc(S(=O)(=O)NC2CC2)ccc1N1CCOCC1]

$^1$H NMR (400 MHz, DMSO-$d_6$) δ: 0.4-0.5 (m, 4H), 2.1 (m, 1H), 2.82-2.9 (m, 4H), 3.8-3.9 (m, 4H), 7.38 (m, 2H), 7.42 (m, 1H), 7.5-7.61 (m, 2H), 7.85 (s, 1H), 8.1 (s, 1H), 8.3 (s, 1H), 8.6 (s, 1H), 10.0 (s, 1H). LCMS: Calculated for $C_{21}H_{23}F_3N_4O_4S$: 484.49, Observed: 485.30 $(M+H)^+$.

N-cyclopropyl-4-(1,4-oxazepan-4-yl)-3-(3-(3-(trifluoromethyl)phenyl)ureido)benzenesulfonamide (349)

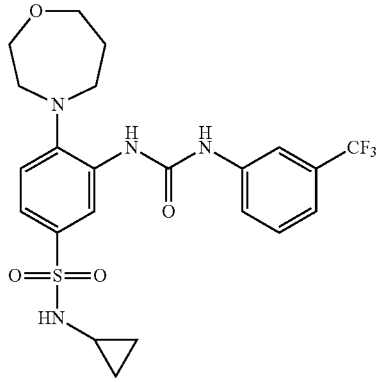 [SMILES: O=C(Nc1cccc(C(F)(F)F)c1)Nc1cc(S(=O)(=O)NC2CC2)ccc1N1CCCOCC1]

$^1$H NMR (400 MHz, DMSO-$d_6$) δ: 0.35-0.52 (m, 4H), 2.0 (t, 2H), 2.15 (m, 1H), 3.1-3.2 (m, 4H), 3.8-3.9 (m, 4H), 7.3-7.4 (m, 3H), 7.5-7.62 (m, 2H), 7.8 (s, 1H), 8.02 (s, 1H), 8.2 (s, 1H), 8.45 (s, 1H), 9.85 (s, 1H). LCMS: Calculated for $C_{22}H_{25}F_3N_4O_4S$: 498.52, Observed: 499.20 $(M+H)^+$.

Example 2: In Vitro Assays for IDH1m (R132H or R132C) Inhibitors

Assays were conducted in a volume of 76 μl assay buffer (150 mM NaCl, 10 mM $MgCl_2$, 20 mM Tris pH 7.5, 0.03% bovine serum albumin) as follows in a standard 384-well plate: To 25 ul of substrate mix (8 uM NADPH, 2 mM aKG), 1 μl of test compound was added in DMSO. The plate was centrifuged briefly, and then 25 μl of enzyme mix was added (0.2 μg/ml IDH1 R132H) followed by a brief centrifugation and shake at 100 RPM. The reaction was incubated for 50 minutes at room temperature, then 25 μl of detection mix (30 μM resazurin, 36 μg/ml) was added and the mixture further incubated for 5 minutes at room temperature. The conversion of resazurin to resorufin was detected by fluorescent spectroscopy at Ex544 Em590 c/o 590.

Representative compounds of formula (I) set forth in Tables 1 and 2 were tested in this assay and the results are set forth below in Table 4. As used in Table 4, "A" refers to an inhibitory activity against IDH1 R132H with an $IC_{50} \leq 1.0$ μM; "B" refers to an inhibitory activity against IDH1 R132H with an $IC_{50}$ between 1.0 μM and 10.0 μM; "C" refers to an inhibitory activity against IDH1 R132H with an $IC_{50} \geq 10.0$ μM.

TABLE 4

IDH1 Inhibitory Activities of Representative Compounds of Formula (I)

| Cpd No | IDH R132H IC50 (uM) |
|---|---|
| 205 | B |
| 206 | B |

TABLE 4-continued

| IDH1 Inhibitory Activities of Representative Compounds of Formula (I) | |
|---|---|
| Cpd No | IDH R132H IC50 (uM) |
| 207 | B |
| 208 | B |
| 209 | B |
| 210 | B |
| 211 | B |
| 212 | B |
| 213 | B |
| 214 | B |
| 215 | B |
| 216 | B |
| 217 | B |
| 218 | B |
| 219 | B |
| 220 | B |
| 221 | B |
| 222 | B |
| 223 | B |
| 224 | B |
| 225 | B |
| 227 | B |
| 228 | B |
| 229 | B |
| 230 | B |
| 231 | B |
| 232 | B |
| 233 | B |
| 234 | B |
| 235 | B |
| 236 | B |
| 237 | B |
| 238 | B |
| 239 | B |
| 240 | B |
| 241 | B |
| 242 | B |
| 243 | B |
| 244 | B |
| 245 | B |
| 246 | B |
| 247 | B |
| 248 | B |
| 249 | B |
| 250 | B |
| 251 | B |
| 252 | B |
| 253 | B |
| 254 | B |
| 255 | B |
| 256 | B |
| 257 | B |
| 258 | B |
| 259 | B |
| 260 | B |
| 261 | B |
| 262 | B |
| 263 | B |
| 264 | B |
| 265 | B |
| 266 | B |
| 267 | B |
| 268 | B |
| 269 | B |
| 270 | B |
| 271 | B |
| 272 | B |
| 273 | B |
| 274 | B |
| 275 | B |
| 276 | B |
| 277 | B |
| 278 | B |
| 279 | B |
| 280 | B |
| 282 | B |

TABLE 4-continued

| IDH1 Inhibitory Activities of Representative Compounds of Formula (I) | |
|---|---|
| Cpd No | IDH R132H IC50 (uM) |
| 283 | B |
| 284 | B |
| 285 | B |
| 286 | B |
| 287 | B |
| 288 | B |
| 289 | B |
| 290 | B |
| 291 | B |
| 292 | B |
| 293 | B |
| 294 | B |
| 295 | B |
| 296 | B |
| 297 | B |
| 298 | B |
| 299 | B |
| 301 | B |
| 302 | B |
| 303 | B |
| 304 | A |
| 305 | B |
| 306 | B |
| 308 | B |
| 309 | B |
| 310 | B |
| 311 | B |
| 312 | B |
| 313 | B |
| 314 | B |
| 315 | B |
| 316 | B |
| 317 | B |
| 318 | B |
| 319 | B |
| 320 | B |
| 321 | B |
| 322 | B |
| 323 | B |
| 324 | B |
| 325 | B |
| 326 | B |
| 327 | B |
| 328 | B |
| 329 | B |
| 330 | B |
| 331 | B |
| 332 | B |
| 333 | B |
| 334 | B |
| 335 | B |
| 336 | B |
| 351 | B |

Example 2B: Cellular Assays for IDH1m (R132H or R132C) Inhibitors

Cells (HT1080 or U87MG) are grown in T125 flasks in DMEM containing 10% FBS, lx penicillin/streptomycin and 500 ug/mL G418 (present in U87MG cells only). They are harvested by trypsin and seeded into 96 well white bottom plates at a density of 5000 cell/well in 100 µl/well in DMEM with 10% FBS. No cells are placed in columns 1 and 12. Cells are incubated overnight at 37° C. in 5% $CO_2$. The next day test compounds are made up at 2× the final concentration and 100 µl is added to each cell well. The final concentration of DMSO is 0.2% and the DMSO control wells are plated in row G. The plates are then placed in the incubator for 48 hours. At 48 hours, 100 µl of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 μl of Promega Cell Titer Glo reagent is added to each well of media. The cell plate is then placed on an orbital shaker for 10 minutes and allowed to sit at room temperature for 20 minutes. The plate is then read for luminescence with an integration time of 500 ms.

Example 3: IDH2 Enzymatic and Cell Assays

Enzymatic Assay.

Compounds were assayed for IDH2 R140Q inhibitory activity through a cofactor depletion assay. Compounds were preincubated with enzyme, then the reaction was started by the addition of NADPH and α-KG, and allowed to proceed for 60 minutes under conditions previously demonstrated to be linear with respect for time for consumption of both cofactor and substrate. The reaction was terminated by the addition of a second enzyme, diaphorase, and a corresponding substrate, resazurin. Diaphorase reduces resazurin to the highly fluorescent resorufin with the concomitant oxidation of NADPH to NADP, both halting the IDH2 reaction by depleting the available cofactor pool and facilitating quantitation of the amount of cofactor remaining after a specific time period through quantitative production of an easily detected fluorophore.

Specifically, into each of 12 wells of a 384-well plate, 1 μl of compound dilution series was placed, followed by the addition of 40 μl of buffer (50 mM potassium phosphate, pH 7.5; 150 mM NaCl; 10 mM $MgCl_2$, 10% glycerol, 0.05% bovine serum albumin, 2 mM beta-mercaptoethanol) containing 1.25 μg/ml IDH2 R140Q. The compound was then incubated for one hour at room temperature with the enzyme; before starting the IDH2 reaction with the addition of 10 μl of substrate mix containing 50 μM NADPH and 6.3 mM α-KG in the buffer described above. After a further one hour of incubation at room temperature, the reaction was halted and the remaining NADPH measured through conversion of resazurin to resorufin by the addition of 25 μl Stop Mix (36 μg/ml diaphorase enzyme and 60 μM resazurin; in buffer). After one minute of incubation the plate was read on a plate reader at Ex544/Em590.

Representative compounds of formula (I) set forth in Tables 1 and 2 were tested in this assay and the results are set forth below in Table 5. As used in Table 5, values indicated as "D" represent an $IC_{50}$ of less than 100 nM; values indicated as "E" represent an $IC_{50}$ of between 100 nM and 1 μM; values indicated as "F" represent an $IC_{50}$ of greater than 1 μM to 10 μM; values indicated as "G" represent an $IC_{50}$ of greater than 10 μM.

TABLE 5

Enzymatic Activity of Representative Compounds of Formula (I).

| Cmpd No | Enz R140Q |
|---|---|
| 1 | E |
| 2 | E |
| 3 | E |
| 4 | E |
| 5 | E |
| 6 | E |
| 7 | E |

TABLE 5-continued

Enzymatic Activity of Representative Compounds of Formula (I).

| Cmpd No | Enz R140Q |
|---|---|
| 8 | E |
| 9 | E |
| 10 | E |
| 11 | E |
| 12 | E |
| 13 | F |
| 14 | F |
| 15 | F |
| 16 | F |
| 17 | F |
| 18 | F |
| 19 | F |
| 20 | F |
| 21 | F |
| 22 | F |
| 23 | F |
| 24 | F |
| 25 | E |
| 26 | F |
| 27 | E |
| 28 | E |
| 29 | F |
| 30 | E |
| 31 | D |
| 32 | D |
| 33 | E |
| 34 | E |
| 35 | E |
| 36 | E |
| 37 | E |
| 38 | E |
| 39 | E |
| 40 | E |
| 41 | E |
| 42 | E |
| 43 | E |
| 44 | E |
| 45 | D |
| 46 | E |
| 47 | E |
| 48 | F |
| 49 | E |
| 50 | E |
| 51 | F |
| 52 | F |
| 53 | F |
| 54 | F |
| 55 | F |
| 56 | F |
| 57 | F |
| 58 | F |
| 59 | F |
| 60 | F |
| 61 | F |
| 62 | F |
| 63 | F |
| 64 | F |
| 65 | F |
| 66 | E |
| 67 | E |
| 68 | E |
| 69 | E |
| 70 | E |
| 71 | E |
| 72 | E |
| 73 | F |
| 74 | E |
| 76 | E |
| 77 | E |
| 78 | E |
| 79 | E |
| 80 | E |
| 81 | E |
| 82 | E |
| 83 | E |
| 84 | E |

TABLE 5-continued

Enzymatic Activity of Representative Compounds of Formula (I).

| Cmpd No | Enz R140Q |
|---|---|
| 85 | E |
| 86 | E |
| 87 | E |
| 88 | E |
| 89 | E |
| 90 | E |
| 91 | E |
| 92 | E |
| 93 | E |
| 94 | E |
| 95 | F |
| 96 | F |
| 97 | E |
| 98 | E |
| 99 | F |
| 100 | E |
| 101 | E |
| 102 | E |
| 103 | E |
| 104 | F |
| 105 | E |
| 106 | E |
| 107 | F |
| 108 | E |
| 109 | F |
| 110 | F |
| 111 | E |
| 112 | E |
| 113 | E |
| 114 | E |
| 115 | E |
| 116 | E |
| 117 | E |
| 118 | E |
| 119 | E |
| 120 | E |
| 121 | E |
| 122 | E |
| 123 | E |
| 124 | E |
| 125 | E |
| 126 | E |
| 127 | E |
| 128 | E |
| 129 | E |
| 130 | E |
| 131 | E |
| 132 | E |
| 133 | E |
| 134 | E |
| 135 | E |
| 136 | E |
| 137 | F |
| 138 | E |
| 139 | E |
| 140 | F |
| 141 | F |
| 142 | G |
| 143 | F |
| 144 | F |
| 145 | F |
| 146 | F |
| 147 | F |
| 148 | F |
| 149 | F |
| 150 | F |
| 151 | E |
| 152 | E |
| 153 | F |
| 154 | E |
| 155 | E |
| 156 | E |
| 157 | F |
| 158 | E |
| 159 | E |
| 160 | E |
| 161 | E |
| 162 | E |
| 163 | E |
| 164 | E |
| 165 | E |
| 166 | E |
| 167 | E |
| 168 | E |
| 169 | E |
| 170 | E |
| 171 | E |
| 172 | F |
| 173 | E |
| 174 | F |
| 352 | E |
| 175 | E |
| 176 | E |
| 177 | D |
| 178 | E |
| 179 | E |
| 180 | E |
| 181 | E |
| 183 | E |
| 184 | E |
| 185 | E |
| 186 | E |
| 187 | E |
| 188 | E |
| 189 | E |
| 190 | E |
| 191 | E |
| 192 | E |
| 193 | F |
| 194 | D |
| 195 | E |
| 196 | D |
| 197 | D |
| 198 | E |
| 199 | E |
| 200 | F |
| 201 | E |
| 202 | E |
| 203 | E |
| 204 | F |
| 353 | E |
| 354 | E |
| 355 | E |
| 356 | F |
| 357 | F |
| 358 | E |
| 359 | E |
| 337 | E |
| 338 | E |
| 339 | E |
| 340 | F |
| 341 | F |
| 342 | E |
| 343 | F |
| 344 | F |
| 345 | E |
| 346 | F |
| 347 | F |
| 348 | F |
| 349 | E |
| 350 | F |

Example 3B: U87MG pLVX-IDH2 R140Q-neo Cell Based Assay

Cells are grown in T125 flasks in DMEM containing 10% FBS, 1× penicillin/streptomycin and 500 µg/mL G418. They are harvested by trypsin and seeded into 96 well white bottom plates at a density of 5000 cell/well in 100 µl/well in DMEM with 10% FBS. No cells are plated in columns 1 and 12. Cells are incubated overnight at 37° C. in 5% $CO_2$. The next day compounds are made up at 2× concentration and 100 μl is added to each cell well. The final concentration of DMSO is 0.2% and the DMSO control wells are plated in row G. The plates are then placed in the incubator for 48 hours. At 48 hours, 100 μl of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 μl of reagent is added to each well of media. The cell plate is then placed on an orbital shaker for 10 minutes and then allowed to sit at room temperature for 20 minutes. The plate is then read for luminescence with an integration time of 500 ms.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A compound of Formula (III) or a pharmaceutically acceptable salt thereof, wherein:

(III)

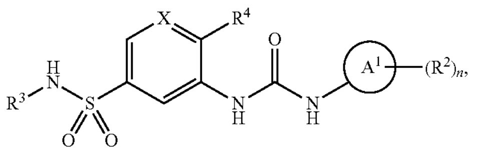

X is CH or N;

$A^1$ is $C_{3-8}$ cycloalkyl, aryl, heteroaryl or heterocyclyl;

each $R^2$ is independently halo, hydroxyl, $C_{1-6}$ alkyl, $C_{2-6}$ alkenyl, $C_{2-6}$ alkynyl, $C_{1-6}$ alkoxy, $C_{1-6}$ thioalkoxy, $C_{1-6}$ haloalkyl, $C_{1-6}$ haloalkoxy, $C_{1-6}$ alkyl-OH, aryl, aralkyl, aryloxy, —$NO^2$, —C(O)—O—$C_{1-6}$ alkyl, —$S(O)_2$—NH-aryl, —$S(O)_2$—$C_{1-6}$ alkyl or —S(O)—$C_{1-6}$ alkyl, wherein each said aryl moiety may be substituted with 0-3 occurrences of $R^6$;

$R^3$ is $C_{1-6}$ alkyl, $C_{2-6}$ alkenyl, $C_{3-8}$ cycloalkyl, aryl, aralkyl, heteroaryl, heteroaralkyl or heterocyclyl, each of which may be substituted with 0-3 occurrences of $R^6$;

$R^4$ is $C_{2-6}$ alkenyl, $C_{2-6}$ alkynyl, $C_{1-6}$ thioalkyl, $C_{3-8}$ cycloalkyl, $C_{3-8}$ cycloalkenyl, aryl, heteroaryl, heterocyclyl, —S(O)—$C_{1-6}$ alkyl, —$S(O)_2$—$C_{1-6}$ alkyl, —O-aryl, —O-heteroaryl, —O-heterocyclyl, —$N(R^5)$—$C_{1-6}$ alkyl or —$N(R^5)$-aryl, wherein each $C_{1-6}$ alkyl, $C_{2-6}$ alkynyl, $C_{1-6}$ thioalkyl, aryl, heteroaryl, heterocyclyl, —S(O)—$C_{1-6}$ alkyl, —$S(O)_2$—$C_{1-6}$ alkyl, —O-aryl, —O-heteroaryl, —O-heterocyclyl, —$N(R^5)$—$C_{1-6}$ alkyl or $N(R^5)$-aryl is independently substituted with 0-3 occurrences of $R^7$;

each $R^5$ is independently hydrogen or $C_{1-6}$ alkyl;

each $R^6$ is independently halo, hydroxyl, $C_{1-6}$ alkyl, $C_{1-6}$ haloalkyl, $C_{1-6}$ alkoxy, $C_{3-8}$ cycloalkyl, cyano, $NO_2$, —$CO_2H$, —C(O)—$C_{1-6}$ alkyl, —$S(O)_2$—$C_{1-6}$ alkyl, —O—$S(O)_2$—$C_{1-6}$ alkyl, —O—$C_{1-6}$ alkyl-C(O)OH, —O—$C_{1-6}$ alkyl-C(O)—O—$C_{1-6}$ alkyl, —$N(R^5)$—C(O)—$C_{1-6}$ alkyl, —$N(R^5)$—$C_{1-6}$ alkyl-C(O)—O—$C_{1-6}$ alkyl, aryl, heteroaryl or heterocyclyl; or adjacent $R^6$ moieties, taken together with the atoms to which they are attached form a heterocyclyl;

each $R^7$ is independently $C_{1-6}$ alkyl, $C_{1-6}$ alkoxy, $C_{3-8}$ cycloalkyl, hydroxyl, halo, —NHC(O)—$C_{1-6}$ alkyl, —$S(O)_2$—$C_{1-6}$ alkyl, aryl, heteroaryl or heterocyclyl; and n is 0, 1, 2, 3 or 4;

provided that:

(1) when $A^1$ is phenyl, X is CH, and $R^4$ 1-piperidinyl, 1-pyrrolidinyl, N-morpholinyl, or N-azepanyl, then $R^3$ is not phenyl optionally substituted with 0-3 occurrences of $R^6$; and (2) the compound is not N-(2,5-dichlorophenyl)-4-(diethylamino)-3-[[[(4-nitrophenyl)amino]carbonyl]amino]-benzenesulfonamide.

2. A compound of Formula (IV) or a pharmaceutically acceptable salt thereof, wherein:

(IV)

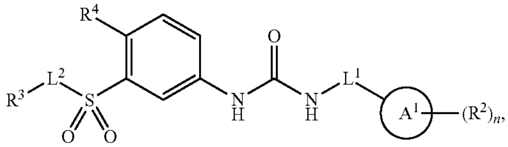

$L^1$ is a bond;

$A^1$ is $C_{3-8}$ cycloalkyl, aryl, heteroaryl or heterocyclyl;

$L^2$ is —$NR^5$—;

each $R^2$ is independently halo, hydroxyl, $C_{1-6}$ alkyl, $C_{2-6}$ alkenyl, $C_{2-6}$ alkynyl, $C_{1-6}$ alkoxy, $C_{1-6}$ thioalkoxy, $C_{1-6}$ haloalkyl, $C_{1-6}$ haloalkoxy, $C_{1-6}$ alkyl-OH, aryl, aralkyl, aryloxy, —$NO^2$, —C(O)—O—$C_{1-6}$ alkyl, —$S(O)_2$—NH-aryl, —$S(O)_2$—$C_{1-6}$ alkyl or —S(O)—$C_{1-6}$ alkyl, wherein each said aryl moiety may be substituted with 0-3 occurrences of $R^6$;

$R^3$ is $C_{2-6}$ alkenyl, $C_{3-8}$ cycloalkyl, aryl, aralkyl, heteroaryl, heteroaralkyl or heterocyclyl, each of which may be substituted with 0-3 occurrences of $R^6$;

$R^4$ is $C_{1-6}$ alkyl, $C_{2-6}$ alkenyl, $C_{2-6}$ alkynyl, $C_{1-6}$ thioalkyl, $C_{3-8}$ cycloalkyl, $C_{3-8}$ cycloalkenyl, aryl, heteroaryl, —S(O)—$C_{1-6}$ alkyl, —$S(O)_2$—$C_{1-6}$ alkyl, —O-aryl, —O-heteroaryl, —O-heterocyclyl, —$N(R^5)$—$C_{1-6}$ alkyl or —$N(R^5)$-aryl, wherein each $C_{1-6}$ alkyl, $C_{2-6}$ alkynyl, $C_{1-6}$ alkoxy, $C_{1-6}$ thioalkyl, aryl, heteroaryl, S(O)—$C_{1-6}$ alkyl, —$S(O)_2$—$C_{1-6}$ alkyl, —O-aryl, —O-heteroaryl, —O-heterocyclyl, —$N(R^5)$—$C_{1-6}$ alkyl or —$N(R^5)$-aryl is independently substituted with 0-3 occurrences of $R^7$;

each $R^5$ is independently hydrogen or $C_{1-6}$ alkyl;

each $R^6$ is independently hydroxyl, $C_{1-6}$ alkyl, $C_{1-6}$ haloalkyl, $C_{3-8}$ cycloalkyl, cyano, $NO_2$, —$CO_2H$, —C(O)—$C_{1-6}$ alkyl, —$S(O)_2$—$C_{1-6}$ alkyl, —O—$S(O)_2$—$C_{1-6}$ alkyl, —O—$C_{1-6}$ alkyl-C(O)OH, —O—$C_{1-6}$ alkyl-C(O)—O—$C_{1-6}$ alkyl, —$N(R^5)$—C(O)—$C_{1-6}$ alkyl, —$N(R^5)$—$C_{1-6}$ alkyl-C(O)—O—$C_{1-6}$ alkyl, aryl, heteroaryl or heterocyclyl; or adjacent $R^6$ moieties, taken together with the atoms to which they are attached form a heterocyclyl;

each $R^7$ is independently $C_{1-6}$ alkyl, $C_{1-6}$ alkoxy, $C_{3-8}$ cycloalkyl, hydroxyl, halo, —NHC(O)—$C_{1-6}$ alkyl, —$S(O)_2$—$C_{1-6}$ alkyl, aryl, heteroaryl or heterocyclyl; and n is 1, 2, 3 or 4;

provided that:

when $R^5$ is H, and $R^4$ is methyl, then $R^3$ is not methyl.

3. The compound of claim 2 or a pharmaceutically acceptable salt thereof, wherein the compound is selected from:
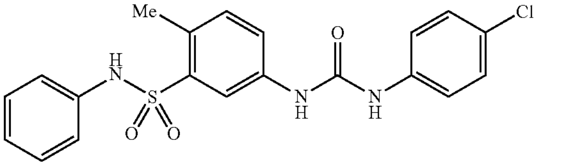
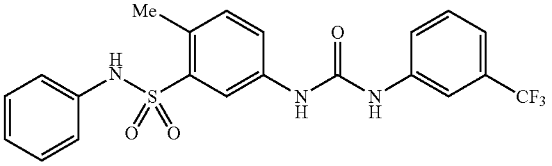
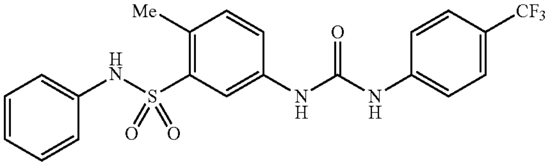
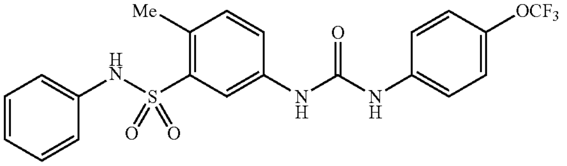
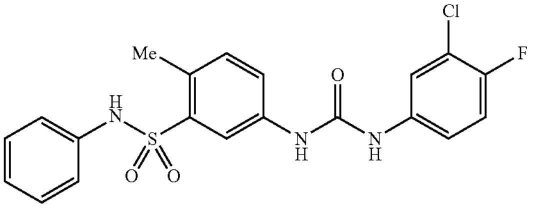
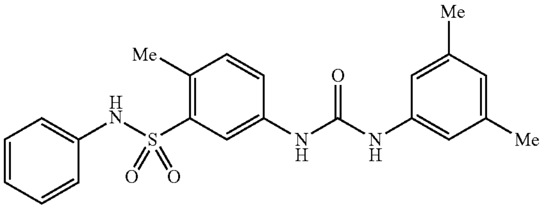
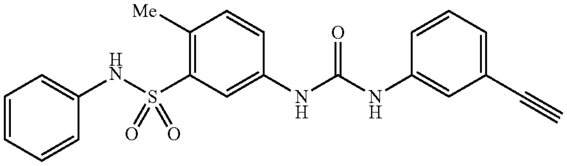
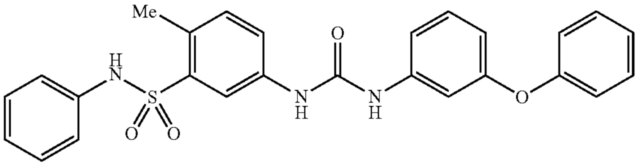
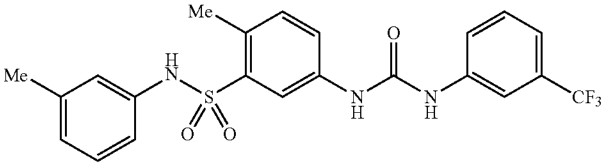

-continued
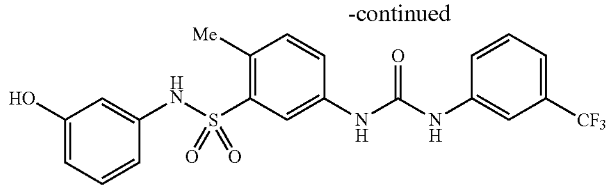
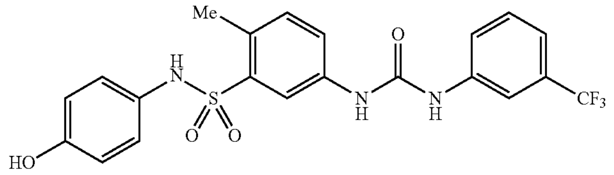
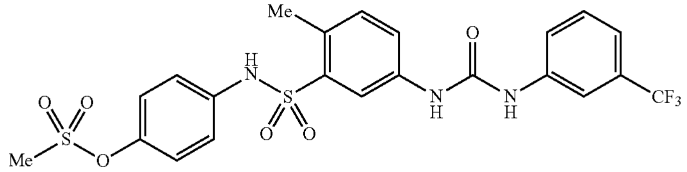
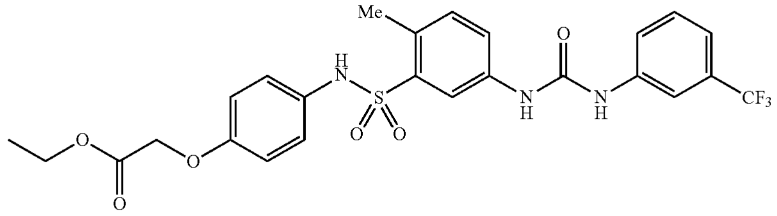
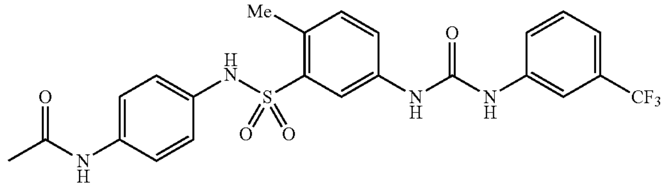
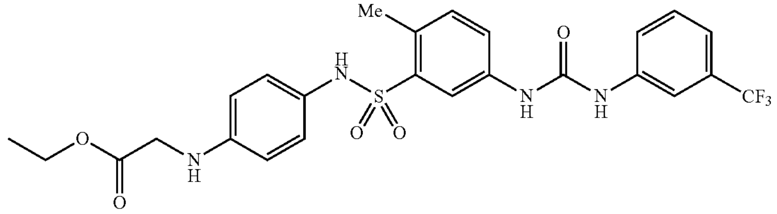
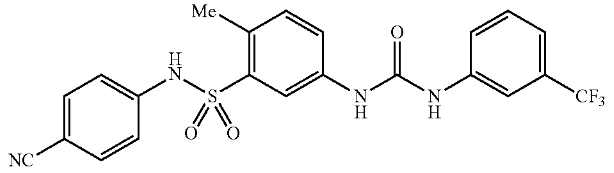
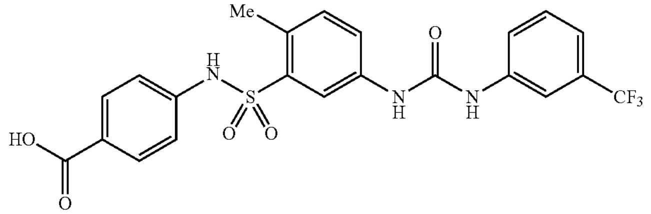
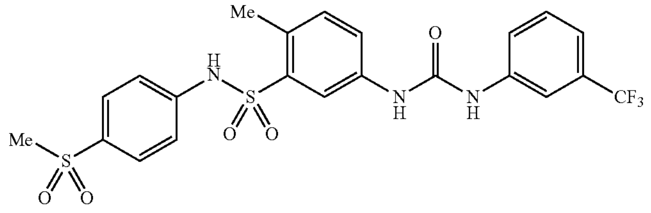

-continued
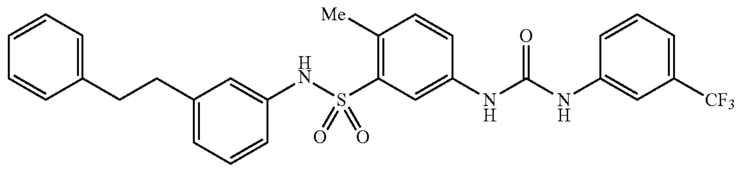
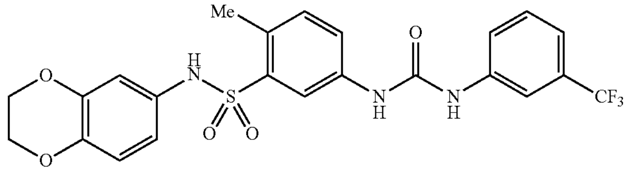
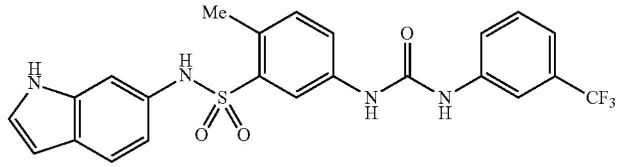
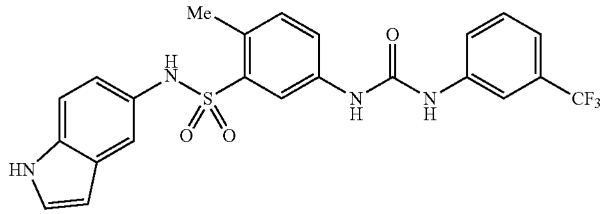
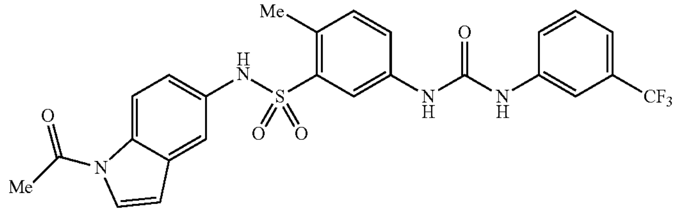
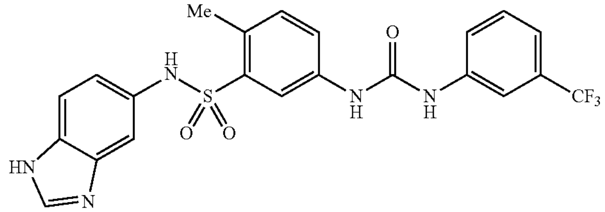
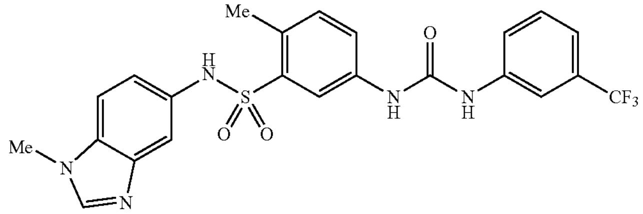
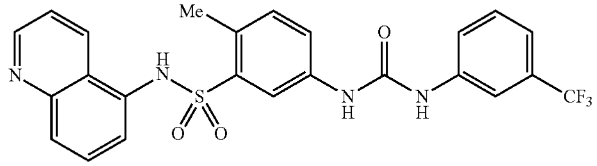

-continued
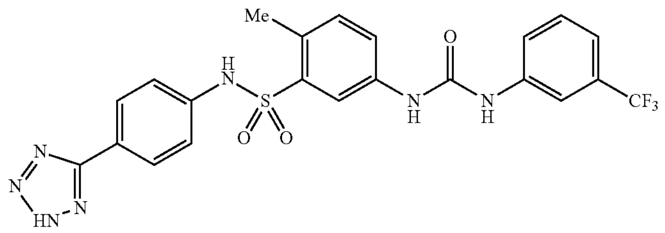
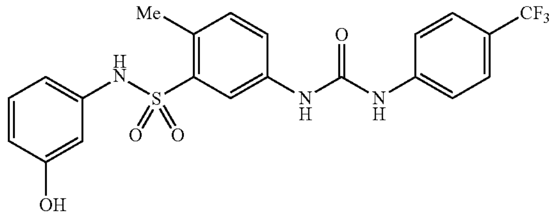
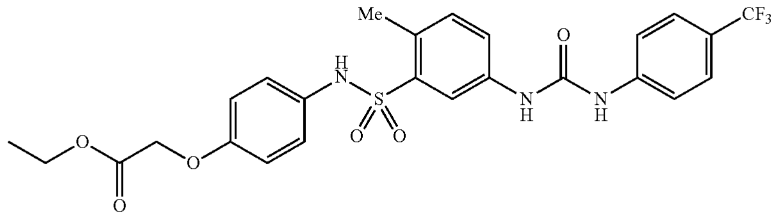
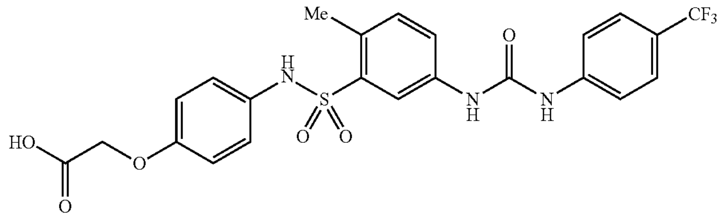
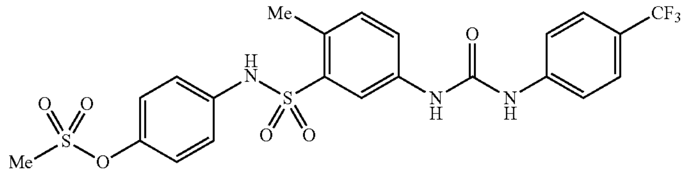
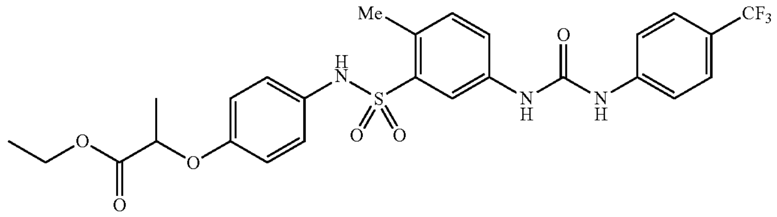
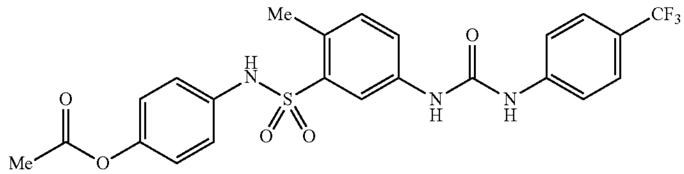
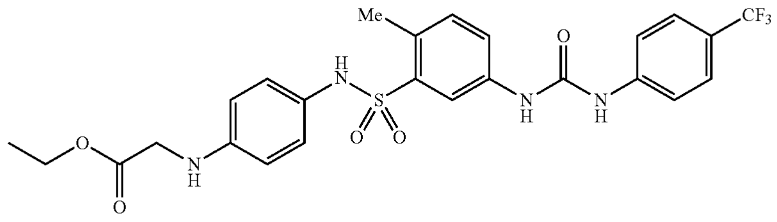

-continued
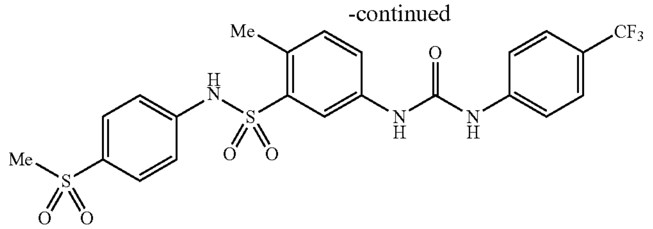
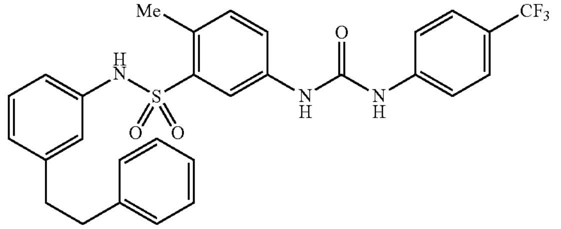
and
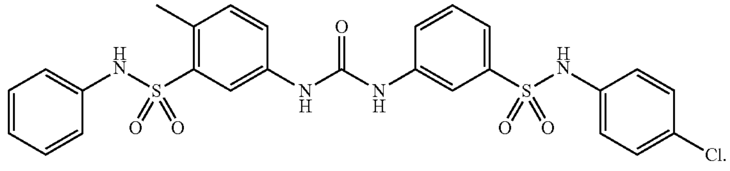
4. The compound of claim 1 or a pharmaceutically acceptable salt thereof, wherein the compound is selected from:
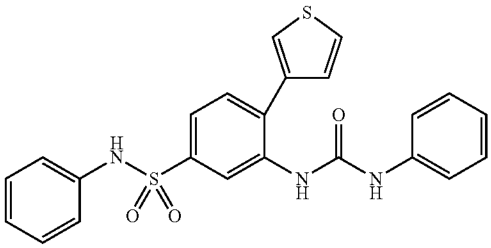
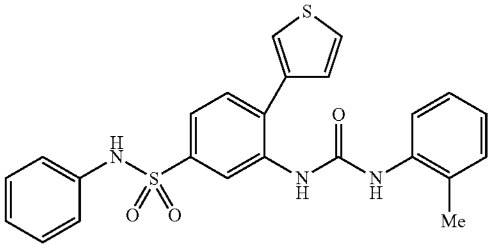
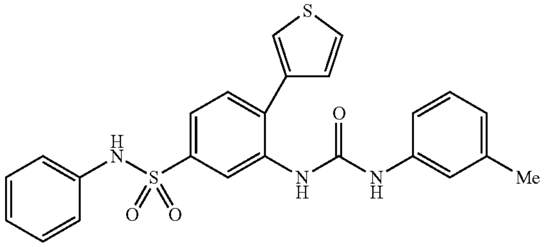
-continued
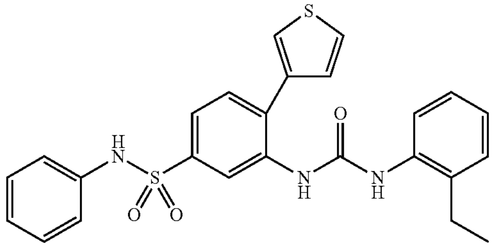
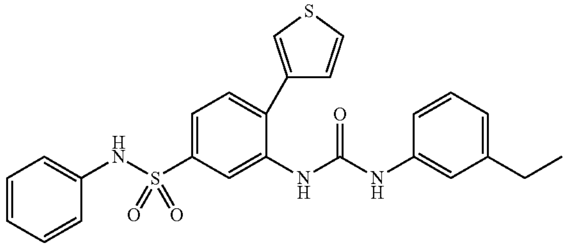
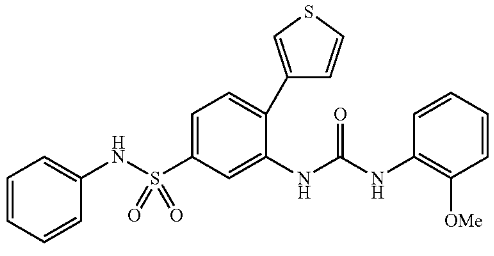
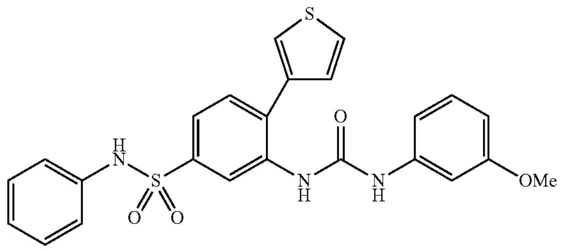

-continued
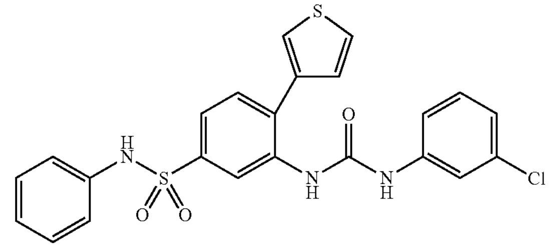
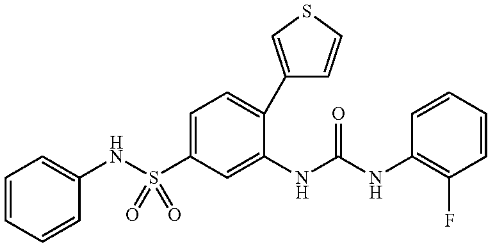
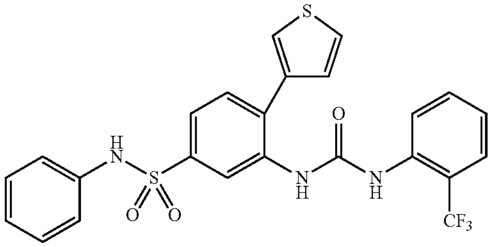
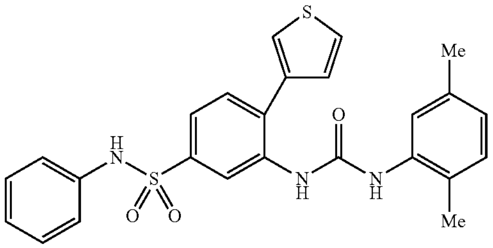
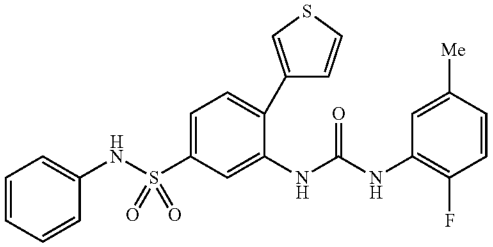
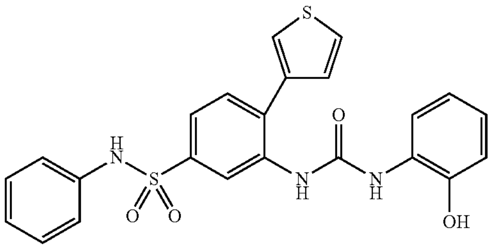
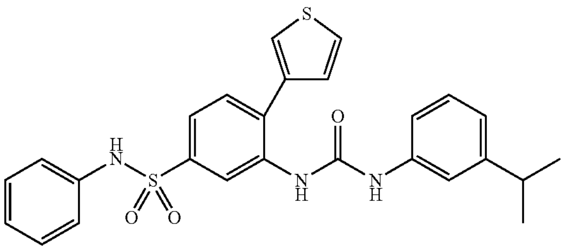
-continued
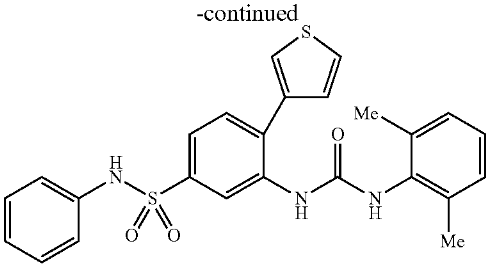
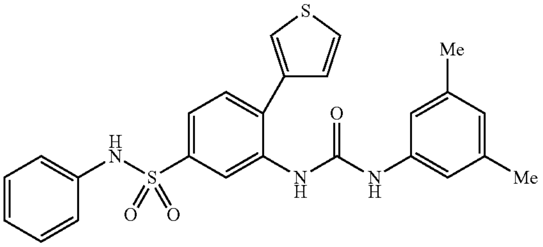
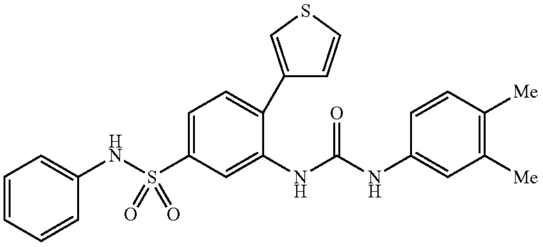
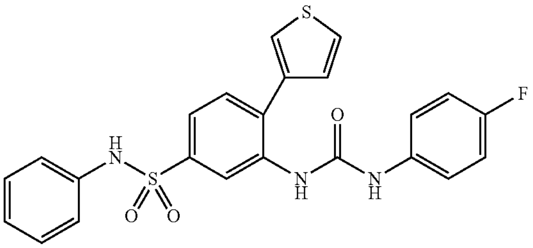
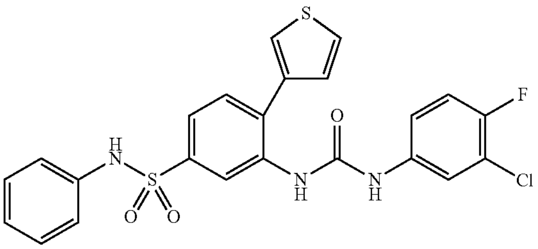
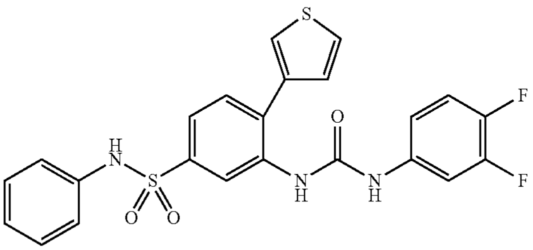
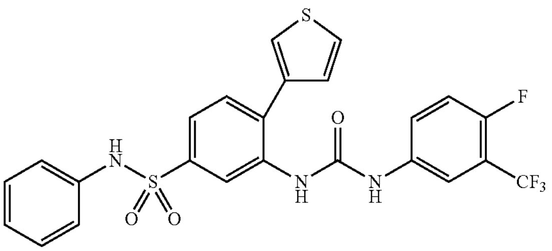

-continued
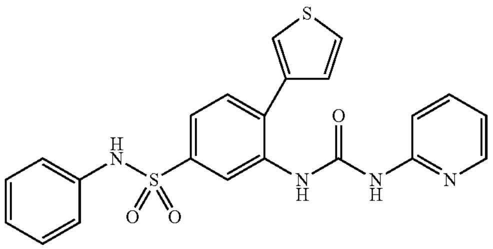
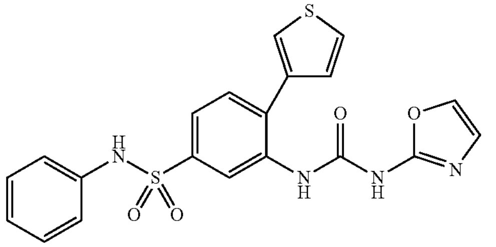
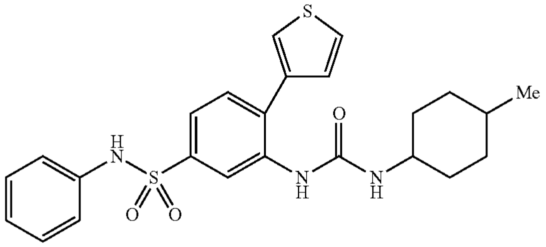
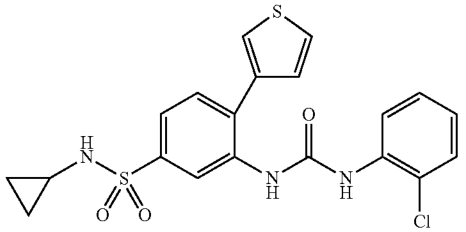
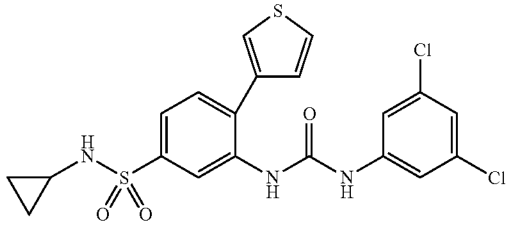
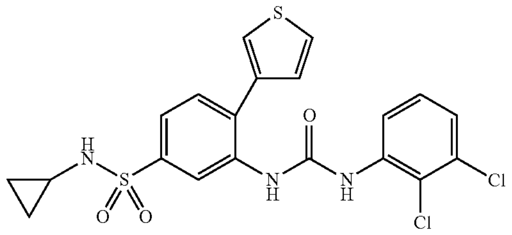
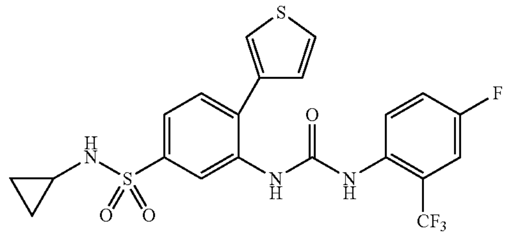
-continued
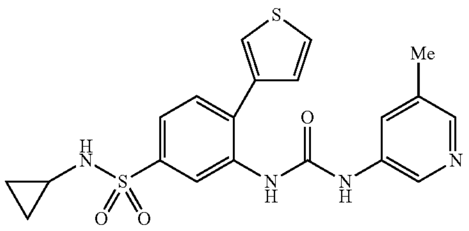
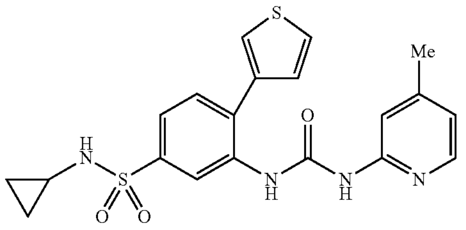
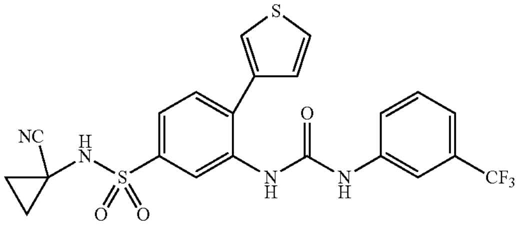
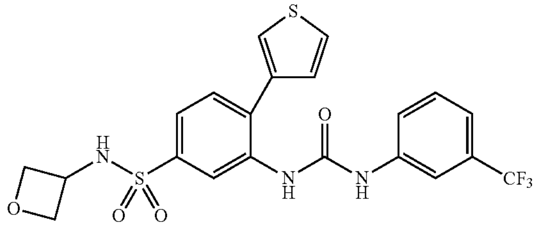
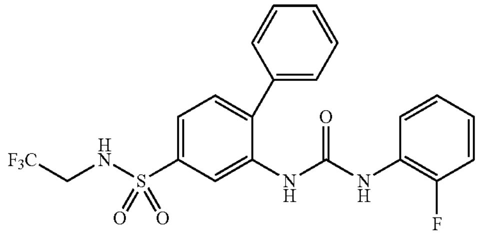
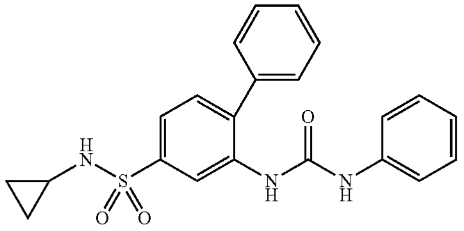
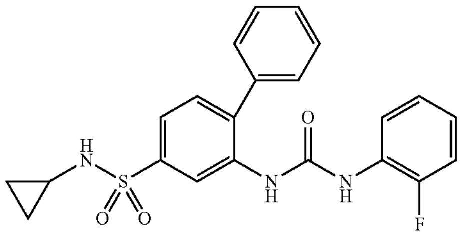

-continued
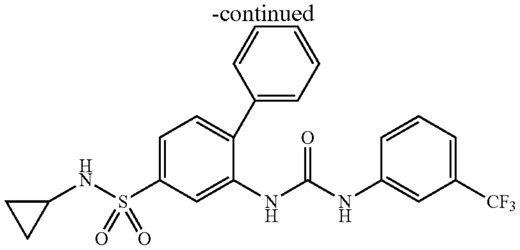
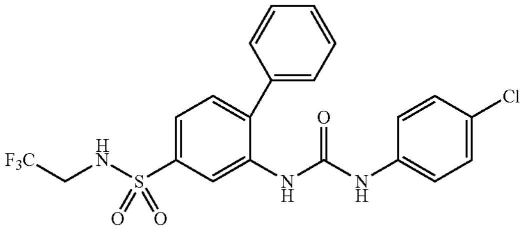
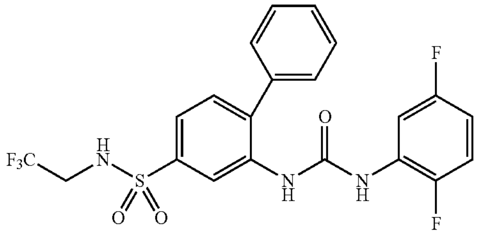
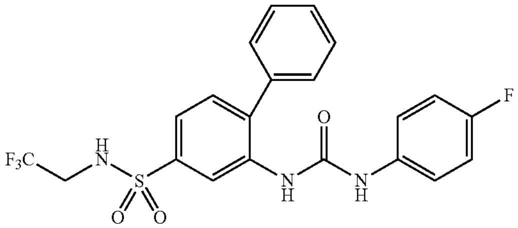
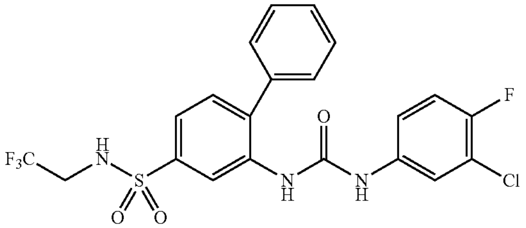
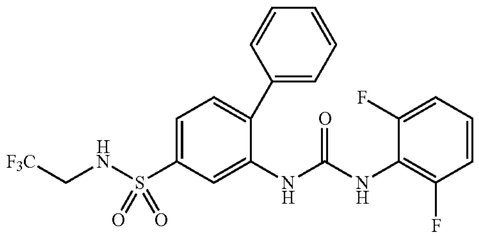
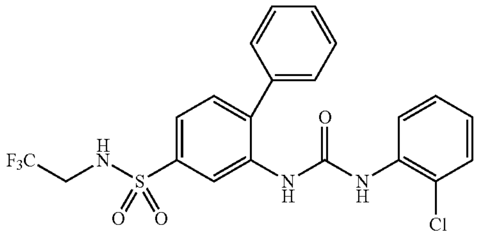
-continued
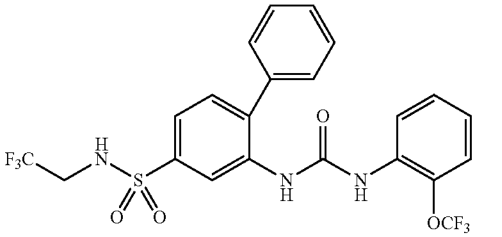
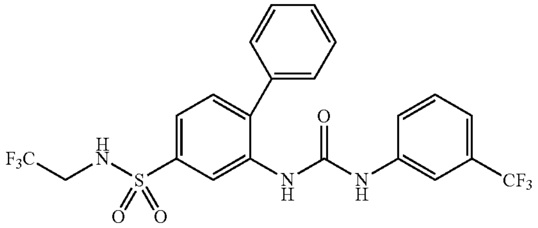
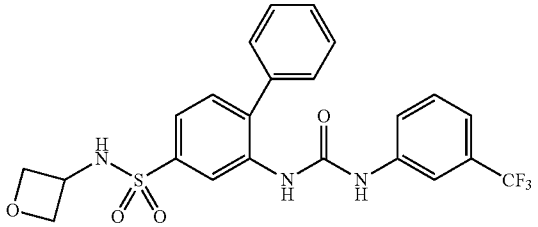
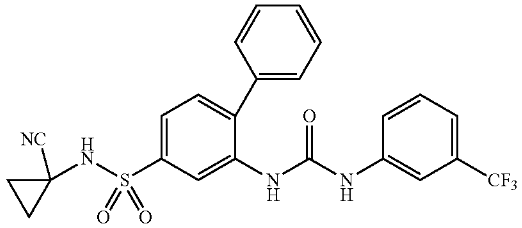
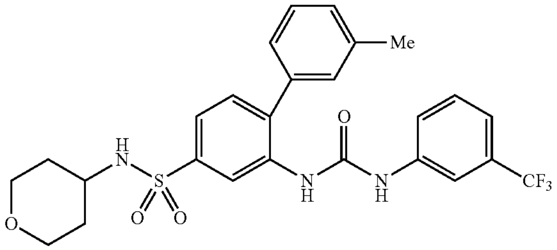
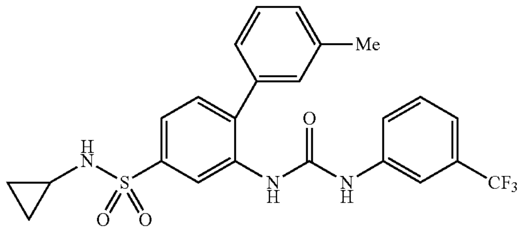
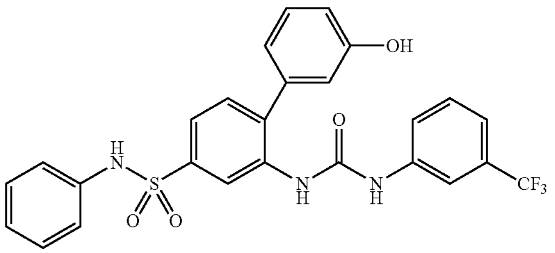

-continued
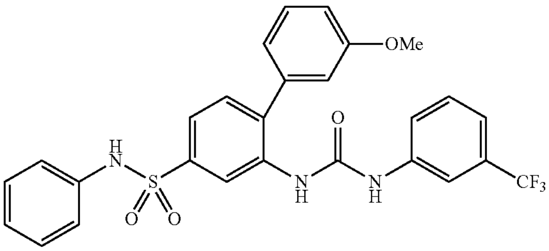
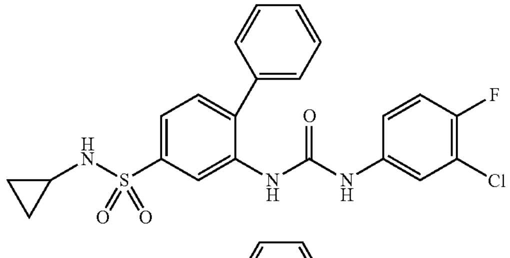
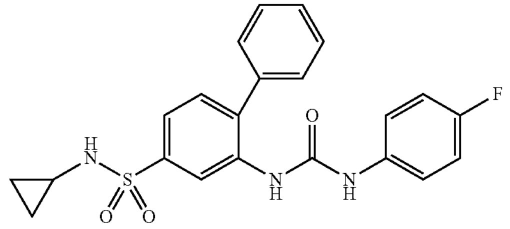
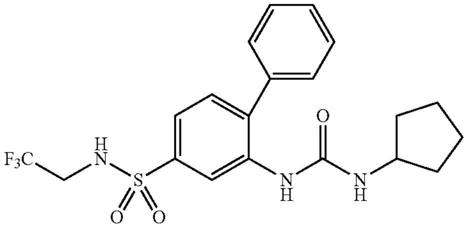
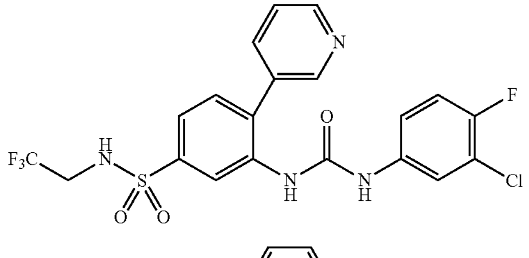
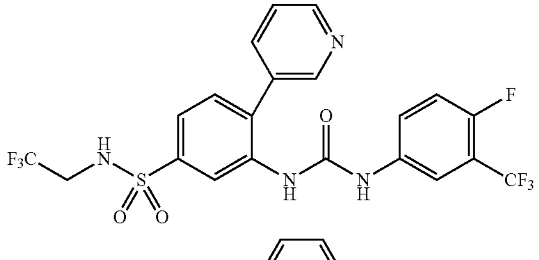
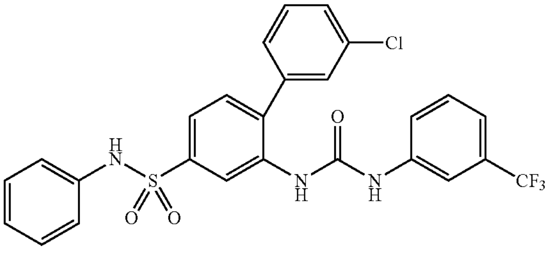
-continued
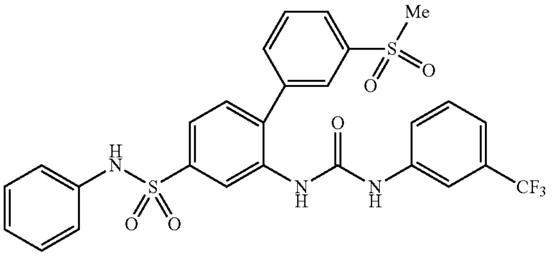
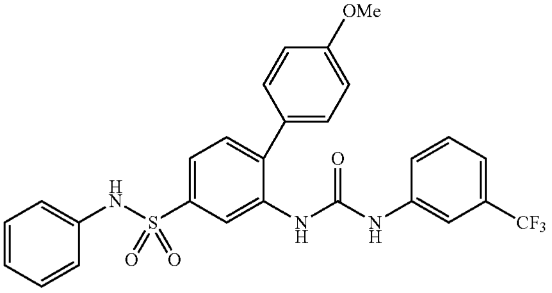
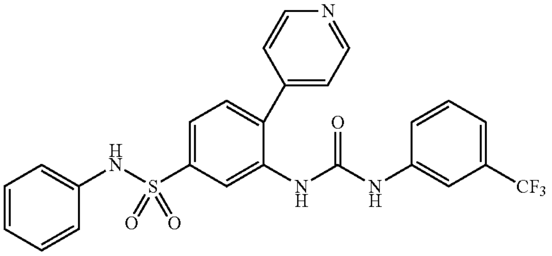
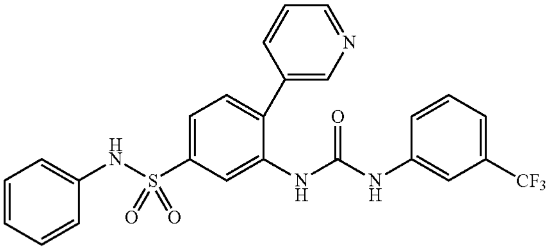
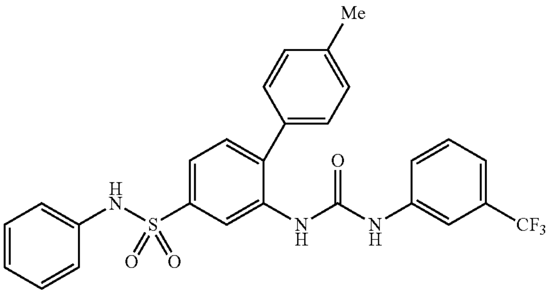
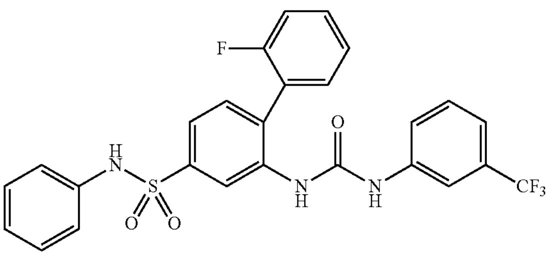

-continued
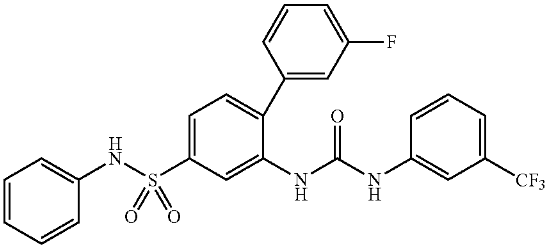
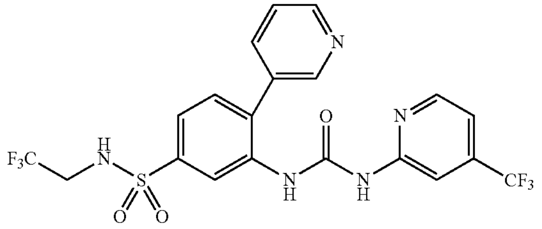
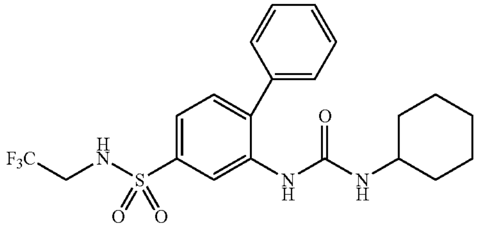
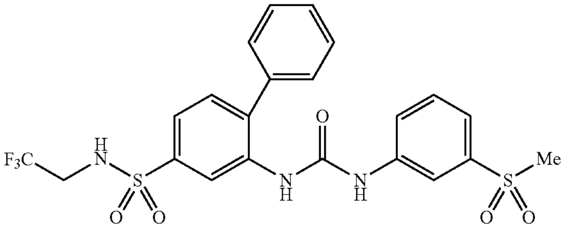
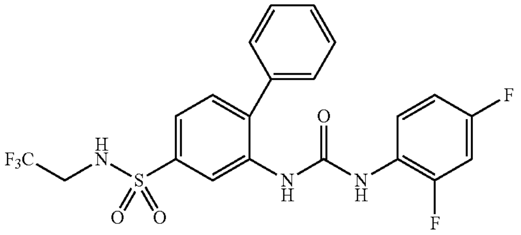
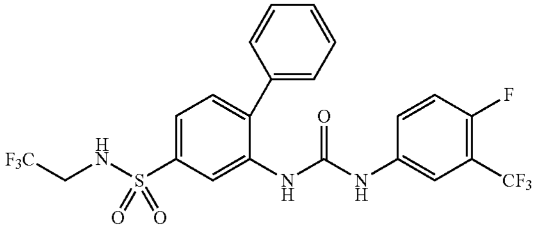
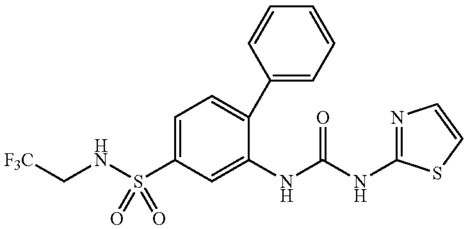
-continued
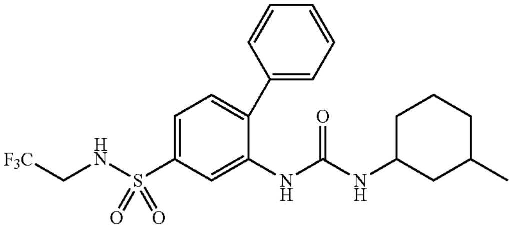
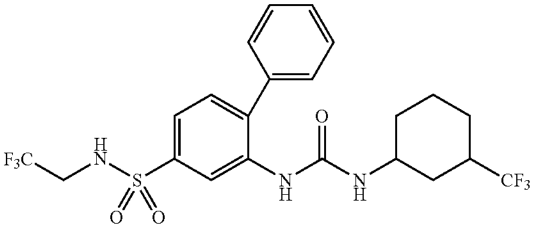
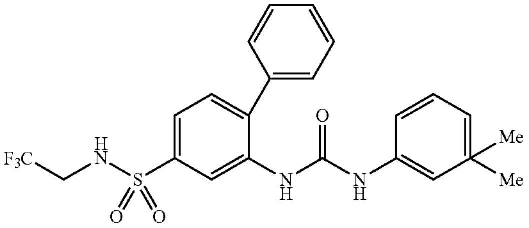
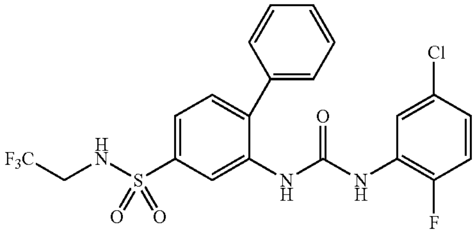
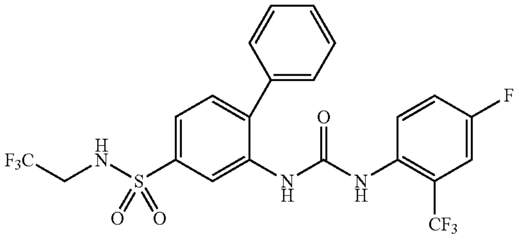
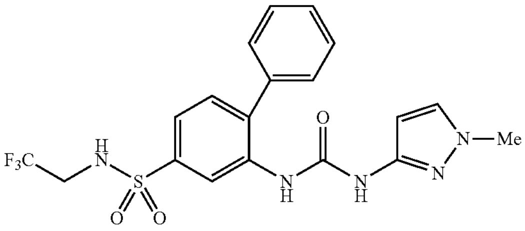
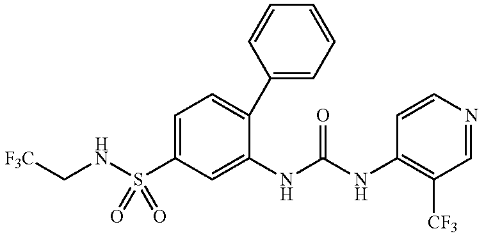

-continued
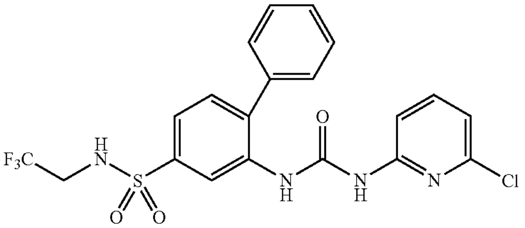
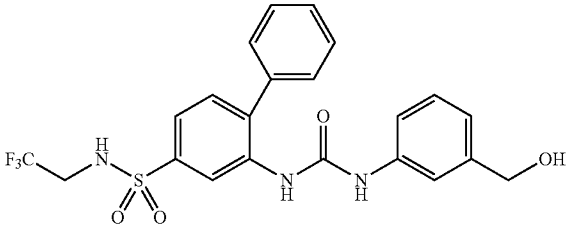
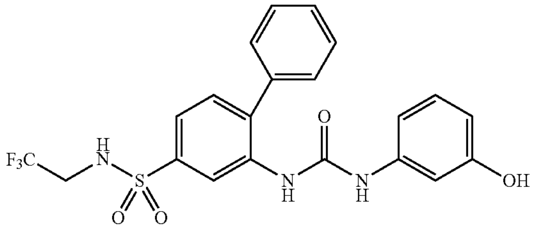
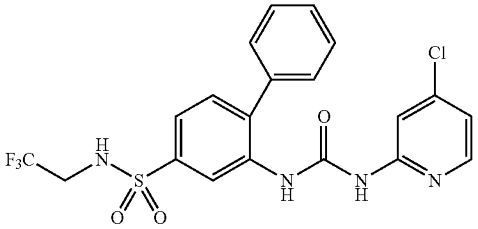
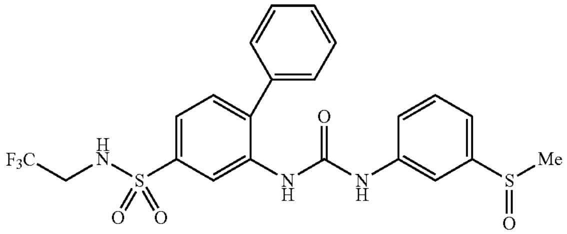
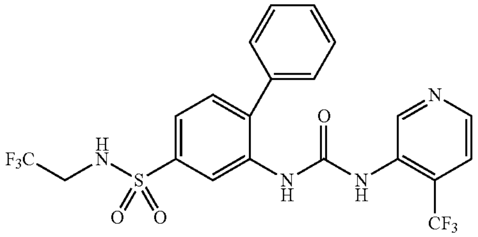
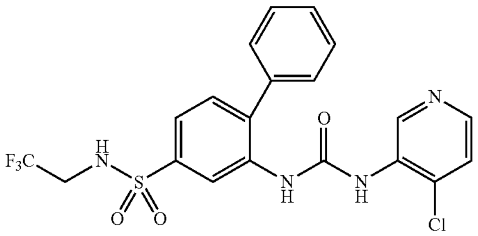
-continued
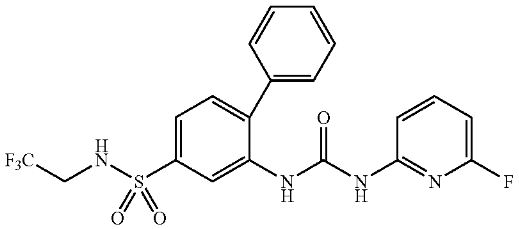
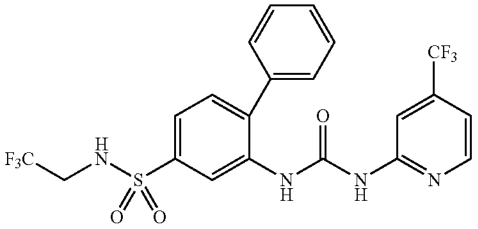
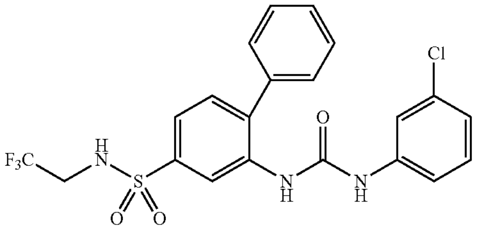
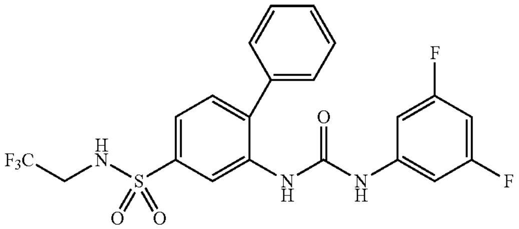
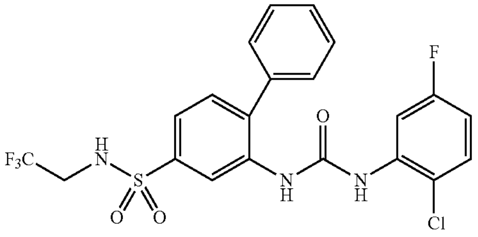
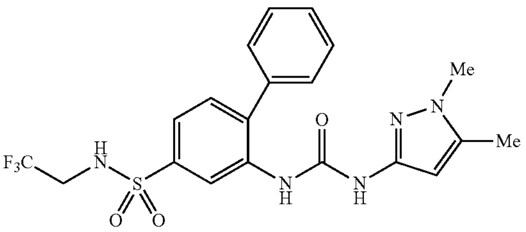
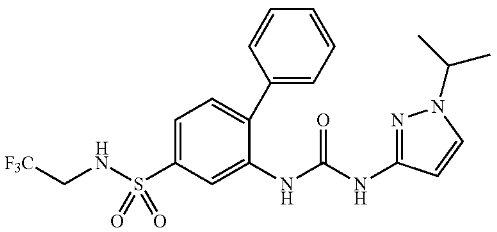

-continued
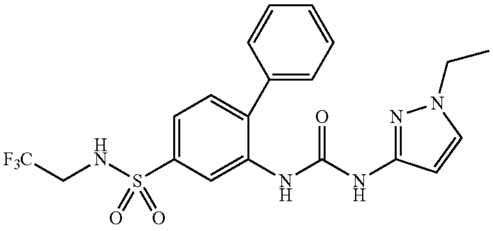
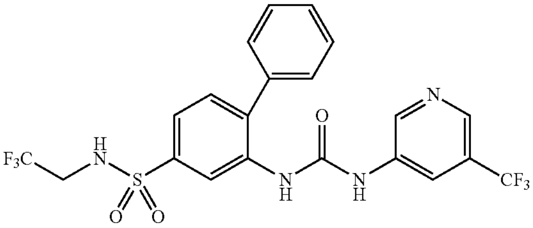
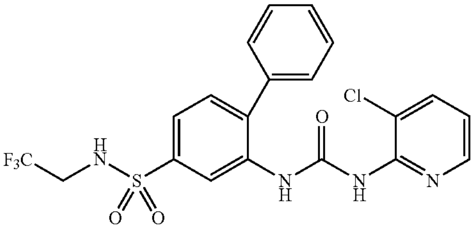
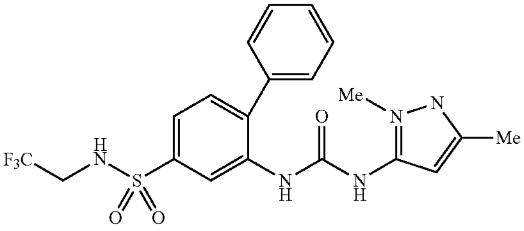
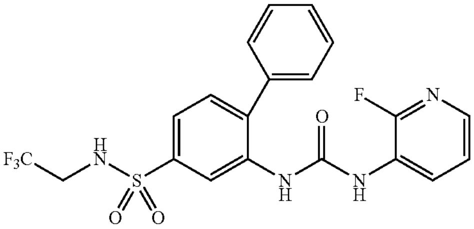
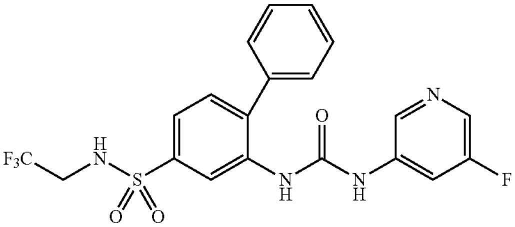
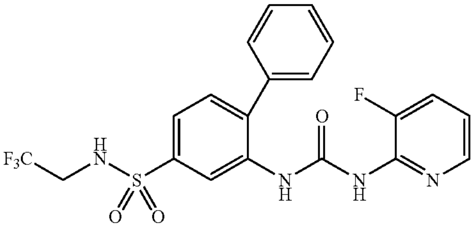
-continued
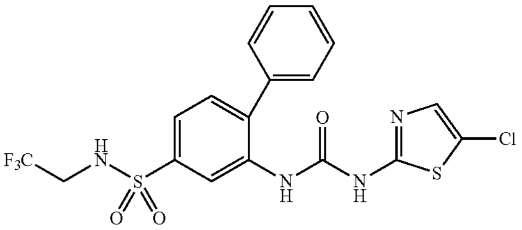
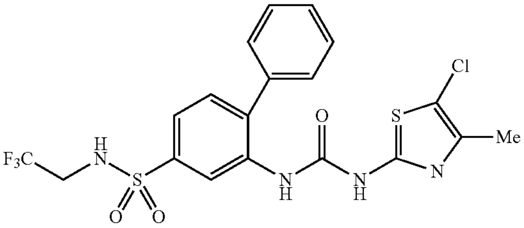
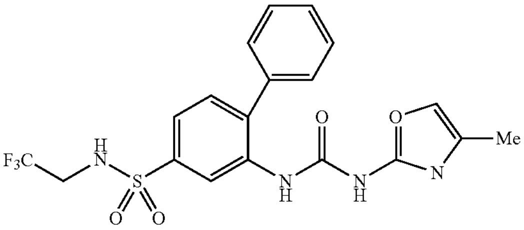
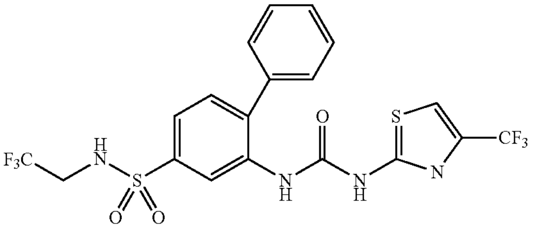
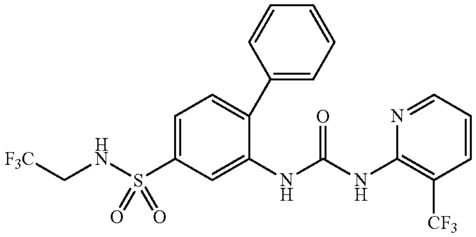
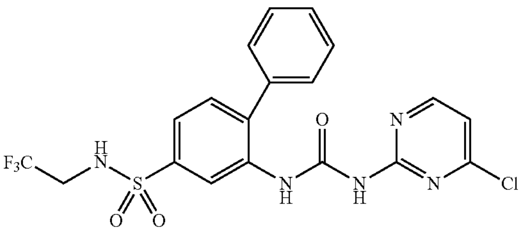
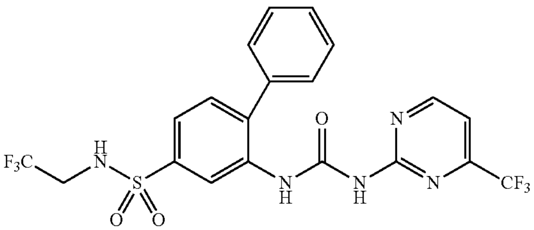

-continued
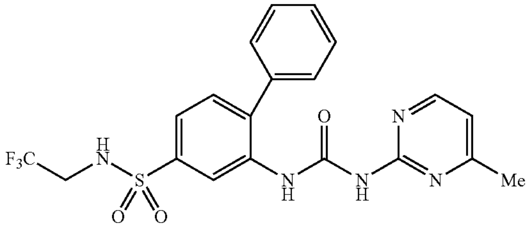
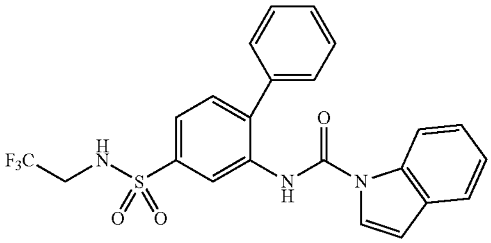
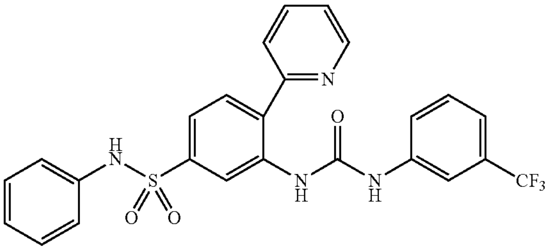
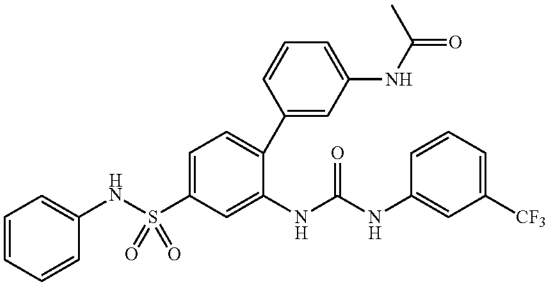
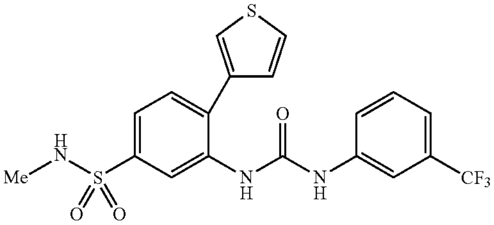
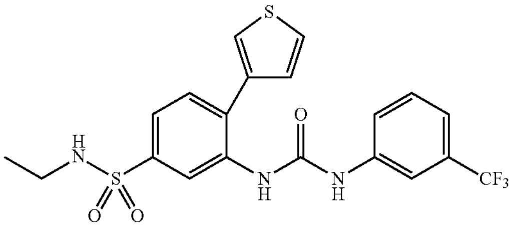
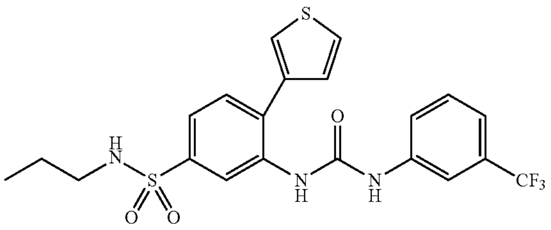
-continued
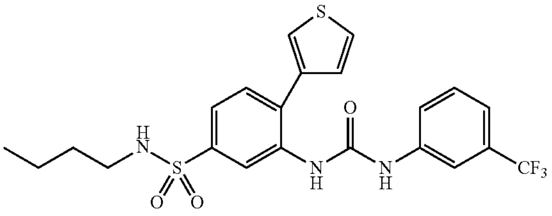
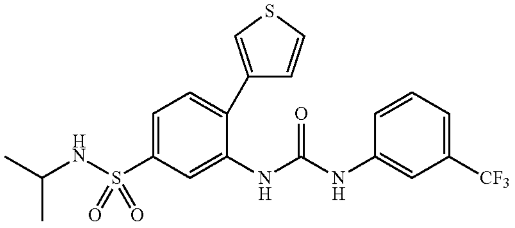
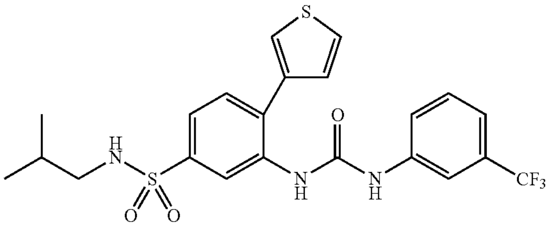
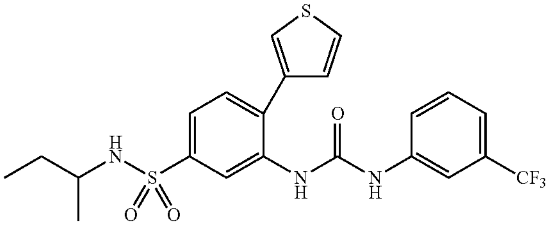
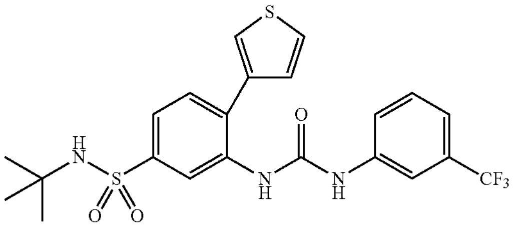
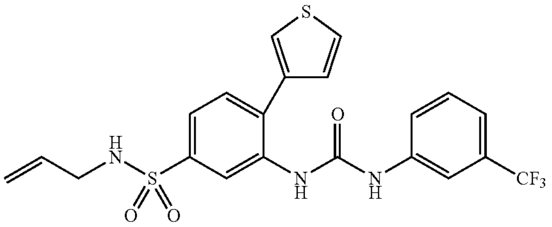
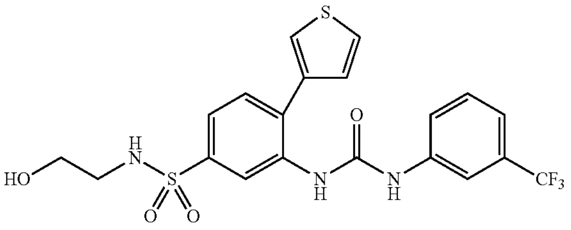

-continued
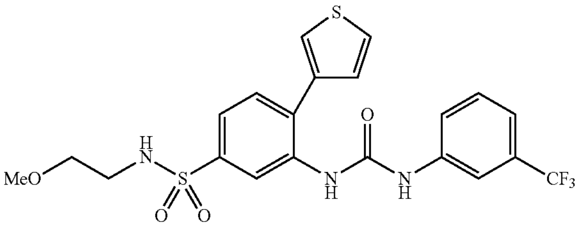
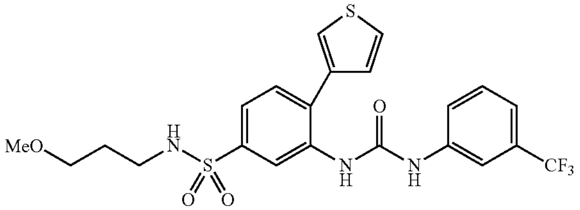
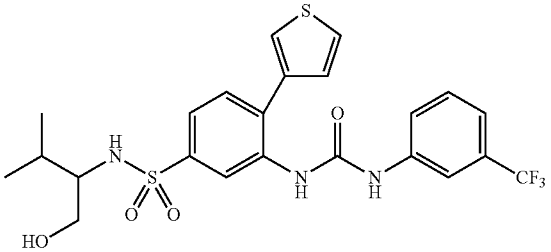
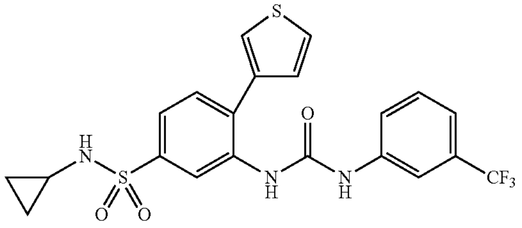
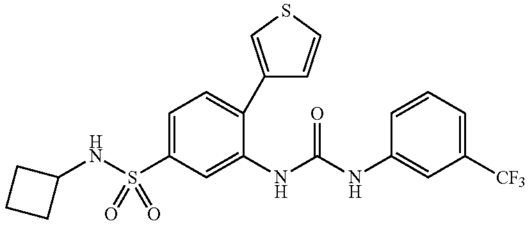
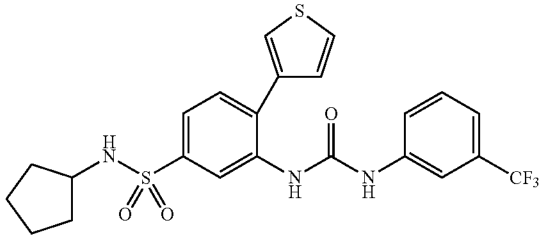
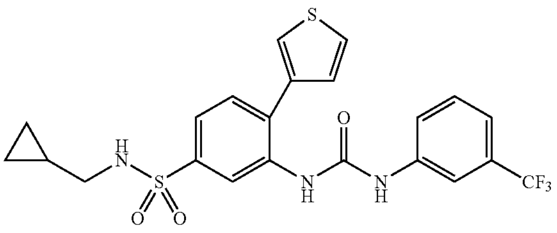
-continued
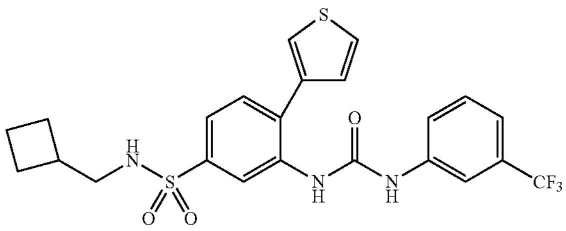
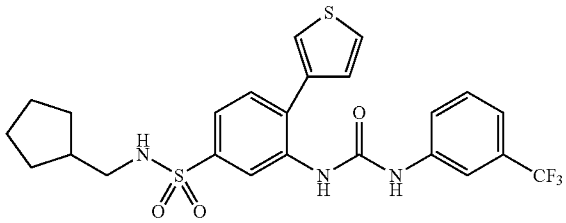
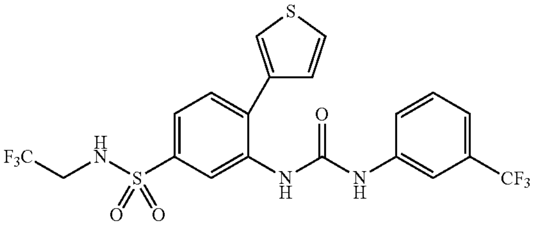
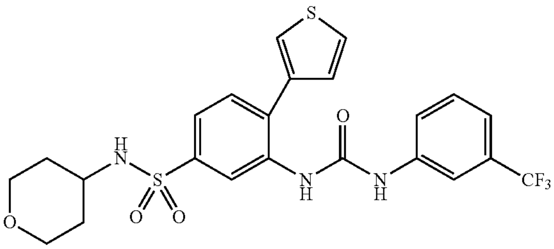
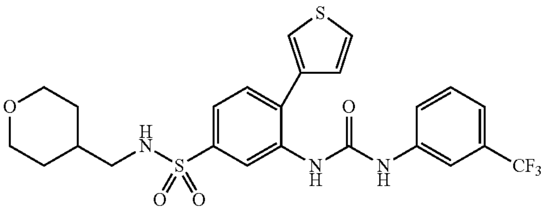
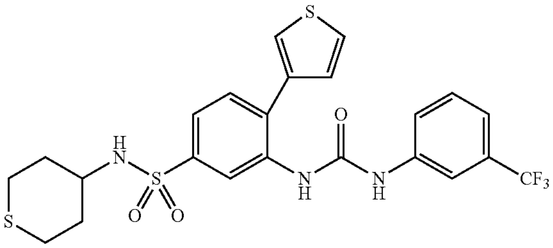
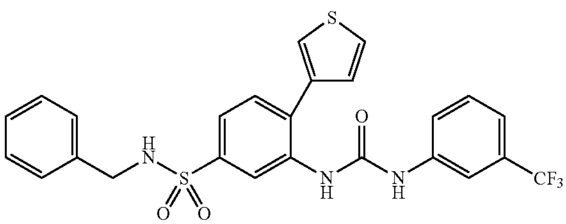

-continued
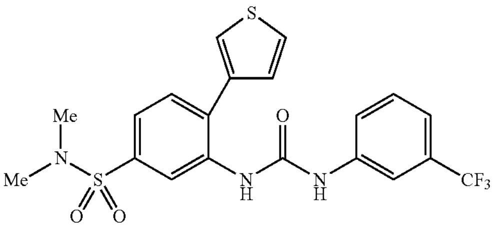
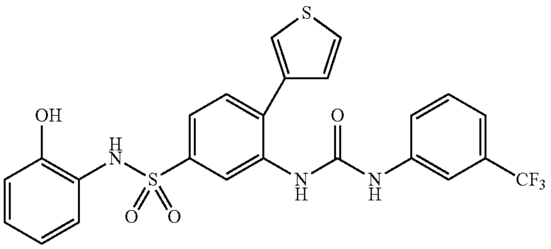
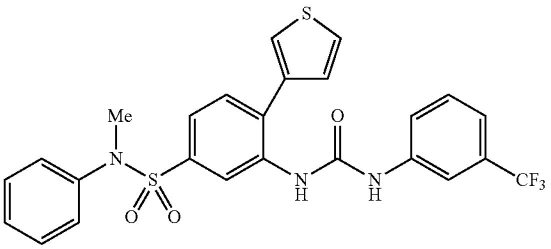
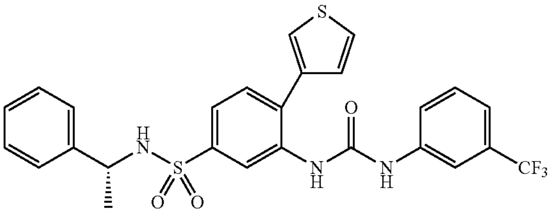
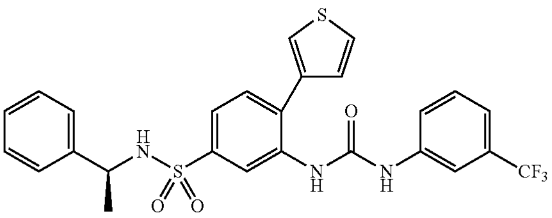
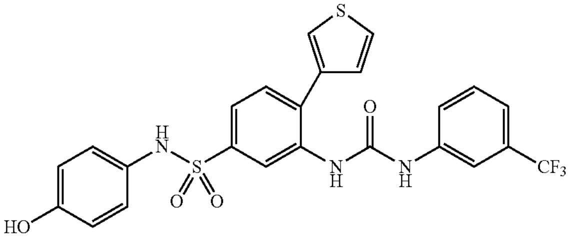
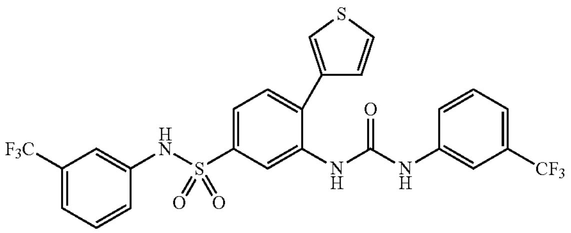
-continued
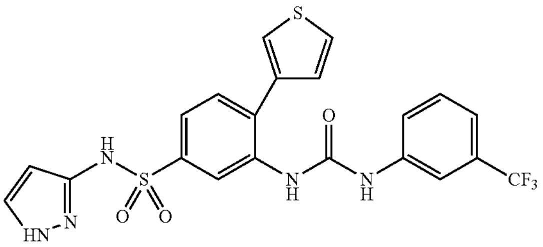
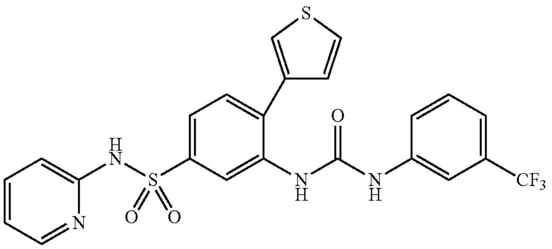
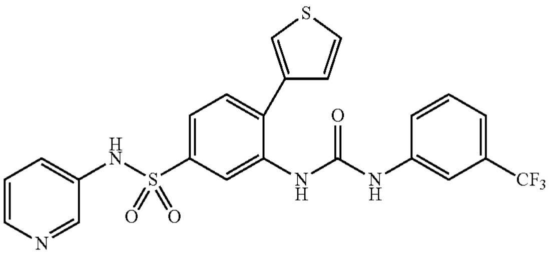
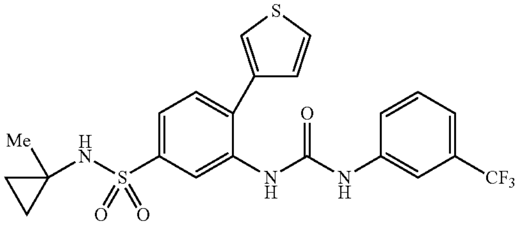
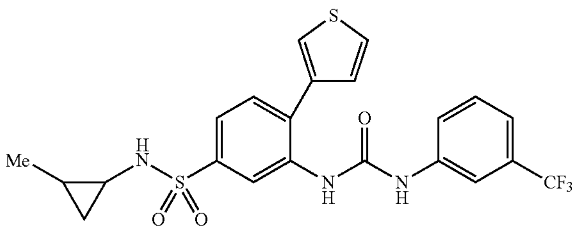
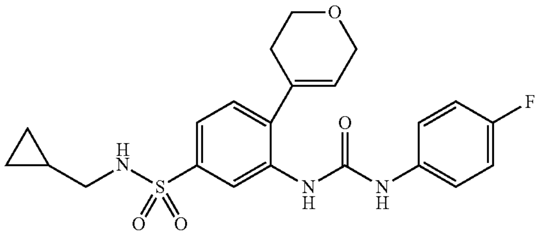
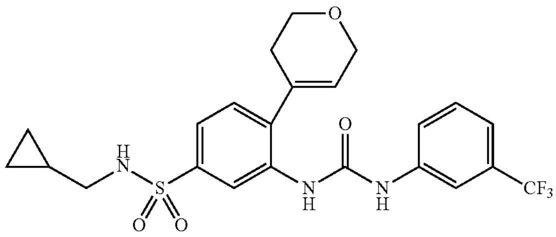

-continued
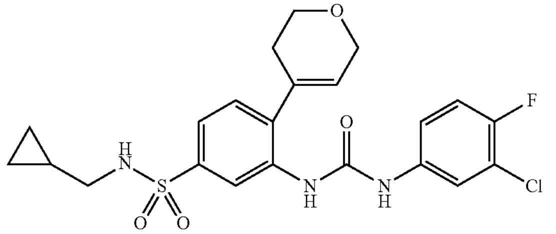
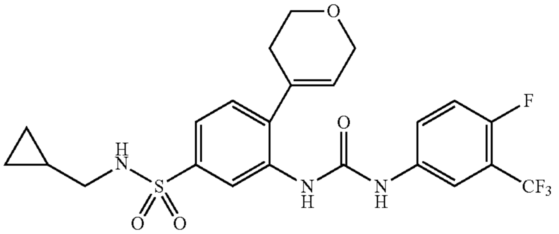
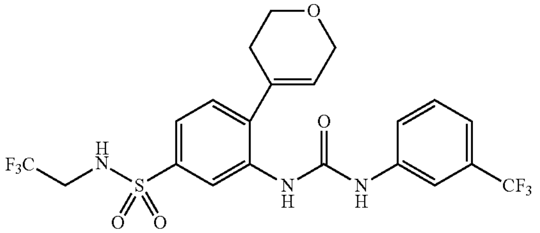
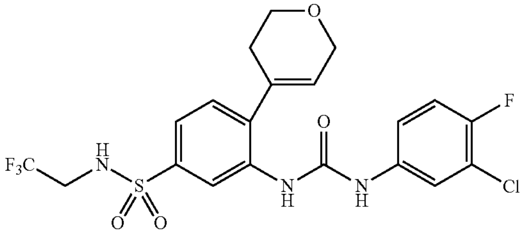
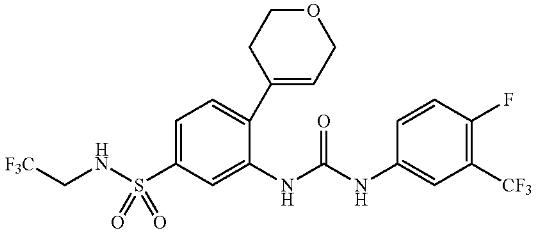
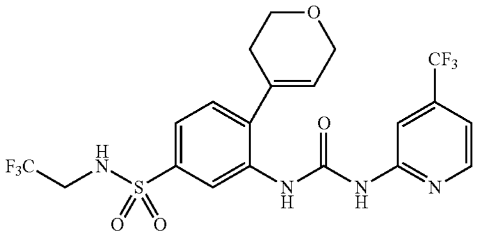
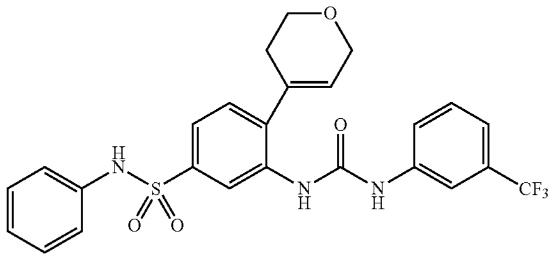
-continued
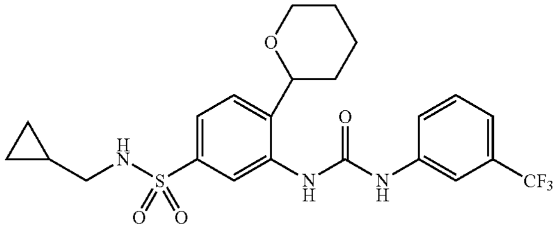
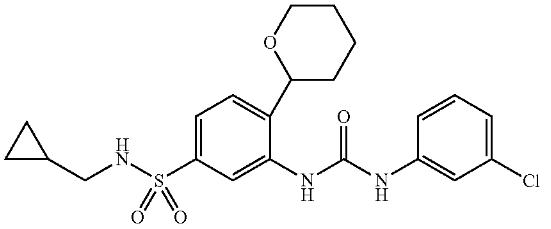
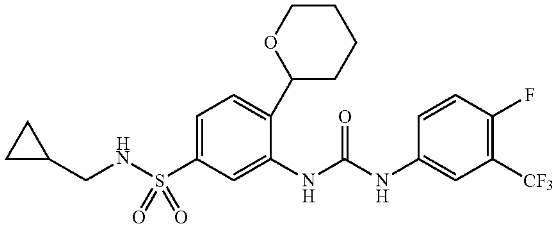
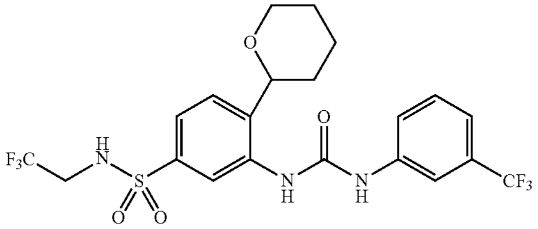
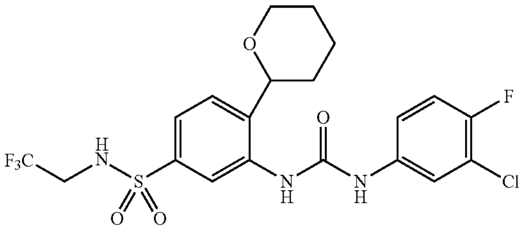
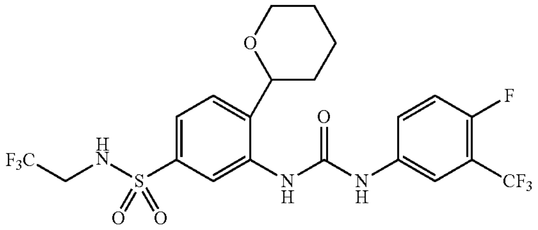
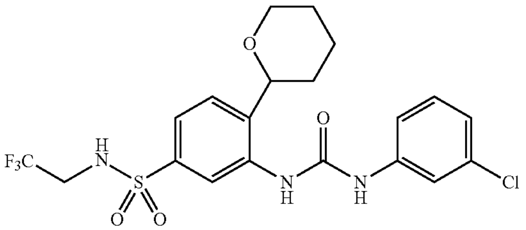

-continued
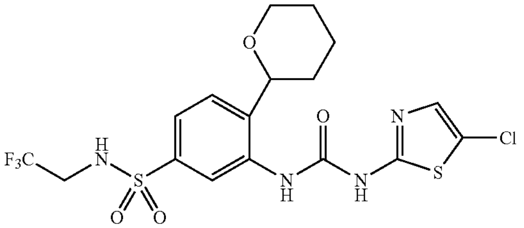
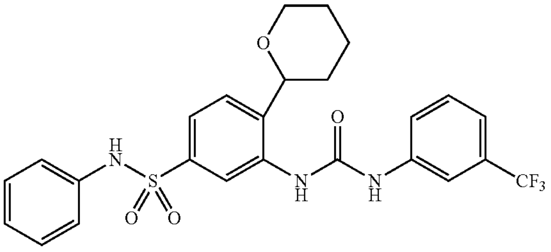
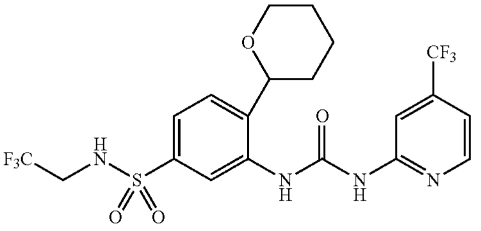
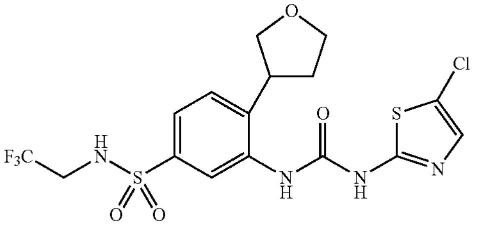
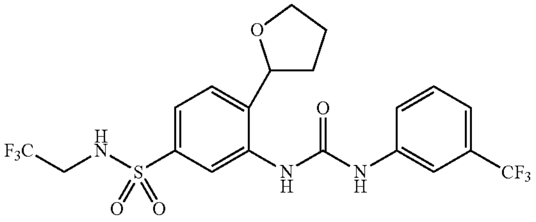
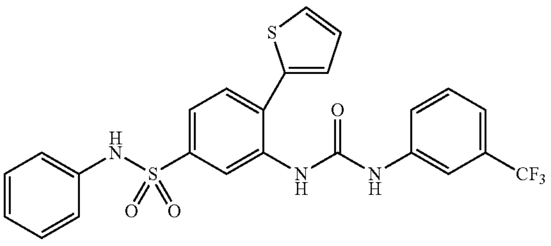
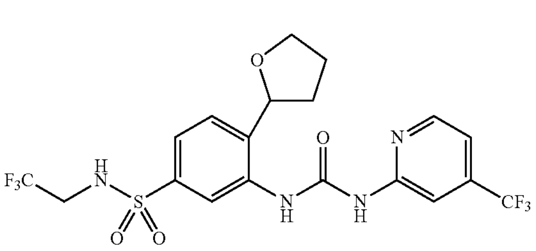
-continued
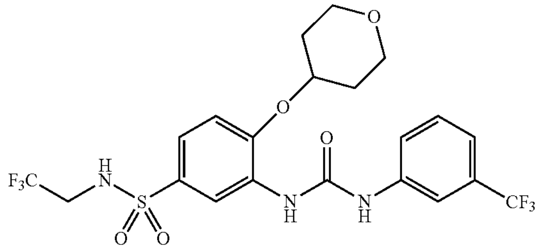
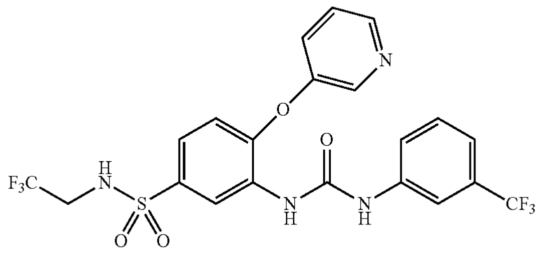 [SMILES: O=C(Nc1cccc(C(F)(F)F)c1)Nc1cc(S(=O)(=O)NCC(F)(F)F)ccc1Oc1cccnc1]
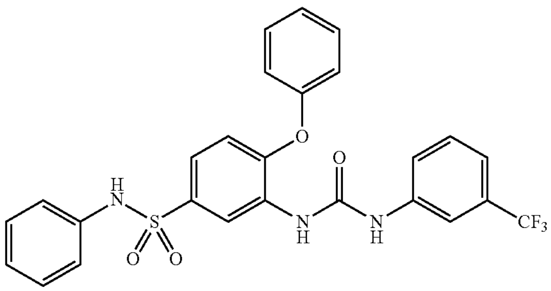
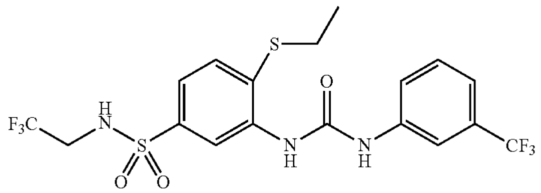
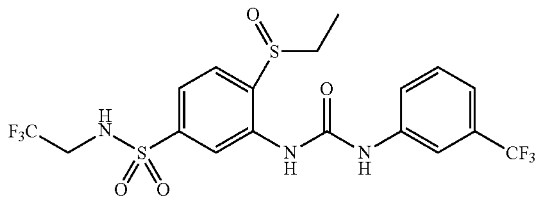
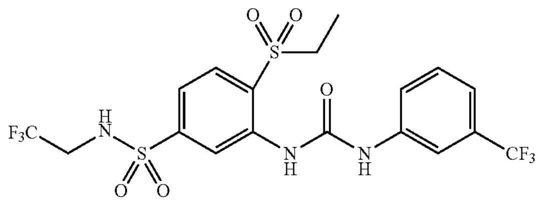
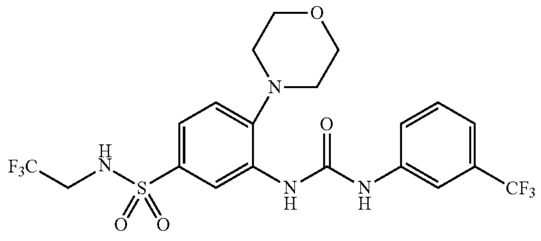 [SMILES: O=C(Nc1cccc(C(F)(F)F)c1)Nc1cc(S(=O)(=O)NCC(F)(F)F)ccc1N1CCOCC1]

-continued
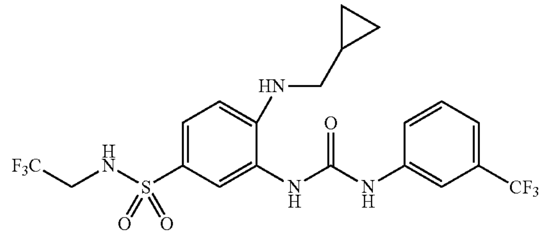
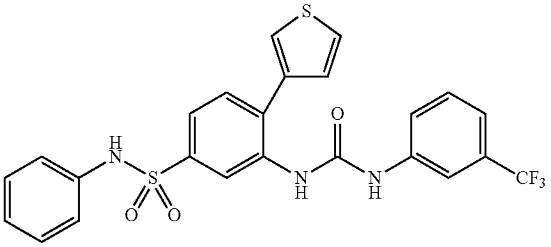
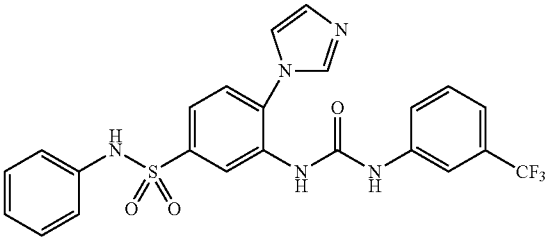
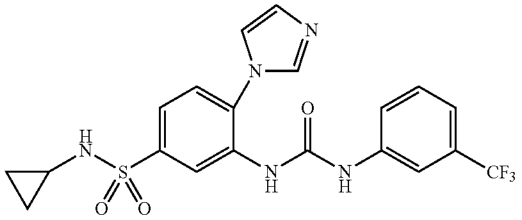
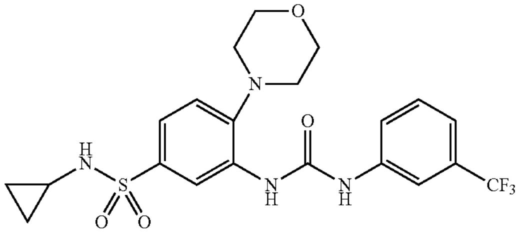
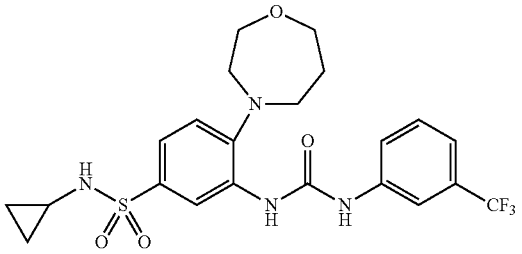
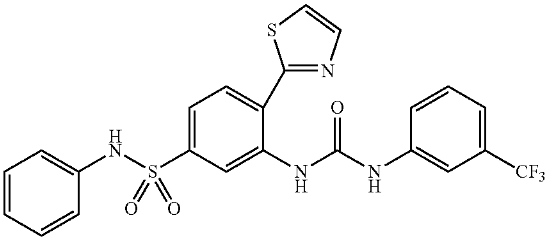
-continued
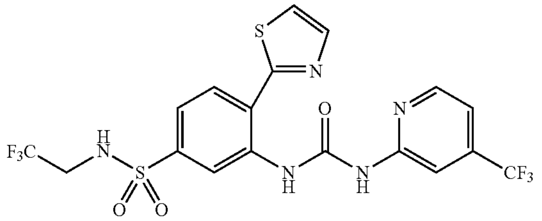
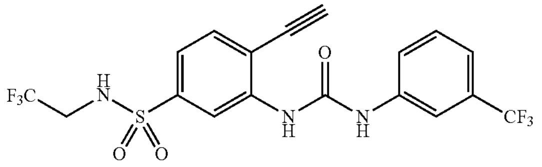
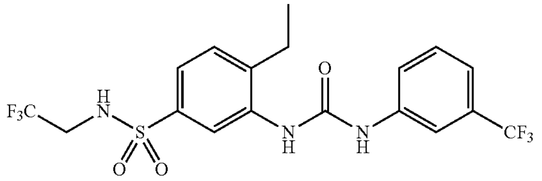
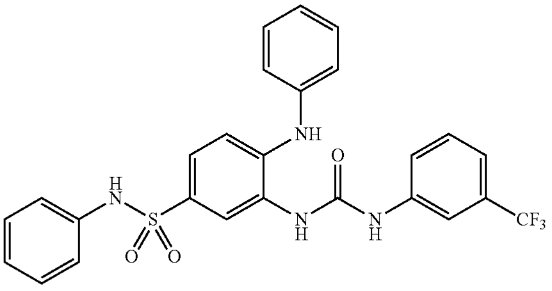
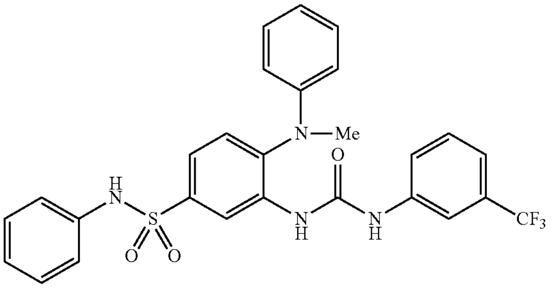
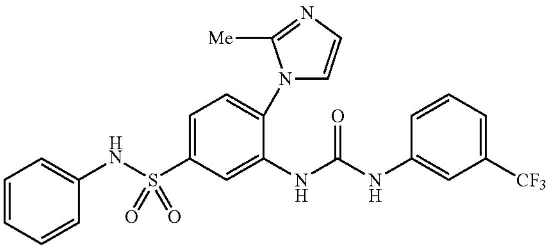
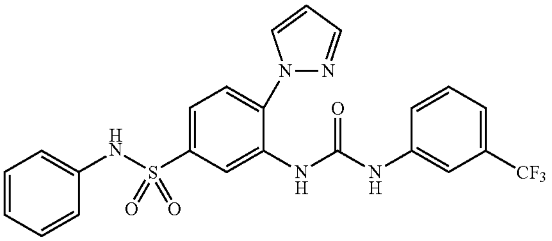

-continued

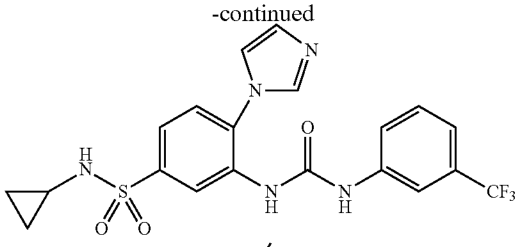

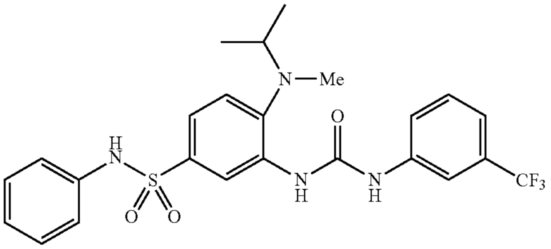

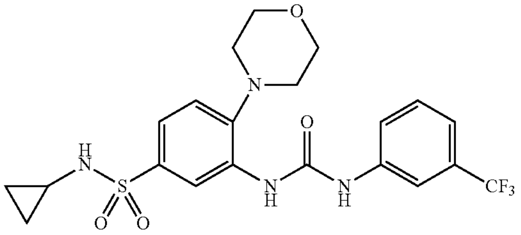

and

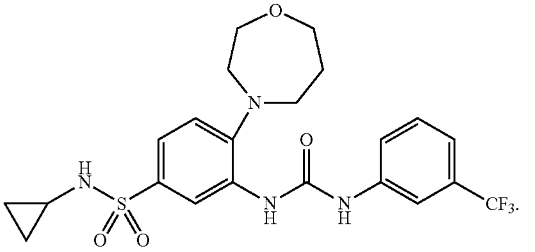

5. A pharmaceutical composition comprising a compound of claim 1 or pharmaceutically acceptable salt thereof, and a pharmaceutically acceptable carrier.

6. The composition of claim 5, comprising an additional cancer therapeutic agent.

7. A compound of or pharmaceutically acceptable salt thereof, wherein the compound is a compound of Formula (IIIa), wherein:

(IIIa)

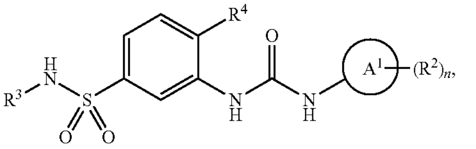

$A^1$ is aryl;

each $R^2$ is independently $C_{1-6}$ haloalkyl or $C_{1-6}$ haloalkoxy;

$R^3$ is $C_{1-6}$ alkyl, $C_{3-8}$ cycloalkyl, or heterocyclyl, each of which may be substituted with 0-3 occurrences of $R^6$;

$R^4$ is $C_{1-6}$ alkyl, $C_{1-6}$ alkoxy, $C_{1-6}$ thioalkyl, aryl, heteroaryl, heterocyclyl, or —$S(O)_2$—$C_{1-6}$ alkyl, wherein each $C_{1-6}$ alkyl, $C_{1-6}$ alkoxy, $C_{1-6}$ thioalkyl, aryl, heteroaryl, or —$S(O)_2$—$C_{1-6}$ alkyl is independently substituted with 0-3 occurrences of $R^7$;

each $R^6$ is independently $C_{1-6}$ alkyl, $C_{1-6}$ haloalkyl, cyano, or heterocyclyl; or adjacent $R^6$ moieties, taken together with the atoms to which they are attached form a heterocyclyl;

each $R^7$ is independently $C_{1-6}$ alkyl, $C_{1-6}$ alkoxy, $C_{3-8}$ cycloalkyl, hydroxyl, halo, —NHC(O)—$C_{1-6}$ alkyl, —$S(O)_2$—$C_{1-6}$ alkyl, aryl, heteroaryl or heterocyclyl; and n is 0, 1, 2, 3 or 4;

provided that:

(1) when $R^4$ is methyl, then $R^3$ is not methyl;

(2 ) when $R^4$ is methoxy, then $R^3$ is not cyclopropyl.

8. The compound of claim 1 or pharmaceutically acceptable salt thereof, wherein the compound is selected from:

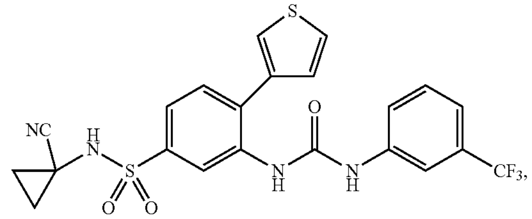

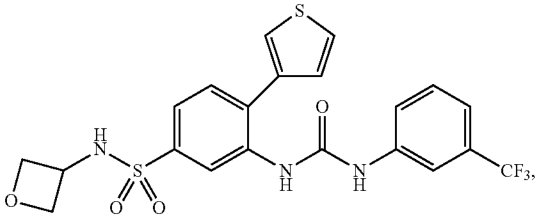

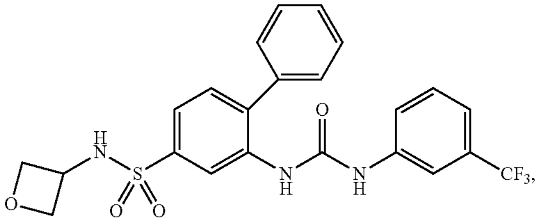

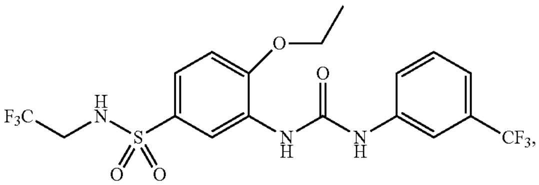

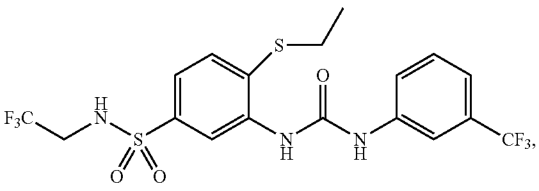

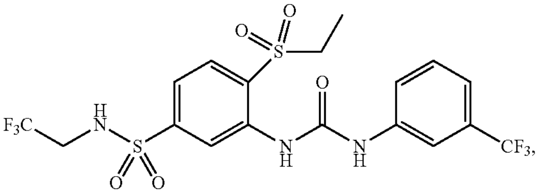

and

-continued

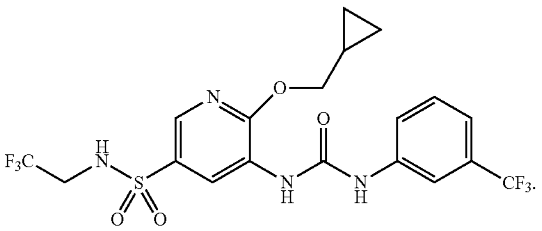

9. The compound of claim 2 or pharmaceutically acceptable salt thereof, wherein the compound is selected from:

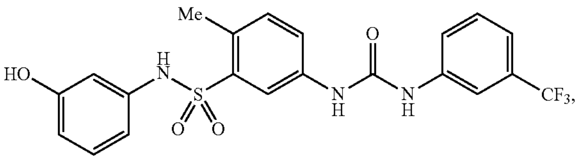

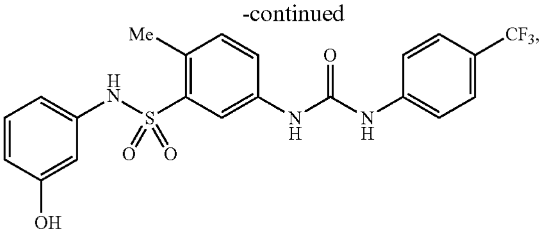

and

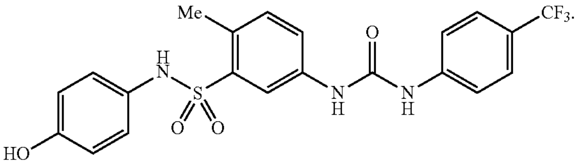

10. A pharmaceutical composition comprising a compound of claim 2 or pharmaceutically acceptable salt thereof, and a pharmaceutically acceptable carrier.

11. The pharmaceutical composition of claim 10, comprising an additional cancer therapeutic agent.

* * * * *